US012365886B2

(12) United States Patent
Babe et al.

(10) Patent No.: US 12,365,886 B2
(45) Date of Patent: Jul. 22, 2025

(54) ENGINEERED ROBUST HIGH Tm-PHYTASE CLADE POLYPEPTIDES AND FRAGMENTS THEREOF

(71) Applicant: DUPONT NUTRITION BIOSCIENCES APS, Copenhagen K (DK)

(72) Inventors: Lilia Maria Babe, Palo Alto, CA (US); Trine Christensen, Copenhagen K (DK); Svend Haaning, Copenhagen K (DK); Hye-Sook Kim, Hockessin, DE (US); Rie Mejldal, Copenhagen K (DK); Igor Nikolaev, Oegstgeest (NL); Jahnavi Chandra Prasad, Wilmington, DE (US); Sina Pricelius, Oegstgeest (NL); Jens Frisbaek Sorensen, Copenhagen K (NL); Robin Anton Sorg, Oegstgeest (NL)

(73) Assignee: International N&H Denmark APS, Kongens Lyngby (DK)

( * ) Notice: Subject to any disclaimer, the term of this patent is extended or adjusted under 35 U.S.C. 154(b) by 275 days.

(21) Appl. No.: 17/294,909

(22) PCT Filed: Nov. 20, 2019

(86) PCT No.: PCT/US2019/062335
§ 371 (c)(1),
(2) Date: May 18, 2021

(87) PCT Pub. No.: WO2020/106796
PCT Pub. Date: May 28, 2020

(65) Prior Publication Data
US 2024/0174993 A1  May 30, 2024

Related U.S. Application Data

(60) Provisional application No. 62/887,714, filed on Aug. 16, 2019, provisional application No. 62/851,122, filed on May 22, 2019, provisional application No. 62/769,713, filed on Nov. 20, 2018.

(51) Int. Cl.
*C12N 9/16* (2006.01)
*A23K 20/189* (2016.01)
*A23K 50/10* (2016.01)
*A23K 50/30* (2016.01)
*A23K 50/75* (2016.01)
*C12N 15/80* (2006.01)

(52) U.S. Cl.
CPC .............. *C12N 9/16* (2013.01); *A23K 20/189* (2016.05); *A23K 50/10* (2016.05); *A23K 50/30* (2016.05); *A23K 50/75* (2016.05); *C12N 15/80* (2013.01); *C12Y 301/03026* (2013.01)

(58) Field of Classification Search
CPC .......... C12N 9/16; C12N 15/80; C12N 15/63; A23K 20/189; A23K 50/10; A23K 50/30; A23K 50/75; A23K 10/16; A23K 40/10; C12Y 301/03026; C12Y 301/03
See application file for complete search history.

(56) References Cited

U.S. PATENT DOCUMENTS

| | | | |
|---|---|---|---|
| 5,246,853 | A | 9/1993 | Clarkson et al. |
| 5,281,526 | A | 1/1994 | Goo et al. |
| 5,475,101 | A | 12/1995 | Ward et al. |
| 6,022,725 | A | 2/2000 | Fowler et al. |
| 6,110,719 | A | 8/2000 | Kretz |
| 6,183,740 | B1 | 2/2001 | Short et al. |
| 6,268,328 | B1 | 7/2001 | Mitchinson et al. |
| 6,287,841 | B1 | 9/2001 | Mulleners et al. |
| 7,081,563 | B2 | 7/2006 | Lanahan et al. |
| 7,754,469 | B2 | 7/2010 | Baltzley et al. |
| 8,053,221 | B2 | 11/2011 | Miasnikov et al. |
| 8,101,391 | B2 | 1/2012 | Sjoeholm et al. |
| 8,143,046 | B2 | 3/2012 | Cervin et al. |
| 8,206,962 | B2 | 6/2012 | Lassen et al. |
| 8,460,656 | B2 | 6/2013 | De Maria et al. |
| 8,507,240 | B2 | 8/2013 | Lassen et al. |
| 8,557,552 | B2 | 10/2013 | Silverman et al. |
| 8,557,555 | B2 | 10/2013 | Haefner et al. |
| 9,365,840 | B2 | 6/2016 | Sjoeholm et al. |
| 2009/0280090 | A1 | 11/2009 | Rehberger et al. |
| 2012/0090042 | A1* | 4/2012 | Sjoeholm ........... C12N 15/8243 800/13 |

(Continued)

FOREIGN PATENT DOCUMENTS

| | | |
|---|---|---|
| CN | 102007211 A | 4/2011 |
| CN | 103502443 A | 1/2014 |
| EP | 3222714 B1 | 10/2019 |

(Continued)

OTHER PUBLICATIONS

Sadowski MI, Jones DT. The sequence-structure relationship and protein function prediction. Curr Opin Struct Biol. Jun. 2009;19(3):357-62. doi: 10.1016/j.sbi.2009.03.008. Epub May 4, 2009. PMID: 19406632. (Year: 2009).*

(Continued)

*Primary Examiner* — Robert B Mondesi
*Assistant Examiner* — Alexander B Pastora

(57) ABSTRACT

Engineered robust high Tm-phytase clade polypeptides and fragments thereof are described herein. Also described are methods of making such engineered robust high Tm-phytase clade and fragments thereof and use thereof in enhancing animal performance.

12 Claims, 59 Drawing Sheets
Specification includes a Sequence Listing.

(56) References Cited

U.S. PATENT DOCUMENTS

| | | | | |
|---|---|---|---|---|
| 2013/0108738 A1* | 5/2013 | Haefner | | C12N 9/16 435/320.1 |
| 2016/0083700 A1 | 3/2016 | Tan et al. | | |

FOREIGN PATENT DOCUMENTS

| | | |
|---|---|---|
| EP | 3883388 A1 | 9/2021 |
| JP | 2011519274 A | 7/2011 |
| JP | 2014513945 A | 9/2014 |
| RU | 2227159 C2 | 4/2004 |
| WO | 198906270 A1 | 7/1989 |
| WO | 198906279 A1 | 7/1989 |
| WO | 199206209 A1 | 4/1992 |
| WO | 1992012645 A1 | 8/1992 |
| WO | 199219729 A1 | 11/1992 |
| WO | 199425583 A1 | 11/1994 |
| WO | 1997016076 A1 | 5/1997 |
| WO | 199820115 A1 | 5/1998 |
| WO | 2007044968 A2 | 4/2007 |
| WO | 2008116878 A1 | 10/2008 |
| WO | 2009129489 A2 | 10/2009 |
| WO | 2010034835 A2 | 4/2010 |
| WO | 2011063308 A2 | 5/2011 |
| WO | 2011117397 A1 | 9/2011 |
| WO | 2012110778 A2 | 8/2012 |
| WO | 2012143862 A1 | 10/2012 |
| WO | 2013029013 A1 | 2/2013 |
| WO | 2013119470 A1 | 8/2013 |
| WO | 2014120638 A1 | 8/2014 |
| WO | 2015012890 A1 | 1/2015 |
| WO | 2015197871 A1 | 12/2015 |
| WO | 2017001701 A1 | 1/2017 |
| WO | 2020106796 A1 | 5/2020 |

OTHER PUBLICATIONS

Seffernick JL, de Souza ML, Sadowsky MJ, Wackett LP. Melamine deaminase and atrazine chlorohydrolase: 98 percent identical but functionally different. J Bacteriol. Apr. 2001;183(8):2405-10. doi: 10.1128/JB.183.8.2405-2410.2001. PMID: 11274097; PMCID: PMC95154. (Year: 2001).*

Tang S, Edwards EA. Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318. PMID: 23479748; PMCID: PMC3638459. (Year: 2013).*

Witkowski A. etal. "Conversion of a β-Ketoacyl Synthase to a Malonyl Decarboxylase by Replacement of the Active-Site Cysteine with Glutamine", Biochemistry 1999, 38, p. 11643-11650, doi:10.1021/bi990993h.

Seffernick J. L. etal. "Melamine Deaminase and Atrazine Chlorohydrolase: 98 Percent Identical but Functionally Different", Journal of Bacteriology, 2001, v.183, No. 8, p. 2405-2410, DOI: 10.1128/JB.183.8.2405-2410.2001.

Broun etal. "Catalytic Plasticity of Fatty Acid Modification Enzymes Underlying Chemical Diversity of Plant Lipids", Science, 1998, v.282, p. 1315-1317, DOI: 10.1126/science.282.5392.1315.

Whisstock J. C. etal. "Prediction of protein function from protein sequence and structure", Quarterly Reviews of Biophysics 36, 3 2003, p. 307-340. DOI:10.1017/S0033583503003901.

Database UniProt [online] Mar. 28, 2018 (Mar. 28, 2018) "SubName:Full=AppA family phytase/histidine-type acid phosphatase {ECO:00003131EMBL:PNK98773.1};", retrieved from EBI accession No. Uniprot: A0A2J9H2M2 Database accession No. A0A2J9H2M2.

Database UniProt [online] Nov. 2, 2016 (Nov. 2, 2016) "SubName:Full= 4-phytase / acid phosphatase {ECO:00003131EMBL:SCM51102.1}; EC=3.1.3.2 {ECO:00003131EMBL:SCM51102.1}; EC=3.1.3.26 {ECO:00003131EMBL:SCM51102.1};", retrieved from EBI accession No. UNIPROT: A0A1C6YW96 Database accession No. A0A1C6YW96.

Ariza et al., "Degradation of Phytate by the 6-Phytase from Hafnia alvei: A Combined Structural and Solution Study", Plos one. 2013. Vol. 8. No. 5. p. e65062, 14 pgs.

Truncated nef protein [Human immunodeficiency virus 1]; GenBank: AAL65331.1; Accession: AAL65331, accessed on Oct. 24, 2023, via www.ncbi.nlm.nih.gov/protein/AAL65331, 1 pg.

Menezes-Blackburn, et al., "Performance of Seven Commercial Phytases in an in Vitro Simulation of Poultry Digestive Tract", JAFC; vol. 63, Issue 27, Jun. 25, 2015, 8 pgs.

Novikova, et al., "Review: From Structure and Functions of Steroidogenic Enzymes to New Technologies of Gene Engineering", Feb. 10, 2009, Biochemistry (Mosc), Dec. 2009;74(13):1482-504.

Database Geneseq [Online]: Nov. 24, 2011, "Obesumbacterium proteus phytase", EBI accession No. GSP: AZN41740, XP002797585, 2 pgs.

Database Geneseq [Online]: Dec. 20, 2012, Mature *Hafnia* sp.-*Y. mollaretii* phytase fusion protein mutant PhV-123, EBI accession No. GSP: BAE68993, XP002797586, 3 pgs.

* cited by examiner

| P/C | A | C | D | E | F | G | H | I | K | L |
|---|---|---|---|---|---|---|---|---|---|---|
|  | 2.6320 | 3.9435 | 2.9107 | 3.0286 | 3.5450 | 2.6663 | 3.4973 | 3.2298 | 3.1466 | 2.2238 |
| COMP | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 1/S | 2.4849 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 2/E | * | * | 2.4849 | 0.0870 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 3/A | 0.2877 | * | * | 2.4849 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 4/A | 0.0572 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0870 | * | 2.4849 | 0.6932 | 0.6932 | 0.6932 | 0.6932 |  |  |  |
| 5/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.0000 | * |  |  |  |
| 6/A | 0.6932 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 7/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 8/Y | * | * | * | * | 2.8904 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 9/H | * | * | * | * | * | * | 0.2513 | * | 2.4849 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 10/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 11/D | * | * | 0.5878 | 2.8904 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 12/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 13/A | 0.1495 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 14/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1A*

| M | N | P | Q | R | S | T | V | W | Y |
|---|---|---|---|---|---|---|---|---|---|
| 3.5243 | 3.0080 | 2.5298 | 2.6977 | 3.3919 | 3.0918 | 2.6672 | 2.7745 | 4.0613 | 3.4286 |
| 2.9957 | 2.9957 | 2.9957 | 2.9957 | 2.9957 | 2.9957 | 2.9957 | 2.9957 | 2.9957 | 2.9957 |
| * | * | * | * | * | 0.0870 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 1.7918 | * | * | * |
| 2.9957 | 2.9957 | 2.9957 | 2.9957 | 2.9957 | 2.9957 | 2.9957 | 2.9957 | 2.9957 | 2.9957 |
| * | * | * | 2.8904 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 2.4849 | * | * | * | 0.8755 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 2.4849 | * | * | * | * | * | * | * | * | 0.1495 |
| 2.9957 | 2.9957 | 2.9957 | 2.9957 | 2.9957 | 2.9957 | 2.9957 | 2.9957 | 2.9957 | 2.9957 |
| * | * | * | 1.9741 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.9445 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 1.9741 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |

*FIG. 1A (Continued)*

| P/C | A | C | D | E | F | G | H | I | K | L |
|---|---|---|---|---|---|---|---|---|---|---|
| 15/I | * | * | * | * | * | * | * | 0.1178 | * | 2.1972 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 16/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 17/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 18/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 19/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 20/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 21/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 22/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 23/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 24/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 25/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 26/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 27/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 28/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 29/Q | * | * | * | 2.8904 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1B*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0572 | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1B (Continued)*

| P/C | A | C | D | E | F | G | H | I | K | L |
|---|---|---|---|---|---|---|---|---|---|---|
| 30/L | * | * | * | * | * | * | * | * | * | 0.3646 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 31/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 32/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 33/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 34/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 35/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 36/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 37/Y | * | * | * | * | * | * | 3.5835 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 38/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 39/W | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 40/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 41/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 42/W | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 43/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 44/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1C*

| M | N | P | Q | R | S | T | V | W | Y |
|---|---|---|---|---|---|---|---|---|---|
| * | * | * | * | * | * | 1.1856 | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 2.1972 | * | * | * | * | * | * | * | 0.1495 |
| 2.9957 | 2.9957 | 2.9957 | 2.9957 | 2.9957 | 2.9957 | 2.9957 | 2.9957 | 2.9957 | 2.9957 |
| * | * | * | 1.9741 | * | * | 0.1495 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | 0.0000 | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |

*FIG. 1C(Continued)*

| P/C | A | C | D | E | F | G | H | I | K | L |
|---|---|---|---|---|---|---|---|---|---|---|
| 45/P | * | * | * | * | * | * | * | * | 3.5835 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 46/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 47/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 48/Y | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 49/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 50/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 51/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 52/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 53/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 54/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 55/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 56/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 57/V | * | * | * | * | * | * | * | 3.5835 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 58/S | * | * | * | * | * | * | * | * | 1.1856 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 59/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1D*

| M | N | P | Q | R | S | T | V | W | Y |
|---|---|---|---|---|---|---|---|---|---|
| * | * | 0.0282 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0282 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.3646 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1D(Continued)*

| P/C | A | C | D | E | F | G | H | I | K | L |
|---|---|---|---|---|---|---|---|---|---|---|
| 60/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 61/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 62/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 63/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 64/Y | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 65/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 66/Q | * | * | * | 3.5835 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 67/Y | * | * | * | * | * | * | * | * | 3.5835 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 68/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 69/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 70/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 71/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 72/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 73/L | * | * | * | * | * | * | * | 2.8904 | * | 0.0572 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 74/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1E*

| M | N | P | Q | R | S | T | V | W | Y |
|---|---|---|---|---|---|---|---|---|---|
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0282 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 3.5835 | * | * | * | 2.1972 | 0.1823 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1E(Continued)*

| P/C | A | C | D | E | F | G | H | I | K | L |
|---|---|---|---|---|---|---|---|---|---|---|
| 75/S | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 76/R | 2.8904 | * | * | * | * | * | * | * | 0.8109 | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 77/D | * | * | 0.0870 | 2.4849 | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 78/r | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 79/C | * | 0.0000 | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 80/P | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 81/T | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 82/A | 0.0870 | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 83/N | * | * | 2.4849 | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 84/D | 2.8904 | * | 0.0572 | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 85/V | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 86/Y | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 87/V | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 88/W | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 89/T | 2.4849 | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |

*FIG. 1F*

| M | N | P | Q | R | S | T | V | W | Y |
|---|---|---|---|---|---|---|---|---|---|
| * | * | 2.4849 | * | * | 0.0870 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.6932 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 1.1856 | * | * | 0.7503 | 1.5041 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | 2.4849 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0870 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | 0.0000 | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0870 | * | * | * |
| 2.9957 | 2.9957 | 2.9957 | 2.9957 | 2.9957 | 2.9957 | 2.9957 | 2.9957 | 2.9957 | 2.9957 |

*FIG. 1F (Continued)*

| P/C | A | C | D | E | F | G | H | I | K | L |
|---|---|---|---|---|---|---|---|---|---|---|
| 90/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 91/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 92/N | 2.8904 | * | 1.7918 | * | * | 3.5835 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 93/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 94/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 95/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 96/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 97/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 98/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 99/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 100/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 101/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 102/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 103/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 104/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1G*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | 0.2877 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1G(Continued)*

| P/C | A | C | D | E | F | G | H | I | K | L |
|---|---|---|---|---|---|---|---|---|---|---|
| 105/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 106/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 107/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 108/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 109/E | * | * | * | 0.5390 | * | 1.7918 | * | * | 2.4849 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 110/C | * | 0.0000 | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 111/D | 2.4849 | * | 0.3254 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 112/L | * | * | * | * | * | * | * | 2.4849 | * | 0.0870 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 113/T | 2.8904 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 114/I | * | * | * | * | * | * | * | 0.0282 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 115/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 116/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 117/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 118/s | * | * | * | * | * | * | * | * | 2.4849 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 119/D | * | * | 0.3646 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1H*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 1.9741 | 3.5835 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 1.6376 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0572 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 3.5835 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.8755 | * | 3.5835 | * | 0.7503 | * | * | * | * |
| 2.9957 | 2.9957 | 2.9957 | 2.9957 | 2.9957 | 2.9957 | 2.9957 | 2.9957 | 2.9957 | 2.9957 |
| * | 1.1856 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1H(Continued)*

| P/C | A | C | D | E | F | G | H | I | K | L |
|---|---|---|---|---|---|---|---|---|---|---|
| 120/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 121/K | * | * | * | * | * | * | 3.5835 | * | 0.1178 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 122/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 123/V | 1.7918 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 124/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 125/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 126/L | * | * | * | * | * | * | * | * | * | 0.1495 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 127/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 128/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 129/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 130/L | * | * | * | * | * | * | * | * | * | 0.4925 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 131/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 132/A | 0.2162 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 133/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 134/I | * | * | * | * | * | * | * | 0.0282 | * | 3.5835 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1I*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 2.8904 | 3.5835 | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.2513 | * | * | * | 1.5041 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.1823 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 1.9741 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.9445 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 1.6376 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1I(Continued)*

| P/C | A | C | D | E | F | G | H | I | K | L |
|---|---|---|---|---|---|---|---|---|---|---|
| 135/C | * | 0.0000 | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 136/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 137/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 138/D | * | * | 0.0282 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 139/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 140/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 141/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 142/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 143/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 144/Q | * | * | * | 3.5835 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 145/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 146/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 147/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 148/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 149/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1J*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 3.5835 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 2.8904 | 0.0572 | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 3.5835 | 0.0282 | * | * |
| 2.9957 | 2.9957 | 2.9957 | 2.9957 | 2.9957 | 2.9957 | 2.9957 | 2.9957 | 2.9957 | 2.9957 |
| * | * | * | 0.0282 | * | * | * | * | * | 3.5835 |
| 2.9957 | 2.9957 | 2.9957 | 2.9957 | 2.9957 | 2.9957 | 2.9957 | 2.9957 | 2.9957 | 2.9957 |
| * | * | * | 0.0282 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1J(Continued)*

| P/C | A | C | D | E | F | G | H | I | K | L |
|---|---|---|---|---|---|---|---|---|---|---|
| 150/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 151/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 152/M | * | * | * | * | * | 2.8904 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 153/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 154/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 155/D | * | * | 0.0572 | 2.8904 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 156/K | * | * | * | 2.8904 | * | * | * | * | 0.1178 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 157/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 158/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 159/Q | * | * | 2.8904 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 160/H | * | * | * | * | * | * | 0.1178 | * | 3.5835 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 161/Y | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 162/R | 1.9741 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 163/P | 1.9741 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 164/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1K*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0572 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 2.8904 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0572 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 3.5835 | * | * | * | * | 2.8904 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |
| * | * | * | 3.5835 | 0.1823 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.1495 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1K(Continued)*

| P/C | A | C | D | E | F | G | H | I | K | L |
|---|---|---|---|---|---|---|---|---|---|---|
| 165/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 166/A | 0.1178 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 167/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 168/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 169/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 170/N | 3.5835 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 171/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 172/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 173/N | * | * | 2.8904 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 174/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 175/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 176/K | 3.5835 | * | * | * | * | * | * | * | 0.0282 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 177/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 178/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 179/Y | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1L*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 2.1972 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | 0.0870 | * | * | * | 2.8904 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0572 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |

*FIG. 1L(Continued)*

| P/C | A | C | D | E | F | G | H | I | K | L |
|---|---|---|---|---|---|---|---|---|---|---|
| 180/C | * | 0.0000 | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 181/Q | 2.4849 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 182/R | * | * | * | * | * | * | 2.8904 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 183/H | * | * | * | * | * | * | 0.0282 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 184/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 185/G | * | * | * | * | * | 0.4925 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 186/E | * | * | 1.0186 | 0.4480 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 187/K | * | * | * | 3.5835 | * | * | * | * | 0.5390 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 188/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 189/C | * | 0.0000 | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 190/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 191/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 192/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 193/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 194/A | 0.6932 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1M*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.5390 | 1.0986 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.9445 | 0.5878 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 3.5835 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.9445 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.9445 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.1495 | * | * | * | 1.9741 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.4925 | * | 0.9445 | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.6932 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1M(Continued)*

| P/C | A | C | D | E | F | G | H | I | K | L |
|---|---|---|---|---|---|---|---|---|---|---|
| 195/F | * | * | * | * | 0.1495 | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 196/P | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 197/S | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 198/Y | * | * | * | * | * | * | * | * | 0.7503 | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 199/L | * | * | * | * | * | * | * | * | * | 0.0000 |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 200/N | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 201/I | * | * | * | * | * | * | * | 0.0000 | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 202/S | * | * | * | * | * | 3.5835 | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 203/D | * | * | 0.0000 | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 204/D | * | * | 0.0000 | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 205/G | * | * | * | * | * | 0.0000 | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 206/N | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 207/E | * | * | * | 0.0000 | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 208/V | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 209/Q | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |

*FIG. 1N*

| M | N | P | Q | R | S | T | V | W | Y |
|---|---|---|---|---|---|---|---|---|---|
| 1.9741 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 3.5835 | * | * | * | * | 0.6932 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0282 | * | * | * | 3.5835 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.1823 | 1.9741 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1N(Continued)*

| P/C | A | C | D | E | F | G | H | I | K | L |
|---|---|---|---|---|---|---|---|---|---|---|
| 210/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 211/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 212/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 213/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 214/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 215/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 216/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 217/S | * | * | * | * | * | 3.5835 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 218/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 219/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 220/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 221/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 222/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 223/I | * | * | * | * | * | * | * | 0.0282 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 224/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 10*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0282 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 3.5835 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1O(Continued)*

| P/C | A | C | D | E | F | G | H | I | K | L |
|---|---|---|---|---|---|---|---|---|---|---|
| 225/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 226/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 227/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 228/Y | * | * | * | * | * | * | 3.5835 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 229/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 230/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 231/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 232/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 233/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 234/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 235/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 236/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 237/W | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 238/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 239/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1P*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0282 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | 0.0000 | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1P(Continued)*

| P/C | A | C | D | E | F | G | H | I | K | L |
|---|---|---|---|---|---|---|---|---|---|---|
| 240/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 241/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 242/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 243/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 244/Q | * | * | * | 3.5835 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 245/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 246/W | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 247/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 248/D | 1.2809 | * | 0.3254 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 249/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 250/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 251/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 252/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 253/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 254/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

FIG. 1Q

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0282 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | 0.0000 | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1Q(Continued)*

| P/C | A | C | D | E | F | G | H | I | K | L |
|---|---|---|---|---|---|---|---|---|---|---|
| 255/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 256/Q | * | * | * | * | * | * | 1.1856 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 257/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 258/D | * | * | 0.0282 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 259/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 260/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 261/E | * | * | * | 0.4055 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 262/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 263/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 264/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 265/Y | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 266/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 267/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 268/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 269/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1R*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.9445 | * | * | * | * | * | 1.1856 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 3.5835 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 1.2809 | * | 2.8904 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

FIG. 1R(Continued)

| P/C | A | C | D | E | F | G | H | I | K | L |
|---|---|---|---|---|---|---|---|---|---|---|
| 270/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 271/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 272/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 273/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 274/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 275/L | * | * | * | * | * | * | * | * | * | 0.0870 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 276/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 277/T | 3.5835 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 278/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 279/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 280/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 281/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 282/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 283/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 284/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1S*

| M | N | P | Q | R | S | T | V | W | Y |
|---|---|---|---|---|---|---|---|---|---|
| * | 0.1823 | * | 1.7918 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 2.4849 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0282 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 2.8904 | * | 0.0572 | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 2.4849 | * | * | 0.0870 | * | * | * | * |
| 2.9957 | 2.9957 | 2.9957 | 2.9957 | 2.9957 | 2.9957 | 2.9957 | 2.9957 | 2.9957 | 2.9957 |

*FIG. 1S(Continued)*

| P/C | A | C | D | E | F | G | H | I | K | L |
|---|---|---|---|---|---|---|---|---|---|---|
| 285/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 286/T | 2.8904 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 287/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 288/A | 0.4055 | * | * | 1.0986 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 289/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 290/E | * | * | * | 0.4055 | * | * | * | * | 1.0986 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 291/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 292/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 293/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 294/I | * | * | * | * | * | * | * | 0.0282 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 295/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 296/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 297/D | * | * | 0.2162 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 298/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 299/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1T*

| M | N | P | Q | R | S | T | V | W | Y |
|---|---|---|---|---|---|---|---|---|---|
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0572 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.4055 | 1.0986 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 3.5835 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0000 | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 1.6376 | * | * | * | * |
| 2.9957 | 2.9957 | 2.9957 | 2.9957 | 2.9957 | 2.9957 | 2.9957 | 2.9957 | 2.9957 | 2.9957 |
| * | 1.7918 | * | * | * | * | * | 0.1823 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1T(Continued)*

| P/C | A | C | D | E | F | G | H | I | K | L |
|---|---|---|---|---|---|---|---|---|---|---|
| 300/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 301/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 302/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 303/L | * | * | * | * | * | * | * | 2.8904 | * | 0.0572 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 304/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 305/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 306/H | * | * | * | * | * | * | 0.0000 | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 307/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 308/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 309/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 310/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 311/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 312/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 313/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 314/G | 1.5041 | * | * | * | * | 0.2513 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1U*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1U(Continued)*

| P/C | A | C | D | E | F | G | H | I | K | L |
|---|---|---|---|---|---|---|---|---|---|---|
| 315/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 316/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 317/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 318/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 319/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 320/T | 3.5835 | * | 1.0186 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 321/W | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 322/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 323/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 324/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 325/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 326/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 327/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 328/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 329/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1V*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.4925 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | 0.0000 | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1V(Continued)*

| P/C | A | C | D | E | F | G | H | I | K | L |
|---|---|---|---|---|---|---|---|---|---|---|
| 330/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 331/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 332/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 333/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 334/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 335/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 336/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 337/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 338/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 339/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 340/L | * | * | * | * | * | * | * | * | * | 0.1178 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 341/W | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 342/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 343/D | * | * | 0.0000 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 344/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1W*

| M | N | P | Q | R | S | T | V | W | Y |
|---|---|---|---|---|---|---|---|---|---|
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 2.1972 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | 0.0000 | * |
| 2.9957 | 2.9957 | 2.9957 | 2.9957 | 2.9957 | 2.9957 | 2.9957 | 2.9957 | 2.9957 | 2.9957 |
| * | * | * | * | 1.1856 | 0.3646 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1W(Continued)*

| P/C | A | C | D | E | F | G | H | I | K | L |
|---|---|---|---|---|---|---|---|---|---|---|
| 345/E | 1.5041 | * | 1.3863 | 0.6391 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 346/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 347/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 348/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 349/Y | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 350/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 351/S | 3.5835 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 352/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 353/K | * | * | * | 2.4849 | * | * | 0.8755 | * | 0.6932 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 354/M | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 355/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 356/Y | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 357/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 358/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 359/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1X*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.0282 | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 0.0000 | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0000 |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1X(Continued)*

| P/C | A | C | D | E | F | G | H | I | K | L |
|---|---|---|---|---|---|---|---|---|---|---|
| 360/A | 0.0572 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 361/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 362/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 363/R | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 364/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 365/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 366/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 367/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 368/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 369/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 370/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 371/K | * | * | * | * | * | * | * | * | 0.0000 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 372/E | * | * | * | 0.0000 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 373/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 374/A | 0.0000 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1Y*

| M | N | P | Q | R | S | T | V | W | Y |
|---|---|---|---|---|---|---|---|---|---|
| * | * | * | * | * | * | 2.8904 | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0000 | * | * | * | * | * |
| 2.9957 | 2.9957 | 2.9957 | 2.9957 | 2.9957 | 2.9957 | 2.9957 | 2.9957 | 2.9957 | 2.9957 |
| * | 0.0000 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| 1.2809 | * | * | 0.3254 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1Y(Continued)*

| P/C | A | C | D | E | F | G | H | I | K | L |
|---|---|---|---|---|---|---|---|---|---|---|
| 375/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 376/S | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 377/N | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 378/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 379/L | * | * | * | * | * | * | * | 3.5835 | * | 0.0282 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 380/K | * | * | * | 3.5835 | * | * | * | * | 0.0282 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 381/I | * | * | * | * | * | * | * | 0.0000 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 382/P | * | * | * | 3.5835 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 383/G | * | * | * | * | * | 0.0000 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 384/C | * | 0.0000 | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 385/D | * | * | 0.0282 | 3.5835 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 386/D | * | * | 0.0282 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 387/Q | * | * | * | * | * | * | * | 3.5835 | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 388/T | * | * | * | * | * | 3.5835 | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 389/A | 0.0282 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1Z*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | 0.4480 | 1.0186 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0282 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | 3.5835 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0282 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0282 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 3.5835 | * | * | * |
| 2.9957 | 2.9957 | 2.9957 | 2.9957 | 2.9957 | 2.9957 | 2.9957 | 2.9957 | 2.9957 | 2.9957 |

*FIG. 1Z(Continued)*

| P/C | A | C | D | E | F | G | H | I | K | L |
|---|---|---|---|---|---|---|---|---|---|---|
| 390/E | * | * | 3.5835 | 0.0282 | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 391/G | * | * | * | * | * | 0.0282 | * | * | 3.5835 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 392/Y | * | * | * | * | * | * | * | * | * | 3.5835 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 393/C | * | 0.0000 | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 394/P | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 395/L | * | * | * | * | * | * | * | * | * | 0.0000 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 396/D | * | * | 0.1823 | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 397/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 398/F | * | * | * | * | 0.0000 | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 399/T | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 400/R | * | * | * | * | * | * | * | * | 3.5835 | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 401/L | * | * | * | * | * | * | * | * | * | 0.0282 |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 402/V | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 403/N | 3.5835 | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |
| 404/Q | * | * | * | * | * | * | * | * | * | * |
|  | 2.9957 | 2.9957 | 2.9957 | 2.9957 | 2.9957 | 2.9957 | 2.9957 | 2.9957 | 2.9957 | 2.9957 |
|  | 0.0000 | * | * | 0.6932 | 0.6932 | 0.6932 | 0.6932 |  |  |  |

*FIG. 1AA*

| M | N | P | Q | R | S | T | V | W | Y |
|---|---|---|---|---|---|---|---|---|---|
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | 0.0282 |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0282 | 3.5835 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 1.7918 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | 0.0000 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 3.5835 | * | * | 0.0282 | * | * | * |
| 2.9957 | 2.9957 | 2.9957 | 2.9957 | 2.9957 | 2.9957 | 2.9957 | 2.9957 | 2.9957 | 2.9957 |
| * | * | * | * | 0.0572 | * | * | 3.5835 | * | * |
| 2.9957 | 2.9957 | 2.9957 | 2.9957 | 2.9957 | 2.9957 | 2.9957 | 2.9957 | 2.9957 | 2.9957 |
| * | * | * | * | 3.5835 | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0000 | * | * |
| 2.9957 | 2.9957 | 2.9957 | 2.9957 | 2.9957 | 2.9957 | 2.9957 | 2.9957 | 2.9957 | 2.9957 |
| * | 0.0282 | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0282 | 3.5835 | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1AA(Continued)*

| P/C | A | C | D | E | F | G | H | I | K | L |
|---|---|---|---|---|---|---|---|---|---|---|
| 405/V | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 406/V | * | * | * | * | * | * | * | 2.8904 | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 407/E | * | * | * | 0.0000 | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 408/P | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 409/A | 0.0000 | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 410/C | * | 0.0000 | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 411/Q | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.6932 | 0.6932 | | | |
| 412/L | * | * | * | * | * | * | * | 1.5041 | * | 0.2513 |
| | 2.9957 | 2.9957 | 2.9957 | 2.9957 | 2.9957 | 2.9957 | 2.9957 | 2.9957 | 2.9957 | 2.9957 |
| | 0.1178 | * | 2.1972 | 0.6932 | 0.6932 | 0.6932 | 0.6932 | | | |
| 413/P | * | * | * | * | * | * | * | * | * | * |
| | 2.9957 | 2.9957 | 2.9957 | 2.9957 | 2.9957 | 2.9957 | 2.9957 | 2.9957 | 2.9957 | 2.9957 |
| | 0.0000 | * | * | 0.6932 | 0.6932 | 0.0000 | * | | | |

*FIG. 1BB*

| M | N | P | Q | R | S | T | V | W | Y |
|---|---|---|---|---|---|---|---|---|---|
| * | * | * | * | * | 1.9741 | * | 0.1495 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | 0.0572 | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | 0.0000 | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | * | * | * | * | * | * | * | * |
| 2.9957 | 2.9957 | 2.9957 | 2.9957 | 2.9957 | 2.9957 | 2.9957 | 2.9957 | 2.9957 | 2.9957 |
| * | * | 0.0000 | * | * | * | * | * | * | * |
| 2.9957 | 2.9957 | 2.9957 | 2.9957 | 2.9957 | 2.9957 | 2.9957 | 2.9957 | 2.9957 | 2.9957 |

*FIG. 1BB(Continued)*

SEQUENCE LISTING

<160> NUMBER OF SEQ ID NOS: 104

<210> SEQ ID NO 1
<211> LENGTH: 413
<212> TYPE: PRT
<213> ORGANISM: artificial sequence
<220> FEATURE:
<223> OTHER INFORMATION: PHY-13594 - sequence is synthesized

<400> SEQUENCE: 1

Ser Glu Ala Ala Pro Ala Gly Tyr His Leu Asp Lys Ala Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gln Gly Leu Leu Ser Arg Asp Ser Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asp Ile Lys Gln Val Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Asn Ala Phe Pro Ser Lys Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

```
Leu Val Asn Gln Val Val Glu Pro Ala Cys Gln Leu Pro
            405                 410

<210> SEQ ID NO 2
<211> LENGTH: 413
<212> TYPE: PRT
<213> ORGANISM: artificial sequence
<220> FEATURE:
<223> OTHER INFORMATION: PHY-10931- sequence is synthesized

<400> SEQUENCE: 2

Ser Glu Thr Ala Pro Ala Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Asn Gln Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gly Leu Leu Ser Arg Asp Arg Cys Pro
65              70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Gln Cys Pro Leu
            100                 105                 110

Thr Ile His His Gln Ser Asn Ile Lys Val Val Asp Pro Leu Phe His
        115                 120                 125

Pro Leu Lys Thr Gly Ile Cys Ser Met Asp Lys Thr Gln Val Gln Gln
    130                 135                 140

Ala Val Glu Lys Gln Ala Gly Met Pro Ile Asp Lys Leu Asn Gln Tyr
145                 150                 155                 160

Tyr Ala Pro Glu Leu Ser Leu Met Ser Asn Val Leu Asn Phe Pro Lys
                165                 170                 175

Ser Pro Tyr Cys Arg Gln His Ser Val Glu Lys Pro Cys Asp Phe Ala
            180                 185                 190

Gln Met Phe Pro Ser Lys Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu His Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Asn Lys Ile Leu Phe Leu Ala
    290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Ala Gly Thr Gln Tyr Val Ser Val
            340                 345                 350
```

-continued

```
His Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 3
<211> LENGTH: 413
<212> TYPE: PRT
<213> ORGANISM: artificial sequence
<220> FEATURE:
<223> OTHER INFORMATION: PHY-10957- sequence is synthesized

<400> SEQUENCE: 3

Ser Glu Ala Ala Pro Ser Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Ser Leu Met Gly Gly Phe Tyr
        50                  55                  60

Arg Gln Trp Phe Gln Gln Gly Ile Leu Ser Lys Glu Arg Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Lys Cys Pro Leu
            100                 105                 110

Thr Ile His His Gln Ser Asn Ile Lys Val Val Asp Pro Leu Phe His
        115                 120                 125

Pro Leu Lys Thr Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Gln His Ser Val Glu Lys Pro Cys Asp Phe Ala
            180                 185                 190

Asn Ala Phe Pro Ser Lys Leu Asn Ile Thr Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
    290                 295                 300
```

```
Gly His Asp Thr Asn Ile Ala Asn Ile Ala Gly Met Leu Gly Met Asp
305                 310                 315                 320

Trp Thr Leu Pro Gly Gln Pro Asp Asn Thr Pro Pro Gly Gly Ala Leu
            325                 330                 335

Leu Phe Glu Leu Trp Arg Asp Lys Glu Gly Thr Gln Tyr Val Ser Val
        340                 345                 350

Lys Met Val Tyr Gln Thr Leu Ala Gln Leu Arg Asn Gln Thr Pro Leu
    355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Val Thr Phe Thr Arg
385                 390                 395                 400

Leu Val Asn Gln Val Val Glu Pro Ala Cys Gln Ile Pro
                405                 410
```

<210> SEQ ID NO 4
<211> LENGTH: 413
<212> TYPE: PRT
<213> ORGANISM: artificial sequence
<220> FEATURE:
<223> OTHER INFORMATION: PHY-11569- sequence is synthesized

<400> SEQUENCE: 4

```
Ser Glu Thr Ala Pro Ser Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gln Gly Leu Leu Ser Lys Asp Asn Cys Pro
65                  70                  75                  80

Thr Ala Asn Asp Val Tyr Val Trp Thr Asp Val Asp Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asn Ile Lys Val Val Asp Pro Met Phe His
        115                 120                 125

Pro Leu Lys Thr Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Ala Pro Glu Leu Ala Leu Met Ser Ala Val Leu Asn Phe Pro Ala
                165                 170                 175

Ser Pro Tyr Cys Gln Gln His Ser Val Asp Lys Pro Cys Asp Phe Ala
            180                 185                 190

Asn Ala Phe Pro Ser Lys Leu Asn Ile Thr Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala His
                245                 250                 255
```

```
Phe Asp Leu Met Ser Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Asn Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Arg Asp Lys Ala Gly Thr Gln Tyr Val Ser Val
            340                 345                 350

His Met Val Tyr Gln Thr Leu Ala Gln Leu Arg Asn Gln Thr Pro Leu
                355                 360                 365

Thr Leu Lys Glu Pro Ala Gly Thr Val Pro Leu Lys Ile Pro Gly Cys
370                 375                 380

Asp Asp Gln Thr Ala Glu Gly Tyr Cys Pro Leu Val Thr Phe Thr Arg
385                 390                 395                 400

Leu Val Asn Gln Ser Val Glu Pro Ala Cys Gln Leu Pro
                405                 410

<210> SEQ ID NO 5
<211> LENGTH: 413
<212> TYPE: PRT
<213> ORGANISM: artificial sequence
<220> FEATURE:
<223> OTHER INFORMATION: PHY-11658- sequence is synthesized

<400> SEQUENCE: 5

Ser Glu Ala Ala Pro Ser Gly Tyr His Leu Asp Lys Ala Val Leu Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Trp Phe Gln Gln Gln Gly Leu Leu Ser Lys Asp Arg Cys Pro
65                  70                  75                  80

Thr Ala Asn Asp Val Tyr Val Trp Ala Asp Val Gly Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asp Ile Lys Gln Val Asp Pro Met Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Gln His Ser Val Glu Lys Pro Cys Asp Phe Ala
            180                 185                 190

Gln Met Phe Pro Ser Lys Leu Asn Ile Thr Asp Asp Gly Asn Glu Val
        195                 200                 205
```

-continued

```
Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Gln Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Arg Trp Ser Asp Lys Asp Gly Thr Gln Tyr Val Ser Val
            340                 345                 350

His Met Val Tyr Gln Thr Leu Ala Gln Leu Arg Asn Gln Thr Pro Leu
        355                 360                 365

Thr Leu Lys Glu Pro Ala Gly Thr Val Pro Leu Lys Ile Pro Gly Cys
    370                 375                 380

Asp Asp Gln Thr Ala Glu Gly Tyr Cys Pro Leu Val Thr Phe Thr Arg
385                 390                 395                 400

Leu Val Asn Gln Ser Val Glu Pro Ala Cys Gln Leu Pro
                405                 410
```

<210> SEQ ID NO 6
<211> LENGTH: 413
<212> TYPE: PRT
<213> ORGANISM: artificial sequence
<220> FEATURE:
<223> OTHER INFORMATION: PHY-11673- sequence is synthesized

<400> SEQUENCE: 6

```
Ser Glu Ala Ala Pro Ser Gly Tyr His Leu Asp Lys Ala Val Ile Leu
1               5                   10                  15

Ser Arg His Gly Val Arg Ala Pro Thr Lys Met Thr Glu Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Ser Leu Met Gly Gly Phe Tyr
        50                  55                  60

Arg Gln Tyr Phe Gln Gln Gly Leu Leu Ser Lys Asp Arg Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Pro Leu
            100                 105                 110

Thr Ile His His Gln Ser Asn Ile Lys Val Val Asp Pro Leu Phe His
        115                 120                 125

Pro Val Lys Thr Gly Leu Cys Ser Met Asp Lys Thr Gln Val Gln Gln
    130                 135                 140

Ala Val Glu Lys Gln Ala Gly Met Pro Ile Asp Lys Leu Asn Asp Lys
145                 150                 155                 160
```

Tyr Ala Pro Glu Leu Ala Leu Met Ser Asn Val Leu Asn Phe Pro Lys
            165                 170                 175

Ser Pro Tyr Cys Arg Gln His Ser Val Glu Lys Pro Cys Asp Phe Ala
        180                 185                 190

Gln Met Phe Pro Ser Lys Leu Ser Ile Gly Asp Asp Gly Asn Glu Val
    195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Lys Leu His Asn Ala His
            245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Glu
        275                 280                 285

Ser Lys Leu Pro Asp Ile Ser Pro Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Arg Asp Lys Asp Gly Thr Gln Tyr Val Ser Val
            340                 345                 350

His Met Val Tyr Gln Thr Leu Ala Gln Leu Arg Asn Gln Thr Pro Leu
        355                 360                 365

Thr Leu Lys Glu Pro Ala Gly Thr Val Pro Leu Lys Ile Pro Gly Cys
    370                 375                 380

Asp Asp Gln Thr Ala Glu Gly Tyr Cys Pro Leu Val Thr Phe Thr Val
385                 390                 395                 400

Leu Val Asn Gln Ser Val Glu Pro Ala Cys Gln Leu Pro
            405                 410

<210> SEQ ID NO 7
<211> LENGTH: 413
<212> TYPE: PRT
<213> ORGANISM: artificial sequence
<220> FEATURE:
<223> OTHER INFORMATION: PHY-11680- sequence is synthesized

<400> SEQUENCE: 7

Ser Glu Thr Ala Pro Ser Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gln Gly Leu Leu Ser Lys Asp Asn Cys Pro
65                  70                  75                  80

Thr Ala Asn Asp Val Tyr Val Trp Thr Asp Val Asp Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asn Ile Lys Val Val Asp Pro Leu Phe His
            115                 120                 125

Pro Leu Lys Thr Gly Ile Cys Ser Met Asp Lys Thr Gln Val Gln Gln
            130                 135                 140

Ala Val Glu Lys Gln Ala Gly Met Pro Ile Asp Lys Leu Asn Asp His
145                 150                 155                 160

Tyr Arg Pro Glu Leu Ser Leu Met Ser Asn Val Leu Asn Phe Pro Lys
                165                 170                 175

Ser Pro Tyr Cys Gln Arg His Ser Gly Glu Lys Thr Cys Asp Phe Ala
            180                 185                 190

Asn Ala Phe Pro Ser Lys Leu Ile Ile Thr Asp Asp Gly Asn Lys Val
            195                 200                 205

Ala Leu Glu Gly Ala Val Gly Leu Ser Ser Thr Leu Ala Glu Ile Phe
        210                 215                 220

Leu Leu Glu Tyr Ala Gln Gly Met Pro Lys Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
        290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Arg Asp Lys Glu Gly Thr Gln Tyr Val Ser Val
            340                 345                 350

Lys Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Ile Pro
                405                 410

<210> SEQ ID NO 8
<211> LENGTH: 413
<212> TYPE: PRT
<213> ORGANISM: artificial sequence
<220> FEATURE:
<223> OTHER INFORMATION: PHY-11895- sequence is synthesized

<400> SEQUENCE: 8

Ser Glu Ala Ala Pro Ser Gly Tyr His Leu Asp Lys Ala Val Leu Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Ser Leu Met Gly Gly Phe Tyr
        50                  55                  60

Arg Gln Trp Phe Gln Gln Gly Leu Leu Ser Arg Asp Arg Cys Pro
 65                  70                  75                  80

Thr Ala Asn Asp Val Tyr Val Trp Thr Asp Val Asn Gln Arg Thr Arg
                 85                  90                  95

Lys Thr Gly Glu Ala Phe Leu Ala Gly Leu Ala Pro Gly Cys Asp Leu
            100                 105                 110

Thr Ile His His Gln Lys Asn Ile Lys Val Val Asp Pro Leu Phe His
        115                 120                 125

Pro Leu Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Ala Pro Glu Leu Ser Leu Met Ser Asn Val Leu Asn Phe Pro Lys
                165                 170                 175

Ser Pro Tyr Cys Gln Arg His Ser Gly Glu Lys Thr Cys Asp Phe Ala
            180                 185                 190

Asn Ala Phe Pro Ser Lys Leu Asn Ile Ser Asp Asp Gly Asn Glu Val
        195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala His
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Ser Val Lys Ile Leu Phe Leu Ala
290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Ala Gly Thr Gln Tyr Val Ser Val
            340                 345                 350

His Met Val Tyr Gln Thr Leu Thr Gln Leu Arg Asn Gln Thr Pro Leu
        355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 9
<211> LENGTH: 413
<212> TYPE: PRT
<213> ORGANISM: artificial sequence
<220> FEATURE:
<223> OTHER INFORMATION: PHY-11932- sequence is synthesized

<400> SEQUENCE: 9

Ser Glu Thr Ala Pro Ala Gly Tyr His Leu Asp Lys Ala Val Ile Leu
1               5                   10                  15

Ser Arg His Gly Val Arg Ala Pro Thr Lys Met Thr Gln Thr Met Arg
        20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Ser Leu Met Gly Gly Phe Tyr
50                      55                  60

Arg Gln Tyr Phe Gln Gln Gly Leu Leu Ser Ala Glu Arg Cys Pro
65              70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Gln Cys Pro Leu
                100                 105                 110

Thr Ile His His Gln Asn Asp Ile Lys Gln Val Asp Pro Met Phe His
            115                 120                 125

Pro Leu Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Asp His
145                 150                 155                 160

Tyr Arg Pro Glu Leu Ser Leu Met Ser Asn Val Leu Asn Phe Pro Lys
                165                 170                 175

Ser Pro Tyr Cys Ala Arg His Ser Gly Asp Lys Pro Cys Asp Phe Ala
            180                 185                 190

Gln Met Met Pro Ser Lys Leu Asn Ile Thr Asp Asp Gly Asn Glu Val
        195                 200                 205

Gln Leu Glu Gly Ala Val Gly Leu Ser Ser Thr Leu Ala Glu Ile Phe
        210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala Gln
            245                 250                 255

Phe Asp Leu Met Glu Arg Thr Pro Tyr Ile Ala Lys His Asn Gly Thr
        260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
290                 295                 300

Gly His Asp Thr Asn Ile Ala Asn Ile Ala Gly Met Leu Gly Met Thr
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Ala Gly Thr Gln Tyr Val Ser Val
            340                 345                 350

His Met Val Tyr Gln Thr Leu Ala Gln Leu Arg Asn Gln Thr Pro Leu
            355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 10
<211> LENGTH: 413

<212> TYPE: PRT
<213> ORGANISM: artificial sequence
<220> FEATURE:
<223> OTHER INFORMATION: PHY-12058- sequence is synthesized

<400> SEQUENCE: 10

```
Ser Glu Ala Ala Pro Ala Gly Tyr His Leu Asp Lys Val Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Lys Phe Gln Gln Gly Leu Leu Ser Lys Asp Arg Cys Pro
65                  70                  75                  80

Thr Ala Asn Asp Val Tyr Val Trp Thr Asp Val Asp Gln Arg Thr Arg
                85                  90                  95

Lys Thr Gly Glu Ala Phe Leu Ala Gly Leu Ala Pro Lys Cys Pro Leu
            100                 105                 110

Thr Ile His His Gln Ser Asn Ile Lys Val Val Asp Pro Leu Phe His
        115                 120                 125

Pro Leu Lys Thr Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ser Leu Met Ser Asn Val Leu Asn Phe Pro Lys
                165                 170                 175

Ser Pro Tyr Cys Ala Gln His Ser Gly Glu Lys Pro Cys Asp Phe Ala
            180                 185                 190

Gln Met Phe Pro Ser Lys Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Ser Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Arg Asp Lys Asp Gly Thr Gln Tyr Val Ser Val
            340                 345                 350

Lys Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
    370                 375                 380
```

-continued

Asp Asp Gln Thr Ala Glu Gly Tyr Cys Pro Leu Asp Thr Phe Thr Arg
385                 390                 395                 400

Leu Val Asn Gln Ser Val Glu Pro Ala Cys Gln Ile Pro
            405                 410

<210> SEQ ID NO 11
<211> LENGTH: 413
<212> TYPE: PRT
<213> ORGANISM: artificial sequence
<220> FEATURE:
<223> OTHER INFORMATION: PHY-12663- sequence is synthesized

<400> SEQUENCE: 11

Ser Glu Ala Ala Pro Ser Gly Tyr His Leu Asp Lys Val Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Trp Phe Gln Gln Gly Leu Leu Ser Lys Asp Arg Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Gln Cys Pro Leu
            100                 105                 110

Thr Ile His His Gln Lys Asn Ile Lys Val Val Asp Pro Leu Phe His
        115                 120                 125

Pro Leu Lys Thr Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Asp Glu Pro Cys Asp Phe Ala
            180                 185                 190

Asn Ala Phe Pro Ser Lys Leu Asn Ile Thr Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Asn Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asn Thr Pro Pro Gly Gly Ala Leu
                325                 330                 335

```
Leu Phe Glu Arg Trp Arg Asp Lys Glu Gly Thr Gln Tyr Val Ser Val
            340                 345                 350

His Met Val Tyr Gln Thr Leu Ala Gln Leu Arg Asn Gln Thr Pro Leu
            355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Ile Pro
                405                 410
```

<210> SEQ ID NO 12
<211> LENGTH: 413
<212> TYPE: PRT
<213> ORGANISM: artificial sequence
<220> FEATURE:
<223> OTHER INFORMATION: PHY-12784- sequence is synthesized

<400> SEQUENCE: 12

```
Ser Glu Ala Ala Pro Ser Gly Tyr His Leu Asp Lys Ala Val Leu Leu
1               5                   10                  15

Ser Arg His Gly Val Arg Ala Pro Thr Lys Met Thr Gln Leu Met Arg
            20                  25                  30

Asp Val Thr Pro Asn Gln Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gly Ile Leu Ser Lys Asp Ser Cys Pro
65                  70                  75                  80

Thr Ala Asn Asp Val Tyr Val Trp Thr Asp Val Asn Gln Arg Thr Arg
            85                  90                  95

Lys Thr Gly Glu Ala Phe Leu Ala Gly Leu Ala Pro Gln Cys Pro Leu
            100                 105                 110

Thr Ile His His Gln Ser Asp Ile Lys Gln Val Asp Pro Met Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln Tyr
145                 150                 155                 160

Tyr Ala Pro Glu Leu Ala Leu Met Ser Asn Val Leu Asn Phe Pro Lys
                165                 170                 175

Ser Pro Tyr Cys Gln Arg His Ser Gly Glu Gln Thr Cys Asp Phe Ala
            180                 185                 190

Gln Met Phe Pro Ser Lys Leu Asn Ile Ser Asp Asp Gly Asn Glu Val
        195                 200                 205

Gln Leu Glu Gly Ala Val Gly Leu Ser Ser Thr Leu Ala Glu Thr Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala Gln
                245                 250                 255

Phe Asp Leu Met Gln Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285
```

```
Arg Glu Leu Pro Asp Ile Ser Pro Ser Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Arg Asp Lys Glu Gly Thr Gln Tyr Val Ser Val
            340                 345                 350

His Met Val Tyr Gln Thr Leu Thr Gln Leu Arg Asn Gln Thr Pro Leu
        355                 360                 365

Thr Leu Lys Glu Pro Ala Gly Thr Val Pro Leu Lys Ile Pro Gly Cys
370                 375                 380

Asp Asp Gln Thr Ala Glu Gly Tyr Cys Pro Leu Val Thr Phe Thr Arg
385                 390                 395                 400

Leu Val Asn Gln Val Val Glu Pro Ala Cys Gln Ile Pro
                405                 410

<210> SEQ ID NO 13
<211> LENGTH: 413
<212> TYPE: PRT
<213> ORGANISM: Artificial Sequence
<220> FEATURE:
<223> OTHER INFORMATION: PHY-13177- sequence is synthesized

<400> SEQUENCE: 13

Ser Glu Ala Ala Pro Ser Gly Tyr His Leu Asp Lys Val Val Ile Leu
1               5                   10                  15

Ser Arg His Gly Val Arg Ala Pro Thr Lys Met Thr Gln Leu Met Arg
            20                  25                  30

Asp Val Thr Pro Asn Gln Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gln Gly Leu Leu Ser Lys Asp Arg Cys Pro
65                  70                  75                  80

Thr Ala Asn Asp Val Tyr Val Trp Ala Asp Val Asn Gln Arg Thr Arg
                85                  90                  95

Lys Thr Gly Glu Ala Phe Leu Ala Gly Leu Ala Pro Arg Cys Asp Leu
            100                 105                 110

Thr Ile His His Gln Lys Asp Ile Lys Gln Val Asp Pro Met Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Ala Gln His Ser Gly Glu Lys Pro Cys Asp Phe Ala
            180                 185                 190

Gln Met Phe Pro Ser Lys Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240
```

```
His Ser Glu Gln Glu Trp Asn Asp Leu Leu Lys Leu His Asn Ala Gln
            245                 250                 255

Phe Asp Leu Met Gln Arg Thr Pro Tyr Ile Ala Lys His Asn Gly Thr
        260                 265                 270

Pro Leu Leu Gln Thr Ile Val Asn Ala Leu Asn Ser Asn Thr Thr Ala
    275                 280                 285

Arg Glu Leu Pro Asp Ile Ser Pro Asp Asn Lys Ile Leu Phe Leu Ala
290                 295                 300

Gly His Asp Thr Asn Ile Ala Asn Ile Gly Met Leu Gly Met Asp
305                 310                 315                 320

Trp Thr Leu Pro Gly Gln Pro Asp Asn Thr Pro Pro Gly Gly Ala Leu
            325                 330                 335

Leu Phe Glu Arg Trp Arg Asp Lys Ala Gly Thr Gln Tyr Val Ser Val
        340                 345                 350

His Met Val Tyr Gln Thr Leu Ala Gln Leu Arg Asn Gln Thr Pro Leu
    355                 360                 365

Thr Leu Lys Glu Pro Ala Gly Thr Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
            405                 410

<210> SEQ ID NO 14
<211> LENGTH: 413
<212> TYPE: PRT
<213> ORGANISM: artificial sequence
<220> FEATURE:
<223> OTHER INFORMATION: PHY-13371- sequence is synthesized

<400> SEQUENCE: 14

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gly Leu Leu Ser Arg Asp Arg Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Gln His Ser Val Glu Gln Pro Cys Asp Phe Ala
            180                 185                 190
```

```
Asn Ala Phe Pro Ser Tyr Leu Asn Ile Ser Asp Asp Gly Asn Glu Val
            195                 200                 205

Gln Leu Glu Gly Ala Val Gly Leu Gly Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala His
                245                 250                 255

Phe Asn Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
    275                 280                 285

Arg Glu Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ala Val
            340                 345                 350

Lys Met Val Tyr Gln Thr Leu Ala Gln Leu Arg Asn Gln Thr Pro Leu
    355                 360                 365

Thr Leu Lys Glu Pro Ala Gly Thr Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Ile Glu Pro Ala Cys Gln Leu Pro
                405                 410

<210> SEQ ID NO 15
<211> LENGTH: 413
<212> TYPE: PRT
<213> ORGANISM: artificial sequence
<220> FEATURE:
<223> OTHER INFORMATION: PHY-13460- sequence is synthesized

<400> SEQUENCE: 15

Ser Glu Ala Ala Pro Ser Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Arg Asp Asn Cys Pro
65                  70                  75                  80

Thr Ala Asn Asp Val Tyr Val Trp Thr Asp Val Ala Gln Arg Thr Arg
                85                  90                  95

Lys Thr Gly Glu Ala Phe Leu Ala Gly Leu Ala Pro Glu Cys Asp Leu
            100                 105                 110

Thr Val His His Gln Asn Asp Ile Lys Gln Val Asp Pro Leu Phe His
    115                 120                 125

Pro Val Lys Ala Gly Ile Cys Ser Met Asn Lys Ser Gln Val Gln Gln
130                 135                 140
```

```
Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Glu Lys Pro Cys Asp Phe Ala
                180                 185                 190

Gln Met Met Pro Ser Lys Leu Asn Ile Ser Asp Asp Gly Asn Glu Val
            195                 200                 205

Gln Leu Glu Gly Ala Val Gly Leu Ser Ser Thr Leu Ala Glu Ile Phe
        210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala Gln
                245                 250                 255

Phe Asp Leu Met Glu Arg Thr Pro Tyr Ile Ala Lys His Asn Gly Thr
                260                 265                 270

Pro Leu Met Gln Thr Ile Val Asn Ala Leu Asn Ser Asn Thr Thr Ala
            275                 280                 285

Arg Glu Leu Pro Asp Ile Ser Pro Asp Val Lys Ile Leu Phe Leu Ala
        290                 295                 300

Gly His Asp Thr Asn Ile Ala Asn Ile Ala Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Gln Thr Pro Leu
            355                 360                 365

Thr Leu Lys Glu Pro Ala Gly Thr Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 16
<211> LENGTH: 413
<212> TYPE: PRT
<213> ORGANISM: artificial sequence
<220> FEATURE:
<223> OTHER INFORMATION: PHY-13513- sequence is synthesized

<400> SEQUENCE: 16

Ser Glu Ala Ala Pro Ser Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
                35                  40                  45

Ile Thr Pro Arg Gly Glu His Leu Val Lys Leu Met Gly Gly Phe Tyr
            50                  55                  60

Arg Gln Tyr Phe Gln Gln Gly Leu Leu Ser Arg Asp Ser Cys Pro
65              70                  75                  80

Thr Ala Asn Asp Val Tyr Val Trp Thr Asp Val Asn Gln Arg Thr Arg
                85                  90                  95
```

-continued

```
Lys Thr Gly Glu Ala Phe Leu Ala Gly Leu Ala Pro Gly Cys Asp Leu
                100                 105                 110

Thr Ile His His Gln Ser Asp Ile Lys Gln Ala Asp Pro Leu Phe His
            115                 120                 125

Pro Val Lys Ala Gly Ile Cys Ser Met Asp Lys Thr Gln Val Gln Gln
        130                 135                 140

Ala Val Glu Lys Gln Ala Gly Gly Pro Ile Glu Thr Leu Asn Gln Arg
145                 150                 155                 160

Tyr Gln Ala Glu Leu Ala Leu Met Ser Ser Val Leu Asp Phe Pro Lys
                165                 170                 175

Ser Pro Tyr Cys Gln Arg His Ser Val Asp Lys Pro Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala His
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Gly Gly Ala Leu
                325                 330                 335

Leu Phe Glu Leu Trp Arg Asp Lys Asp Gly Thr Gln Tyr Val Ser Val
            340                 345                 350

His Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410
```

<210> SEQ ID NO 17
<211> LENGTH: 413
<212> TYPE: PRT
<213> ORGANISM: artificial sequence
<220> FEATURE:
<223> OTHER INFORMATION: PHY-13637- sequence is synthesized

<400> SEQUENCE: 17

```
Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45
```

```
Ile Thr Pro Arg Gly Glu His Leu Val Ser Leu Met Gly Gly Phe Tyr
 50                  55                  60

Arg Gln Tyr Phe Gln Gln Gln Gly Leu Leu Ser Lys Asp Asn Cys Pro
 65                  70                  75                  80

Thr Ala Asn Asp Val Tyr Val Trp Thr Asp Val Asn Gln Arg Thr Arg
                 85                  90                  95

Lys Thr Gly Glu Ala Phe Leu Ala Gly Leu Ala Pro Glu Cys Asp Leu
                100                 105                 110

Thr Ile His His Gln Asn Asp Ile Lys Gln Val Asp Pro Leu Phe His
                115                 120                 125

Pro Leu Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Ser Val Leu Asp Phe Pro Lys
                165                 170                 175

Ser Pro Tyr Cys Gln His His Ser Gly Asp Gln Pro Cys Asp Phe Ala
                180                 185                 190

Gln Met Phe Pro Ser Tyr Leu Asn Ile Ser Asp Asp Gly Asn Glu Val
                195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
                260                 265                 270

Pro Leu Leu Gln Thr Ile Val Asn Ala Leu Asn Ser Asn Thr Thr Ala
                275                 280                 285

Arg Glu Leu Pro Asp Val Ser Pro Asp Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Gln Thr Pro Leu
                355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410
```

<210> SEQ ID NO 18
<211> LENGTH: 413
<212> TYPE: PRT
<213> ORGANISM: artificial sequence
<220> FEATURE:
<223> OTHER INFORMATION: PHY-13705- sequence is synthesized

<400> SEQUENCE: 18

```
Ser Glu Ala Ala Pro Ala Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
                35                  40                  45

Ile Thr Pro Arg Gly Glu His Leu Val Lys Leu Met Gly Gly Phe Tyr
        50                  55                  60

Arg Gln Tyr Phe Gln Gln Gly Leu Leu Ser Arg Asp Ser Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Ala Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Arg Gln His Ser Val Glu Gln Pro Cys Asp Phe Ala
                180                 185                 190

Asn Ala Phe Pro Ser Arg Leu Asn Ile Ser Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Gln Gly Thr
                260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
    290                 295                 300

Gly His Asp Thr Asn Ile Ala Asn Ile Ala Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Gln Thr Pro Leu
                355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Arg Val Val Glu Pro Ala Cys Gln Leu Pro
                405                 410
```

```
<210> SEQ ID NO 19
<211> LENGTH: 413
<212> TYPE: PRT
<213> ORGANISM: artificial sequence
<220> FEATURE:
<223> OTHER INFORMATION: PHY-13713- sequence is synthesized

<400> SEQUENCE: 19

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gly Leu Leu Ser Arg Asp Arg Cys Pro
65                  70                  75                  80

Thr Pro Asp Ala Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asp Ile His Gln Val Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Val Asp Lys Pro Cys Asp Phe Ala
            180                 185                 190

Gln Met Met Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala His
                245                 250                 255

Phe Asp Leu Met Glu Arg Thr Pro Tyr Ile Ala Lys His Gln Gly Thr
            260                 265                 270

Pro Leu Leu Gln Thr Ile Val Asn Ala Leu Asn Ser Asn Thr Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Ala Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Arg Asp Lys Ala Gly Thr Gln Tyr Val Ser Val
            340                 345                 350

Lys Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
```

```
            370                 375                 380
Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 20
<211> LENGTH: 412
<212> TYPE: PRT
<213> ORGANISM: artificial sequence
<220> FEATURE:
<223> OTHER INFORMATION: PHY-13747- sequence is synthesized

<400> SEQUENCE: 20

Ser Glu Ala Ala Pro Ser Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Ser Leu Met Gly Gly Phe Tyr
        50                  55                  60

Arg Gln Tyr Phe Gln Gln Gly Leu Leu Ser Lys Asp Asn Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Asn Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Arg His Ser Gly Glu Lys Pro Cys Asp Phe Ala
            180                 185                 190

Gln Met Met Pro Ser Lys Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Glu Glu Trp Asn Asp Leu Leu Lys Leu His Asn Ala Tyr
                245                 250                 255

Phe Asp Leu Met Gln Arg Thr Pro Tyr Ile Ala Lys His Asn Gly Thr
            260                 265                 270

Pro Leu Met Gln Thr Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
```

```
                    325                 330                 335
Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Gln Thr Pro Leu
            355                 360                 365

Thr Leu Lys Glu Pro Ala Gly Thr Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Ile
                405                 410

<210> SEQ ID NO 21
<211> LENGTH: 412
<212> TYPE: PRT
<213> ORGANISM: artificial sequence
<220> FEATURE:
<223> OTHER INFORMATION: PHY-13779- sequence is synthesized

<400> SEQUENCE: 21

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Thr Met Arg
            20                  25                  30

Asp Val Thr Pro His Gln Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Lys Asp Arg Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Glu Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Gln Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
```

```
            275                 280                 285
Arg Glu Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Ala Gly Thr Gln Tyr Val Ser Val
                340                 345                 350

His Met Val Tyr Gln Thr Leu Ala Gln Leu Arg Asn Met Thr Pro Leu
                355                 360                 365

Thr Leu Lys Glu Pro Ala Gly Thr Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Ile
                405                 410
```

<210> SEQ ID NO 22
<211> LENGTH: 413
<212> TYPE: PRT
<213> ORGANISM: artificial sequence
<220> FEATURE:
<223> OTHER INFORMATION: PHY-13789- sequence is synthesized

<400> SEQUENCE: 22

```
Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
        50                  55                  60

Arg Gln Tyr Phe Gln Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
```

```
                225                 230                 235                 240

His Ser Glu Gln Glu Trp Asn Asp Leu Leu Lys Leu His Asn Ala Tyr
                            245                 250                 255

Phe Asp Leu Met Glu Arg Thr Pro Tyr Ile Ala Lys His Asn Gly Thr
                            260                 265                 270

Pro Leu Leu Gln Thr Ile Val Asn Ala Leu Asn Pro Asn Ala Thr Glu
                            275                 280                 285

Ser Lys Leu Pro Asp Ile Ser Pro Asp Val Lys Ile Leu Phe Leu Ala
                            290                 295                 300

Gly His Asp Thr Asn Ile Ala Asn Ile Gly Gly Met Leu Gly Met Asp
            305                 310                 315                 320

Trp Thr Leu Pro Gly Gln Pro Asp Asn Thr Pro Pro Gly Gly Ala Leu
                            325                 330                 335

Leu Phe Glu Leu Trp Ser Asp Lys Glu Gly Thr Gln Tyr Val Ser Val
                            340                 345                 350

Lys Met Val Tyr Gln Thr Leu Ala Gln Leu Arg Asn Met Thr Pro Leu
                            355                 360                 365

Thr Leu Lys Glu Pro Ala Gly Ser Val Pro Leu Lys Ile Pro Gly Cys
                            370                 375                 380

Asp Asp Gln Thr Ala Glu Gly Tyr Cys Pro Leu Asp Thr Phe Thr Arg
            385                 390                 395                 400

Leu Val Asn Gln Val Val Glu Pro Ala Cys Gln Leu Pro
                            405                 410

<210> SEQ ID NO 23
<211> LENGTH: 413
<212> TYPE: PRT
<213> ORGANISM: artificial sequence
<220> FEATURE:
<223> OTHER INFORMATION: PHY-13798- sequence is synthesized

<400> SEQUENCE: 23

Ser Glu Ala Ala Pro Ala Gly Tyr His Leu Gln Lys Ala Val Ile Leu
            1               5                   10                  15

Ser Arg His Gly Val Arg Ala Pro Thr Lys Met Thr Gln Thr Met Arg
                            20                  25                  30

Asp Val Thr Pro Tyr Thr Trp Pro Glu Trp Pro Val Pro Leu Gly Tyr
                            35                  40                  45

Ile Thr Pro Arg Gly Glu His Leu Val Lys Leu Met Gly Gly Phe Tyr
                50                  55                  60

Arg Gln Tyr Phe Gln Gln Gln Gly Leu Leu Ser Lys Asp Asn Cys Pro
            65                  70                  75                  80

Thr Ala Asn Asp Val Tyr Val Trp Thr Asp Val Ala Gln Arg Thr Arg
                            85                  90                  95

Lys Thr Gly Glu Ala Phe Leu Ala Gly Leu Ala Pro Glu Cys Asp Leu
                            100                 105                 110

Thr Ile His His Gln Asn Asn Ile Ser Gln Val Asp Pro Leu Phe His
                            115                 120                 125

Pro Val Lys Ala Gly Ile Cys Ser Met Asp Lys Thr Gln Val Gln Gln
                            130                 135                 140

Ala Val Glu Lys Gln Ala Gly Met Pro Ile Asp Lys Leu Asn Gln His
            145                 150                 155                 160

Tyr Arg Pro Glu Leu Ala Leu Met Ser Asn Val Leu Asn Phe Pro Lys
                            165                 170                 175

Ser Pro Tyr Cys Gln Arg His Ser Gly Glu Lys Pro Cys Asp Phe Ala
```

```
                    180             185             190
Gln Met Met Pro Ser Lys Leu Asn Ile Ser Asp Asp Gly Asn Glu Val
            195                 200                 205
Gln Leu Glu Gly Ala Val Gly Leu Ser Ser Thr Leu Ala Glu Ile Phe
            210                 215                 220
Leu Leu Glu Tyr Ala Gln Gly Met Pro Val Val Ala Trp Gly Asn Ile
225                 230                 235                 240
His Ser Glu Gln Glu Trp Asn Asp Leu Lys Leu His Asn Ala His
                245                 250                 255
Phe Asp Leu Met Glu Arg Thr Pro Tyr Ile Ala Lys His Asn Gly Thr
            260                 265                 270
Pro Leu Leu Gln Ala Ile Ser Asn Ala Leu Asn Pro Asn Thr Thr Glu
            275                 280                 285
Ser Lys Leu Pro Asp Ile Ser Pro Asp Val Lys Ile Leu Phe Leu Ala
            290                 295                 300
Gly His Asp Thr Asn Ile Ala Asn Ile Gly Gly Met Leu Gly Met Thr
305                 310                 315                 320
Trp Thr Leu Pro Gly Gln Pro Asp Asn Thr Pro Pro Gly Gly Ala Leu
                325                 330                 335
Leu Phe Glu Leu Trp Arg Asp Lys Ala Gly Thr Gln Tyr Val Ser Val
                340                 345                 350
His Met Val Tyr Gln Thr Leu Ala Gln Leu Arg Asn Met Thr Pro Leu
                355                 360                 365
Thr Leu Lys Glu Pro Ala Gly Ser Val Pro Leu Lys Ile Pro Gly Cys
            370                 375                 380
Asp Asp Gln Thr Ala Glu Gly Tyr Cys Pro Leu Asp Thr Phe Thr Arg
385                 390                 395                 400
Leu Val Asn Gln Val Val Glu Pro Ala Cys Gln Leu Pro
                405                 410

<210> SEQ ID NO 24
<211> LENGTH: 413
<212> TYPE: PRT
<213> ORGANISM: artificial sequence
<220> FEATURE:
<223> OTHER INFORMATION: PHY-13868- sequence is synthesized

<400> SEQUENCE: 24

Ser Asp Thr Ala Pro Ala Gly Phe Gln Leu Glu Lys Val Val Ile Leu
1               5                   10                  15
Ser Arg His Gly Val Arg Ala Pro Thr Lys Met Thr Gln Leu Met Arg
                20                  25                  30
Asp Val Thr Pro Tyr Thr Trp Pro Glu Trp Pro Val Pro Leu Gly Tyr
                35                  40                  45
Ile Thr Pro Arg Gly Glu His Leu Ile Ser Leu Met Gly Gly Phe Tyr
            50                  55                  60
Arg Gln Tyr Phe Gln Gln Gln Gly Leu Leu Ser Lys Asp Asn Cys Pro
65                  70                  75                  80
Thr Ala Asn Asp Val Tyr Val Trp Thr Asp Val Asp Gln Arg Thr Arg
                85                  90                  95
Lys Thr Gly Glu Ala Phe Leu Ala Gly Leu Ala Pro Glu Cys Asp Leu
                100                 105                 110
Thr Ile His His Gln Ser Asp Ile Lys Gln Ala Asp Pro Leu Phe His
            115                 120                 125
Pro Val Lys Ala Gly Ile Cys Ser Met Asp Lys Ser Gln Thr Tyr Glu
```

```
                130                 135                 140
Ala Val Glu Lys Gln Ala Gly Gly Pro Ile Glu Thr Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Arg His Ser Gly Asp Lys Thr Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Lys Leu His Asn Ala His
                245                 250                 255

Phe Asp Leu Met Gln Arg Thr Pro Tyr Ile Ala Lys His Gln Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

Glu Met Val Tyr Gln Thr Leu Ala Gln Leu Arg Asn Met Thr Pro Leu
        355                 360                 365

Thr Leu Lys Glu Pro Ala Gly Thr Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 25
<211> LENGTH: 413
<212> TYPE: PRT
<213> ORGANISM: artificial sequence
<220> FEATURE:
<223> OTHER INFORMATION: PHY-13883- sequence is synthesized

<400> SEQUENCE: 25

Ser Glu Ala Ala Pro Ser Gly Tyr Gln Leu Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
        50                  55                  60

Arg Gln Tyr Phe Gln Gln Gln Gly Leu Leu Ser Arg Asp Asn Cys Pro
65                  70                  75                  80

Thr Ala Asn Asp Val Tyr Val Trp Thr Asp Val Asp Gln Arg Thr Arg
```

```
                    85                  90                  95
Lys Thr Gly Glu Ala Phe Leu Ala Gly Leu Ala Pro Gly Cys Asp Leu
                100                 105                 110

Thr Ile His His Gln Asn Asn Ile Ser Gln Ala Asp Pro Leu Phe His
            115                 120                 125

Pro Val Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Arg Gln His Ser Val Glu Gln Pro Cys Asp Phe Ala
            180                 185                 190

Asn Ala Phe Pro Ser Tyr Leu Asn Ile Ser Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala His
                245                 250                 255

Phe Asp Leu Met Gln Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
        290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Arg Asp Lys Asp Gly Thr Gln Tyr Val Ser Val
            340                 345                 350

His Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 26
<211> LENGTH: 413
<212> TYPE: PRT
<213> ORGANISM: artificial sequence
<220> FEATURE:
<223> OTHER INFORMATION: PHY-13885- sequence is synthesized

<400> SEQUENCE: 26

Ser Glu Ala Ala Pro Ser Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
```

```
            35                  40                  45
Ile Thr Pro Arg Gly Glu His Leu Val Ser Leu Met Gly Gly Phe Tyr
 50                  55                  60

Arg Gln Tyr Phe Gln Gln Gly Leu Leu Ser Arg Asp Arg Cys Pro
 65                  70                  75                  80

Thr Ala Asn Asp Val Tyr Val Trp Thr Asp Val Asn Gln Arg Thr Arg
                     85                  90                  95

Lys Thr Gly Glu Ala Phe Leu Ala Gly Leu Ala Pro Glu Cys Asp Leu
                100                 105                 110

Thr Ile His His Gln Asn Asp Ile Lys Gln Val Asp Pro Leu Phe His
            115                 120                 125

Pro Leu Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Gln His Ser Val Glu Gln Pro Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Gln Gly Thr
            260                 265                 270

Pro Leu Leu Gln Thr Ile Val Asn Ala Leu Asn Ser Asn Thr Thr Glu
        275                 280                 285

Ser Lys Leu Pro Asp Ile Ser Pro Ser Val Lys Ile Leu Phe Leu Ala
    290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Asp Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 27
<211> LENGTH: 413
<212> TYPE: PRT
<213> ORGANISM: artificial sequence
<220> FEATURE:
<223> OTHER INFORMATION: PHY-13936- sequence is synthesized
```

```
<400> SEQUENCE: 27

Ser Glu Ala Ala Pro Ala Gly Tyr His Leu Asp Lys Ala Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gly Leu Leu Pro Arg Asp Ser Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Ala Ile
            100                 105                 110

Thr Ile His His Gln Ser Asp Ile Lys Gln Val Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Ala Leu Leu Lys Leu His Asn Ala His
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Glu
        275                 280                 285

Ser Lys Leu Pro Asp Ile Ser Pro Ser Val Lys Ile Leu Phe Leu Ala
    290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
            340                 345                 350

Glu Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410
```

<210> SEQ ID NO 28
<211> LENGTH: 412
<212> TYPE: PRT
<213> ORGANISM: artificial sequence
<220> FEATURE:
<223> OTHER INFORMATION: PHY-14004- sequence is synthesized

<400> SEQUENCE: 28

```
Ala Glu Glu Ala Asn Gly Met Lys Leu Gln Lys Ala Val Ile Leu Ser
1               5                   10                  15

Arg His Gly Val Arg Ala Pro Thr Lys Met Thr Gln Leu Met Arg Asp
            20                  25                  30

Val Thr Pro Tyr Thr Trp Pro Glu Trp Pro Val Pro Leu Gly Tyr Ile
        35                  40                  45

Thr Pro Arg Gly Glu His Leu Val Ser Leu Met Gly Gly Phe Tyr Arg
    50                  55                  60

Gln Tyr Phe Gln Gln Gln Gly Leu Leu Ser Arg Asp Ser Cys Pro Thr
65                  70                  75                  80

Ala Asn Asp Val Tyr Val Trp Thr Asp Val Asn Gln Arg Thr Arg Lys
                85                  90                  95

Thr Gly Glu Ala Phe Leu Ala Gly Leu Ala Pro Gly Cys Asp Leu Thr
            100                 105                 110

Ile His His Gln Asn Asp Ile Lys Gln Val Asp Pro Leu Phe His Pro
        115                 120                 125

Leu Lys Ala Gly Ile Cys Ser Met Asp Lys Thr Gln Val Gln Gln Ala
    130                 135                 140

Val Glu Lys Gln Ala Gly Met Pro Ile Asp Lys Leu Asn Gln His Tyr
145                 150                 155                 160

Arg Pro Glu Leu Ala Leu Met Ser Asn Val Leu Asn Phe Pro Lys Ser
                165                 170                 175

Pro Tyr Cys Gln Arg His Ser Gly Glu Gln Pro Cys Asp Phe Ala Asn
            180                 185                 190

Met Phe Pro Ser Tyr Leu Asn Ile Ser Asp Asp Gly Asn Glu Val Gln
        195                 200                 205

Leu Glu Gly Ala Val Gly Leu Ser Ser Thr Leu Ala Glu Ile Phe Leu
    210                 215                 220

Leu Glu Tyr Ala Gln Gly Met Pro Val Val Ala Trp Gly Asn Ile His
225                 230                 235                 240

Ser Glu Gln Glu Trp Asn Asp Leu Leu Lys Leu His Asn Ala Gln Phe
                245                 250                 255

Asp Leu Met Glu Arg Thr Pro Tyr Ile Ala Lys His Asn Gly Thr Pro
            260                 265                 270

Leu Leu Gln Thr Ile Val Asn Ala Leu Asn Ser Asn Thr Thr Ala Arg
        275                 280                 285

Glu Leu Pro Asp Ile Ser Pro Asp Val Lys Ile Leu Phe Leu Ala Gly
    290                 295                 300

His Asp Thr Asn Ile Ala Asn Ile Ala Gly Met Leu Gly Met Thr Trp
305                 310                 315                 320

Thr Leu Pro Gly Gln Pro Asp Asn Thr Pro Gly Gly Ala Leu Leu
                325                 330                 335

Phe Glu Leu Trp Ser Asp Lys Asp Gly Thr Gln Tyr Val Ser Val His
            340                 345                 350

Met Val Tyr Gln Thr Leu Ala Gln Leu Arg Asn Gln Thr Pro Leu Thr
        355                 360                 365
```

```
Leu Lys Glu Pro Ala Gly Ser Val Pro Leu Lys Ile Pro Gly Cys Asp
    370                 375                 380

Asp Gln Thr Ala Glu Gly Tyr Cys Pro Leu Asp Thr Phe Thr Arg Leu
385                 390                 395                 400

Val Asn Gln Val Val Glu Pro Ala Cys Gln Leu Pro
                405                 410

<210> SEQ ID NO 29
<211> LENGTH: 413
<212> TYPE: PRT
<213> ORGANISM: artificial sequence
<220> FEATURE:
<223> OTHER INFORMATION: PHY-14215- sequence is synthesized

<400> SEQUENCE: 29

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Ser Leu Met Gly Gly Phe Tyr
        50                  55                  60

Arg Gln Tyr Phe Gln Gln Gly Leu Leu Ser Arg Asp Ser Cys Pro
65                  70                  75                  80

Thr Ala Asn Asp Val Tyr Val Trp Thr Asp Val Asp Gln Arg Thr Arg
                85                  90                  95

Lys Thr Gly Glu Ala Phe Leu Ala Gly Leu Ala Pro Gly Cys Asp Leu
                100                 105                 110

Ala Ile His His Gln Gln Asn Ile Thr Gln Val Asp Pro Leu Phe His
                115                 120                 125

Pro Leu Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Arg His Ser Gly Asp Lys Thr Cys Asp Phe Ala
            180                 185                 190

Asn Ala Phe Pro Ser Tyr Leu Asn Ile Ser Asp Asp Gly Asn Lys Val
        195                 200                 205

Ala Leu Asp Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Ser Gln Trp Lys Ser Leu Leu Asn Leu His Asn Ala His
                245                 250                 255

Phe Asn Leu Met Gln Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Asn Lys Ile Leu Phe Leu Ala
    290                 295                 300

Gly His Asp Thr Asn Ile Ala Asn Ile Gly Gly Met Leu Gly Met Thr
305                 310                 315                 320
```

Trp Thr Leu Pro Gly Gln Pro Asp Asn Thr Pro Gly Gly Ala Leu
            325                 330                 335

Leu Phe Glu Leu Trp Arg Asp Lys Glu Gly Thr Gln Tyr Val Ser Val
            340                 345                 350

Glu Met Val Tyr Gln Thr Leu Ala Gln Leu Arg Asn Gln Thr Pro Leu
            355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
            405                 410

<210> SEQ ID NO 30
<211> LENGTH: 413
<212> TYPE: PRT
<213> ORGANISM: artificial sequence
<220> FEATURE:
<223> OTHER INFORMATION: PHY-14256- sequence is synthesized

<400> SEQUENCE: 30

Ser Asp Thr Ala Pro Ala Gly Tyr Gln Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Lys Asp Asn Cys Pro
65                  70                  75                  80

Thr Ala Asn Asp Val Tyr Val Trp Thr Asp Val Asn Gln Arg Thr Arg
            85                  90                  95

Lys Thr Gly Glu Ala Phe Leu Ala Gly Leu Ala Pro Gly Cys Asp Leu
            100                 105                 110

Thr Ile His His Gln Asn Asp Ile Lys Gln Ala Asp Pro Leu Phe His
        115                 120                 125

Pro Leu Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
            165                 170                 175

Ser Pro Tyr Cys Gln Arg His Ser Val Asp Lys Pro Cys Asp Phe Ala
            180                 185                 190

Asn Ala Phe Pro Ser Tyr Leu Asn Ile Ser Asp Asp Gly Asn Glu Val
            195                 200                 205

Gln Leu Glu Gly Ala Val Gly Leu Ser Ser Thr Leu Ala Glu Ile Phe
        210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
            245                 250                 255

Phe Asp Leu Met Gln Arg Thr Pro Tyr Ile Ala Lys His Gln Gly Thr
            260                 265                 270

```
Pro Leu Leu Gln Thr Ile Val Asn Ala Leu Asn Ser Asn Thr Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Ala Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 31
<211> LENGTH: 412
<212> TYPE: PRT
<213> ORGANISM: artificial sequence
<220> FEATURE:
<223> OTHER INFORMATION: PHY-14277- sequence is synthesized

<400> SEQUENCE: 31

Ser Glu Ala Ala Pro Ala Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gln Gly Leu Leu Pro Lys Asp Asn Cys Pro
65              70                  75                  80

Thr Ala Asn Asp Val Tyr Val Trp Thr Asp Val Asn Gln Arg Thr Arg
            85                  90                  95

Lys Thr Gly Glu Ala Phe Leu Ala Gly Leu Ala Pro Glu Cys Asp Leu
            100                 105                 110

Thr Ile His His Gln Asn Asp Ile Lys Gln Val Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Arg His Ser Gly Asp Lys Thr Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220
```

-continued

```
Leu Leu Glu Tyr Ala Gln Gly Met Pro Val Ala Trp Gly Asn Ile
225                 230                 235                 240

His Ser Glu Gln Glu Trp Asn Asp Leu Leu Lys Leu His Asn Ala Gln
            245                 250                 255

Phe Asp Leu Met Glu Arg Thr Pro Tyr Ile Ala Lys His Gln Gly Thr
        260                 265                 270

Pro Leu Leu Gln Thr Ile Val Asn Ala Leu Asn Ser Asn Thr Thr Glu
    275                 280                 285

Ser Lys Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Thr Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Ile
                405                 410

<210> SEQ ID NO 32
<211> LENGTH: 412
<212> TYPE: PRT
<213> ORGANISM: artificial sequence
<220> FEATURE:
<223> OTHER INFORMATION: PHY-14473- sequence is synthesized

<400> SEQUENCE: 32

Ala Glu Glu Gln Asn Gly Met Lys Leu Gln Lys Ala Val Ile Leu Ser
1               5                   10                  15

Arg His Gly Val Arg Ala Pro Thr Lys Met Thr Gln Leu Met Arg Asp
            20                  25                  30

Val Thr Pro Tyr Thr Trp Pro Glu Trp Pro Val Pro Leu Gly Tyr Ile
        35                  40                  45

Thr Pro Arg Gly Glu His Leu Val Ser Leu Met Gly Gly Phe Tyr Arg
    50                  55                  60

Gln Tyr Phe Gln Gln Gly Leu Leu Ser Arg Asp Arg Cys Pro Thr
65                  70                  75                  80

Ala Asn Asp Val Tyr Val Trp Thr Asp Val Asn Gln Arg Thr Arg Lys
                85                  90                  95

Thr Gly Glu Ala Phe Leu Ala Gly Leu Ala Pro Glu Cys Ala Ile Thr
            100                 105                 110

Ile His His Gln Ser Asp Ile Lys Gln Val Asp Pro Leu Phe His Pro
        115                 120                 125

Val Lys Ala Gly Ile Cys Ser Met Asp Lys Thr Gln Val Gln Gln Ala
    130                 135                 140

Val Glu Lys Gln Ala Gly Met Pro Ile Asp Lys Leu Asn Gln His Tyr
145                 150                 155                 160

Arg Pro Glu Leu Ala Leu Met Ser Asn Val Leu Asn Phe Pro Lys Ser
                165                 170                 175
```

Pro Tyr Cys Arg His Gln Ser Gly Asp Lys Thr Cys Asp Phe Ala Asn
                180                 185                 190

Ala Phe Pro Ser Tyr Leu Asn Ile Ser Asp Asp Gly Asn Glu Val Gln
            195                 200                 205

Leu Glu Gly Ala Val Gly Leu Ser Ser Thr Leu Ala Glu Ile Phe Leu
        210                 215                 220

Leu Glu Tyr Ala Gln Gly Met Pro Val Ala Trp Gly Asn Ile His
225                 230                 235                 240

Ser Glu Gln Glu Trp Asn Asp Leu Leu Lys Leu His Asn Ala Gln Phe
                245                 250                 255

Asp Leu Met Glu Arg Thr Pro Tyr Ile Ala Lys His Asn Gly Thr Pro
            260                 265                 270

Leu Leu Gln Thr Ile Val Asn Ala Leu Asn Ser Asn Thr Thr Glu Ser
        275                 280                 285

Lys Leu Pro Asp Ile Ser Pro Asp Val Lys Ile Leu Phe Leu Ala Gly
    290                 295                 300

His Asp Thr Asn Ile Ala Asn Ile Gly Gly Met Leu Gly Met Thr Trp
305                 310                 315                 320

Thr Leu Pro Gly Gln Pro Asp Asn Thr Pro Pro Gly Gly Ala Leu Leu
                325                 330                 335

Phe Glu Leu Trp Ser Asp Lys Glu Gly Thr Gln Tyr Val Ser Val Lys
            340                 345                 350

Met Val Tyr Gln Thr Leu Ala Gln Leu Arg Asn Gln Thr Pro Leu Thr
        355                 360                 365

Leu Lys Glu Pro Ala Gly Ser Val Pro Leu Lys Ile Pro Gly Cys Asp
    370                 375                 380

Asp Gln Thr Ala Glu Gly Tyr Cys Pro Leu Asp Thr Phe Thr Arg Leu
385                 390                 395                 400

Val Asn Gln Val Val Glu Pro Ala Cys Gln Leu Pro
                405                 410

<210> SEQ ID NO 33
<211> LENGTH: 413
<212> TYPE: PRT
<213> ORGANISM: artificial sequence
<220> FEATURE:
<223> OTHER INFORMATION: PHY-14614- sequence is synthesized

<400> SEQUENCE: 33

Ser Glu Ala Ala Pro Ser Gly Tyr His Leu Asp Lys Ala Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Gln Gly Leu Leu Ser Arg Asp Ser Cys Pro
65              70                  75                  80

Thr Ala Asn Asp Val Tyr Val Trp Thr Asp Val Asn Gln Arg Thr Arg
            85                  90                  95

Lys Thr Gly Glu Ala Phe Leu Ala Gly Leu Ala Pro Gly Cys Asp Leu
        100                 105                 110

Thr Ile His His Gln Gln Asn Ile Thr Gln Val Asp Pro Leu Phe His
    115                 120                 125

Pro Val Lys Ala Gly Ile Cys Ser Met Asp Lys Thr Gln Val Gln
            130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Gln His Ser Val Asp Lys Pro Cys Asp Phe Ala
                180                 185                 190

Asn Met Phe Pro Ser Tyr Leu Asn Ile Ser Asp Asp Gly Asn Glu Val
                195                 200                 205

Gln Leu Glu Gly Ala Val Gly Leu Ser Ser Thr Leu Ala Glu Ile Phe
                210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Asn Gly Thr
                260                 265                 270

Pro Leu Leu Gln Thr Ile Val Asn Ala Leu Asn Ser Asn Thr Thr Glu
                275                 280                 285

Ser Lys Leu Pro Asp Ile Ser Pro Asp Val Lys Ile Leu Phe Leu Ala
290                 295                 300

Gly His Asp Thr Asn Ile Ala Asn Ile Ala Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Met Thr Pro Leu
                355                 360                 365

Thr Leu Lys Glu Pro Ala Gly Thr Val Pro Leu Lys Ile Pro Gly Cys
            370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 34
<211> LENGTH: 413
<212> TYPE: PRT
<213> ORGANISM: artificial sequence
<220> FEATURE:
<223> OTHER INFORMATION: PHY-14804- sequence is synthesized

<400> SEQUENCE: 34

Ser Asp Thr Ala Pro Ala Gly Phe Gln Leu Asp Lys Ala Val Ile Leu
1               5                   10                  15

Ser Arg His Gly Val Arg Ala Pro Thr Lys Met Thr Gln Thr Met Arg
                20                  25                  30

Asp Val Thr Pro Tyr Thr Trp Pro Glu Trp Pro Val Pro Leu Gly Tyr
                35                  40                  45

Ile Thr Pro Arg Gly Glu His Leu Val Ser Leu Met Gly Gly Phe Tyr
            50                  55                  60

Arg Gln Tyr Phe Gln Gln Gln Gly Leu Leu Pro Arg Asp Asn Cys Pro
65                  70                  75                  80

```
Thr Ala Asn Asp Val Tyr Val Trp Thr Asp Val Asp Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Glu Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Asp Gly Thr Gln Tyr Val Ser Val
            340                 345                 350

Lys Met Val Tyr Gln Thr Leu Ala Gln Leu Arg Asn Gln Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 35
<211> LENGTH: 413
<212> TYPE: PRT
<213> ORGANISM: artificial sequence
<220> FEATURE:
<223> OTHER INFORMATION: PHY-14945- sequence is synthesized

<400> SEQUENCE: 35

Ser Glu Ala Ala Pro Ala Gly Tyr His Leu Asp Lys Ala Val Ile Leu
1               5                   10                  15

Ser Arg His Gly Val Arg Ala Pro Thr Lys Met Thr Gln Thr Met Arg
            20                  25                  30
```

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
 50                  55                  60

Arg Glu Arg Phe Gln Gln Gln Gly Leu Leu Ser Arg Asp Ser Cys Pro
 65                  70                  75                  80

Thr Ala Asn Asp Val Tyr Val Trp Thr Asp Val Asn Gln Arg Thr Arg
                 85                  90                  95

Lys Thr Gly Glu Ala Phe Leu Ala Gly Leu Ala Pro Glu Cys Ala Ile
                100                 105                 110

Thr Ile His His Gln Ser Asp Ile Lys Gln Val Asp Pro Leu Phe His
            115                 120                 125

Pro Val Lys Ala Gly Ile Cys Ser Met Asp Lys Thr Gln Val Gln Gln
            130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Asn Ala Phe Pro Ser Lys Leu Asn Ile Ser Asp Asp Gly Asn Glu Val
            195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala His
                245                 250                 255

Phe Asp Leu Met Glu Arg Thr Pro Tyr Ile Ala Lys His Asn Gly Thr
                260                 265                 270

Pro Leu Leu Gln Thr Ile Val Asn Ala Leu Asn Ser Asn Thr Thr Ala
            275                 280                 285

Arg Glu Leu Pro Asp Ile Ser Pro Asp Val Lys Ile Leu Phe Leu Ala
            290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Gln Thr Pro Leu
            355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 36
<211> LENGTH: 412
<212> TYPE: PRT
<213> ORGANISM: artificial sequence
<220> FEATURE:

<223> OTHER INFORMATION: PHY-15459- sequence is synthesized

<400> SEQUENCE: 36

```
Ala Glu Pro Gln Asn Gly Met Lys Leu Asp Lys Ala Val Ile Leu Ser
1               5                   10                  15

Arg His Gly Val Arg Ala Pro Thr Lys Met Thr Gln Thr Met Arg Asp
            20                  25                  30

Val Thr Pro Tyr Thr Trp Pro Glu Trp Pro Val Pro Leu Gly Tyr Ile
        35                  40                  45

Thr Pro Arg Gly Glu His Leu Val Ser Leu Met Gly Gly Phe Tyr Arg
    50                  55                  60

Gln Tyr Phe Gln Gln Gly Ile Leu Ser Lys Asp Arg Cys Pro Arg
65                  70                  75                  80

Ala Asn Asp Val Tyr Val Trp Thr Asp Val Asp Gln Arg Thr Arg Lys
                85                  90                  95

Thr Gly Glu Ala Phe Leu Ala Gly Leu Ala Pro Gln Cys Pro Leu Thr
            100                 105                 110

Ile His His Gln Asn Asp Ile Lys Gln Val Asp Pro Met Phe His Pro
        115                 120                 125

Val Lys Gly Gly Ile Cys Ser Met Asp Lys Thr Gln Val Gln Gln Ala
    130                 135                 140

Val Glu Lys Gln Ala Gly Met Pro Ile Asp Lys Leu Asn Asp His Tyr
145                 150                 155                 160

Arg Pro Glu Leu Ala Leu Met Ser Ala Val Leu Asn Phe Pro Ala Ser
                165                 170                 175

Pro Tyr Cys Gln Arg His Ser Gly Glu Gln Pro Cys Asp Phe Ala Gln
            180                 185                 190

Met Met Pro Ser Lys Leu Tyr Ile Thr Asp Asp Gly Asn Glu Val Gln
        195                 200                 205

Leu Glu Gly Ala Val Gly Leu Ser Ser Thr Leu Ala Glu Ile Phe Leu
    210                 215                 220

Leu Glu Tyr Ala Gln Gly Met Pro Val Val Ala Trp Gly Asn Ile His
225                 230                 235                 240

Ser Glu Gln Glu Trp Asn Ala Leu Leu Lys Leu His Asn Ala Tyr Phe
                245                 250                 255

Asp Leu Met Tyr Arg Thr Pro Tyr Ile Ala Lys His Asn Gly Thr Pro
            260                 265                 270

Leu Leu Gln Thr Ile Val Asn Ala Leu Asn Ser Asn Thr Thr Ala Arg
        275                 280                 285

Glu Leu Pro Asp Ile Ser Pro Asp Asn Arg Ile Leu Phe Leu Ala Gly
    290                 295                 300

His Asp Thr Asn Ile Ala Asn Ile Gly Gly Met Leu Gly Met Asp Trp
305                 310                 315                 320

Thr Leu Pro Gly Gln Pro Asp Asn Thr Pro Pro Gly Gly Ala Leu Leu
                325                 330                 335

Phe Glu Leu Trp Ser Asp Lys Glu Gly Thr Gln Tyr Val Ser Val His
            340                 345                 350

Met Val Tyr Gln Thr Leu Ala Gln Leu Arg Asn Gln Thr Pro Leu Thr
        355                 360                 365

Leu Gln Glu Pro Ala Gly Thr Val Pro Leu Lys Ile Pro Ser Cys Asp
    370                 375                 380

Asp Gln Thr Ala Glu Gly Tyr Cys Pro Leu Asp Thr Phe Thr Lys Leu
385                 390                 395                 400
```

```
Val Asn Gln Val Val Glu Pro Ala Cys Gln Ile Pro
            405                 410
```

<210> SEQ ID NO 37
<211> LENGTH: 413
<212> TYPE: PRT
<213> ORGANISM: artificial sequence
<220> FEATURE:
<223> OTHER INFORMATION: PHY-16513- sequence is synthesized

<400> SEQUENCE: 37

```
Ser Glu Ala Ala Pro Ser Gly Tyr His Leu Asp Lys Ala Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Ser Leu Met Gly Gly Phe Tyr
    50                  55                  60

Arg Gln Tyr Phe Gln Met Gln Gly Leu Leu Ser Arg Asp Arg Cys Pro
65                  70                  75                  80

Asn Ala Asn Asp Val Tyr Val Trp Thr Asp Val Asp Gln Arg Thr Arg
                85                  90                  95

Lys Thr Gly Glu Ala Phe Leu Arg Gly Leu Ala Pro Glu Cys Asp Leu
            100                 105                 110

Thr Ile His His Gln Asn Asp Ile Lys Gln Val Asp Pro Met Phe His
        115                 120                 125

Pro Val Lys Gly Gly Ile Cys Ser Met Asp Lys Thr Gln Val Gln Gln
    130                 135                 140

Ala Val Glu Lys Gln Ala Gly Met Pro Ile Asp Lys Leu Asn Asp His
145                 150                 155                 160

Tyr Arg Pro Glu Leu Ala Leu Met Ser Ala Val Leu Asn Phe Pro Ala
                165                 170                 175

Ser Pro Tyr Cys Gln Gln His Ser Val Asp Lys Pro Cys Asp Phe Ala
            180                 185                 190

Asn Ala Phe Pro Ser Lys Leu Asn Ile Thr Asp Asp Gly Asn Glu Val
        195                 200                 205

Ala Leu Asp Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Asn Glu Ser Gln Trp Lys Ser Leu Leu Asn Leu His Asn Ala His
                245                 250                 255

Phe Asn Leu Met His Arg Thr Pro Tyr Ile Ala Lys His Asn Gly Thr
            260                 265                 270

Pro Leu Leu Gln Thr Ile Val Asn Ala Leu Asn Ser Asn Thr Thr Ala
        275                 280                 285

Arg Glu Leu Pro Asp Ile Ser Pro Ser Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Asp Gly Thr Gln Tyr Val Ser Val
            340                 345                 350
```

```
Lys Met Val Tyr Gln Thr Leu Ala Gln Leu Arg Asn Gln Thr Pro Leu
            355                 360                 365

Thr Leu Asn Glu Pro Ala Gly Thr Val Pro Leu Lys Ile Pro Ser Cys
    370                 375                 380

Asp Asp Gln Thr Ala Glu Gly Tyr Cys Pro Leu Asp Thr Phe Thr Val
385                 390                 395                 400

Leu Val Asn Gln Val Val Glu Pro Ala Cys Gln Ile Pro
                405                 410

<210> SEQ ID NO 38
<211> LENGTH: 413
<212> TYPE: PRT
<213> ORGANISM: Buttiauxella noackiae

<400> SEQUENCE: 38

Ser Glu Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Lys Leu Met Gly Gly Phe Tyr
    50                  55                  60

Arg Glu Lys Phe Gln Gln Gln Gly Ile Leu Ser Gln Glu Asn Cys Pro
65                  70                  75                  80

Ala Pro Asn Ser Val Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Glu Lys Asn Gln Ile Gln Gln
    130                 135                 140

Ala Val Glu Lys Glu Ala Gln Thr Pro Ile Asp Asn Leu Asn Gln His
145                 150                 155                 160

Tyr Leu Pro Ser Leu Ala Leu Met Asn Thr Thr Leu Asn Phe Ala Asn
                165                 170                 175

Ser Ala Trp Cys Gln Lys His Ser Val Asp Lys Ser Cys Asp Leu Gly
            180                 185                 190

Gln Ser Met Pro Ser Lys Leu Ser Ile Gln Glu Asn Gly Asn Lys Ile
        195                 200                 205

Thr Leu Asp Gly Ala Ile Gly Leu Ser Ser Thr Leu Ala Glu Ile Phe
    210                 215                 220

Leu Leu Glu Tyr Ala Gln Gly Met Pro Lys Ala Trp Gly Asn Ile
225                 230                 235                 240

His Ser Glu Gln Glu Trp Ala Ala Leu Leu Lys Leu His Asn Thr Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asp Pro Asn Ala Thr Ala
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ser Gly Met Leu Asn Ile Ser
305                 310                 315                 320
```

```
Trp Thr Leu Pro Gly Gln Pro Asp Asn Thr Pro Pro Gly Gly Ala Leu
                325                 330                 335

Val Phe Glu Arg Leu Ala Asp Lys Ala Gly Lys Gln Tyr Val Ser Val
            340                 345                 350

Ser Met Val Tyr Gln Thr Leu Glu Gln Leu His Ala Gln Thr Pro Leu
        355                 360                 365

Ser Leu Lys Glu Pro Ala Gly Ser Val Gln Leu Lys Ile Pro Gly Cys
370                 375                 380

Ser Asp Gln Thr Ala Glu Gly Tyr Cys Pro Leu Pro Thr Phe Thr Arg
385                 390                 395                 400

Val Val Ser Gln Ser Val Glu Pro Gly Cys Gln Leu Gln
                405                 410
```

<210> SEQ ID NO 39
<211> LENGTH: 413
<212> TYPE: PRT
<213> ORGANISM: Citrobacter braakii

<400> SEQUENCE: 39

```
His Ala Glu Glu Gln Asn Gly Met Lys Leu Glu Arg Val Val Ile Val
1               5                   10                  15

Ser Arg His Gly Val Arg Ala Pro Thr Lys Phe Thr Pro Ile Met Lys
            20                  25                  30

Asp Val Thr Pro Asp Gln Trp Pro Gln Trp Asp Val Pro Leu Gly Trp
        35                  40                  45

Leu Thr Pro Arg Gly Gly Glu Leu Val Ser Glu Leu Gly Gln Tyr Gln
50                  55                  60

Arg Leu Trp Phe Thr Ser Lys Gly Leu Leu Asn Asn Gln Thr Cys Pro
65                  70                  75                  80

Ser Pro Gly Gln Val Ala Val Ile Ala Asp Thr Asp Gln Arg Thr Arg
                85                  90                  95

Lys Thr Gly Glu Ala Phe Leu Ala Gly Leu Ala Pro Lys Cys Gln Ile
            100                 105                 110

Gln Val His Tyr Gln Lys Asp Glu Glu Lys Asn Asp Pro Leu Phe Asn
        115                 120                 125

Pro Val Lys Met Gly Lys Cys Ser Phe Asn Thr Leu Lys Val Lys Asn
    130                 135                 140

Ala Ile Leu Glu Arg Ala Gly Gly Asn Ile Glu Leu Tyr Thr Gln Arg
145                 150                 155                 160

Tyr Gln Ser Ser Phe Arg Thr Leu Glu Asn Val Leu Asn Phe Ser Gln
                165                 170                 175

Ser Glu Thr Cys Lys Thr Thr Glu Lys Ser Thr Lys Cys Thr Leu Pro
            180                 185                 190

Glu Ala Leu Pro Ser Glu Phe Lys Val Thr Pro Asp Asn Val Ser Leu
        195                 200                 205

Pro Gly Ala Trp Ser Leu Ser Ser Thr Leu Thr Glu Ile Phe Leu Leu
    210                 215                 220

Gln Glu Ala Gln Gly Met Pro Gln Val Ala Trp Gly Arg Ile Thr Gly
225                 230                 235                 240

Glu Lys Glu Trp Arg Asp Leu Leu Ser Leu His Asn Ala Gln Phe Asp
                245                 250                 255

Leu Leu Gln Arg Thr Pro Glu Val Ala Arg Ser Arg Ala Thr Pro Leu
            260                 265                 270

Leu Asp Met Ile Asp Thr Ala Leu Leu Thr Asn Gly Thr Thr Glu Asn
```

```
                275                 280                 285
Arg Tyr Gly Ile Lys Leu Pro Val Ser Leu Phe Ile Ala Gly His
    290                 295                 300
Asp Thr Asn Leu Ala Asn Leu Ser Gly Ala Leu Asp Leu Lys Trp Ser
305                 310                 315                 320
Leu Pro Gly Gln Pro Asp Asn Thr Pro Gly Gly Glu Leu Val Phe
                325                 330                 335
Glu Lys Trp Lys Arg Thr Ser Asp Asn Thr Asp Trp Val Gln Val Ser
                340                 345                 350
Phe Val Tyr Gln Thr Leu Arg Asp Met Arg Asp Ile Gln Pro Leu Ser
                355                 360                 365
Leu Glu Lys Pro Ala Gly Lys Val Asp Leu Lys Leu Ile Ala Cys Glu
    370                 375                 380
Glu Lys Asn Ser Gln Gly Met Cys Ser Leu Lys Ser Phe Ser Arg Leu
385                 390                 395                 400
Ile Lys Glu Ile Arg Val Pro Glu Cys Ala Val Thr Glu
                    405                 410

<210> SEQ ID NO 40
<211> LENGTH: 415
<212> TYPE: PRT
<213> ORGANISM: Coxiellaceae bacterium

<400> SEQUENCE: 40

Val Val Ala Lys Gly Thr Glu Tyr Thr Leu Gln Gln Val Val Ile Leu
1               5                   10                  15
Ser Arg His Gly Val Arg Ser Pro Ile Lys His Ser Lys Leu Leu Asn
                20                  25                  30
Glu Ile Thr Pro Ser Ser Trp Pro Gln Trp Pro Val Lys Pro Gly Tyr
            35                  40                  45
Leu Thr Pro Arg Gly Lys Leu Leu Met Thr Leu Met Gly Glu Phe Tyr
        50                  55                  60
Gly Asp Tyr Phe Arg Asn Lys Gly Leu Leu Ala Glu His Gly Cys Pro
65              70                  75                  80
Ala Asn Gly Thr Val Tyr Val Gln Thr Asp Val Asp Gln Arg Thr Ile
                85                  90                  95
Leu Ser Gly Trp Ala Leu Leu Ser Gly Met Thr Pro His Cys Arg Phe
            100                 105                 110
Lys Ile His His Gln Glu Asn Leu Lys Arg Ile Asp Pro Leu Phe His
        115                 120                 125
Pro Val Glu Ala Gly Ile Cys Glu Leu Asn Lys Glu Lys Ala Leu Asn
    130                 135                 140
Ala Ile Glu Glu Arg Leu Gly Ala Pro Leu Gln Thr Leu Ser Lys Arg
145                 150                 155                 160
Tyr Ala Ser Pro Leu Ala Gln Met Ser Lys Ile Leu Lys Phe Asp Arg
                165                 170                 175
Ser Pro Tyr Cys Glu Lys Met His Lys Met Gln Lys Ser Cys Asp Phe
                180                 185                 190
Ala Thr Phe Leu Ser Asn Lys Ile Tyr Ile Asn Asn Lys Gly Thr Ile
            195                 200                 205
Leu Leu Arg Gly Pro Val Ser Leu Ser Ser Thr Phe Ala Glu Ile Phe
        210                 215                 220
Leu Leu Gln Asn Ser Gln Gly Met Pro Asp Val Ala Trp His Arg Leu
225                 230                 235                 240
```

```
Lys Gly Glu Ala Asn Trp Glu Ser Leu Leu Ser Leu His Asn Ala Gln
                245                 250                 255

Phe Asp Leu Met Ala Lys Thr Phe Tyr Ile Ser Arg His Glu Gly Thr
            260                 265                 270

Pro Leu Leu Glu Glu Ile Gly Gly Ala Leu Thr His Gln Met Lys Gln
        275                 280                 285

Gln Arg Ile Phe Ser Thr Leu Pro Leu Ser Ala His Asn Arg Val Leu
    290                 295                 300

Phe Leu Val Gly His Asp Val Asn Ile Ala Asn Ile Ala Gly Met Leu
305                 310                 315                 320

Gly Leu Asn Trp Gln Leu Leu Gln Gln Pro Asp Asn Thr Pro Pro Gly
                325                 330                 335

Gly Gly Leu Val Phe Glu Leu Trp Gln Lys Met Asp Asp His Lys His
            340                 345                 350

Tyr Ile Ser Ile Lys Met Phe Tyr Gln Thr Met Val Gln Leu Arg Asn
        355                 360                 365

Lys Gln Lys Met Asp Leu Trp Leu Asn Pro Ala Gly Met Leu Ser Ile
    370                 375                 380

Pro Gly Cys Asp Asn Met Gly Lys Asp Lys Leu Cys Arg Leu Glu Lys
385                 390                 395                 400

Phe Gln Lys Lys Leu Gln Gln Ala Ile Glu Pro Ile Cys Arg Ile
                405                 410                 415

<210> SEQ ID NO 41
<211> LENGTH: 411
<212> TYPE: PRT
<213> ORGANISM: unknown
<220> FEATURE:
<223> OTHER INFORMATION: Enterobacteriaceae WP 094337278.1

<400> SEQUENCE: 41

Ala Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Trp Leu
            35                  40                  45

Thr Pro Arg Gly Gly Glu Leu Ile Ala Tyr Leu Gly His Tyr Gln Arg
        50                  55                  60

Gln Arg Leu Val Ala Asp Gly Leu Leu Ala Lys Lys Gly Cys Pro Gln
65                  70                  75                  80

Pro Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Ser Arg Ala Gly Gly Ser Ile Ala Asp Phe Thr Gly His Arg
145                 150                 155                 160

Gln Thr Ala Phe Arg Glu Leu Glu Arg Val Leu Asn Phe Pro Gln Ser
                165                 170                 175

Asn Leu Cys Leu Asn Arg Glu Lys Gln Asp Glu Ser Cys Ser Leu Thr
            180                 185                 190
```

Gln Ala Leu Pro Ser Glu Leu Lys Val Ser Ala Asp Asn Val Ser Leu
            195                 200                 205

Thr Gly Ala Val Ser Leu Ala Ser Met Leu Thr Glu Ile Phe Leu Leu
            210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Gln Phe Tyr
                245                 250                 255

Leu Leu Gln Arg Thr Pro Glu Val Ala Arg Ser Arg Ala Thr Pro Leu
            260                 265                 270

Leu Asp Leu Ile Met Ala Ala Leu Thr Pro His Pro Gln Lys Gln
            275                 280                 285

Ala Tyr Gly Val Thr Leu Pro Thr Ser Val Leu Phe Ile Ala Gly His
            290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 42
<211> LENGTH: 411
<212> TYPE: PRT
<213> ORGANISM: Escherichia coli

<400> SEQUENCE: 42

Ala Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Trp Leu
        35                  40                  45

Thr Pro Arg Gly Gly Glu Leu Ile Ala Tyr Leu Gly His Tyr Gln Arg
    50                  55                  60

Gln Arg Leu Val Ala Asp Gly Leu Leu Ala Lys Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Asn Ala Asn Val Thr Asp Ala
    130                 135                 140

Ile Leu Ser Arg Ala Gly Gly Ser Ile Ala Asp Phe Thr Gly His Arg
145                 150                 155                 160

Gln Thr Ala Phe Arg Glu Leu Glu Arg Val Leu Asn Phe Pro Gln Ser
            165                 170                 175

Asn Leu Cys Leu Lys Arg Glu Lys Gln Asp Glu Ser Cys Ser Leu Thr
        180                 185                 190

Gln Ala Leu Pro Ser Glu Leu Lys Val Ser Ala Asp Asn Val Ser Leu
    195                 200                 205

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Ser Leu His Asn Ala Gln Phe Tyr
            245                 250                 255

Leu Leu Gln Arg Thr Pro Glu Val Ala Arg Ser Arg Ala Thr Pro Leu
        260                 265                 270

Leu Asp Leu Ile Met Ala Ala Leu Thr Pro His Pro Gln Lys Gln
    275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Thr Pro Pro Gly Gly Glu Leu Val Phe
            325                 330                 335

Glu Arg Trp Arg Arg Leu Ser Asp Asn Ser Gln Trp Ile Gln Val Ser
        340                 345                 350

Leu Val Phe Gln Thr Leu Gln Gln Met Arg Asp Lys Thr Pro Leu Ser
    355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
            385                 390                 395                 400

Val Asn Glu Ala Arg Ile Pro Ala Cys Ser Leu
        405                 410

<210> SEQ ID NO 43
<211> LENGTH: 411
<212> TYPE: PRT
<213> ORGANISM: Hafnia alvei

<400> SEQUENCE: 43

Ser Glu Thr Val Pro Ser Gly Tyr Gln Leu Glu Lys Val Ile Leu
1               5                   10                  15

Ser Arg His Gly Val Arg Ala Pro Thr Lys Met Thr Gln Thr Met Arg
            20                  25                  30

Asp Val Thr Pro Asp Ala Trp Pro Glu Trp Pro Val Lys Leu Gly Tyr
        35                  40                  45

Ile Thr Pro Arg Gly Glu His Leu Val Ser Leu Met Gly Gly Phe Tyr
    50                  55                  60

Arg Gln Thr Phe Gln Gln Leu Gly Ile Leu Ser Lys Asp Arg Cys Pro
65                  70                  75                  80

Thr Ala Asn Asp Val Tyr Val Trp Ala Asp Val Asp Gln Arg Thr Arg
                85                  90                  95

Lys Thr Gly Glu Ala Phe Leu Ala Gly Leu Ala Pro Glu Cys His Leu
            100                 105                 110

Ser Ile His His Gln Gln Asp Ile Lys Gln Ala Asp Pro Leu Phe His

```
                115                 120                 125
Pro Val Lys Ala Gly Val Cys Ser Met Glu Lys Thr Gln Val Gln Gln
    130                 135                 140

Ala Val Glu Gln Gln Ala Gly Met Pro Ile Ala Gln Leu Asn Gln His
145                 150                 155                 160

Tyr Arg Pro Ala Leu Ala Leu Met Ser Arg Val Leu Asn Phe Pro Lys
                165                 170                 175

Ser Ala Tyr Cys Gln Gln His Ser Ala Asp Gln Thr Cys Asp Phe Ala
            180                 185                 190

Gln Ala Met Pro Ser Lys Leu Ser Ile Lys Asp Asp Gly Asn Lys Val
        195                 200                 205

Ala Leu Asp Gly Ala Val Gly Leu Ser Ser Thr Leu Ala Glu Ile Phe
    210                 215                 220

Leu Leu Glu His Ala Gln Gly Met Pro Asn Ala Ala Trp Gly Lys Ile
225                 230                 235                 240

His Ser Glu Gln Asp Trp Asn Ala Leu Leu Ala Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Val Ser Ala Ile Asn Ser Gln Thr Gly Thr
        275                 280                 285

Arg Glu Leu Pro Glu Leu Ser Ala Asp Asn Lys Ile Leu Phe Leu Ala
    290                 295                 300

Gly His Asp Thr Asn Ile Ala Asn Ile Ala Gly Met Leu Gly Leu Ser
305                 310                 315                 320

Trp Thr Leu Pro Gly Gln Pro Asp Asn Thr Pro Gly Gly Ala Leu
                325                 330                 335

Val Phe Glu Arg Trp Ser Asp Lys Ala Gly Lys Tyr Val Ser Val
            340                 345                 350

Gln Met Met Tyr Gln Thr Leu Ala Gln Leu Arg Asn Gln Thr Pro Leu
        355                 360                 365

Thr Leu Asp Glu Pro Ala Gly Ser Val Ala Leu Lys Ile Pro Gly Cys
    370                 375                 380

Asp Asp Gln Thr Ala Gln Gly Tyr Cys Pro Leu Asp Thr Phe Thr Arg
385                 390                 395                 400

Leu Ala Lys Gln Asn Glu Leu Ala Glu Cys Gln
                405                 410

<210> SEQ ID NO 44
<211> LENGTH: 418
<212> TYPE: PRT
<213> ORGANISM: Rouxiella badensis

<400> SEQUENCE: 44

Asp Ala Pro Ala Thr Gln Asn Leu Gln Leu Gln Gln Ala Val Ile Leu
1               5                   10                  15

Ser Arg His Gly Val Arg Ala Pro Thr Lys Gln Thr Lys Lys Met Glu
                20                  25                  30

Gln Val Ala Ala Lys Asp Trp Pro Val Trp Pro Val Lys Phe Gly Tyr
            35                  40                  45

Leu Thr Pro Arg Gly Glu His Leu Val Thr Leu Met Gly Gly Tyr Tyr
        50                  55                  60

Gly Glu Tyr Phe Arg Lys Glu Gly Leu Ile Ser Asp Lys Ser Cys Pro
65                  70                  75                  80
```

-continued

```
Ala Asn Gly Ala Ile Phe Gly Trp Gly Asp Val Asp Gln Arg Thr Arg
             85                  90                  95

Leu Thr Thr Gln Ala Leu Leu Asn Gly Ile Ala Pro Gly Cys His Leu
        100                 105                 110

Asp Ala His Phe Gln Asn Asp Leu Lys Lys Ala Asp Pro Leu Phe His
    115                 120                 125

Ala Leu Lys Ala Lys Val Cys Lys Leu Asp Glu Lys Thr Ala Gln Gln
130                 135                 140

Ala Ile Glu Gln Gln Ala Gly Gly Ser Leu Ser Ala Leu Asp Lys Thr
145                 150                 155                 160

Tyr Ala Pro Gln Leu Gln Leu Met Ser Asn Val Leu Asp Tyr Pro His
                165                 170                 175

Ser Ala Tyr Cys Gln Lys Met Gln Lys Lys Gly Gln Gln Cys Glu Leu
            180                 185                 190

Gly Ile Asn Met Pro Ser Ser Val Lys Val Lys Val Lys Val Lys Glu
        195                 200                 205

Asn Gly Thr Asp Ala Ser Leu Lys Gly Ala Ile Gly Leu Ser Ser Thr
    210                 215                 220

Leu Ala Glu Ile Phe Leu Leu Gln Asp Ala Gln Gly Met Thr Asp Pro
225                 230                 235                 240

Ala Trp Gly Asn Ile Lys Asp Gln Lys Thr Trp Gln Gly Leu Met Ala
                245                 250                 255

Leu His Asn Leu Gln Phe Ser Leu Met Ser Gly Thr Pro Tyr Leu Ala
            260                 265                 270

Lys Ser Asn Gly Thr Pro Ile Leu Gln Ala Ile Asp Ser Ala Leu Gly
        275                 280                 285

Ala Pro Glu Lys Pro Ala Ser Gly Tyr Thr Leu Pro Thr Gly Asn Lys
    290                 295                 300

Leu Leu Ile Leu Gly Gly His Asp Thr Asn Ile Glu Asn Val Ala Gly
305                 310                 315                 320

Ala Leu Gly Leu Asn Trp Ser Leu Asp Gly Gln Pro Asp Asn Thr Pro
                325                 330                 335

Pro Ala Gly Ala Leu Val Phe Glu Arg Trp Gln Ser Arg Thr Ser His
            340                 345                 350

Gln Gln Tyr Ile Ser Leu Lys Met Val Tyr Gln Thr Arg Asp Gln Met
        355                 360                 365

Arg Ser Gln Gln Val Leu Thr Leu Asn Asn Pro Pro Ser Ser Ile Ala
    370                 375                 380

Ile Thr Leu Pro Gly Cys Glu Asn Ile Gly Pro Asn Lys Leu Cys Ala
385                 390                 395                 400

Ile Lys Thr Phe His Gln Val Met Thr Lys Ala Gln Leu Pro Gln Cys
                405                 410                 415

Lys Ile

<210> SEQ ID NO 45
<211> LENGTH: 414
<212> TYPE: PRT
<213> ORGANISM: unknown
<220> FEATURE:
<223> OTHER INFORMATION: Serratia sp. WP 009636981.1

<400> SEQUENCE: 45

Val Ile Pro Ala Pro Gln Asp Leu Gln Leu Gln Gln Ala Val Ile Leu
1               5                  10                  15

Ser Arg His Gly Val Arg Ser Pro Thr Lys Gln Thr Lys Glu Met Lys
```

```
                20                  25                  30
Asp Leu Ala Gly Gln Asp Trp Pro Lys Trp Pro Val Lys Pro Gly Tyr
            35                  40                  45
Leu Thr Pro Arg Gly Gln Gln Leu Val Ser Leu Met Gly Thr Tyr Tyr
        50                  55                  60
Gly Asp Tyr Phe Lys Lys Glu Gly Leu Leu Ser Ser Glu Gln Cys Pro
 65                  70                  75                  80
Gly Asp Ser Glu Val Phe Gly Trp Gly Asp Thr Asp Gln Arg Thr Arg
                85                  90                  95
Leu Thr Thr Gln Thr Leu Leu Ser Ala Ile Ala Pro His Cys His Val
            100                 105                 110
Met Ala Lys Asn Gln Ala Asp Leu Lys Lys Pro Asp Pro Val Phe His
            115                 120                 125
Pro Leu Lys Ala Gly Ile Cys Thr Leu Asp Lys Ala Thr Ala Ile Lys
        130                 135                 140
Ala Ile Asp Lys Glu Ala Gly Gly Ser Leu Asp Ala Leu Asp Gln Thr
145                 150                 155                 160
Tyr Ala Pro Gln Leu Lys Leu Met Ser Gln Val Leu Asn Tyr Pro Gln
                165                 170                 175
Ser Ser Tyr Cys Gln Gln Met Lys Gln Thr Gly Gln Thr Cys Ser Ala
            180                 185                 190
Val Ile Asp Ile Pro Ser Ser Ile Lys Met Lys Lys Gly Thr Glu
            195                 200                 205
Ala Thr Leu Glu Gly Gly Ile Gly Met Ser Ser Thr Phe Ala Glu Asn
        210                 215                 220
Phe Leu Leu Glu Asp Ala Gln Gly Met Gln Asp Val Ala Trp Gly Arg
225                 230                 235                 240
Ile Lys Asp Gln Lys Thr Trp Gln Ala Leu Leu Glu Leu His Asn Leu
                245                 250                 255
Gln Phe Arg Leu Met Ser Gly Thr Pro Tyr Ile Ala Lys Ser Asn Gly
            260                 265                 270
Thr Pro Val Leu Gln Val Ile Asp Asn Ala Phe Gly Ala Ala Ala Pro
        275                 280                 285
Ala Ser Ser Gly Phe Ser Leu Pro Ser Gly Asn Lys Val Leu Ile Leu
        290                 295                 300
Gly Gly His Asp Thr Asn Ile Glu Asn Val Ala Gly Ala Leu Gly Leu
305                 310                 315                 320
Asp Trp Thr Leu Thr Asp Gln Pro Asp His Thr Pro Pro Ala Gly Ala
                325                 330                 335
Leu Met Phe Glu Arg Trp Gln Asp Lys Thr Thr His Gln Gln Tyr Ile
            340                 345                 350
Ser Leu Arg Met Val Tyr Gln Thr Gln Asp Gln Met Arg Thr Gln His
            355                 360                 365
Lys Leu Thr Leu Lys His Pro Pro Met Thr Val Ala Leu Ser Ile Pro
        370                 375                 380
Gly Cys Glu Asn Ile Gly Asp Asn Lys Leu Cys Ala Ile Gly Thr Phe
385                 390                 395                 400
His Gln Val Ile Glu Lys Ala Gln Leu Pro Gln Cys Lys Ile
                405                 410

<210> SEQ ID NO 46
<211> LENGTH: 412
<212> TYPE: PRT
<213> ORGANISM: Yersinia aldovae
```

<400> SEQUENCE: 46

```
Gln Pro Ala Gly Tyr Thr Leu Glu Arg Val Val Ile Leu Ser Arg His
1               5                   10                  15

Gly Val Arg Ser Pro Thr Lys Gln Thr Gln Leu Met Asn Asp Val Thr
            20                  25                  30

Pro Asp Lys Trp Pro Gln Trp Pro Val Lys Ala Gly Tyr Leu Thr Pro
        35                  40                  45

Arg Gly Ala Gln Leu Val Thr Leu Met Gly Gln Phe Tyr Gly Asp Tyr
    50                  55                  60

Phe Arg Ser Lys Gly Leu Leu Ala Gly Cys Pro Ala Glu Gly Val
65                  70                  75                  80

Ile Tyr Ala Gln Ala Asp Ile Asp Gln Arg Thr Arg Leu Thr Gly Gln
                85                  90                  95

Ala Phe Leu Asp Gly Val Ala Pro Asp Cys Gly Leu Lys Val His Tyr
                100                 105                 110

Gln Ala Asp Leu Lys Lys Thr Asp Pro Leu Phe His Pro Val Glu Ala
            115                 120                 125

Gly Val Cys Lys Leu Asp Ala Val Gln Thr Gln Lys Ala Val Glu Glu
    130                 135                 140

His Leu Gly Gly Pro Leu Ser Ser Leu Gly Glu Arg Tyr Thr Lys Pro
145                 150                 155                 160

Phe Ala Gln Met Gly Glu Val Leu Asn Phe Ala Lys Ser Pro Tyr Cys
                165                 170                 175

Lys Thr Arg Gln Gln Asn Asp Lys Thr Cys Asp Phe Ala His Phe Ala
                180                 185                 190

Ala Asn Glu Ile Lys Val Asn Lys Glu Gly Ser Lys Val Ser Leu Asn
            195                 200                 205

Gly Pro Leu Ala Leu Ser Ser Thr Leu Gly Glu Ile Phe Leu Leu Gln
    210                 215                 220

Asn Ala Gln Asn Met Pro Asn Val Ala Trp Asn Arg Leu Ser Gly Thr
225                 230                 235                 240

Glu Asn Trp Ala Ser Leu Leu Ser Leu His Asn Val Gln Phe Asp Leu
                245                 250                 255

Met Ala Lys Thr Pro Tyr Ile Ala Arg His Lys Gly Thr Pro Leu Leu
                260                 265                 270

Gln Gln Ile Asp Ala Ala Leu Thr Leu Gln Pro Asp Ala Leu Gly Gln
            275                 280                 285

Thr Leu Pro Leu Ser Pro Gln Ser Arg Val Leu Phe Ile Gly Gly His
    290                 295                 300

Asp Thr Asn Ile Ala Asn Ile Ala Gly Met Leu Gly Ala Ser Trp Gln
305                 310                 315                 320

Leu Pro Gln Gln Pro Asp Asn Thr Pro Pro Gly Gly Leu Val Phe
                325                 330                 335

Glu Leu Trp Gln Asn Pro Asp Asn His Gln Arg Tyr Val Ala Val Lys
                340                 345                 350

Met Phe Tyr Gln Thr Met Asp Gln Leu Arg Lys Ala Glu Met Leu Asp
                355                 360                 365

Leu Lys Asn Asn Pro Ala Gly Met Ile Ser Val Ala Val Glu Gly Cys
            370                 375                 380

Glu Asn Ser Gly Asp Asp Lys Leu Cys Gln Leu Asp Thr Phe Gln Lys
385                 390                 395                 400

Lys Val Ala Gln Val Ile Glu Pro Ala Cys His Ile
```

-continued

```
                405                 410

<210> SEQ ID NO 47
<211> LENGTH: 415
<212> TYPE: PRT
<213> ORGANISM: Yersinia frederiksenii

<400> SEQUENCE: 47

Val Val Ala Pro Pro Thr Gly Tyr Thr Leu Glu Arg Val Val Ile Leu
1               5                   10                  15

Ser Arg His Gly Val Arg Ser Pro Thr Lys Gln Thr Gln Leu Met Asn
            20                  25                  30

Asp Val Thr Pro Asp Lys Trp Pro Gln Trp Pro Val Lys Ala Gly Tyr
        35                  40                  45

Leu Thr Pro Arg Gly Ala Glu Leu Val Thr Leu Met Gly Gly Phe Tyr
    50                  55                  60

Gly Asp Tyr Phe Arg His Gln Gly Leu Leu Pro Met Gly Cys Pro Ala
65                  70                  75                  80

Asp Gly Ala Ile Tyr Ala Gln Ala Asp Val Asp Gln Arg Thr Arg Leu
                85                  90                  95

Thr Gly Gln Ala Phe Leu Asp Gly Ile Ala Pro Gly Cys Gly Leu Thr
            100                 105                 110

Val His Tyr Gln Ala Asp Leu Lys Lys Ile Asp Pro Leu Phe His Pro
        115                 120                 125

Val Glu Ala Gly Val Cys Gln Leu Asp Ser Thr Gln Thr His Lys Ala
    130                 135                 140

Val Glu Glu Arg Leu Gly Gly Pro Leu Asn Thr Leu Ser Gln Arg Tyr
145                 150                 155                 160

Ala Lys Pro Phe Ala Gln Met Gly Glu Ile Leu Asn Phe Ser Thr Ser
                165                 170                 175

Pro Tyr Cys Gln Ser Leu Gln Gln Thr Gly Lys Thr Cys Asp Phe Ala
            180                 185                 190

Thr Phe Ala Ala Asn Glu Ile Thr Val Asn Lys Ala Gly Thr Lys Val
        195                 200                 205

Ser Leu Ser Gly Pro Leu Ala Leu Ser Ser Thr Leu Gly Glu Ile Phe
    210                 215                 220

Leu Leu Gln Asn Ser Gln Ala Met Pro Asp Val Ala Trp His Arg Leu
225                 230                 235                 240

Asn Gly Ala Glu Asn Trp Ala Ser Leu Leu Ser Leu His Asn Val Gln
                245                 250                 255

Phe Asp Leu Met Ala Lys Thr Pro Tyr Ile Ala Arg His Lys Gly Thr
            260                 265                 270

Pro Leu Leu Gln Gln Ile Glu Thr Ala Leu Leu Gln Arg Asp Ala
        275                 280                 285

Gln Gly Gln Lys Leu Pro Leu Ser Pro Gln Thr Lys Val Leu Phe Leu
    290                 295                 300

Gly Gly His Asp Thr Asn Ile Ala Asn Ile Ala Gly Met Leu Gly Ala
305                 310                 315                 320

Asn Trp Gln Leu Pro Gln Gln Pro Asp Asn Thr Pro Gly Gly Gly
                325                 330                 335

Leu Val Phe Glu Leu Trp Gln Asn Pro Asp Asn His Gln Arg Tyr Val
            340                 345                 350

Ala Val Lys Met Phe Tyr Gln Thr Met Asp Gln Leu Arg Arg Ala Glu
        355                 360                 365
```

```
Lys Leu Asp Leu Lys Asn Asn Pro Ala Gly Ile Val Pro Ile Thr Val
    370                 375                 380
Glu Glu Cys Glu Asn Thr Gly Asp Asn Lys Leu Cys Gln Leu Glu Thr
385                 390                 395                 400
Phe Gln Lys Lys Val Ala Lys Met Ile Glu Pro Ala Cys His Ile
                405                 410                 415

<210> SEQ ID NO 48
<211> LENGTH: 415
<212> TYPE: PRT
<213> ORGANISM: Yersinia kristensenii

<400> SEQUENCE: 48

Leu Ala Ala Gln Ser Thr Gly Tyr Thr Leu Glu Arg Val Val Ile Leu
1               5                   10                  15
Ser Arg His Gly Val Arg Ser Pro Thr Lys Gln Thr Gln Leu Met Asn
                20                  25                  30
Asp Val Thr Pro Asp Lys Trp Pro Gln Trp Pro Val Lys Ala Gly Tyr
            35                  40                  45
Leu Thr Pro Arg Gly Ala Gly Leu Val Thr Leu Met Gly Gly Phe Tyr
        50                  55                  60
Gly Asp Tyr Phe Arg Ser Tyr Gly Leu Leu Pro Ala Gly Cys Pro Ala
65                  70                  75                  80
Asp Glu Ser Ile Tyr Val Gln Ala Asp Val Asp Gln Arg Thr Arg Leu
                85                  90                  95
Thr Gly Gln Ala Phe Leu Asp Gly Ile Ala Pro Asp Cys Gly Leu Lys
            100                 105                 110
Val His Tyr Gln Ala Asp Leu Lys Lys Ile Asp Pro Leu Phe His Thr
        115                 120                 125
Val Glu Ala Gly Val Cys Lys Leu Asp Pro Glu Lys Thr His Gln Ala
    130                 135                 140
Val Glu Lys Arg Leu Gly Gly Pro Leu Asn Glu Leu Ser Gln Arg Tyr
145                 150                 155                 160
Ala Lys Pro Phe Ala Leu Met Gly Glu Val Leu Asn Phe Ser Ala Ser
                165                 170                 175
Pro Tyr Cys Asn Ser Leu Gln Gln Lys Gly Lys Thr Cys Asp Phe Ala
            180                 185                 190
Thr Phe Ala Ala Asn Glu Ile Glu Val Asn Lys Glu Gly Thr Lys Val
        195                 200                 205
Ser Leu Ser Gly Pro Leu Ala Leu Ser Ser Thr Leu Gly Glu Ile Phe
    210                 215                 220
Leu Leu Gln Asn Ser Gln Ala Met Pro Asp Val Ala Trp Asn Arg Leu
225                 230                 235                 240
Ser Gly Glu Glu Asn Trp Ile Ser Leu Leu Ser Leu His Asn Ala Gln
                245                 250                 255
Phe Asp Leu Met Ala Lys Thr Pro Tyr Ile Ala Arg His Lys Gly Thr
            260                 265                 270
Pro Leu Leu Gln Gln Ile Asp Thr Ala Leu Val Leu Gln Arg Asp Ala
        275                 280                 285
Gln Gly Gln Thr Leu Pro Leu Ser Pro Gln Thr Lys Leu Leu Phe Leu
    290                 295                 300
Gly Gly His Asp Thr Asn Ile Ala Asn Ile Ala Gly Met Leu Gly Ala
305                 310                 315                 320
Asn Trp Gln Leu Pro Gln Gln Pro Asp Asn Thr Pro Pro Gly Gly Gly
                325                 330                 335
```

Leu Val Phe Glu Leu Trp Gln Asn Pro Asp Asn His Gln Arg Tyr Val
                340                 345                 350

Ala Val Lys Met Phe Tyr Gln Thr Met Glu Gln Leu Arg Asn Ala Asp
                355                 360                 365

Lys Leu Asp Leu Lys Asn Asn Pro Ala Arg Ile Val Pro Ile Ala Ile
370                 375                 380

Glu Gly Cys Glu Asn Glu Gly Asp Asn Lys Leu Cys Gln Leu Glu Thr
385                 390                 395                 400

Phe Gln Lys Lys Val Ala Gln Val Ile Glu Pro Thr Cys His Ile
                405                 410                 415

<210> SEQ ID NO 49
<211> LENGTH: 415
<212> TYPE: PRT
<213> ORGANISM: Yersinia mollaretii

<400> SEQUENCE: 49

Val Ala Ala Pro Ala Ala Gly Tyr Thr Leu Glu Arg Val Val Ile Leu
1               5                   10                  15

Ser Arg His Gly Val Arg Ser Pro Thr Lys Gln Thr Gln Leu Met Asn
                20                  25                  30

Asp Val Thr Pro Asp Lys Trp Pro Gln Trp Pro Val Gln Ala Gly Tyr
                35                  40                  45

Leu Thr Pro Arg Gly Ala Gln Leu Val Thr Leu Met Gly Gly Phe Tyr
            50                  55                  60

Gly Asp Tyr Phe Arg Ser Gln Gly Leu Leu Pro Thr Gly Cys Pro Ala
65              70                  75                  80

Asp Gly Thr Leu Tyr Ala Gln Ala Asp Ile Asp Gln Arg Thr Arg Leu
                85                  90                  95

Thr Gly Gln Ala Phe Leu Asp Gly Ile Ala Pro Gly Cys Asp Leu Lys
            100                 105                 110

Val His Tyr Gln Ala Asp Leu Lys Lys Val Asp Pro Leu Phe His Pro
            115                 120                 125

Val Glu Ala Gly Val Cys Gln Leu Asp Ser Ala Gln Thr His Gln Ala
130                 135                 140

Ile Glu Ala Arg Leu Gly Ala Pro Leu Ser Glu Leu Ser Gln Arg Tyr
145                 150                 155                 160

Ala Lys Pro Phe Ala Gln Met Gly Glu Ile Leu Asn Phe Ala Ala Ser
                165                 170                 175

Pro Tyr Cys Lys Ser Leu Gln Gln Gln Gly Lys Ser Cys Asp Phe Ala
            180                 185                 190

Thr Phe Ala Ala Asn Glu Val Lys Val Asn Gln Gln Gly Thr Lys Val
            195                 200                 205

Ser Leu Ser Gly Pro Leu Ala Leu Ser Ser Thr Leu Gly Glu Ile Phe
210                 215                 220

Leu Leu Gln Asn Ser Gln Gly Met Pro Asp Val Ala Trp His Arg Leu
225                 230                 235                 240

Ser Gly Ala Glu Asn Trp Val Ser Leu Leu Ser Leu His Asn Ala Gln
                245                 250                 255

Phe Asp Leu Met Ala Lys Thr Pro Tyr Ile Ala Arg His Lys Gly Thr
                260                 265                 270

Pro Leu Leu Gln Gln Ile Met Thr Ala Leu Val Leu Gln Arg Lys Gly
            275                 280                 285

Gln Gly Gln Thr Leu Pro Leu Ser Glu Gln Thr Lys Leu Leu Phe Leu

```
                290                 295                 300
Gly Gly His Asp Thr Asn Ile Ala Asn Ile Gly Gly Met Leu Gly Ala
305                 310                 315                 320

Asn Trp Gln Leu Pro Gln Gln Pro Asp Asn Thr Pro Gly Gly Gly
                325                 330                 335

Leu Val Phe Glu Leu Trp Gln Asn Pro Asp Asn His Gln Gln Tyr Val
                340                 345                 350

Ala Val Lys Met Phe Tyr Gln Thr Met Asp Gln Leu Arg Asn Ser Glu
                355                 360                 365

Lys Leu Asp Leu Lys Ser His Pro Ala Gly Ile Val Pro Ile Glu Ile
                370                 375                 380

Glu Ser Cys Glu Asn Ile Gly Thr Asp Lys Leu Cys Gln Leu Asp Thr
385                 390                 395                 400

Phe Gln Lys Arg Val Ala Gln Val Ile Glu Pro Ala Cys His Ile
                405                 410                 415

<210> SEQ ID NO 50
<211> LENGTH: 415
<212> TYPE: PRT
<213> ORGANISM: Yersinia rohdei

<400> SEQUENCE: 50

Val Ile Thr Ala Pro Ala Gly Tyr Thr Leu Glu Arg Val Val Ile Leu
1               5                   10                  15

Ser Arg His Gly Val Arg Ser Pro Thr Lys Gln Thr Gln Leu Met Asn
                20                  25                  30

Glu Val Thr Pro Asp Lys Trp Pro Gln Trp Pro Val Lys Ala Gly Tyr
                35                  40                  45

Phe Asp Leu Met Ala Lys Thr Pro Tyr Ile Ala Arg His Lys Gly Thr
            260                 265                 270

Pro Leu Leu Gln Gln Ile Asn Thr Ala Leu Val Leu Gln Arg Asp Ala
        275                 280                 285

Gln Gly Gln Thr Leu Pro Leu Ser Pro Gln Thr Lys Val Leu Phe Leu
    290                 295                 300

Gly Gly His Asp Thr Asn Ile Ala Asn Ile Ala Gly Met Leu Gly Ala
305                 310                 315                 320

Asn Trp Gln Leu Pro Gln Gln Pro Asp Asn Thr Pro Pro Gly Gly Gly
                325                 330                 335

Leu Val Phe Glu Leu Trp Gln His Pro Asp Asn His Gln Arg Tyr Val
        340                 345                 350

Ala Val Lys Met Phe Tyr Gln Thr Met Asp Gln Leu Arg Asn Val Glu
    355                 360                 365

Lys Leu Asn Leu Thr Thr Asn Pro Ala Gly Ile Ile Pro Ile Ala Val
370                 375                 380

Glu Gly Cys Glu Asn Met Gly Asp Asp Lys Leu Cys Gln Leu Glu Thr
385                 390                 395                 400

Phe Glu Lys Lys Ile Ala Gln Val Ile Glu Pro Ala Cys His Ile
                405                 410                 415

<210> SEQ ID NO 51
<211> LENGTH: 410
<212> TYPE: PRT
<213> ORGANISM: Escherichia coli

<400> SEQUENCE: 51

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
            245                 250                 255

Leu Gln Arg Thr Pro Glu Val Ala Arg Ser Arg Ala Thr Pro Leu Leu
        260                 265                 270

Asp Leu Ile Lys Thr Ala Leu Thr Pro His Pro Pro Gln Lys Gln Ala
    275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 52
<211> LENGTH: 413
<212> TYPE: PRT
<213> ORGANISM: unknown
<220> FEATURE:
<223> OTHER INFORMATION: US8101391-0002

<400> SEQUENCE: 52

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Arg Leu Gln Gln
    130                 135                 140

Ala Val Glu Lys Glu Ala Gln Thr Pro Ile Glu Asn Leu Asn Gln His
145                 150                 155                 160

Tyr Ile Pro Ser Leu Ala Leu Met Asn Thr Thr Leu Asn Phe Ser Thr
                165                 170                 175

```
Ser Ala Trp Cys Gln Lys His Ser Ala Asp Lys Ser Cys Asp Leu Ala
            180                 185                 190
Gln Ser Met Pro Ser Lys Leu Ser Ile Lys Asp Asn Gly Asn Lys Val
        195                 200                 205
Ala Leu Asp Gly Ala Val Gly Leu Ser Ser Thr Leu Ala Glu Ile Phe
210                 215                 220
Leu Leu Glu Tyr Ala Gln Gly Met Pro Gln Ala Ala Trp Gly Lys Ile
225                 230                 235                 240
His Ser Glu Gln Asp Trp Ala Glu Leu Leu Lys Leu His Asn Ala Gln
                245                 250                 255
Phe Asp Leu Met Ala Arg Thr Pro Tyr Ile Ala Arg His Asn Gly Thr
            260                 265                 270
Pro Leu Leu Gln Ala Ile Ser Asn Ala Leu Asp Pro Asn Ala Thr Ala
        275                 280                 285
Ser Lys Leu Pro Asp Ile Ser Pro Asp Asn Lys Ile Leu Phe Ile Ala
    290                 295                 300
Gly His Asp Thr Asn Ile Ala Asn Ile Ser Gly Met Leu Asn Met Arg
305                 310                 315                 320
Trp Thr Leu Pro Gly Gln Pro Asp Asn Thr Pro Pro Gly Gly Ala Leu
                325                 330                 335
Ile Phe Glu Arg Leu Ala Asp Lys Ala Gly Lys Gln Tyr Val Ser Val
            340                 345                 350
Ser Met Val Tyr Gln Thr Leu Glu Gln Leu Arg Ala Gln Thr Pro Leu
        355                 360                 365
Ser Leu Lys Glu Pro Ala Gly Ser Val Gln Leu Lys Ile Pro Gly Cys
    370                 375                 380
Asn Asp Gln Thr Ala Glu Gly Tyr Cys Pro Leu Pro Thr Phe Lys Arg
385                 390                 395                 400
Val Val Ser Gln Ser Glu Glu Pro Gly Cys Gln Leu Gln
                405                 410

<210> SEQ ID NO 53
<211> LENGTH: 413
<212> TYPE: PRT
<213> ORGANISM: unknown
<220> FEATURE:
<223> OTHER INFORMATION: US8101391-0004

<400> SEQUENCE: 53

Ser Asp Thr Pro Ala Ser Gly Tyr Gln Ile Glu Lys Val Val Ile Leu
1               5                   10                  15
Ser Arg His Gly Val Arg Ala Pro Thr Lys Met Thr Gln Thr Met Arg
            20                  25                  30
Asp Val Thr Pro Asn Ser Trp Pro Glu Trp Pro Val Lys Leu Gly Tyr
        35                  40                  45
Ile Thr Pro Arg Gly Glu His Leu Ile Ser Leu Met Gly Gly Phe Tyr
    50                  55                  60
Arg Gln Lys Phe Gln Gln Lys Gly Ile Leu Ser Gln Gly Ser Cys Pro
65                  70                  75                  80
Thr Pro Asn Ser Ile Tyr Val Trp Ala Asp Val Asp Gln Arg Thr Leu
                85                  90                  95
Lys Thr Gly Glu Ala Phe Leu Ala Gly Leu Ala Pro Gln Cys Gly Leu
            100                 105                 110
Thr Ile His His Gln Gln Asn Leu Glu Lys Ala Asp Pro Leu Phe His
        115                 120                 125
```

Pro Val Lys Ala Gly Thr Cys Ser Met Asp Lys Thr Gln Val Gln Gln
    130                 135                 140

Ala Val Glu Lys Glu Ala Gln Met Pro Ile Glu Asn Leu Asn Gln His
145                 150                 155                 160

Tyr Ile Pro Ser Leu Ala Leu Met Asn Thr Thr Leu Asn Phe Ser Thr
                165                 170                 175

Ser Ala Trp Cys Gln Lys His Ser Ala Asp Lys Ser Cys Asp Leu Ala
            180                 185                 190

Gln Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Thr Gln
                245                 250                 255

Phe Asp Leu Met Ala Arg Thr Pro Tyr Ile Ala Ala His Asn Gly Thr
            260                 265                 270

Pro Leu Leu Gln Thr Ile Ser Asn Ala Leu Glu Pro Lys Ala Asp Val
        275                 280                 285

Ser Lys Leu Pro Asp Ile Ser Ser Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Ile Ser Val
            340                 345                 350

Ser Met Val Tyr Gln Thr Leu Glu Gln Leu Arg Ala Gln Thr Pro Leu
        355                 360                 365

Ser Leu Asn Glu Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Pro
                405                 410

<210> SEQ ID NO 54
<211> LENGTH: 413
<212> TYPE: PRT
<213> ORGANISM: Pyrococcus yayanosi

<400> SEQUENCE: 54

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu

```
            85                  90                  95
Lys Thr Gly Glu Ala Phe Leu Ala Gly Leu Ala Pro Glu Cys His Leu
            100                 105                 110

Thr Ile His His Gln Gln Asp Ile Lys Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Lys
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 55
<211> LENGTH: 411
<212> TYPE: PRT
<213> ORGANISM: Obesumbacterium proteus

<400> SEQUENCE: 55

Ser Glu Thr Glu Pro Ser Gly Tyr Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Ala Trp Pro Glu Trp Pro Val Lys Leu Gly Tyr
        35                  40                  45
```

```
Ile Thr Pro Arg Gly Glu His Leu Val Ser Leu Met Gly Gly Phe Tyr
 50                  55                  60

Arg Gln Lys Phe Gln Gln Leu Gly Ile Leu Ser Lys Gly Arg Cys Pro
 65                  70                  75                  80

Thr Ala Asn Asp Val Tyr Val Trp Ala Asp Val Asp Gln Arg Thr Arg
                     85                  90                  95

Lys Thr Gly Glu Ala Phe Leu Ala Gly Leu Ala Pro Glu Cys His Leu
                100                 105                 110

Ser Ile His His Gln Gln Asp Ile Lys Gln Ala Asp Pro Leu Phe His
                115                 120                 125

Pro Val Lys Ala Gly Val Cys Thr Met Glu Lys Thr Gln Val Gln Gln
130                 135                 140

Ala Val Glu Gln Gln Ala Gly Met Pro Ile Asp Gln Leu Asn Gln His
145                 150                 155                 160

Tyr Arg Pro Ala Leu Ala Leu Met Ser Ser Val Leu Asn Phe Pro Lys
                165                 170                 175

Ser Thr Tyr Cys Gln Gln His Ser Ala Asp Gln Thr Cys Asp Leu Ala
                180                 185                 190

Gln Ala Met Pro Ser Lys Leu Ser Ile Lys Asp Asn Gly Asn Lys Val
                195                 200                 205

Ala Leu Asp Gly Ala Val Gly Leu Ser Ser Thr Leu Ala Glu Ile Phe
210                 215                 220

Leu Leu Glu Tyr Ala Gln Gly Met Pro Asp Ala Ala Trp Gly Lys Ile
225                 230                 235                 240

His Ser Glu Gln Asp Trp Asn Ala Leu Leu Thr Leu His Asn Ala Gln
                245                 250                 255

Phe Asp Leu Met Ser Arg Thr Pro Tyr Ile Ala Lys His Asn Gly Thr
                260                 265                 270

Pro Leu Leu Gln Thr Ile Val Ser Ala Ile Asn Ser Gln Pro Ser Ser
                275                 280                 285

Arg Glu Leu Pro Glu Leu Ser Ala Asp Asn Lys Ile Leu Phe Pro Ala
                290                 295                 300

Gly His Asp Thr Asn Ile Ala Asn Ile Ala Gly Met Phe Gly Met Ser
305                 310                 315                 320

Trp Ala Leu Pro Gly Gln Pro Asp Asn Thr Pro Pro Gly Gly Ala Leu
                325                 330                 335

Val Phe Glu Arg Trp Ser Asp Lys Thr Gly Lys Lys Tyr Val Ser Val
                340                 345                 350

Gln Met Met Tyr Gln Thr Leu Ala Gln Leu Arg Asn Gln Thr Pro Leu
                355                 360                 365

Thr Leu Asp Lys Pro Ala Gly Ser Val Ala Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Ala Lys Gln Asn Glu Leu Val Glu Cys Gln
                405                 410

<210> SEQ ID NO 56
<211> LENGTH: 413
<212> TYPE: PRT
<213> ORGANISM: unknown
<220> FEATURE:
<223> OTHER INFORMATION: US8143046-0001

<400> SEQUENCE: 56
```

```
Asn Asp Thr Pro Ala Ser Gly Tyr Gln Val Glu Lys Val Val Ile Leu
 1               5                  10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Ser Gln Gly Ser Cys Pro
 65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Glu Cys His Leu
                100                 105                 110

Thr Ile His His Gln Gln Asp Ile Lys Lys Ala Asp Pro Leu Phe His
            115                 120                 125

Pro Val Lys Ala Gly Thr Cys Ser Met Asp Lys Thr Gln Val Gln Gln
        130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
            195                 200                 205

Ala Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
                260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
            290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

```
<210> SEQ ID NO 57
<211> LENGTH: 413
<212> TYPE: PRT
<213> ORGANISM: unknown
<220> FEATURE:
<223> OTHER INFORMATION: US8143046-0003US8143046-0003

<400> SEQUENCE: 57
```

| | | | | | | | | | | | | | | | |
|---|---|---|---|---|---|---|---|---|---|---|---|---|---|---|---|
| Asn | Asp | Thr | Pro | Ala | Ser | Gly | Tyr | Gln | Val | Glu | Lys | Val | Val | Ile | Leu |
| 1 | | | | 5 | | | | | 10 | | | | | 15 | |
| Ser | Arg | His | Gly | Val | Arg | Ala | Pro | Thr | Lys | Met | Thr | Gln | Thr | Met | Arg |
| | | | 20 | | | | | 25 | | | | | 30 | | |
| Asp | Val | Thr | Pro | Asn | Thr | Trp | Pro | Glu | Trp | Pro | Val | Lys | Leu | Gly | Tyr |
| | | | 35 | | | | 40 | | | | | 45 | | | |
| Ile | Thr | Pro | Arg | Gly | Glu | His | Leu | Ile | Ser | Leu | Met | Gly | Gly | Phe | Tyr |
| | 50 | | | | | 55 | | | | | 60 | | | | |
| Arg | Gln | Lys | Phe | Gln | Gln | Gln | Gly | Ile | Leu | Ser | Gln | Gly | Ser | Cys | Pro |
| 65 | | | | | 70 | | | | | 75 | | | | | 80 |
| Thr | Pro | Asn | Ser | Ile | Tyr | Val | Trp | Thr | Asp | Val | Ala | Gln | Arg | Thr | Leu |
| | | | | 85 | | | | | 90 | | | | | 95 | |
| Lys | Thr | Gly | Glu | Ala | Phe | Leu | Ala | Gly | Leu | Ala | Pro | Gln | Cys | Gly | Leu |
| | | | 100 | | | | | 105 | | | | | 110 | | |
| Thr | Ile | His | His | Gln | Gln | Asn | Leu | Glu | Lys | Ala | Asp | Pro | Leu | Phe | His |
| | | | 115 | | | | | 120 | | | | | 125 | | |
| Pro | Val | Lys | Ala | Gly | Ile | Cys | Ser | Met | Asp | Lys | Thr | Gln | Val | Gln | Gln |
| | | | 130 | | | | 135 | | | | | 140 | | | |
| Ala | Val | Glu | Lys | Glu | Ala | Gln | Thr | Pro | Ile | Asp | Asn | Leu | Asn | Gln | His |
| 145 | | | | | 150 | | | | | 155 | | | | | 160 |
| Tyr | Ile | Pro | Ser | Leu | Ala | Leu | Met | Asn | Thr | Thr | Leu | Asn | Phe | Ser | Lys |
| | | | | 165 | | | | | 170 | | | | | 175 | |
| Ser | Pro | Trp | Cys | Gln | Lys | His | Ser | Ala | Asp | Lys | Ser | Cys | Asp | Leu | Gly |
| | | | 180 | | | | | 185 | | | | | 190 | | |
| Leu | Ser | Met | Pro | Ser | Lys | Leu | Ser | Ile | Lys | Asp | Asn | Gly | Asn | Glu | Val |
| | | | 195 | | | | | 200 | | | | | 205 | | |
| Ser | Leu | Asp | Gly | Ala | Ile | Gly | Leu | Ser | Ser | Thr | Leu | Ala | Glu | Ile | Phe |
| 210 | | | | | 215 | | | | | 220 | | | | | |
| Leu | Leu | Glu | Tyr | Ala | Gln | Gly | Met | Pro | Gln | Ala | Ala | Trp | Gly | Asn | Ile |
| 225 | | | | | 230 | | | | | 235 | | | | | 240 |
| His | Ser | Glu | Gln | Glu | Trp | Ala | Leu | Leu | Lys | Leu | His | Asn | Val | Tyr | |
| | | | | 245 | | | | | 250 | | | | | 255 | |
| Phe | Asp | Leu | Met | Glu | Arg | Thr | Pro | Tyr | Ile | Ala | Arg | His | Lys | Gly | Thr |
| | | | 260 | | | | | 265 | | | | | 270 | | |
| Pro | Leu | Leu | Gln | Ala | Ile | Ser | Asn | Ala | Leu | Asn | Pro | Asn | Ala | Thr | Glu |
| | | | 275 | | | | | 280 | | | | | 285 | | |
| Ser | Lys | Leu | Pro | Asp | Ile | Ser | Pro | Asp | Asn | Lys | Ile | Leu | Phe | Ile | Ala |
| | 290 | | | | | 295 | | | | | 300 | | | | |
| Gly | His | Asp | Thr | Asn | Ile | Ala | Asn | Ile | Ala | Gly | Met | Leu | Asn | Met | Arg |
| 305 | | | | | 310 | | | | | 315 | | | | | 320 |
| Trp | Thr | Leu | Pro | Gly | Gln | Pro | Asp | Asn | Thr | Pro | Pro | Gly | Gly | Ala | Leu |
| | | | | 325 | | | | | 330 | | | | | 335 | |
| Val | Phe | Glu | Arg | Leu | Ala | Asp | Lys | Ser | Gly | Lys | Gln | Tyr | Val | Ser | Val |
| | | | 340 | | | | | 345 | | | | | 350 | | |
| Ser | Met | Val | Tyr | Gln | Thr | Leu | Glu | Gln | Leu | Arg | Ser | Gln | Thr | Pro | Leu |
| | | | | 355 | | | | | 360 | | | | | 365 | |
| Ser | Leu | Asn | Gln | Pro | Ala | Gly | Ser | Val | Gln | Leu | Lys | Ile | Pro | Gly | Cys |

-continued

```
            370             375             380
Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 58
<211> LENGTH: 411
<212> TYPE: PRT
<213> ORGANISM: Citrobacter braakii

<400> SEQUENCE: 58

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asn Val
                20                  25                  30

Thr Pro Asp Gln Trp Pro Gln Trp Asp Val Pro Leu Gly Trp Leu Thr
                35                  40                  45

Pro Arg Gly Gly Glu Leu Val Ser Glu Leu Gly Gln Tyr Gln Arg Leu
50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
                115                 120                 125

Lys Met Gly Lys Cys Ser Phe Asn Thr Leu Gln Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
                180                 185                 190

Leu Pro Ser Glu Leu Lys Val Thr Pro Asp Asn Val Ser Leu Pro Gly
                195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
                260                 265                 270

Met Ile Asp Thr Ala Leu Leu Thr Asn Gly Thr Thr Glu Asn Arg Tyr
                275                 280                 285

Gly Ile Lys Leu Pro Val Ser Leu Leu Phe Ile Ala Gly His Asp Thr
                290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335
```

Trp Lys Arg Thr Ser Asp Asn Thr Asp Trp Val Gln Val Ser Phe Val
                340                 345                 350

Tyr Gln Thr Leu Arg Asp Met Arg Asp Ile Gln Pro Leu Ser Leu Glu
            355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 59
<211> LENGTH: 413
<212> TYPE: PRT
<213> ORGANISM: unknown
<220> FEATURE:
<223> OTHER INFORMATION: US8557555-0013

<400> SEQUENCE: 59

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asn Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ser Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Ala Ser
        275                 280                 285

```
Arg Pro Leu Pro Asp Ile Ser Pro Asp Asn Lys Ile Leu Phe Ile Ala
    290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Ala Leu
                325                 330                 335

Val Phe Glu Arg Trp Val Asp Asn Ala Gly Lys Pro Tyr Val Ser Val
                340                 345                 350

Asn Met Val Tyr Gln Thr Leu Ala Gln Leu His Asp Gln Thr Pro Leu
                355                 360                 365

Thr Leu Gln His Pro Ala Gly Ser Val Arg Leu Asn Ile Pro Gly Cys
370                 375                 380

Ser Asp Gln Thr Pro Asp Gly Tyr Cys Pro Leu Ser Thr Phe Ser Arg
385                 390                 395                 400

Leu Val Asn His Ser Val Glu Pro Ala Cys Gln Leu Pro
                405                 410

<210> SEQ ID NO 60
<211> LENGTH: 414
<212> TYPE: PRT
<213> ORGANISM: unknown
<220> FEATURE:
<223> OTHER INFORMATION: US8557555-0024

<400> SEQUENCE: 60

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Thr Asp Val Asn Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Thr Gln Val Asp Pro Leu Phe His
        115                 120                 125

Pro Val Lys Ala Gly Ile Cys Ser Met Asn Lys Ser Gln Thr Tyr Glu
    130                 135                 140

Ala Val Glu Lys Gln Ala Gly Gly Pro Ile Glu Thr Leu Asn Gln Arg
145                 150                 155                 160

Tyr Gln Ala Glu Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Asn Ile Ser Asp Asp Gly Asn Glu Val
        195                 200                 205

Gln Leu Glu Gly Ala Val Gly Leu Gly Ser Thr Leu Ala Glu Ile Phe
    210                 215                 220

Leu Leu Glu Tyr Ala Gln Gly Met Pro Val Val Ala Trp Gly Asn Ile
225                 230                 235                 240
```

```
His Asn Glu Ser Gln Trp Lys Ser Leu Leu Asn Leu His Asn Ala His
                245                 250                 255

Phe Asn Leu Met His Arg Thr Pro Tyr Ile Ala Lys His Gln Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Gly Met Leu Gly Met Asn
305                 310                 315                 320

Trp Thr Leu Pro Gly Gln Pro Asp Asn Thr Pro Pro Gly Gly Leu
                325                 330                 335

Val Phe Glu Leu Trp Gln Asn Pro Asp Asn His Gln Gln Tyr Val Ala
            340                 345                 350

Val Lys Met Ile Tyr Gln Thr Met Asp Gln Leu Arg Asn Ser Glu Lys
        355                 360                 365

Leu Asp Leu Lys Ser Asn Pro Ala Gly Ile Val Pro Ile Glu Ile Glu
370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys Gln Ile
                405                 410

<210> SEQ ID NO 61
<211> LENGTH: 411
<212> TYPE: PRT
<213> ORGANISM: E. coli K12

<400> SEQUENCE: 61

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Glu Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Arg Arg Ala Gly Gly Ser Ile Ala Asp Phe Thr His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asp Val Ser Leu
        195                 200                 205
```

Thr Gly Ala Val Ser Leu Ala Ser Met Leu Thr Glu Ile Phe Leu Leu
210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
            245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
            275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
                340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 62
<211> LENGTH: 413
<212> TYPE: PRT
<213> ORGANISM: unknown
<220> FEATURE:
<223> OTHER INFORMATION: WO2010034835-0001

<400> SEQUENCE: 62

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
    50                  55                  60

Arg Glu Arg Phe Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
                100                 105                 110

Ala Ile His His Gln Gln Asn Thr Gln Gln Ala Asp Pro Leu Phe His
            115                 120                 125

Pro Val Lys Ala Gly Ile Cys Ser Met Asp Lys Ser Gln Val His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ala Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asn Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Thr Ser
        275                 280                 285

Arg Pro Leu Pro Asp Ile Ser Pro Asp Asn Lys Ile Leu Phe Ile Ala
    290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Ala Leu
                325                 330                 335

Val Phe Glu Arg Trp Val Asp Asn Ala Gly Lys Pro Tyr Val Ser Val
            340                 345                 350

Asn Met Val Tyr Gln Thr Leu Ala Gln Leu His Asp Gln Ala Pro Leu
        355                 360                 365

Thr Leu Gln His Pro Ala Gly Ser Val Arg Leu Asn Ile Pro Gly Cys
    370                 375                 380

Ser Asp Gln Thr Pro Asp Gly Tyr Cys Pro Leu Ser Thr Phe Ser Arg
385                 390                 395                 400

Leu Val Ser His Ser Val Glu Pro Ala Cys Gln Leu Pro
                405                 410

<210> SEQ ID NO 63
<211> LENGTH: 20
<212> TYPE: PRT
<213> ORGANISM: T. reesei

<400> SEQUENCE: 63

Met Gln Thr Phe Gly Ala Phe Leu Val Ser Phe Leu Ala Ala Ser Gly
1               5                   10                  15

Leu Ala Ala Ala
            20

<210> SEQ ID NO 64
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 64

Ser Glu Ala Ala Pro Ala Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
                35                  40                  45

Ile Thr Pro Arg Gly Glu His Leu Val Ser Leu Met Gly Gly Phe Tyr
 50                  55                  60

Arg Gln Tyr Phe Gln Gln Gln Gly Leu Leu Ser Arg Asp Arg Cys Pro
 65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
                100                 105                 110

Thr Ile His His Gln Ser Asp Ile Lys Gln Val Asp Pro Leu Phe His
                115                 120                 125

Pro Leu Lys Ala Gly Ile Cys Ser Met Asp Lys Thr Gln Val Gln Gln
                130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Glu Lys Pro Cys Asp Phe Ala
                180                 185                 190

Asn Ala Phe Pro Ser Tyr Leu Asn Ile Ser Asp Asp Gly Asn Glu Val
                195                 200                 205

Gln Leu Glu Gly Ala Val Gly Leu Ser Ser Thr Leu Ala Glu Ile Phe
                210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Asn Gly Thr
                260                 265                 270

Pro Leu Leu Gln Thr Ile Val Asn Ala Leu Asn Ser Asn Thr Thr Ala
                275                 280                 285

Arg Glu Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Gln Thr Pro Leu
                355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 65
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 65

Ser Glu Ala Ala Pro Ala Gly Tyr His Leu Asp Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Ile Lys Leu Met Gly Gly Phe Tyr
    50                  55                  60

Arg Gln Tyr Phe Gln Gln Gln Gly Leu Leu Ser Lys Asp Arg Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asp Ile Lys Gln Val Asp Pro Leu Phe His
        115                 120                 125

Pro Val Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Val Asp Lys Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala His
                245                 250                 255

Phe Asp Leu Met Glu Arg Thr Pro Tyr Ile Ala Lys His Asn Gly Thr
            260                 265                 270

Pro Leu Met Gln Thr Ile Val Asn Ala Leu Asn Ser Asn Thr Thr Glu
        275                 280                 285

Arg Lys Leu Pro Asp Ile Ser Pro Asp Val Lys Ile Leu Phe Leu Ala
290                 295                 300

Gly His Asp Thr Asn Ile Ala Asn Ile Ala Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro

-continued

```
               405                 410

<210> SEQ ID NO 66
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 66

Ser Glu Ala Ala Pro Ala Gly Tyr His Leu Asp Lys Val Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Lys Asp Arg Cys Pro
65                  70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asp Ile Lys Gln Val Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Gln His Ser Gly Asp Lys Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala His
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Thr Thr Glu
        275                 280                 285

Ser Glu Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Asp Gly Thr Gln Tyr Val Ser Val
            340                 345                 350

Lys Met Val Tyr Gln Thr Leu Ala Gln Leu Arg Asn Met Thr Pro Leu
```

```
                    355                 360                 365
Thr Leu Lys Glu Pro Ala Gly Ser Val Pro Leu Lys Ile Pro Gly Cys
            370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 67
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 67

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
```

```
                305                 310                 315                 320
Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Met Thr Pro Leu
                355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 68
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 68

Ser Glu Thr Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
                35                  40                  45

Ile Thr Pro Arg Gly Glu His Leu Val Lys Leu Met Gly Gly Phe Tyr
        50                  55                  60

Arg Gln Tyr Phe Gln Gln Gly Leu Leu Ser Arg Asp Asn Cys Pro
65              70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
                100                 105                 110

Thr Ile His His Gln Ser Asp Ile Lys Gln Val Asp Pro Leu Phe His
            115                 120                 125

Pro Leu Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
                180                 185                 190

Gln Met Phe Pro Ser Tyr Leu Asn Ile Ser Asp Gly Asn Glu Val
            195                 200                 205

Gln Leu Glu Gly Ala Val Gly Leu Ser Ser Thr Leu Ala Glu Ile Phe
        210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
```

```
                260                 265                 270
Pro Leu Leu Gln Thr Ile Val Asn Ala Leu Asn Pro Asn Ala Thr Glu
            275                 280                 285

Ser Lys Leu Pro Asp Ile Ser Pro Asp Val Lys Ile Leu Phe Leu Ala
            290                 295                 300

Gly His Asp Thr Asn Ile Ala Asn Ile Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
            370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 69
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 69

Ser Glu Ala Ala Pro Ser Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
        50                  55                  60

Arg Gln Tyr Phe Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
```

```
                 210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                    245                 250                 255

Phe Asp Leu Met Glu Arg Thr Pro Tyr Ile Ala Lys His Asn Gly Thr
                260                 265                 270

Pro Leu Leu Gln Thr Ile Val Asn Ala Leu Asn Pro Asn Ala Thr Glu
            275                 280                 285

Ser Lys Leu Pro Asp Ile Ser Pro Asp Val Lys Ile Leu Phe Leu Ala
        290                 295                 300

Gly His Asp Thr Asn Ile Ala Asn Ile Gly Gly Met Leu Gly Met Asp
305                 310                 315                 320

Trp Thr Leu Pro Gly Gln Pro Asn Thr Pro Pro Gly Gly Ala Leu
                    325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                    405                 410
```

<210> SEQ ID NO 70
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 70

```
Ser Glu Ala Ala Pro Ser Gly Tyr His Leu Asp Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
                35                  40                  45

Ile Thr Pro Arg Gly Glu His Leu Val Ser Leu Met Gly Gly Phe Tyr
            50                  55                  60

Arg Gln Tyr Phe Gln Gln Gln Gly Leu Leu Ser Arg Asp Arg Cys Pro
65              70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
```

```
                165                 170                 175
Ser Pro Tyr Cys Arg Gln His Ser Val Glu Gln Pro Cys Asp Phe Ala
            180                 185                 190

Asn Ala Phe Pro Ser Tyr Leu Asn Ile Ser Asp Asp Gly Asn Glu Val
            195                 200                 205

Gln Leu Glu Gly Ala Val Gly Leu Ser Ser Thr Leu Ala Glu Ile Phe
            210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Gln
            245                 250                 255

Phe Asp Leu Met Glu Arg Thr Pro Tyr Ile Ala Lys His Gln Gly Thr
            260                 265                 270

Pro Leu Leu Gln Thr Ile Val Asn Ala Leu Asn Ser Asn Thr Thr Glu
            275                 280                 285

Ser Lys Leu Pro Asp Ile Ser Pro Ser Val Lys Ile Leu Phe Leu Ala
            290                 295                 300

Gly His Asp Thr Asn Ile Ala Asn Ile Gly Gly Met Leu Gly Met Thr
305                 310                 315                 320

Trp Thr Leu Pro Gly Gln Pro Asp Asn Thr Pro Pro Gly Gly Ala Leu
            325                 330                 335

Val Phe Glu Leu Trp Ser Asp Lys Asp Gly Thr Gln Tyr Val Ser Val
            340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
            370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
            405                 410

<210> SEQ ID NO 71
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 71

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
            50                  55                  60

Arg Gln Tyr Phe Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
            85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
```

115                 120                 125
Pro Leu Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Asp Gln Pro Cys Asp Phe Ala
            180                 185                 190

Gln Met Phe Pro Ser Tyr Leu Asn Ile Ser Asp Gly Asn Glu Val
        195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 72
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 72

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Arg Asp Asn Cys Pro

```
            65                  70                  75                  80
Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Ala
        275                 280                 285

Ser Lys Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 73
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 73

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
```

```
                20                  25                  30
Asp Val Thr Pro Tyr Thr Trp Pro Glu Trp Pro Val Pro Leu Gly Tyr
            35                  40                  45
Ile Thr Pro Arg Gly Glu His Leu Val Lys Leu Met Gly Gly Phe Tyr
        50                  55                  60
Arg Gln Tyr Phe Gln Gln Gln Gly Leu Leu Ser Arg Asp Asn Cys Pro
65                  70                  75                  80
Thr Pro Asp Asp Val Tyr Val Trp Thr Asp Val Asn Gln Arg Thr Arg
                85                  90                  95
Lys Thr Gly Glu Ala Phe Leu Ala Gly Leu Ala Pro Glu Cys Asp Leu
            100                 105                 110
Thr Ile His His Gln Ser Asp Ile Lys Gln Val Asp Pro Leu Phe His
        115                 120                 125
Pro Leu Lys Ala Gly Ile Cys Ser Met Asp Lys Thr Gln Val Gln Gln
        130                 135                 140
Ala Val Glu Lys Gln Ala Gly Met Pro Ile Asp Lys Leu Asn Gln His
145                 150                 155                 160
Tyr Arg Ala Glu Leu Ala Leu Met Ser Asn Val Leu Asn Phe Pro Lys
                165                 170                 175
Ser Pro Tyr Cys Gln Arg His Ser Gly Glu Gln Pro Cys Asp Phe Ala
            180                 185                 190
Gln Met Phe Pro Ser Tyr Leu Asn Ile Ser Asp Asp Gly Asn Glu Val
        195                 200                 205
Gln Leu Glu Gly Ala Val Gly Leu Ser Ser Thr Leu Ala Glu Ile Phe
    210                 215                 220
Leu Leu Glu Tyr Ala Gln Gly Met Pro Val Val Ala Trp Gly Asn Ile
225                 230                 235                 240
His Ser Glu Gln Glu Trp Asn Asp Leu Leu Lys Leu His Asn Ala Tyr
                245                 250                 255
Phe Asp Leu Met Glu Arg Thr Pro Tyr Ile Ala Lys His Asn Gly Thr
            260                 265                 270
Pro Leu Leu Gln Thr Ile Val Asn Ala Leu Asn Pro Asn Ala Thr Glu
        275                 280                 285
Ser Lys Leu Pro Asp Ile Ser Pro Asp Val Lys Ile Leu Phe Leu Ala
    290                 295                 300
Gly His Asp Thr Asn Ile Ala Asn Ile Gly Gly Met Leu Gly Met Asp
305                 310                 315                 320
Trp Thr Leu Pro Gly Gln Pro Asp Asn Thr Pro Gly Gly Ala Leu
                325                 330                 335
Leu Phe Glu Leu Trp Ser Asp Lys Ala Gly Thr Gln Tyr Val Ser Val
            340                 345                 350
Lys Met Val Tyr Gln Thr Leu Ala Gln Leu Arg Asn Met Thr Pro Leu
        355                 360                 365
Thr Leu Lys Glu Pro Ala Gly Ser Val Pro Leu Lys Ile Pro Gly Cys
    370                 375                 380
Asp Asp Gln Thr Ala Glu Gly Tyr Cys Pro Leu Asp Thr Phe Thr Arg
385                 390                 395                 400
Leu Val Asn Gln Val Val Glu Pro Ala Cys Gln Leu Pro
                405                 410

<210> SEQ ID NO 74
<211> LENGTH: 413
<212> TYPE: PRT
<213> ORGANISM: Artificial Sequence
```

<220> FEATURE:
<223> OTHER INFORMATION: Sequence is synthesized

<400> SEQUENCE: 74

Ser Glu Ala Ala Pro Ala Gly Tyr Gln Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 75
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 75

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

```
Lys Met Val Tyr Gln Thr Leu Ala Gln Leu Arg Asn Met Thr Pro Leu
                355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 76
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 76

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
        50                  55                  60

Arg Gln Tyr Phe Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Val Lys Ile Leu Phe Leu Ala
    290                 295                 300
```

```
Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
            325                 330                 335

Val Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
            370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 77
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 77

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Ile Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255
```

```
Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
            275                 280                 285

Ser Lys Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410
```

<210> SEQ ID NO 78
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 78

```
Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
        50                  55                  60

Arg Gln Tyr Phe Gln Gln Gln Gly Leu Leu Ser Arg Asp Ser Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205
```

```
Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
            245                 250                 255

Phe Asp Leu Met Glu Arg Thr Pro Tyr Ile Ala Lys His Asn Gly Thr
        260                 265                 270

Pro Leu Leu Gln Thr Ile Val Asn Ala Leu Asn Pro Asn Ala Thr Glu
    275                 280                 285

Ser Lys Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
            325                 330                 335

Leu Phe Glu Leu Trp Ser Asp Lys Glu Gly Thr Gln Tyr Val Ser Val
        340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 79
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 79

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Thr Gln Val Gln Gln
    130                 135                 140

Ala Val Glu Lys Gln Ala Gly Met Pro Ile Asp Lys Leu Asn Gln His
145                 150                 155                 160
```

```
Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Ser Asn Ala Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 80
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 80

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
        50                  55                  60

Arg Gln Tyr Phe Gln Gln Gln Gly Leu Leu Ser Arg Asp Asn Cys Pro
65                  70                  75                  80

Thr Pro Asp Asp Val Tyr Val Trp Asp Val Asn Gln Arg Thr Arg
                85                  90                  95

Lys Thr Gly Glu Ala Phe Leu Ala Gly Leu Ala Pro Glu Cys Asp Leu
            100                 105                 110
```

Thr Ile His His Gln Ser Asp Ile Lys Gln Val Asp Pro Leu Phe His
            115                 120                 125

Pro Leu Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Lys Pro Cys Asp Phe Ala
            180                 185                 190

Gln Met Phe Pro Ser Tyr Leu Asn Ile Ser Asp Gly Asn Glu Val
        195                 200                 205

Gln Leu Glu Gly Ala Val Gly Leu Ser Ser Thr Leu Ala Glu Ile Phe
        210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Val Lys Ile Leu Phe Leu Ala
        290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 81
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 81

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

```
Arg Gln Tyr Phe Gln Gln Gly Leu Leu Ser Arg Asp Asn Cys Pro
 65                  70                  75                  80

Thr Pro Asp Asp Val Tyr Val Trp Thr Asp Val Asn Gln Arg Thr Arg
                 85                  90                  95

Lys Thr Gly Glu Ala Phe Leu Ala Gly Leu Ala Pro Gly Cys Asp Leu
            100                 105                 110

Thr Ile His His Gln Ser Asp Ile Lys Gln Val Asp Pro Leu Phe His
            115                 120                 125

Pro Leu Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
            195                 200                 205

Ala Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
            275                 280                 285

Ser Lys Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
            370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 82
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 82

Ser Glu Ala Ala Pro Ala Gly Tyr His Leu Gln Lys Ala Val Ile Leu
1                5                  10                  15
```

Ser Arg His Gly Val Arg Ala Pro Thr Lys Met Thr Gln Leu Met Arg
              20                  25                  30

Asp Val Thr Pro Tyr Thr Trp Pro Glu Trp Pro Val Pro Leu Gly Tyr
              35                  40                  45

Ile Thr Pro Arg Gly Glu His Leu Val Lys Leu Met Gly Gly Phe Tyr
50                  55                  60

Arg Gln Tyr Phe Gln Gln Gly Leu Leu Ser Lys Asp Asn Cys Pro
65                  70                  75                  80

Thr Pro Asp Asp Val Tyr Val Trp Thr Asp Val Asn Gln Arg Thr Arg
              85                  90                  95

Lys Thr Gly Glu Ala Phe Leu Ala Gly Leu Ala Pro Glu Cys Asp Leu
              100                 105                 110

Thr Ile His His Gln Ser Asp Ile Lys Gln Val Asp Pro Leu Phe His
              115                 120                 125

Pro Leu Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
              165                 170                 175

Ser Pro Tyr Cys Gln Arg His Ser Gly Glu Gln Pro Cys Asp Phe Ala
              180                 185                 190

Gln Met Phe Pro Ser Tyr Leu Asn Ile Ser Asp Asp Gly Asn Glu Val
              195                 200                 205

Gln Leu Glu Gly Ala Val Gly Leu Ser Ser Thr Leu Ala Glu Ile Phe
              210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
              245                 250                 255

Phe Asp Leu Met Glu Arg Thr Pro Tyr Ile Ala Lys His Asn Gly Thr
              260                 265                 270

Pro Leu Leu Gln Thr Ile Val Asn Ala Leu Asn Pro Asn Ala Thr Glu
              275                 280                 285

Ser Lys Leu Pro Asp Ile Ser Pro Asp Val Lys Ile Leu Phe Leu Ala
              290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
              325                 330                 335

Leu Phe Glu Leu Trp Ser Asp Lys Glu Gly Thr Gln Tyr Val Ser Val
              340                 345                 350

Lys Met Val Tyr Gln Thr Leu Ala Gln Leu Arg Asn Met Thr Pro Leu
              355                 360                 365

Thr Leu Lys Glu Pro Ala Gly Ser Val Pro Leu Lys Ile Pro Gly Cys
              370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
              405                 410

<210> SEQ ID NO 83
<211> LENGTH: 413

```
<212> TYPE: PRT
<213> ORGANISM: Artificial Sequence
<220> FEATURE:
<223> OTHER INFORMATION: Sequence is synthesized

<400> SEQUENCE: 83

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Gln Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Gly Gly Ala Leu
                325                 330                 335

Leu Phe Glu Leu Trp Ser Asp Lys Glu Gly Thr Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
    370                 375                 380
```

```
Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
            405                 410

<210> SEQ ID NO 84
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 84

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Lys Leu Met Gly Gly Phe Tyr
        50                  55                  60

Arg Gln Tyr Phe Gln Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285

Arg Lys Leu Pro Asp Ile Ser Pro Asp Val Lys Ile Leu Phe Leu Ala
290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335
```

```
Leu Phe Glu Leu Trp Ser Asp Lys Glu Gly Thr Gln Tyr Val Ser Val
                340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 85
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 85

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gly Leu Leu Ser Arg Asp Asn Cys Pro
65                  70                  75                  80

Thr Pro Asp Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Ser Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190

Gln Met Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
                245                 250                 255

Phe Asp Leu Met Glu Arg Thr Pro Tyr Ile Ala Lys His Asn Gly Thr
            260                 265                 270

Pro Leu Leu Gln Thr Ile Val Asn Ala Leu Asn Pro Asn Ala Thr Glu
        275                 280                 285
```

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Glu Gly Lys Gln Tyr Val Ser Val
                340                 345                 350

Lys Met Val Tyr Gln Thr Leu Ala Gln Leu Arg Asn Met Thr Pro Leu
            355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 86
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 86

Ser Glu Ala Ala Pro Ser Gly Tyr His Leu Asp Lys Ala Val Ile Leu
1               5                   10                  15

Ser Arg His Gly Val Arg Ala Pro Thr Lys Met Thr Gln Leu Met Arg
                20                  25                  30

Asp Val Thr Pro Tyr Thr Trp Pro Glu Trp Pro Val Pro Leu Gly Tyr
            35                  40                  45

Ile Thr Pro Arg Gly Glu His Leu Val Ser Leu Met Gly Gly Phe Tyr
        50                  55                  60

Arg Gln Tyr Phe Gln Gln Gly Leu Leu Ser Arg Asp Arg Cys Pro
65              70                  75                  80

Thr Ala Asn Asp Val Tyr Val Trp Thr Asp Val Asn Gln Arg Thr Arg
                85                  90                  95

Lys Thr Gly Glu Ala Phe Leu Ala Gly Leu Ala Pro Glu Cys Asp Leu
            100                 105                 110

Thr Ile His His Gln Asn Asp Ile Lys Gln Val Asp Pro Leu Phe His
        115                 120                 125

Pro Leu Lys Ala Gly Ile Cys Ser Met Asp Lys Thr Gln Val Gln Gln
    130                 135                 140

Ala Val Glu Lys Gln Ala Gly Met Pro Ile Asp Lys Leu Asn Gln His
145                 150                 155                 160

Tyr Arg Pro Glu Leu Ala Leu Met Ser Asn Val Leu Asn Phe Pro Lys
                165                 170                 175

Ser Pro Tyr Cys Arg Gln His Ser Val Glu Gln Pro Cys Asp Phe Ala
            180                 185                 190

Asn Ala Phe Pro Ser Tyr Leu Asn Ile Ser Asp Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

```
His Ser Glu Gln Glu Trp Asn Asp Leu Leu Lys Leu His Asn Ala Gln
                245                 250                 255

Phe Asp Leu Met Glu Arg Thr Pro Tyr Ile Ala Lys His Gln Gly Thr
            260                 265                 270

Pro Leu Leu Gln Thr Ile Val Asn Ala Leu Asn Ser Asn Thr Thr Glu
        275                 280                 285

Ser Lys Leu Pro Asp Ile Ser Pro Ser Val Lys Ile Leu Phe Leu Ala
    290                 295                 300

Gly His Asp Thr Asn Ile Ala Asn Ile Gly Met Leu Gly Met Thr
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Asp Gly Lys Gln Tyr Val Ser Val
            340                 345                 350

Lys Met Val Tyr Gln Thr Leu Ala Gln Leu Arg Asn Met Thr Pro Leu
        355                 360                 365

Thr Leu Lys Glu Pro Ala Gly Ser Val Pro Leu Lys Ile Pro Gly Cys
    370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 87
<211> LENGTH: 413
<212> TYPE: PRT
<213> ORGANISM: Artificial Sequence
<220> FEATURE:
<223> OTHER INFORMATION: Sequence is synthesized

<400> SEQUENCE: 87

Ser Glu Ala Ala Pro Ala Gly Tyr His Leu Gln Lys Ala Val Ile Leu
1               5                   10                  15

Ser Arg His Gly Val Arg Ala Pro Thr Lys Met Thr Gln Leu Met Arg
            20                  25                  30

Asp Val Thr Pro Tyr Thr Trp Pro Glu Trp Pro Val Pro Leu Gly Tyr
        35                  40                  45

Ile Thr Pro Arg Gly Glu His Leu Val Lys Leu Met Gly Gly Phe Tyr
    50                  55                  60

Arg Gln Tyr Phe Gln Gln Gly Leu Leu Ser Arg Asp Asn Cys Pro
65              70                  75                  80

Thr Pro Asp Asp Val Tyr Val Trp Thr Asp Val Asn Gln Arg Thr Arg
            85                  90                  95

Lys Thr Gly Glu Ala Phe Leu Ala Gly Leu Ala Pro Glu Cys Asp Leu
        100                 105                 110

Thr Ile His His Gln Ser Asp Ile Lys Gln Ala Asp Pro Leu Phe His
    115                 120                 125

Pro Leu Lys Ala Gly Ile Cys Ser Met Asp Lys Thr Gln Val Gln Gln
        130                 135                 140

Ala Val Glu Lys Gln Ala Gly Met Pro Ile Asp Lys Leu Asn Gln His
145                 150                 155                 160

Tyr Arg Ala Glu Leu Ala Leu Met Ser Asn Val Leu Asn Phe Pro Lys
                165                 170                 175

Ser Pro Tyr Cys Gln Arg His Ser Gly Glu Gln Pro Cys Asp Phe Ala
            180                 185                 190
```

Gln Met Phe Pro Ser Tyr Leu Asn Ile Ser Asp Gly Asn Glu Val
        195                 200                 205

Gln Leu Glu Gly Ala Val Gly Leu Ser Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Ser Glu Gln Glu Trp Asn Asp Leu Leu Lys Leu His Asn Ala Tyr
            245                 250                 255

Phe Asp Leu Met Glu Arg Thr Pro Tyr Ile Ala Lys His Asn Gly Thr
                260                 265                 270

Pro Leu Leu Gln Thr Ile Val Asn Ala Leu Asn Pro Asn Ala Thr Glu
            275                 280                 285

Ser Lys Leu Pro Asp Ile Ser Pro Asp Val Lys Ile Leu Phe Leu Ala
    290                 295                 300

Gly His Asp Thr Asn Ile Ala Asn Ile Gly Gly Met Leu Gly Met Asp
305                 310                 315                 320

Trp Thr Leu Pro Gly Gln Pro Asp Asn Thr Pro Pro Gly Gly Ala Leu
                325                 330                 335

Leu Phe Glu Leu Trp Ser Asp Lys Gly Thr Gln Tyr Val Ser Val
            340                 345                 350

Lys Met Val Tyr Gln Thr Leu Ala Gln Leu Arg Asn Met Thr Pro Leu
    355                 360                 365

Thr Leu Lys Glu Pro Ala Gly Ser Val Pro Leu Lys Ile Pro Gly Cys
        370                 375                 380

Asp Asp Gln Thr Ala Glu Gly Tyr Cys Pro Leu Asp Thr Phe Thr Arg
385                 390                 395                 400

Leu Val Asn Gln Val Val Glu Pro Ala Cys Gln Leu Pro
                405                 410

<210> SEQ ID NO 88
<211> LENGTH: 13
<212> TYPE: PRT
<213> ORGANISM: Artificial Sequence
<220> FEATURE:
<223> OTHER INFORMATION: Sequence is synthesized

<400> SEQUENCE: 88

Asn Asp Thr Pro Ala Ser Gly Tyr Gln Val Glu Lys Val
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Sequence is synthesized

<400> SEQUENCE: 89

His Ala Glu Glu Gln Asn Gly Met Lys Leu Glu Arg Val
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Sequence is synthesized

<400> SEQUENCE: 90

Ser Ala Ala Glu Pro Ala Val Arg His Leu Glu Arg Val

<210> SEQ ID NO 91
<211> LENGTH: 13
<212> TYPE: PRT
<213> ORGANISM: Artificial Sequence
<220> FEATURE:
<223> OTHER INFORMATION: Sequence is synthesized

<400> SEQUENCE: 91

Ser Glu Ala Ala Pro Ala Gly Tyr His Leu Asp Lys Ala
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Sequence is synthesized

<400> SEQUENCE: 92

Ser Glu Ala Ala Pro Ala Gly Tyr His Leu Gln Lys Ala
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Sequence is synthesized

<400> SEQUENCE: 93

Ser Glu Ala Ala Pro Ser Gly Tyr His Leu Asp Lys Ala
1               5                   10

<210> SEQ ID NO 94
<211> LENGTH: 88
<212> TYPE: PRT
<213> ORGANISM: Artificial Sequence
<220> FEATURE:
<223> OTHER INFORMATION: Sequence is synthesized

<400> SEQUENCE: 94

Gln Pro Asp Asn Thr Pro Pro Gly Gly Ala Leu Val Phe Glu Arg Trp
1               5                   10                  15

Val Asp Asn Ala Gly Lys Pro Tyr Val Ser Val Asn Met Val Tyr Gln
                20                  25                  30

Thr Leu Ala Gln Leu His Asp Gln Ala Pro Leu Thr Leu Gln His Pro
            35                  40                  45

Ala Gly Ser Val Arg Leu Asn Ile Pro Gly Cys Ser Asp Gln Thr Pro
        50                  55                  60

Asp Gly Tyr Cys Pro Leu Ser Thr Phe Ser Arg Leu Val Ser His Ser
65                  70                  75                  80

Val Glu Pro Ala Cys Gln Leu Pro
                85

<210> SEQ ID NO 95
<211> LENGTH: 89
<212> TYPE: PRT
<213> ORGANISM: Artificial Sequence
<220> FEATURE:
<223> OTHER INFORMATION: Sequence is synthesized

<400> SEQUENCE: 95

Gln Pro Asp Asn Thr Pro Pro Gly Gly Gly Leu Val Phe Glu Leu Trp
1               5                   10                  15

Gln Asn Pro Asp Asn His Gln Gln Tyr Val Ala Val Lys Met Phe Tyr
            20                  25                  30

Gln Thr Met Asp Gln Leu Arg Asn Ser Glu Lys Leu Asp Leu Lys Ser
        35                  40                  45

His Pro Ala Gly Ile Val Pro Ile Glu Ile Glu Gly Cys Glu Asn Ile
    50                  55                  60

Gly Thr Asp Lys Leu Cys Gln Leu Asp Thr Phe Gln Lys Arg Val Ala
65                  70                  75                  80

Gln Val Ile Glu Pro Ala Cys His Ile
                85

<210> SEQ ID NO 96
<211> LENGTH: 88
<212> TYPE: PRT
<213> ORGANISM: Artificial Sequence
<220> FEATURE:
<223> OTHER INFORMATION: Sequence is synthesized

<400> SEQUENCE: 96

Gln Pro Asp Asn Thr Pro Pro Gly Gly Ala Leu Val Phe Glu Arg Leu
1               5                   10                  15

Ala Asp Lys Ser Gly Lys Gln Tyr Val Ser Val Ser Met Val Tyr Gln
            20                  25                  30

Thr Leu Glu Gln Leu Arg Ser Gln Thr Pro Leu Ser Leu Asn Gln Pro
        35                  40                  45

Ala Gly Ser Val Gln Leu Lys Ile Pro Gly Cys Asn Asp Gln Thr Ala
    50                  55                  60

Glu Gly Tyr Cys Pro Leu Ser Thr Phe Thr Arg Val Val Ser Gln Ser
65                  70                  75                  80

Val Glu Pro Gly Cys Gln Leu Gln
                85

<210> SEQ ID NO 97
<211> LENGTH: 88
<212> TYPE: PRT
<213> ORGANISM: Artificial Sequence
<220> FEATURE:
<223> OTHER INFORMATION: Sequence is synthesized

<400> SEQUENCE: 97

Gln Pro Asp Asn Thr Pro Pro Gly Gly Ala Leu Leu Phe Glu Leu Trp
1               5                   10                  15

Ser Asp Lys Glu Gly Thr Gln Tyr Val Ser Val Lys Met Val Tyr Gln
            20                  25                  30

Thr Leu Ala Gln Leu Arg Asn Gln Thr Pro Leu Thr Leu Lys Glu Pro
        35                  40                  45

Ala Gly Ser Val Pro Leu Lys Ile Pro Gly Cys Asp Asp Gln Thr Ala
    50                  55                  60

Glu Gly Tyr Cys Pro Leu Asp Thr Phe Thr Arg Leu Val Asn Gln Val
65                  70                  75                  80

Val Glu Pro Ala Cys Gln Leu Pro
                85

<210> SEQ ID NO 98
<211> LENGTH: 88
<212> TYPE: PRT
<213> ORGANISM: Artificial Sequence
<220> FEATURE:
<223> OTHER INFORMATION: Sequence is synthesized

<400> SEQUENCE: 98

```
Gln Pro Asp Asn Thr Pro Pro Gly Gly Ala Leu Leu Phe Glu Leu Trp
1               5                   10                  15

Ser Asp Lys Glu Gly Thr Gln Tyr Val Ser Val Lys Met Val Tyr Gln
            20                  25                  30

Thr Leu Ala Gln Leu Arg Asn Met Thr Pro Leu Thr Leu Lys Glu Pro
        35                  40                  45

Ala Gly Ser Val Pro Leu Lys Ile Pro Gly Cys Asp Asp Gln Thr Ala
    50                  55                  60

Glu Gly Tyr Cys Pro Leu Asp Thr Phe Thr Arg Leu Val Asn Gln Val
65                  70                  75                  80

Val Glu Pro Ala Cys Gln Leu Pro
                85
```

<210> SEQ ID NO 99
<211> LENGTH: 88
<212> TYPE: PRT
<213> ORGANISM: Artificial Sequence
<220> FEATURE:
<223> OTHER INFORMATION: Sequence is synthesized

<400> SEQUENCE: 99

```
Gln Pro Asp Asn Thr Pro Pro Gly Gly Ala Leu Leu Phe Glu Leu Trp
1               5                   10                  15

Ser Asp Lys Asp Gly Thr Gln Tyr Val Ser Val Lys Met Val Tyr Gln
            20                  25                  30

Thr Leu Ala Gln Leu Arg Asn Met Thr Pro Leu Thr Leu Lys Glu Pro
        35                  40                  45

Ala Gly Ser Val Pro Leu Lys Ile Pro Gly Cys Asp Asp Gln Thr Ala
    50                  55                  60

Glu Gly Tyr Cys Pro Leu Asp Thr Phe Thr Arg Leu Val Asn Gln Val
65                  70                  75                  80

Val Glu Pro Ala Cys Gln Leu Pro
                85
```

<210> SEQ ID NO 100
<211> LENGTH: 312
<212> TYPE: PRT
<213> ORGANISM: Artificial Sequence
<220> FEATURE:
<223> OTHER INFORMATION: Sequence is synthesized

<400> SEQUENCE: 100

```
Val Ile Leu Ser Arg His Gly Val Arg Ala Pro Thr Lys Met Thr Gln
1               5                   10                  15

Thr Met Arg Asp Val Thr Pro Tyr Thr Trp Pro Glu Trp Pro Val Pro
            20                  25                  30

Leu Gly Tyr Ile Thr Pro Arg Gly Glu His Leu Val Ser Leu Met Gly
        35                  40                  45

Gly Phe Tyr Arg Gln Tyr Phe Gln Gln Gln Gly Leu Leu Ser Arg Asp
    50                  55                  60

Ser Cys Pro Thr Ala Asn Asp Val Tyr Val Trp Thr Asp Val Asn Gln
65                  70                  75                  80

Arg Thr Arg Lys Thr Gly Glu Ala Phe Leu Ala Gly Leu Ala Pro Glu
                85                  90                  95
```

Cys Asp Leu Thr Ile His His Gln Asn Asp Ile Lys Gln Val Asp Pro
            100                 105                 110

Leu Phe His Pro Val Lys Ala Gly Ile Cys Ser Met Asp Lys Thr Gln
        115                 120                 125

Val Gln Gln Ala Val Glu Lys Gln Ala Gly Met Pro Ile Asp Lys Leu
    130                 135                 140

Asn Gln His Tyr Arg Pro Glu Leu Ala Leu Met Ser Asn Val Leu Asn
145                 150                 155                 160

Phe Pro Lys Ser Pro Tyr Cys Gln Arg His Ser Gly Glu Gln Pro Cys
                165                 170                 175

Asp Phe Ala Asn Ala Phe Pro Ser Lys Leu Asn Ile Ser Asp Asp Gly
            180                 185                 190

Asn Glu Val Gln Leu Glu Gly Ala Val Gly Leu Ser Ser Thr Leu Ala
        195                 200                 205

Glu Ile Phe Leu Leu Glu Tyr Ala Gln Gly Met Pro Val Val Ala Trp
210                 215                 220

Gly Asn Ile His Ser Glu Gln Glu Trp Asn Asp Leu Leu Lys Leu His
225                 230                 235                 240

Asn Ala Gln Phe Asp Leu Met Glu Arg Thr Pro Tyr Ile Ala Lys His
                245                 250                 255

Asn Gly Thr Pro Leu Leu Gln Thr Ile Val Asn Ala Leu Asn Ser Asn
            260                 265                 270

Thr Thr Glu Ser Lys Leu Pro Asp Ile Ser Pro Asp Val Lys Ile Leu
        275                 280                 285

Phe Leu Ala Gly His Asp Thr Asn Ile Ala Asn Ile Gly Gly Met Leu
    290                 295                 300

Gly Met Thr Trp Thr Leu Pro Gly
305                 310

<210> SEQ ID NO 101
<211> LENGTH: 312
<212> TYPE: PRT
<213> ORGANISM: Artificial Sequence
<220> FEATURE:
<223> OTHER INFORMATION: Sequence is synthesized

<400> SEQUENCE: 101

Val Ile Leu Ser Arg His Gly Val Arg Ala Pro Thr Lys Met Thr Gln
1               5                   10                  15

Leu Met Arg Asp Val Thr Pro Tyr Thr Trp Pro Glu Trp Pro Val Pro
            20                  25                  30

Leu Gly Tyr Ile Thr Pro Arg Gly Glu His Leu Val Lys Leu Met Gly
        35                  40                  45

Gly Phe Tyr Arg Gln Tyr Phe Gln Gln Gln Gly Leu Leu Ser Arg Asp
    50                  55                  60

Asn Cys Pro Thr Pro Asp Asp Val Tyr Val Trp Thr Asp Val Asn Gln
65                  70                  75                  80

Arg Thr Arg Lys Thr Gly Glu Ala Phe Leu Ala Gly Leu Ala Pro Glu
                85                  90                  95

Cys Asp Leu Thr Ile His His Gln Ser Asp Ile Lys Gln Val Asp Pro
            100                 105                 110

Leu Phe His Pro Leu Lys Ala Gly Ile Cys Ser Met Asp Lys Thr Gln
        115                 120                 125

Val Gln Gln Ala Val Glu Lys Gln Ala Gly Met Pro Ile Asp Lys Leu
    130                 135                 140

Asn Gln His Tyr Arg Ala Glu Leu Ala Leu Met Ser Asn Val Leu Asn
145                 150                 155                 160

Phe Pro Lys Ser Pro Tyr Cys Gln Arg His Ser Gly Glu Gln Pro Cys
            165                 170                 175

Asp Phe Ala Gln Met Phe Pro Ser Tyr Leu Asn Ile Ser Asp Asp Gly
        180                 185                 190

Asn Glu Val Gln Leu Glu Gly Ala Val Gly Leu Ser Ser Thr Leu Ala
    195                 200                 205

Glu Ile Phe Leu Leu Glu Tyr Ala Gln Gly Met Pro Val Val Ala Trp
210                 215                 220

Gly Asn Ile His Ser Glu Gln Glu Trp Asn Asp Leu Leu Lys Leu His
225                 230                 235                 240

Asn Ala Tyr Phe Asp Leu Met Glu Arg Thr Pro Tyr Ile Ala Lys His
            245                 250                 255

Asn Gly Thr Pro Leu Leu Gln Thr Ile Val Asn Ala Leu Asn Pro Asn
        260                 265                 270

Ala Thr Glu Ser Lys Leu Pro Asp Ile Ser Pro Asp Val Lys Ile Leu
    275                 280                 285

Phe Leu Ala Gly His Asp Thr Asn Ile Ala Asn Ile Gly Gly Met Leu
290                 295                 300

Gly Met Asp Trp Thr Leu Pro Gly
305                 310

<210> SEQ ID NO 102
<211> LENGTH: 312
<212> TYPE: PRT
<213> ORGANISM: Artificial Sequence
<220> FEATURE:
<223> OTHER INFORMATION: Sequence is synthesized

<400> SEQUENCE: 102

Val Ile Leu Ser Arg His Gly Val Arg Ala Pro Thr Lys Met Thr Gln
1               5                   10                  15

Leu Met Arg Asp Val Thr Pro Tyr Thr Trp Pro Glu Trp Pro Val Pro
            20                  25                  30

Leu Gly Tyr Ile Thr Pro Arg Gly Glu His Leu Val Ser Leu Met Gly
        35                  40                  45

Gly Phe Tyr Arg Gln Tyr Phe Gln Gln Gln Gly Leu Leu Ser Arg Asp
    50                  55                  60

Arg Cys Pro Thr Ala Asn Asp Val Tyr Val Trp Thr Asp Val Asn Gln
65                  70                  75                  80

Arg Thr Arg Lys Thr Gly Glu Ala Phe Leu Ala Gly Leu Ala Pro Glu
            85                  90                  95

Cys Asp Leu Thr Ile His His Gln Asn Asp Ile Lys Gln Val Asp Pro
        100                 105                 110

Leu Phe His Pro Leu Lys Ala Gly Ile Cys Ser Met Asp Lys Thr Gln
    115                 120                 125

Val Gln Gln Ala Val Glu Lys Gln Ala Gly Met Pro Ile Asp Lys Leu
130                 135                 140

Asn Gln His Tyr Arg Pro Glu Leu Ala Leu Met Ser Asn Val Leu Asn
145                 150                 155                 160

Phe Pro Lys Ser Pro Tyr Cys Arg Gln His Ser Val Glu Gln Pro Cys
            165                 170                 175

Asp Phe Ala Asn Ala Phe Pro Ser Tyr Leu Asn Ile Ser Asp Asp Gly
        180                 185                 190

```
Asn Glu Val Gln Leu Glu Gly Ala Val Gly Leu Ser Ser Thr Leu Ala
            195                 200                 205

Glu Ile Phe Leu Leu Glu Tyr Ala Gln Gly Met Pro Val Val Ala Trp
        210                 215                 220

Gly Asn Ile His Ser Glu Gln Glu Trp Asn Asp Leu Leu Lys Leu His
225                 230                 235                 240

Asn Ala Gln Phe Asp Leu Met Glu Arg Thr Pro Tyr Ile Ala Lys His
            245                 250                 255

Gln Gly Thr Pro Leu Leu Gln Thr Ile Val Asn Ala Leu Asn Ser Asn
        260                 265                 270

Thr Thr Glu Ser Lys Leu Pro Asp Ile Ser Pro Ser Val Lys Ile Leu
275                 280                 285

Phe Leu Ala Gly His Asp Thr Asn Ile Ala Asn Ile Gly Gly Met Leu
        290                 295                 300

Gly Met Thr Trp Thr Leu Pro Gly
305                 310
```

<210> SEQ ID NO 103
<211> LENGTH: 312
<212> TYPE: PRT
<213> ORGANISM: Artificial Sequence
<220> FEATURE:
<223> OTHER INFORMATION: Sequence is synthesized

<400> SEQUENCE: 103

```
Val Ile Leu Ser Arg His Gly Val Arg Ala Pro Thr Lys Met Thr Gln
1               5                   10                  15

Leu Met Arg Asp Val Thr Pro Tyr Thr Trp Pro Glu Trp Pro Val Pro
            20                  25                  30

Leu Gly Tyr Ile Thr Pro Arg Gly Glu His Leu Val Ser Leu Met Gly
        35                  40                  45

Gly Phe Tyr Arg Gln Tyr Phe Gln Gln Gln Gly Leu Leu Ser Arg Asp
    50                  55                  60

Arg Cys Pro Thr Ala Asn Asp Val Tyr Val Trp Thr Asp Val Asn Gln
65                  70                  75                  80

Arg Thr Arg Lys Thr Gly Glu Ala Phe Leu Ala Gly Leu Ala Pro Glu
            85                  90                  95

Cys Asp Leu Thr Ile His His Gln Ser Asp Ile Lys Gln Val Asp Pro
        100                 105                 110

Leu Phe His Pro Leu Lys Ala Gly Ile Cys Ser Met Asp Lys Thr Gln
    115                 120                 125

Val Gln Gln Ala Val Glu Lys Gln Ala Gly Met Pro Ile Asp Lys Leu
130                 135                 140

Asn Gln His Tyr Arg Pro Glu Leu Ala Leu Met Ser Asn Val Leu Asn
145                 150                 155                 160

Phe Pro Lys Ser Pro Tyr Cys Gln Arg His Ser Gly Glu Lys Pro Cys
            165                 170                 175

Asp Phe Ala Asn Ala Phe Pro Ser Tyr Leu Asn Ile Ser Asp Asp Gly
        180                 185                 190

Asn Glu Val Gln Leu Glu Gly Ala Val Gly Leu Ser Ser Thr Leu Ala
    195                 200                 205

Glu Ile Phe Leu Leu Glu Tyr Ala Gln Gly Met Pro Val Val Ala Trp
        210                 215                 220

Gly Asn Ile His Ser Glu Gln Glu Trp Asn Asp Leu Leu Lys Leu His
225                 230                 235                 240
```

```
Asn Ala Gln Phe Asp Leu Met Glu Arg Thr Pro Tyr Ile Ala Lys His
            245                 250                 255

Asn Gly Thr Pro Leu Leu Gln Thr Ile Val Asn Ala Leu Asn Ser Asn
            260                 265                 270

Thr Thr Ala Arg Glu Leu Pro Asp Ile Ser Pro Asp Val Lys Ile Leu
            275                 280                 285

Phe Leu Ala Gly His Asp Thr Asn Ile Ala Asn Ile Gly Gly Met Leu
            290                 295                 300

Gly Met Thr Trp Thr Leu Pro Gly
305                 310
```

<210> SEQ ID NO 104
<211> LENGTH: 431
<212> TYPE: PRT
<213> ORGANISM: Artificial Sequence
<220> FEATURE:
<223> OTHER INFORMATION: Sequence is synthesized

<400> SEQUENCE: 104

```
Met Arg Val Leu Leu Val Ala Leu Ala Leu Ala Leu Ala Leu Ala Ser
1               5                   10                  15

Ala Thr Ser Ala Ala Gln Ser Glu Pro Glu Leu Lys Leu Glu Ser Val
            20                  25                  30

Val Ile Val Ser Arg His Gly Val Arg Ala Pro Thr Lys Ala Thr Gln
            35                  40                  45

Leu Met Gln Asp Val Thr Pro Asp Ala Trp Pro Thr Trp Pro Val Lys
        50                  55                  60

Leu Gly Glu Leu Thr Pro Arg Gly Gly Glu Leu Ile Ala Tyr Leu Gly
65                  70                  75                  80

His Tyr Trp Arg Gln Arg Leu Val Ala Asp Gly Leu Leu Pro Lys Cys
                85                  90                  95

Gly Cys Pro Gln Ser Gly Gln Val Ala Ile Ile Ala Asp Val Asp Glu
            100                 105                 110

Arg Thr Arg Lys Thr Gly Glu Ala Phe Ala Ala Gly Leu Ala Pro Asp
            115                 120                 125

Cys Ala Ile Thr Val His Thr Gln Ala Asp Thr Ser Ser Pro Asp Pro
        130                 135                 140

Leu Phe Asn Pro Leu Lys Thr Gly Val Cys Gln Leu Asp Asn Ala Asn
145                 150                 155                 160

Val Thr Asp Ala Ile Leu Glu Arg Ala Gly Gly Ser Ile Ala Asp Phe
                165                 170                 175

Thr Gly His Tyr Gln Thr Ala Phe Arg Glu Leu Glu Arg Val Leu Asn
            180                 185                 190

Phe Pro Gln Ser Asn Leu Cys Leu Lys Arg Glu Lys Gln Asp Glu Ser
            195                 200                 205

Cys Ser Leu Thr Gln Ala Leu Pro Ser Glu Leu Lys Val Ser Ala Asp
        210                 215                 220

Cys Val Ser Leu Thr Gly Ala Val Ser Leu Ala Ser Met Leu Thr Glu
225                 230                 235                 240

Ile Phe Leu Leu Gln Gln Ala Gln Gly Met Pro Glu Pro Gly Trp Gly
                245                 250                 255

Arg Ile Thr Asp Ser His Gln Trp Asn Thr Leu Leu Ser Leu His Asn
            260                 265                 270

Ala Gln Phe Asp Leu Leu Gln Arg Thr Pro Glu Val Ala Arg Ser Arg
            275                 280                 285
```

-continued

```
Ala Thr Pro Leu Leu Asp Leu Ile Lys Thr Ala Leu Thr Pro His Pro
    290             295                 300

Pro Gln Lys Gln Ala Tyr Gly Val Thr Leu Pro Thr Ser Val Leu Phe
305             310                 315                     320

Ile Ala Gly His Asp Thr Asn Leu Ala Asn Leu Gly Gly Ala Leu Glu
                325                 330                 335

Leu Asn Trp Thr Leu Pro Gly Gln Pro Asp Asn Thr Pro Pro Gly Gly
            340             345                 350

Glu Leu Val Phe Glu Arg Trp Arg Arg Leu Ser Asp Asn Ser Gln Trp
        355             360                 365

Ile Gln Val Ser Leu Val Phe Gln Thr Leu Gln Gln Met Arg Asp Lys
    370             375                 380

Thr Pro Leu Ser Leu Asn Thr Pro Pro Gly Glu Val Lys Leu Thr Leu
385             390                 395                     400

Ala Gly Cys Glu Glu Arg Asn Ala Gln Gly Met Cys Ser Leu Ala Gly
                405                 410                 415

Phe Thr Gln Ile Val Asn Glu Ala Arg Ile Pro Ala Cys Ser Leu
                420                 425             430
```

ENGINEERED ROBUST HIGH Tm-PHYTASE CLADE POLYPEPTIDES AND FRAGMENTS THEREOF

CROSS-REFERENCE TO RELATED APPLICATIONS

This application is a U.S. National Stage Application under 35 U.S.C. § 371 of International Application No. PCT/US2019/062335, filed Nov. 20, 2019, which in turn claims priority to U.S. Provisional Patent Application No. 62/769,713, filed Nov. 20, 2018, U.S. Provisional Patent Application No. 62/851,122, filed May 22, 2019, and U.S. Provisional Patent Application No. 62/887,714, filed Aug. 16, 2019, the disclosures of each of which are incorporated by reference herein in their entireties.

STATEMENT REGARDING FEDERALLY SPONSORED RESEARCH OR DEVELOPMENT

Not applicable.

THE NAMES OF THE PARTIES TO JOINT RESEARCH AGREEMENT

Not applicable.

INCORPORATION-BY-REFERENCE OF A MATERIAL SUBMITTED ON A READ-ONLY OPTICAL DISC, AS A TEXT FILE OR AN XML FILE VIA THE PATENT ELECTRONIC SYSTEM

The sequence listing provided in the file named 20191115_NB41175-WO-PCT_Sequence Listing_ST25 with a size of 324 KB which was created on Nov. 15, 2019 and which is filed herewith, is incorporated by reference herein in its entirety.

STATEMENT REGARDING PRIOR DISCLOSURES BY THE INVENTOR OR A JOINT INVENTOR

Not applicable.

BACKGROUND OF THE INVENTION

Phytase is the most commonly used exogenous enzyme in feed for monogastric animals. Phytase can reduce the antinutritional effect of phytate and improve the digestibility of phosphorous, calcium, amino acids and energy, as well as reduce the negative impact of inorganic phosphorous excretion to the environment.

Phytate is the major storage form of phosphorus in cereals and legumes. However, monogastric animals such as pig, poultry and fish are not able to efficiently metabolize or absorb phytate (or phytic acid) in their diet and therefore it is excreted, leading to phosphorous pollution in areas of intense livestock production. Moreover, phytic acid also acts as an anti-nutritional agent in monogastric animals by chelating metal agents such as calcium, copper and zinc and forming insoluble complexes with proteins and amino acids in various segments of the digestive tract.

It has long been assumed that non-ruminant animals lack endogenous phytase and are, thus, incapable of utilizing phytate. However, endogenous mucosal phosphatases and bacterial phytases have been described to have activity in the small intestine and caeca of poultry. Maenz, D. D.; Classen, H. L., Phytase activity in the small intestinal brush border membrane of the chicken. *Poult Sci* 1998, 77, 557-63. Abudabos, A. M., Phytate phosphorus utilization and intestinal phytase activity in laying hens. *Italian Journal of Animal Science* 2012, 11, e8. Zeller, E.; Schollenberger, M.; Kuhn, I.; Rodehutscord, M. In order to provide sufficient phosphates for growth and health of these animals, inorganic phosphate is added to their diets. Such addition can be costly and further increases pollution problems.

Through the action of phytase, phytate is generally hydrolysed to give lower inositol-phosphates and inorganic phosphate. Phytases are useful as additives to animal feeds where they improve the availability of organic phosphorus to the animal and decrease phosphate pollution of the environment (Wodzinski R J, Ullah A H. Adv Appl Microbiol. 42, 263-302 (1996)).

A number of phytases of fungal (Wyss M. et al., *Appl. Environ. Microbiol.* 65 (2), 367-373 (1999); Berka R. M. et al., *Appl. Environ. Microbiol.* 64 (11), 4423-4427 (1998); Lassen S. et al., *Appl. Environ. Microbiol.* 67 (10), 4701-4707 (2001)) and bacterial (Greiner R. et al *Arch. Biochem. Biophys.* 303 (1), 107-113 (1993); Kerovuo et al., *Appl. Environ. Microbiol.* 64 (6), 2079-2085 (1998); Kim H. W. et al., *Biotechnol. Lett.* 25, 1231-1234 (2003); Greiner R. et al., *Arch. Biochem. Biophys.* 341 (2), 201-206 (1997); Yoon S. J. et al., *Enzyme and microbial technol.* 18, 449-454 (1996); Zinin N. V. et al., *FEMS Microbiol. Lett.* 236, 283-290 (2004)) origin have been described in the literature.

U.S. Pat. No. 8,053,221 issued to Miasnikov et al. on Nov. 8, 2011, relates to phytases derived from the bacterium, *Buttiauxella* sp. and variant/modified forms thereof selected and/or engineered for improved characteristics compared to the wild-type (parent) enzyme.

U.S. Pat. No. 6,110,719 issued to Short on Aug. 29, 2000 and U.S. Pat. No. 6,183,740 issued to short et al. on Feb. 6, 2001 relates to phytase enzymes derived from *Escherichia coli* B.

U.S. Pat. No. 9,365,840 issued to Sjoeholm et al. on Jun. 4, 2016 relates to polypeptides having phytase activity.

U.S. Pat. No. 8,206,962 issued to Lassen et al. on Jun. 26, 2011 and U.S. Pat. No. 8,507,240 issued to Lassen et al. on Aug. 13, 2013 relate to Hafnia phytase variants.

U.S. Pat. No. 8,557,552 issued to Haefner et al. on Oct. 15, 2013 relates to synthetic phytase variants.

WO2015/012890 having international publication date Jan. 29, 2015 relates to polypeptides having phytase activity.

New generations of phytases have been developed over the last decade. However, none of these phytases has a suitable robustness when applied to feed in a liquid form prior to conditioning and pelleting to withstand the high levels of stress under commercially relevant feed pelleting conditions. Therefore, thermostable phytase products on the market suitable for commercial pelleting are dry products and many have protective coatings to retain activity. However, application of phytases in a liquid form to feed is desirable, because, for example, phytase added in a liquid form will be evenly distributed and immediately released in the animal when delivered via feed. There remains a need for such phytases and fragments thereof which are robust when applied in a liquid form prior to conditioning and pelleting under commercially relevant conditions and remain capable of improving animal performance.

FIELD OF THE INVENTION

The field pertains to engineered robust high Tm-phytase clade polypeptides and fragments thereof, methods of production of such engineered robust high Tm-phytase clade polypeptides and fragments thereof and use thereof for enhancing animal performance.

BRIEF SUMMARY OF THE INVENTION

In a first embodiment, there is disclosed an engineered phytase polypeptide (such as a biosynthetic bacterial 6-phytase) or a fragment thereof comprising phytase activity having at least 82% sequence identity with the amino acid sequence set forth in SEQ ID NO:1.

In a second embodiment, there is disclosed the engineered phytase polypeptide or fragment thereof of embodiment 1, wherein the amino acid sequence of the engineered phytase polypeptide or fragment thereof has a Hidden Markov Model (HMM) score of at least 1200 as set forth in Table 11 for the high Tm phytase clade polypeptides and fragments thereof.

In a third embodiment, there is disclosed an engineered phytase polypeptide or core domain fragment thereof having at least 78% sequence identity with amino acid positions 14-325 corresponding to the amino acid sequence set forth in SEQ ID NO:1.

In a fourth embodiment, there is disclosed an engineered phytase polypeptide or fragment thereof (such as those of embodiments 1, 2, or 3) having in-feed pelleting recovery of at least about 50% when applied in MLA at 95° C. for 30 seconds, using a standard in-feed pelleting recovery test as described in Example 5.

In a fifth embodiment, there is disclosed an engineered phytase polypeptide or fragment thereof (such as those of embodiments 1, 2, 3, or 4) having a ratio of in-feed pelleting recoveries of at least about 0.7 when applied in MLA at 95° C. for 30 seconds as compared to application in MLA at 80° C. for 30 seconds, using a standard in-feed pelleting test as described in Example 5.

In a sixth embodiment, there is disclosed an engineered phytase polypeptide or fragment thereof of embodiment 1, 2, 3, 4, or 5 wherein said polypeptide or fragment there comprises a Tm temperature of at least about 92.5° C. under differential scanning calorimetric assay conditions described in Example 3.

In a seventh embodiment, there is disclosed the engineered phytase polypeptide or fragment thereof of embodiment 6 wherein said polypeptide or fragment thereof comprises a specific activity of at least about 100 U/mg at pH 3.5 under assay conditions described in Example 3.

In an eighth embodiment, there is disclosed the engineered phytase polypeptide or fragment thereof of embodiment 1, 2, 3, 4, 5, 6, or 7 wherein a) said phytase polypeptide comprises an amino acid sequence selected from the group consisting of SEQ ID NO:2, SEQ ID NO: 3, SEQ ID NO:4, SEQ ID NO:5, SEQ ID NO:6, SEQ ID NO:7, SEQ ID NO:8, SEQ ID NO: 9, SEQ ID NO: 10, SEQ ID NO: 11, SEQ ID NO: 12, SEQ ID NO: 13, SEQ ID NO: 14, SEQ ID NO: 16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO: 27, SEQ ID NO:28, SEQ ID NO:29, SEQ ID NO:30, SEQ ID NO:31, SEQ ID NO:32, SEQ ID: NO: 33, SEQ ID NO:34, SEQ ID NO:35, SEQ ID NO:36, SEQ ID NO:37, and SEQ ID NO: 64; or b) said phytase polypeptide comprises an amino acid sequence selected from the group consisting of SEQ ID NO:67, SEQ ID NO:68, SEQ ID NO:69, SEQ ID NO:70, SEQ ID NO: 71, SEQ ID NO: 72, SEQ ID NO: 73, SEQ ID NO:74, SEQ ID NO:75, SEQ ID NO: 76, SEQ ID NO: 77, SEQ ID NO:78, SEQ ID NO:79, SEQ ID NO:80, SEQ ID NO:81, SEQ ID NO:82, SEQ ID NO:83, SEQ ID NO:84, SEQ ID NO: 85, SEQ ID NO:86, and SEQ ID NO:87.

In a ninth embodiment, there is disclosed an animal feed, feedstuff, feed additive composition or premix of comprising the engineered phytase polypeptide or fragment thereof of embodiment 1, 2, 3 4, 5, 6, 7, or 8 wherein the engineered phytase polypeptide or fragment thereof may be used (i) alone or (ii) in combination with a direct fed microbial comprising at least one bacterial strain or (iii) with at least one other enzyme or (iv) in combination with a direct fed microbial comprising at least one bacterial strain and at least one other enzyme, or (v) any of (i), (ii), (iii) or (iv) further comprising at least one other feed additive component and, optionally, the engineered phytase polypeptide or fragment thereof is present in an amount of at least about 0.1 g/ton feed.

In a tenth embodiment, there is disclosed a recombinant construct comprising a regulatory sequence functional in a production host operably linked to a nucleotide sequence encoding the engineered phytase polypeptide or fragment thereof of embodiment 1, 2, 3, 4, 5, 6, 7, or 8.

In an eleventh embodiment, the production host is selected from the group consisting of bacterial, fungi, yeast, plants and algae.

In a twelfth embodiment, there is disclosed a method for producing an engineered phytase polypeptide or fragment thereof comprising:
  (a) transforming a production host with the recombinant construct of embodiment 9; and
  (b) culturing the production host of step (a) under conditions whereby the engineered phytase polypeptide or fragment thereof is produced.

In a thirteenth embodiment, the engineered phytase polypeptide or fragment thereof made by the method of the tenth embodiment optionally is recovered from the production host.

In a fourteenth embodiment, there is disclosed a phytase-containing culture supernatant obtained by the methods of embodiment ten or eleven.

In a fifteenth embodiment, there is disclosed a polynucleotide sequence encoding the engineered phytase polypeptide or fragment thereof of embodiment 1, 2, 3, 4, 5, 6, 7, or 8.

In a sixteenth embodiment, there is described a dried enzyme composition for use in animal feed comprising the engineered phytase polypeptide or fragment thereof of embodiment 1, 2, 3, 4, 5, 6, 7, or 8.

In a seventeenth embodiment, there is disclosed the dried enzyme composition of embodiment 15 wherein dried enzyme composition is a granulated feed additive composition.

In an eighteenth embodiment, there is disclosed liquid enzyme composition for use in animal feed comprising the engineered phytase polypeptide or fragment thereof of embodiment 1, 2, 3, 4, 5, 6, 7, or 8.

In a nineteenth embodiment, there is disclosed a method for improving the nutritional value of an animal feed, wherein the engineered phytase or fragment thereof of embodiment 1, 2, 3, 4, 5, 6, 7, or 8 is added to animal feed.

In a twentieth embodiment, there is disclosed a method for improving animal performance on one or more metrics comprising administering an effective amount of the engineered phytase polypeptide of embodiment 1, 2, 3, 4, 5, 6, 7, or 8 or the animal feed, feedstuff, feed additive composition or premix of embodiment 9 or 10 to the animal.

In a twenty-first embodiment, there is disclosed the method of embodiment 20, wherein the one or more metrics is selected from the group consisting of increased feed efficiency, increased weight gain, reduced feed conversion ratio, improved digestibility of nutrients or energy in a feed, improved nitrogen retention, improved ability to avoid the negative effects of necrotic enteritis, and improved immune response.

In a twenty-second embodiment, there is disclosed the method of embodiment 20 or 21, wherein the animal is a monogastric animal selected from the group consisting of swine and poultry.

In a twenty-third embodiment, there is disclosed the method of embodiment 22, wherein the swine is selected from the group consisting of piglets, growing pigs, and sows.

In a twenty-fourth embodiment, there is disclosed the method of embodiment 22, wherein the poultry is selected from the group consisting of turkeys, ducks, chickens, broiler chicks, layers, geese, pheasants, quail, and emus.

In a twenty-fifth embodiment, there is disclosed the method of embodiment 20 or 21, wherein the animal is a ruminant animal selected from the group consisting of cattle, young calves, goats, sheep, giraffes, bison, moose, elk, yaks, water buffalo, deer, reindeer, caribou, camels, alpacas, llamas, antelope, pronghorn and nilgai.

BRIEF DESCRIPTION OF THE SEVERAL VIEWS OF THE DRAWING(S)

FIGS. 1A-1BB (panels A to 1BB) shows the HMM probability scores for each position along the polypeptide sequence of the High Tm-phytase clade. The composite scores (COMP) for the HMM are shown on the top 3 panels of FIG. 1A, in bold. The position (P) and consensus (C) for each amino acid are shown in column 1 under P/C.

Figure 2:
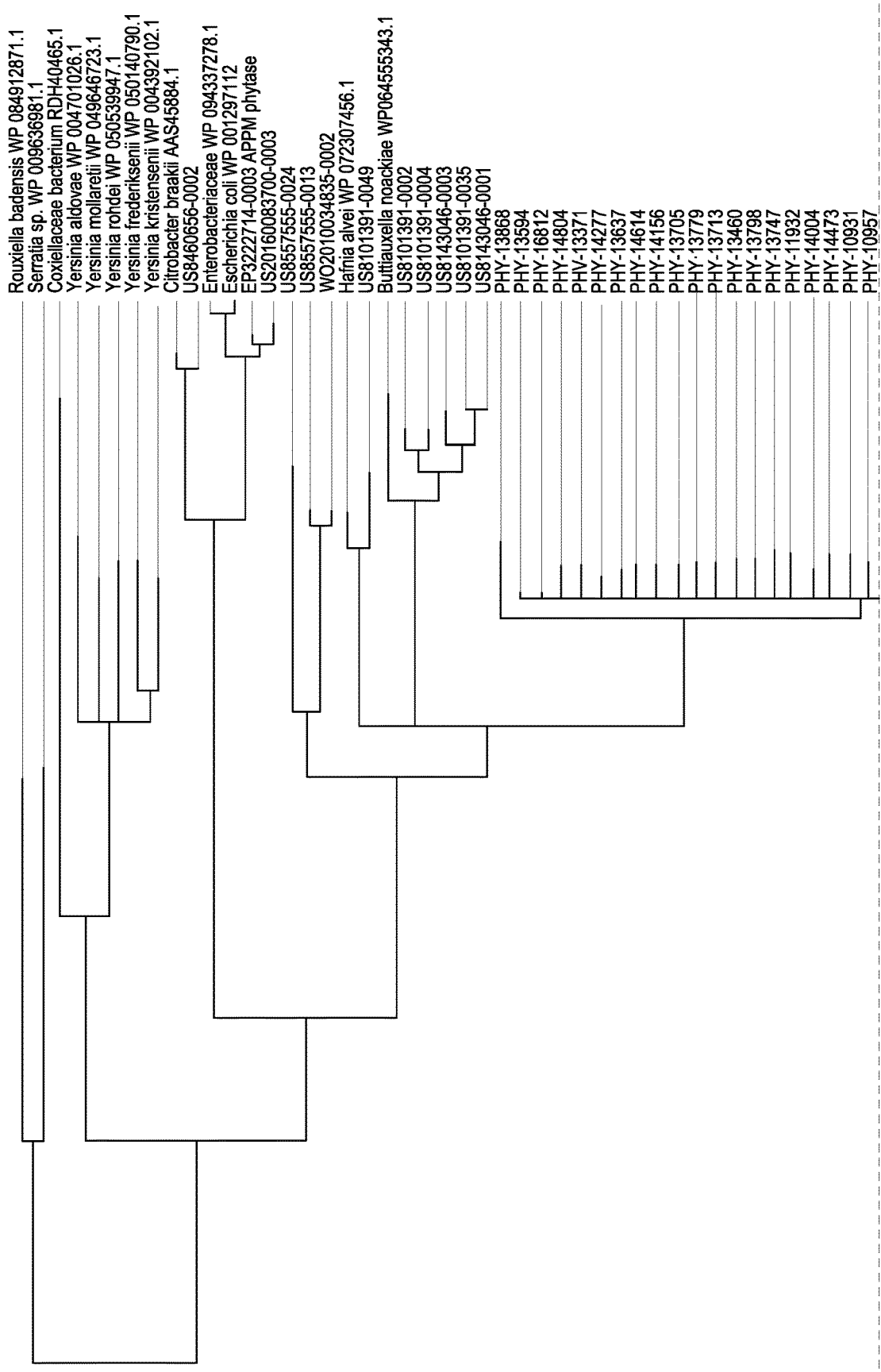
FIG. 2 depicts a phylogenetic tree showing the relatedness among various phytases including the engineered phytase polypeptides and fragments thereof described herein based upon similarities and differences in the amino acid sequence.
Figure 2:
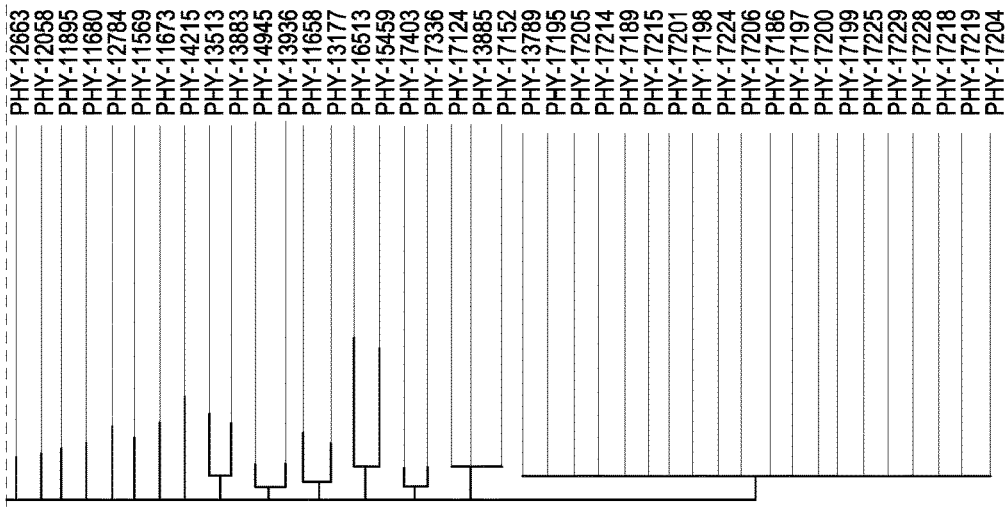

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5 (a-bis), and Section 208 and Annex C of the Administrative Instructions. The symbols and format used for nucleotide and amino acid sequence data comply with the rules set forth in 37 C.F.R. § 1.822. SEQ ID NO:1 corresponds to the predicted mature sequence of engineered phytase PHY-13594.

SEQ ID NO:2 corresponds to the predicted mature sequence of engineered phytase PHY-10931.

SEQ ID NO:3 corresponds to the predicted mature sequence of engineered phytase PHY-10957.

SEQ ID NO:4 corresponds to the predicted mature sequence of engineered phytase PHY-11569.

SEQ ID NO:5 corresponds to the predicted mature sequence of engineered phytase PHY-11658.

SEQ ID NO:6 corresponds to the predicted mature sequence of engineered phytase PHY-11673.

SEQ ID NO:7 corresponds to the predicted mature sequence of engineered phytase PHY-11680.

SEQ ID NO:8 corresponds to the predicted mature sequence of engineered phytase PHY-11895.

SEQ ID NO:9 corresponds to the predicted mature sequence of engineered phytase PHY-11932.

SEQ ID NO:10 corresponds to the predicted mature sequence of engineered phytase PHY-12058.

SEQ ID NO:11 corresponds to the predicted mature sequence of engineered phytase PHY-12663.

SEQ ID NO:12 corresponds to the predicted mature sequence of engineered phytase PHY-12784.

SEQ ID NO:13 corresponds to the predicted mature sequence of engineered phytase PHY-13177.

SEQ ID NO:14 corresponds to the predicted mature sequence of engineered phytase PHY-13371

SEQ ID NO:15 corresponds to the predicted mature sequence of engineered phytase PHY-13460.

SEQ ID NO: 16 corresponds to the predicted mature sequence of engineered phytase PHY-13513.

SEQ ID NO:17 corresponds to the predicted mature sequence of engineered phytase PHY-13637.

SEQ ID NO:18 corresponds to the predicted mature sequence of engineered phytase PHY-13705.

SEQ ID NO: 19 corresponds to the predicted mature sequence of engineered phytase PHY-13713.

SEQ ID NO:20 corresponds to the predicted mature sequence of engineered phytase PHY-13747.

SEQ ID NO:21 corresponds to the predicted mature sequence of engineered phytase PHY-13779.

SEQ ID NO:22 corresponds to the predicted mature sequence of engineered phytase PHY-13789.

SEQ ID NO:23 corresponds to the predicted mature sequence of engineered phytase PHY-13798.

SEQ ID NO:24 corresponds to the predicted mature sequence of engineered phytase PHY-13868.

SEQ ID NO:25 corresponds to the predicted mature sequence of engineered phytase PHY-13883.

SEQ ID NO:26 corresponds to the predicted mature sequence of engineered phytase PHY-13885.

SEQ ID NO:27 corresponds to the predicted mature sequence of engineered phytase PHY-13936.

SEQ ID NO:28 corresponds to the predicted mature sequence of engineered phytase PHY-14004.

SEQ ID NO:29 corresponds to the predicted mature sequence of engineered phytase PHY-14215.

SEQ ID NO:30 corresponds to the predicted mature sequence of engineered phytase PHY-14256.

SEQ ID NO:31 corresponds to the predicted mature sequence of engineered phytase PHY-14277.

SEQ ID NO:32 corresponds to the predicted mature sequence of engineered phytase PHY-14473.

SEQ ID NO:33 corresponds to the predicted mature sequence of engineered phytase PHY-14614.

SEQ ID NO:34 corresponds to the predicted mature sequence of engineered phytase PHY-14804.

SEQ ID NO:35 corresponds to the predicted mature sequence of engineered phytase PHY-14945.

SEQ ID NO:36 corresponds to the predicted mature sequence of engineered phytase PHY-15459.

SEQ ID NO:37 corresponds to the predicted mature sequence of engineered phytase PHY-16513.

SEQ ID NO:38 corresponds to *Buttiauxella noackiae* WP 064555343.1.

SEQ ID NO:39 corresponds to *Citrobacter braakii* AAS45884.1

SEQ ID NO:40 corresponds to Coxiellaceae bacterium RDH40465.1.

SEQ ID NO:41 corresponds to Enterobacteriaceae WP 094337278.1.

SEQ ID NO:42 corresponds to *Escherichia coli* WP 001297112.

SEQ ID NO:43 corresponds to *Hafnia alvei* WP 072307456.1.

SEQ ID NO:44 corresponds to *Rouxiella badensis* WP 084912871.1.

SEQ ID NO:45 corresponds to *Serratia* sp. WP 009636981.1.

SEQ ID NO:46 corresponds to *Yersinia aldovae* WP 004701026.1.

SEQ ID NO:47 corresponds to *Yersinia frederiksenii* WP 050140790.1.

SEQ ID NO:48 corresponds to *Yersinia kristensenii* WP 004392102.1.

SEQ ID NO:49 corresponds to *Yersinia mollaretii* WP 049646723.1.

SEQ ID NO:50 corresponds to *Yersinia rohdei* WP 050539947.1.

SEQ ID NO:51 corresponds to SEQ ID NO:3 in EP322271.

SEQ ID NO:52 corresponds to SEQ ID NO:2 in U.S. Pat. No. 8,101,391.

SEQ ID NO:53 corresponds to SEQ ID NO:4 in U.S. Pat. No. 8,101,391.

SEQ ID NO:54 corresponds to SEQ ID NO:35 in U.S. Pat. No. 8,101,391.

SEQ ID NO:55 corresponds to SEQ ID NO:49 in U.S. Pat. No. 8,101,391.

SEQ ID NO:56 corresponds to SEQ ID NO:1 in U.S. Pat. No. 8,143,046.

SEQ ID NO:57 corresponds to SEQ ID NO:3 in U.S. Pat. No. 8,143,046.

SEQ ID NO:58 corresponds to SEQ ID NO:2 in U.S. Pat. No. 8,460,656.

SEQ ID NO:59 corresponds to SEQ ID NO:13 in U.S. Pat. No. 8,557,555.

SEQ ID NO:60 corresponds to SEQ ID NO:24 in U.S. Pat. No. 8,557,555.

SEQ ID NO:61 corresponds to SEQ ID NO:3 in US20160083700.

SEQ ID NO:62 corresponds to SEQ ID NO:1 in WO2010034835-0002.

SEQ ID NO:63 corresponds to the *T. reesei* aspartate protease signal sequence.

SEQ ID NO:64 corresponds to the predicted mature sequence of engineered phytase PHY-16812.

SEQ ID NO:65 corresponds to the predicted mature sequence of engineered phytase PHY-17403.

SEQ ID NO:66 corresponds to the predicted mature sequence of engineered phytase PHY-17336.

SEQ ID NO:67 corresponds to the predicted mature sequence of engineered phytase PHY-17225.

SEQ ID NO:68 corresponds to the predicted mature sequence of engineered phytase PHY-17186.

SEQ ID NO:69 corresponds to the predicted mature sequence of engineered phytase PHY-17195.

SEQ ID NO:70 corresponds to the predicted mature sequence of engineered phytase PHY-17124

SEQ ID NO:71 corresponds to the predicted mature sequence of engineered phytase PHY-17189.

SEQ ID NO:72 corresponds to the predicted mature sequence of engineered phytase PHY-17218.

SEQ ID NO:73 corresponds to the predicted mature sequence of engineered phytase PHY-17219.

SEQ ID NO:74 corresponds to the predicted mature sequence of engineered phytase PHY-17204.

SEQ ID NO:75 corresponds to the predicted mature sequence of engineered phytase PHY-17215.

SEQ ID NO:76 corresponds to the predicted mature sequence of engineered phytase PHY-17201.

SEQ ID NO:77 corresponds to the predicted mature sequence of engineered phytase PHY-17205

SEQ ID NO:78 corresponds to the predicted mature sequence of engineered phytase PHY-17224.

SEQ ID NO:79 corresponds to the predicted mature sequence of engineered phytase PHY-17200.

SEQ ID NO:80 corresponds to the predicted mature sequence of engineered phytase PHY-17198.

SEQ ID NO:81 corresponds to the predicted mature sequence of engineered phytase PHY-17199.

SEQ ID NO:82 corresponds to the predicted mature sequence of engineered phytase PHY-17214.

SEQ ID NO:83 corresponds to the predicted mature sequence of engineered phytase PHY-17197.

SEQ ID NO:84 corresponds to the predicted mature sequence of engineered phytase PHY-17228

SEQ ID NO:85 corresponds to the predicted mature sequence of engineered phytase PHY-17229.

SEQ ID NO:86 corresponds to the predicted mature sequence of engineered phytase PHY-17152.

SEQ ID NO:87 corresponds to the predicted mature sequence of engineered phytase PHY-17206.

SEQ ID NO:88 corresponds to the *Buttiauxella* NCIMB 41248 N-terminus.

SEQ ID NO:89 corresponds to the *C. braakii* AAS45884 N-terminus.

SEQ ID NO:90 corresponds to the *E. tarda* YP007628727 N-terminus.

SEQ ID NO:91 corresponds to the PHY-13594 N-terminus.

SEQ ID NO:92 corresponds to the PHY-13789 N-terminus.

SEQ ID NO:93 corresponds to the PHY-13885 N-terminus.

SEQ ID NO:94 corresponds to the C-terminus SEQ ID NO:1 in WO2010034835-0002.

SEQ ID NO:95 corresponds to the *Y. mollaretii* WP032813045 C-terminus.

SEQ ID NO:96 corresponds to the *Buttiauxella* NCIMB 41248 C-terminus.

SEQ ID NO:97 corresponds to the PHY-13594 C-terminus.

SEQ ID NO:98 corresponds to the PHY-13789 C-terminus.

SEQ ID NO:99 corresponds to the PHY-13885 C-terminus.

SEQ ID NO:100 corresponds to the PHY-13594 core region.

SEQ ID NO: 101 corresponds to the PHY-13789 core region.

SEQ ID NO:102 corresponds to the PHY-13885 core region.

SEQ ID NO: 103 corresponds to the PHY-16812 core region.

SEQ ID NO: 104 corresponds to SEQ ID NO:4 in U.S. Pat. No. 7,081,563.

DETAILED DESCRIPTION OF THE INVENTION

All patents, patent applications, and publications cited are incorporated herein by reference in their entirety.

In this disclosure, many terms and abbreviations are used. The following definitions apply unless specifically stated otherwise.

As used herein, the singular forms "a," "an," and "the" include plural references unless the context clearly dictates otherwise. For example, the term "a compound" or "at least one compound" may include a plurality of compounds, including mixtures thereof. The terms "a," "an," "the," "one or more," and "at least one," for example, can be used interchangeably herein.

The term "and/or" and "or" are used interchangeably herein and refer to a specific disclosure of each of the two specified features or components with or without the other. Thus, the term "and/or" as used in a phrase such "A and/or B" herein is intended to include "A and B," "A or B," "A" (alone), and "B" alone. Likewise, the term "and/or" as used a phrase such as "A, B and/or C" is intended to encompass each of the following aspects: A, B and C; A, B or C; A or C; A or B; B or C; A and C; A and B; B and C; A (alone); B (alone); and C (alone).

Words using the singular include the plural, and vice versa.

The terms "comprises," "comprising," "includes," "including," "having" and their conjugates are used interchangeably and mean "including but not limited to." It is understood that wherever aspects are described herein with the language "comprising," otherwise analogous aspects described in terms of "consisting of" and/or "consisting essentially of" are also provided.

The term "consisting of" means "including and limited to."

The term "consisting essentially of" means the specified material of a composition, or the specified steps of a methods, and those additional materials or steps that do not materially affect the basic characteristics of the material or method.

Throughout this application, various embodiments can be presented in a range format. It should be understood that the description in range format is merely for convenience and brevity and should not be construed as an inflexible limitation on the scope of the embodiments described herein. Accordingly, the description of a range should be considered to have specifically disclosed all the possible subranges as well as individual numerical values within that range. For example, description of a range, such as from 1 to 6 should be considered to have specifically disclosed subranges such as from 1 to 2, from 1 to 3, from 1 to 4 and from 1 to 5, from 2 to 3, from 2 to 4, from 2 to 5, from 2 to 6, from 3 to 4, from 3 to 5, from 3 to 6, etc. as well as individual numbers within that range, for example, 1, 2, 3, 4, 5 and 6. This applies regardless of the breadth of the range.

The term "about" as used herein can allow for a degree of variability in a value or range, for example, within 10%, within 5%, or within 1% of a stated value or of a stated limit of a range.

The term "phytase" (myo-inositol hexakisphosphate phosphohydrolase) refers to a class of phosphatase enzymes that catalyzes the hydrolysis of phytic acid (myo-inositol hexakisphosphate or IP6)—an indigestible, organic form of phosphorus that is found in grains and oil seeds—and releases a usable form of inorganic phosphorus.

The terms "animal" and "subject" are used interchangeably herein and refer to any organism belonging to the kingdom Animalia and includes, without limitation, mammals (excluding humans), non-human animals, domestic animals, livestock, farm animals, zoo animals, breeding stock and the like. For example, there can be mentioned all non-ruminant and ruminant animals. In an embodiment, the animal is a non-ruminant, i.e., mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment, the animal is a ruminant animal including, but not limited to, cattle, young calves, goats, sheep, giraffes, bison, moose, elk, yaks, water buffalo, deer, camels, alpacas, llamas, antelope, pronghorn and nilgai.

The term "clade", also known as a monophyletic group, refers to a group of organisms or related sequences that have a common ancestor and all its lineal descendants.

The term "$T_m$" is the temperature at which a protein denatures or the free energy of the unfolded and folded states is equal and half of the population is unfolded and the other half is folded. The thermal unfolding behavior of enzymes is typically studied using calorimetry or optical techniques such as circular dichroism, fluorescence or light scattering.

The term "High Tm-phytase clade" refers to a clade of phytase polypeptides or fragments thereof having a Tm of at least 92.5° using differential scanning calorimetry as described below in Example 3. The terms "high Tm-phytase clade polypeptides" and "engineered phytase polypeptides and fragments thereof" are used interchangeably herein.

The terms "mixer liquid application" and "MLA" are used interchangeably herein and refer to animal feed production wherein heat sensitive compounds, specifically, enzymes can be applied in a liquid form to animal feed prior to conditioning and pelleting and remain functional in the feed after conditioning and pelleting.

A "feed" means any natural or artificial diet, meal or the like or components of such meals intended or suitable for being eaten, taken in, digested, by a non-human animal, respectively. Preferably term "feed" is used with reference to products that are fed to animals in the rearing of livestock. The terms "feed" and "animal feed" are used interchangeably herein.

A "feed additive" as used herein refers to one or more ingredients, products of substances (e.g., cells), used alone or together, in nutrition (e.g., to improve the quality of a food (e.g., an animal feed), to improve an animal's performance and/or health, and/or to enhance digestibility of a food or materials within a food.

As used herein, the term "food" is used in a broad sense—and covers food and food products in any form for humans as well as food for animals (i.e. a feed).

The food or feed may be in the form of a solution or as a solid-depending on the use and/or the mode of application and/or the mode of administration. In some embodiments, the enzymes mentioned herein may be used as—or in the preparation or production of—a food or feed substance.

As used herein the term "food or feed ingredient" includes a formulation, which is or can be added to foods or foodstuffs and includes formulations which can be used at low levels in a wide variety of products. The food ingredient may be in the form of a solution or as a solid-depending on the use and/or the mode of application and/or the mode of administration. The enzymes described herein may be used as a food or feed ingredient or in the preparation or production. The enzymes may be—or may not be added to—food supplements. Feed compositions for monogastric animals typically include compositions comprising plant products which contain phytate. Such compositions include, but are not limited to, cornmeal, soybean meal, rapeseed meal, cottonseed meal, maize, wheat, barley and sorghum-based feeds.

As used herein, the term "pelleting" refers to the production of pellets which can be solid, rounded, spherical and cylindrical tablets, particularly feed pellets and solid, extruded animal feed. One example of a known feed pelleting manufacturing process generally includes admixing together food or feed ingredients at least 1 minutes at room temperature, transferring the admixture to a surge bin, conveying the admixture to a steam conditioner (i.e., conditioning), optionally transferring the steam conditioned admixture to an expander, transferring the admixture to the pellet mill or extruder, and finally transferring the pellets into a pellet cooler. (Fairfield, D. 1994. Chapter 10, Pelleting Cost Center. In Feed Manufacturing Technology IV. (McEllhiney, editor), American Feed Industry Association, Arlington, Va., pp. 110-139.).

The term "pellet" refers to a composition of animal feed (usually derived from grain) that has been subjected to a heat treatment, such as a steam treatment (i.e., conditioning), and pressed or extruded through a machine. The pellet may incorporate enzyme in the form of a liquid preparation or a dry preparation. The dry preparation may be coated or not coated and may be in the form of a granule. The term "granule" is used for particles composed of enzymes (such as a phytase, for example, any of the engineered phytase polypeptides disclosed herein) and other chemicals such as salts and sugars, and may be formed using any of a variety of techniques, including fluid bed granulation approaches to form layered granules.

The terms "in-feed pelleting recovery", "recovered activity" or "activity recovery" refer to the ratio of (i) the activity of a feed enzyme after a treatment involving one or more of the following stressors: heating, increased pressure, increased pH, decreased pH, storage, drying, exposure to surfactant(s), exposure to solvent(s), and mechanical stress to (ii) the activity of the enzyme before the treatment. The recovered activity may be expressed as a percentage. The percent recovered activity is calculated as follows:

$$\% \text{ recovered activity} = \frac{(\text{activity after treatment})}{(\text{activity before treatment})} \times 100\%$$

A phytase can exhibit stability by showing any of improved "in-feed pelleting recovery", "recovered activity," "thermostability," or "inactivity reversibility."

In the context of pelleting experiments, the "activity before treatment" can be approximated by measuring the phytase activity present in the mash that does not undergo treatment in a manner that is otherwise matched to the phytase that does undergo treatment. For example, the phytase in the untreated mash is handled and stored for a similar time and under similar conditions as the phytase in the treated mash, to control for possible interactions or other effects outside of the specified treatment per se.

The terms "in-feed pelleting recovery test" and "standard in-feed pelleting test" are used interchangeably herein and refer to a test to measure or assess the stability of a feed enzyme to withstand the heat treatment of conditioning and pelleting.

For example, such an in-feed pelleting recovery test is set forth in Example 5 below.

The term phytase activity in relation to determination in solid or liquid preparations means 1 FTU (phytase unit) which is defined as the amount of enzyme required to release 1 micromole of inorganic orthophosphate from a 5.0 mM Sodium phytate substrate (from rice) in one minute under the reaction conditions, pH 5.5 at 37° C., which are also defined in the ISO 2009 phytase assay—A standard assay for determining phytase activity found at *International Standard ISO/DIS* 30024:1-17, 2009.

Alternatively, as used herein one unit of phytase (U) can be defined as the quantity of enzyme that releases 1 micromole of inorganic orthophosphate from a 0.2 mM sodium phytate substrate (from rice) in one minute under the reaction conditions 25° C., at pH 5.5 or 3.5 respectively in the Malachite Green assay as is illustrated in Example 3.

The term "specific activity" as used herein is the number of enzyme units per ml divided by the concentration of (total) protein in mg/ml. Specific activity values are therefore usually quoted as units/mg. Alternatively, specific activity is the number of enzyme units per ml divided by the concentration of phytase in mg/ml.

The term "differential scanning calorimetry" or "DSC" as used herein is a thermoanalytical technique in which the difference in the amount of heat required to increase the temperature of a sample and reference is measured as a function of temperature. Both the sample and reference are maintained at nearly the same temperature throughout the experiment. Generally, the temperature program for a DSC analysis is designed such that the sample holder temperature increases linearly as a function of time. The reference sample should have a well-defined heat capacity over the range of temperatures to be scanned.

The term "prebiotic" means a non-digestible food ingredient that beneficially affects the host by selectively stimulating the growth and/or the activity of one or a limited number of beneficial bacteria.

The term "direct-fed microbial" ("DFM") as used herein is source of live (viable) microorganisms that when applied in sufficient numbers can confer a benefit to the recipient thereof, i.e., a probiotic. A DFM can comprise one or more of such microorganisms such as bacterial strains. Categories of DFMs include *Bacillus*, Lactic Acid Bacteria and Yeasts. Thus, the term DFM encompasses one or more of the following: direct fed bacteria, direct fed yeast, direct fed yeast and combinations thereof.

Bacilli are unique, gram-positive rods that form spores. These spores are very stable and can withstand environmental conditions such as heat, moisture and a range of pH. These spores germinate into active vegetative cells when ingested by an animal and can be used in meal and pelleted diets. Lactic Acid Bacteria are gram-positive cocci that produce lactic acid which are antagonistic to pathogens. Since Lactic Acid Bacteria appear to be somewhat heat-sensitive, they are not used in pelleted diets. Types of Lactic Acid Bacteria include *Bifidobacterium, Lactobacillus* and *Streptococcus*.

The terms "probiotic," "probiotic culture," and "DFM" are used interchangeably herein and define live microorganisms (including bacteria or yeasts for example) which, when for example ingested or locally applied in sufficient numbers, beneficially affects the host organism, i.e. by conferring one or more demonstrable health benefits on the host organism such as a health, digestive, and/or performance benefit. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut. Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a subject.

The term "CFU" as used herein means "colony forming units" and is a measure of viable cells in which a colony represents an aggregate of cells derived from a single progenitor cell.

The term "isolated" means a substance in a form or environment that does not occur in nature and does not reflect the extent to which an isolate has been purified, but indicates isolation or separation from a native form or native environment. Non-limiting examples of isolated substances include (1) any non-naturally occurring substance, (2) any substance including, but not limited to, any host cell, enzyme, engineered enzyme, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated. The terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The terms "purify," "purified," and purification mean to make substantially pure or clear from unwanted components, material defilement, admixture or imperfection. For example, as applied to nucleic acids or polypeptides, purification generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

The terms "peptides", "proteins" and "polypeptides are used interchangeably herein and refer to a polymer of amino acids joined together by peptide bonds. A "protein" or "polypeptide" comprises a polymeric sequence of amino acid residues. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine(S) is represented as "G087S" or "G87S". When describing modifications, a position followed by amino acids listed in parentheses indicates a list of substitutions at that position by any of the listed amino acids. For example, 6(L, I) means position 6 can be substituted with a leucine or isoleucine. At times, in a sequence, a slash (/) is used to define substitutions, e.g. F/V, indicates that the position may have a phenylalanine or valine at that position.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or enzyme without the signal peptide sequence and propeptide sequence.

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant/engineered nucleic acids and protein sequences produced in the laboratory or modification of the wild-type sequence).

As used herein with regard to amino acid residue positions, "corresponding to" or "corresponds to" or "correspond to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question.

The term "amino acid" refers to the basic chemical structural unit of a protein or polypeptide. The following abbreviations used herein to identify specific amino acids can be found in Table 1.

TABLE 1

| One and Three Letter Amino Acid Abbreviations | | |
|---|---|---|
| Amino Acid | Three-Letter Abbreviation | One-Letter Abbreviation |
| Alanine | Ala | A |
| Arginine | Arg | R |
| Asparagine | Asn | N |

TABLE 1-continued

One and Three Letter Amino Acid Abbreviations

| Amino Acid | Three-Letter Abbreviation | One-Letter Abbreviation |
|---|---|---|
| Thermostable serine acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

It would be recognized by one of ordinary skill in the art that modifications of amino acid sequences disclosed herein can be made while retaining the function associated with the disclosed amino acid sequences. For example, it is well known in the art that alterations in a gene which result in the production of a chemically equivalent amino acid at a given site, but do not affect the functional properties of the encoded protein are common.

The term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

The term "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "intron" means any nucleotide sequence within a gene that is removed by RNA splicing during maturation of the final RNA product. The term "intron' refers to both the DNA sequence within a gene and the corresponding sequence in the RNA transcripts.

The term "coding sequence" refers to a nucleotide sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding sites, and stem-loop structures.

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The terms "regulatory sequence" or "control sequence" are used interchangeably herein and refer to a segment of a nucleotide sequence which is capable of increasing or decreasing expression of specific genes within an organism. Examples of regulatory sequences include, but are not limited to, promoters, signal sequence, operators and the like. As noted above, regulatory sequences can be operably linked in sense or antisense orientation to the coding sequence/gene of interest.

"Promoter" or "promoter sequences" refer a regulatory sequence that is involved in binding RNA polymerase to initiate transcription of a gene. The promoter may be an inducible promoter or a constitutive promoter. A preferred promoter used in the invention is Trichoderma reesei cbh1, which is an inducible promoter.

The "3' non-coding sequences" refer to DNA sequences located downstream of a coding sequence and include sequences encoding regulatory signals capable of affecting mRNA processing or gene expression, such as termination of transcription.

The term "transformation" as used herein refers to the transfer or introduction of a nucleic acid molecule into a host organism. The nucleic acid molecule may be introduced as a linear or circular form of DNA. The nucleic acid molecule may be a plasmid that replicates autonomously, or it may integrate into the genome of a production host. Production hosts containing the transformed nucleic acid are referred to as "transformed" or "recombinant" or "transgenic" organisms or "transformants".

The terms "recombinant" and "engineered" refer to an artificial combination of two otherwise separated segments of nucleic acid sequences, e.g., by chemical synthesis or by the manipulation of isolated segments of nucleic acids by genetic engineering techniques. For example, DNA in which one or more segments or genes have been inserted, either naturally or by laboratory manipulation, from a different molecule, from another part of the same molecule, or an artificial sequence, resulting in the introduction of a new sequence in a gene and subsequently in an organism. The terms "recombinant", "transgenic", "transformed", "engineered", "genetically engineered" and "modified for exogenous gene expression" are used interchangeably herein.

The terms "recombinant construct", "expression construct", "recombinant expression construct" and "expression cassette" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature.

Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened to obtain lines displaying the desired expression level and pattern. Such screening may be accomplished using standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The terms "production host", "host" and "host cell" are used interchangeably herein and refer to any plant, organism, or cell of any plant or organism, whether human or non-human into which a recombinant construct can be stably or transiently introduced to express a gene. This term encompasses any progeny of a parent cell, which is not identical to the parent cell due to mutations that occur during propagation.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs.

As used herein, "% identity" or percent identity" or "PID" refers to protein sequence identity. Percent identity may be determined using standard techniques known in the art. Useful algorithms include the BLAST® algorithms (See, Altschul et al., *J Mol Biol*, 215:403-410, 1990; and Karlin and Altschul, Proc Natl Acad Sci USA, 90:5873-5787, 1993). The BLAST® program uses several search parameters, most of which are set to the default values. The NCBI® BLAST® algorithm finds the most relevant sequences in terms of biological similarity but is not recommended for query sequences of less than 20 residues (Altschul et al., *Nucleic Acids Res*, 25:3389-3402, 1997; and Schaffer et al., *Nucleic Acids Res*, 29:2994-3005, 2001). Exemplary default BLAST® parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST® parameters for amino acid sequence searches include: Word size=3; E-value cut-off=10; Scoring Matrix=BLOSUM62; Gap Opening=11; and Gap extension=1. A percent (%) amino acid sequence identity value is determined by the number of matching identical residues divided by the total number of residues of the "reference" sequence. BLAST® algorithms refer to the "reference" sequence as the "query" sequence.

As used herein, "homologous proteins" or "homologous phytases" refers to proteins that have distinct similarity in primary, secondary, and/or tertiary structure. Protein homology can refer to the similarity in linear amino acid sequence when proteins are aligned. Homologous search of protein sequences can be done using BLAST®P and PSI-BLAST® from NCBI® BLAST® with threshold (E-value cut-off) at 0.001. (Altschul S F, Madde T L, Shaffer A A, Zhang J, Zhang Z, Miller W, Lipman D J. Gapped BLAST® and PSI BLAST® a new generation of protein database search programs. *Nucleic Acids Res* 1997 Set 1; 25 (17): 3389-402). Using this information, proteins sequences can be grouped.

Sequence alignments and percent identity calculations may be performed using the Megalign program of the LASERGENER bioinformatics computing suite (DNASTAR Inc., Madison, WI), the AlignX program of VECTOR NTI® v. 7.0 (Informax, Inc., Bethesda, MD), or the EMBOSS Open Software Suite (EMBL-EBIR; Rice et al., *Trends in Genetics* 16, (6): 276-277 (2000)). Multiple alignment of the sequences can be performed using the CLUSTAL method (such as CLUSTALW; for example, version 1.83) of alignment (Higgins and Sharp, *CABIOS*, 5:151-153 (1989); Higgins et al., *Nucleic Acids Res.* 22:4673-4680 (1994); and Chenna et al., *Nucleic Acids Res* 31 (13): 3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=−1, protein GAPDIST-4, and KTUPLE=1. In one embodiment, a fast or slow alignment is used with the default settings where a slow alignment. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5. Alternatively, multiple sequence alignment may be derived using MAFFT alignment from Gencious® version 10.2.4 with default settings, scoring matrix BLOSUM62, gap open penalty 1.53 and offset value 0.123.

The MUSCLE program (Robert C. Edgar. MUSCLE: multiple sequence alignment with high accuracy and high throughput *Nucl. Acids Res*. (2004) 32 (5): 1792-1797) is yet another example of a multiple sequence alignment algorithm.

A phylogenetic or evolutionary tree is depicted in FIG. 2 shows the relatedness among various phytases including the engineered phytase polypeptides and fragments thereof based upon similarities and differences in the amino acid sequence.

Another way to identify sequence similarities is to generate a Hidden Markov Model (HMM). HMMs are probabilistic frameworks where the observed data (such as a DNA or amino acid sequence) are modeled on a series of outputs (or emissions) generated by one of several (hidden) internal states. HMMs are frequently used for the statistical analysis of multiple DNA sequence alignments. They can be used to identify genomic features such as ORFs, insertions, deletions, substitutions and protein domains, amongst many others. HMMs can also be used to identify homologies; the widely used Pfam database (Punta et al., 2012), for example, is a database of protein families identified using HMMs. HMMs can be significantly more accurate than the workhorse of sequence comparison tools, BLAST® (Basic Local Alignment Search Tool), first produced in 1990 (Altschul et al., 1990, 1997). Accordingly, the polypeptide sequences of the High Tm Phytase Clade polypeptides and fragments thereof shown in Example 4 were used to generate a Hidden Markov Model (HMM) to identify sequence similarities.

The term "engineered phytase polypeptide" means that the polypeptide is not naturally occurring and has phytase activity.

It is noted that a fragment of the engineered phytase polypeptide is a portion or subsequence of the engineered phytase polypeptide that is capable of functioning like the engineered phytase polypeptide, i.e., it retains phytase activity.

The term "vector" refers to a polynucleotide sequence designed to introduce nucleic acids into one or more cell types. Vectors include, but are not limited to, cloning vectors, expression vectors, shuttle vectors, plasmids, phage particles, cassettes and the like.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "expression", as used herein, refers to the production of a functional end-product (e.g., an mRNA or a protein) in either precursor or mature form. Expression may also refer to translation of mRNA into a polypeptide.

Expression of a gene involves transcription of the gene and translation of the mRNA into a precursor or mature protein. "Mature" protein refers to a post-translationally processed polypeptide; i.e., one from which any signal sequence, pre- or propeptides present in the primary translation product have been removed. "Precursor" protein refers to the primary product of translation of mRNA; i.e., with pre- and propeptides still present. Pre- and propeptides may be but are not limited to intracellular localization signals. "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

Thus, in one embodiment, there is described a recombinant construct comprising a regulatory sequence functional in a production host operably linked to a nucleotide sequence encoding an engineered phytase polypeptide and fragments thereof as described herein.

This recombinant construct may comprise a regulatory sequence functional in a production host operably linked to a nucleotide sequence encoding any of the engineered phytase polypeptide and fragments thereof described herein. Furthermore, the production host is selected from the group consisting of bacteria, fungi, yeast, plants or algae. The preferred production host is the filamentous fungus, *Trichoderma reesei*.

Alternatively, it may be possible to use cell-free protein synthesis as described in Chong, Curr Protoc *Mol Biol.* 2014; 108:16.30.1-16.30.11.

Also described herein is a method for producing an engineered phytase polypeptide or fragment thereof comprising:
(a) transforming a production host with the recombinant construct described herein; and
(b) culturing the production host of step (a) under conditions whereby the engineered phytase polypeptide or fragment thereof is produced.

Optionally, the engineered phytase polypeptide or fragment thereof may be recovered from the production host.

In another aspect, a phytase-containing culture supernatant can be obtained by any of the methods disclosed herein.

In another embodiment, there is described a polynucleotide sequence encoding any of the engineered phytase polypeptides or fragments thereof as described herein.

Possible initiation control regions or promoters that can be included in the expression vector are numerous and familiar to those skilled in the art. A "constitutive promoter" is a promoter that is active under most environmental and developmental conditions. An "inducible" or "repressible" promoter is a promoter that is active under environmental or developmental regulation. In some embodiments, promoters are inducible or repressible due to changes in environmental factors including but not limited to, carbon, nitrogen or other nutrient availability, temperature, pH, osmolarity, the presence of heavy metal(s), the concentration of inhibitor(s), stress, or a combination of the foregoing, as is known in the art. In some embodiments, the inducible or repressible promoters are inducible or repressible by metabolic factors, such as the level of certain carbon sources, the level of certain energy sources, the level of certain catabolites, or a combination of the foregoing as is known in the art.

In one embodiment, the promoter is one that is native to the host cell. For example, in some instances when *Trichoderma reesei* is the host, the promoter can be a native *T. reesei* promoter such as the cbh1 promoter which is deposited in GenBank® under Accession Number D86235. Other suitable non-limiting examples of promoters useful for fungal expression include, cbh2, egl1, egl2, egl3, egl4, egl5, xyn1, and xyn2, repressible acid phosphatase gene (phoA) promoter of *P. chrysogenus* (see e.g., Graessle et al., (1997) *Appl. Environ. Microbiol.,* 63:753-756), glucose repressible PCKI promoter (see e.g., Leuker et al., (1997), *Gene,* 192:235-240), maltose inducible, glucose-repressible MET3 promoter (see Liu et al., (2006), *Eukary. Cell,* 5:638-649), pKi promoter and cpc 1 promoter. Other examples of useful promoters include promoters from *A. awamori* and *A. niger* glucoamylase genes (see e.g., Nunberg et al., (1984) *Mol. Cell Biol.* 15 4:2306-2315 and Boel et al., (1984) *EMBO J.* 3:1581-1585). Also, the promoters of the *T. reesei* xln1 gene may be useful (see e.g., EPA 137280A1).

DNA fragments which control transcriptional termination may also be derived from various genes native to a preferred production host cell. In certain embodiments, the inclusion of a termination control region is optional. In certain embodiments, the expression vector includes a termination control region derived from the preferred host cell.

The terms "production host", "production host cell", "host cell" and "host strains" are used interchangeable herein and mean a suitable host for an expression vector or DNA construct comprising a polynucleotide encoding phytase polypeptide or fragment thereof. The choice of a production host can be selected from the group consisting of bacteria, fungi, yeast, plants and algae. Typically, the choice will depend upon the gene encoding the engineered phytase polypeptide or fragment thereof and its source.

Specifically, host strains are preferably filamentous fungal cells. In a preferred embodiment of the invention, "host cell" means both the cells and protoplasts created from the cells of a filamentous fungal strain and particularly a *Trichoderma* sp. or an *Aspergillus* sp.

The term "filamentous fungi" refers to all filamentous forms of the subdivision Eumycotina (Sec, Alexopoulos, C. J. (1962), *INTRODUCTORY MYCOLOGY*, Wiley, New York). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolismis obligatory aerobic. In the present invention, the filamentous fungal parent cell may be a cell of a species of, but not limited to, *Trichoderma*, (e.g., *Trichoderma reesei* (previously classified as *T. longibrachiatum* and currently also known as *Hypocrea jecorina*), *Trichoderma viride*, *Trichoderma koningii*, *Trichoderma harzianum*); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *A. oryzae*, *A. niger*, and *A. awamori*), *Fusarium* sp., *Neurospora* sp., *Hypocrea* sp., and *Emericella* sp. (See also, Innis et al., (1985) Sci. 228:21-26).

As used herein, the term "*Trichoderma*" or "*Trichoderma* sp." refer to any fungal genus previously or currently classified as *Trichoderma*.

An expression cassette can be included in the production host, particularly in the cells of microbial production hosts. The production host cells can be microbial hosts found within the fungal families and which grow over a wide range of temperature, pH values, and solvent tolerances. For example, it is contemplated that any of bacteria, yeast, plants, algae, or fungi such as filamentous fungi, may suitably host the expression vector.

Inclusion of the expression cassette in the production host cell may be used to express the protein of interest so that it may reside intracellularly, extracellularly, or a combination of both inside and outside the cell. Extracellular expression renders recovery of the desired protein from a fermentation product more facile than methods for recovery of protein produced by intracellular expression.

Methods for transforming nucleic acids into filamentous fungi such as *Aspergillus* spp., e.g., *A. oryzae* or *A. niger, H. grisea, H. insolens,* and *T. reesei.* are well known in the art. A suitable procedure for transformation of *Aspergillus* host cells is described, for example, in EP238023.

A suitable procedure for transformation of *Trichoderma* host cells is described, for example, in Steiger et al 2011, *Appl. Environ. Microbiol.* 77:114-121. Uptake of DNA into the host *Trichoderma* sp. strain is dependent upon the calcium ion concentration. Generally, between about 10 mM $CaCl_2$) and 50 mM $CaCl_2$) is used in an uptake solution. Besides the need for the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes, thus permitting the contents of the medium to be delivered into the cytoplasm of the *Trichoderma* sp. strain and the plasmid DNA is transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of 105 to 107/mL, preferably $2\times10^6$/mL are used in transformation. A volume of 100 μL of these protoplasts or cells in an appropriate solution (e.g., 1.2 M sorbitol; 50 mM $CaCl_2$)) are mixed with the desired DNA. Generally, a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. (see, e.g., U.S. Pat. Nos. 6,022,725 and 6,268,328, both of which are incorporated by reference).

Preferably, genetically stable transformants are constructed with vector systems whereby the nucleic acid encoding the phytase polypeptide or fragment thereof is stably integrated into a host strain chromosome. Transformants are then purified by known techniques.

After the expression vector is introduced into the cells, the transfected or transformed cells are cultured under conditions favoring expression of genes under control of the promoter sequences.

Generally, cells are cultured in a standard medium containing physiological salts and nutrients (see, e.g., Pourquic, J. et al., BIOCHEMISTRY AND GENETICS OF CELLULOSE DEGRADATION, eds. Aubert, J. P. et al., *Academic Press*, pp. 71-86, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present invention.

Culture-conditions are also standard, (e.g., cultures are incubated at approximately 28° C. in appropriate medium in shake cultures or fermenters until desired levels of phytase expression are achieved). Preferred culture conditions for a given filamentous fungus are known in the art and may be found in the scientific literature and/or from the source of the fungi such as the American Type Culture Collection and Fungal Genetics Stock Center.

After fungal growth has been established, the cells are exposed to conditions effective to cause or permit the expression of a phytase and particularly a phytase as defined herein. In cases where a phytase coding sequence is under the control of an inducible promoter, the inducing agent (e.g., a sugar, metal salt or antimicrobial), is added to the medium at a concentration effective to induce phytase expression. An engineered phytase polypeptide or fragment thereof secreted from the host cells can be used, with minimal post-production processing, as a whole broth preparation.

The preparation of a spent whole fermentation broth of a recombinant microorganism can be achieved using any cultivation method known in the art resulting in the expression of an engineered phytase polypeptide or fragment thereof.

The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

After fermentation, a fermentation broth is obtained, the microbial cells and various suspended solids, including residual raw fermentation materials, are removed by conventional separation techniques in order to obtain a phytase solution. Filtration, centrifugation, microfiltration, rotary vacuum drum filtration, ultrafiltration, centrifugation followed by ultrafiltration, extraction, or chromatography, or the like, are generally used.

It is possible to optionally recover the desired protein from the production host. In another aspect, an engineered phytase polypeptide or fragment thereof containing culture supernatant is obtained by using any of the methods known to those skilled in the art.

Examples of these techniques include, but are not limited to, affinity chromatography (Tilbeurgh et a., (1984) *FEBS Lett.* 16:215), ion-exchange chromatographic methods (Goyal et al., (1991) *Biores. Technol.* 36:37; Fliess et al., (1983) *Eur. J. Appl. Microbiol. Biotechnol.* 17:314; Bhikhabhai et al, (1984) *J. Appl. Biochem.* 6:336; and Ellouz et al., (1987) *Chromatography* 396:307), including ion-exchange using materials with high resolution power (Medve et al., (1998) *J. Chromatography A* 808:153), hydrophobic interaction chromatography (Sec, Tomaz and Queiroz, (1999) *J. Chromatography A* 865:123; two-phase partitioning (Sec, Brumbauer, et al., (1999) *Bioseparation* 7:287); ethanol precipitation; reverse phase HPLC, chromatography on silica or on a cation-exchange resin such as DEAE, chromatofocusing, SDS-PAGE, ammonium sulfate precipitation, and gel filtration (e.g., Sephadex® G-75). The degree of purification desired will vary depending on the use of the engineered phytase polypeptide or fragment thereof. In some embodiments, purification will not be necessary.

On the other hand, it may be desirable to concentrate a solution containing an engineered phytase polypeptide or fragment thereof in order to optimize recovery. Use of unconcentrated solutions requires increased incubation time in order to collect the enriched or purified enzyme precipitate. The enzyme containing solution is concentrated using conventional concentration techniques until the desired enzyme level is obtained. Concentration of the enzyme containing solution may be achieved by any of the techniques discussed herein. Exemplary methods of enrichment and purification include but are not limited to rotary vacuum filtration and/or ultrafiltration.

In addition, concentration of the desired protein product may be performed using, e.g., a precipitation agent, such as a metal halide precipitation agent. The metal halide precipitation agent, sodium chloride, can also be used as a preservative. The metal halide precipitation agent is used in an amount effective to precipitate the engineered phytase polypeptide or fragment thereof. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing. Generally, at least about 5% w/v (weight/volume) to about 25% w/v of metal halide is added to the concentrated enzyme solution, and usually at least 8% w/v.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of the organic compound precipitation agents can take place prior to, simultaneously with or subsequent to the addition of the metal halide precipitation agent, and the addition of both precipitation agents, organic compound and metal halide, may be carried out sequentially or simultaneously. Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. Additional organic compounds also include but are not limited to 4-hydroxybenzoic acid methyl ester (named methyl PARABEN), 4-hydroxybenzoic acid propyl ester (named propyl PARABEN). For further descriptions, see, e.g., U.S. Pat. No. 5,281,526. Addition of the organic compound precipitation agent provides the advantage of high flexibility of the precipitation conditions with respect to pH, temperature, concentration, precipitation agent, protein concentration, and time of incubation. Generally, at least about 0.01% w/v and no more than about 0.3% w/v of organic compound precipitation agent is added to the concentrated enzyme solution.

After the incubation period, the enriched or purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further enrichment or purification of the enzyme precipitate can be obtained by washing the precipitate with water. For example, the enriched or purified enzyme precipitate is washed with water containing the metal halide precipitation agent, or with water containing the metal halide and the organic compound precipitation agents.

Sometimes it is advantageous to delete genes from expression hosts, where the gene deficiency can be cured by an expression vector. Where it is desired to obtain a fungal host cell having one or more inactivated genes known methods may be used (e.g, methods disclosed in U.S. Pat. Nos. 5,246,853, 5,475,101 and WO92/06209). Gene inactivation may be accomplished by complete or partial deletion, by insertional inactivation or by any other means which renders a gene nonfunctional for its intended purpose (such that the gene is prevented from expression of a functional protein).

Any gene from a *Trichoderma* sp. or other filamentous fungal host, which has been cloned can be deleted, for example cbh1, cbh2, egl1 and egl2 genes. In some embodiments, gene deletion may be accomplished by inserting a form of the desired gene to be inactivated into a plasmid by methods known in the art. The deletion plasmid is then cut at an appropriate restriction enzyme site(s), internal to the desired gene coding region, and the gene coding sequence or part thereof is replaced with a selectable marker. Flanking DNA sequences from the locus of the gene to be deleted (preferably between about 0.5 to 2.0 kb) remain on either side of the marker gene. An appropriate deletion plasmid will generally have unique restriction enzyme sites present therein to enable the fragment containing the deleted gene, including the flanking DNA sequences and the selectable markers gene to be removed as a single linear piece.

Depending upon the host cell used post-transcriptional and/or post-translational modifications may be made. One non-limiting example of a post-transcriptional and/or post-translational modification is "clipping" or "truncation" of a polypeptide. In another instance, this clipping may result in taking a mature phytase polypeptide and further removing N or C-terminal amino acids to generate truncated forms of the phytase that retain enzymatic activity.

Other examples of post-transcriptional or post-translational modifications include, but are not limited to, myristoylation, glycosylation, truncation, lipidation and tyrosine, serine or threonine phosphorylation. The skilled person will appreciate that the type of post-transcriptional or post-translational modifications that a protein may undergo may depend on the host organism in which the protein is expressed.

Further sequence modifications of polypeptides post expression may occur. This includes, but is not limited to, oxidation, deglycosylation, glycation, etc. It is known that glycation can affect the activity of phytase when subjected to incubation with glucose or other reducing sugars especially at temperatures above 30° C. and neutral or alkaline pH. Protein engineering to eliminate Lysine residues can be used to prevent such modification. An example of this can be found in U.S. Pat. No. 8,507,240. For example, yeast expression can result in highly glycosylated polypeptides resulting in an apparent increased molecular weight. Also, WO2013/119470 (incorporated by reference herein) having international publication date Aug. 15, 2013 relates to phytases having increased stability believed to be due to increased glycosylation.

The term "glycosylation" as used herein refers to the attachment of glycans to molecules, for example to proteins. Glycosylation may be an enzymatic reaction. The attachment formed may be through covalent bonds. The phrase "highly glycosylated" refers to a molecule such as an enzyme which is glycosylated in many sites and at all or nearly all the available glycosylation sites, for instance N-linked glycosylation sites. Alternatively, or in addition to, the phrase "highly glycosylated" can refer to extensive glycolytic branching (such as, the size and number of glycolytic moieties associated with a particular N-linked glycosylation site) at all or substantially all N-linked glycosylation sites. In some embodiments, the engineered phytase polypeptide is glycosylated at all or substantially all consensus N-linked glycosylation sites (i.e. an NXS/T consensus N-linked glycosylation site).

The term "glycan" as used herein refers to a polysaccharide or oligosaccharide, or the carbohydrate section of a glycoconjugate such as a glycoprotein. Glycans may be homo- or heteropolymers of monosaccharide residues. They may be linear or branched molecules.

A phytase may have varying degrees of glycosylation. It is known that such glycosylations may improve stability during storage and in applications. Extensive The activity of any of the engineered phytase polypeptides or fragments thereof disclosed herein can be determined as discussed above.

As those skilled in the art will appreciate, enzymes are fragile proteins always under threat in the harsh environment of the feed mill. Extremes of temperature, pressure, friction, pH and microbial activity can degrade or destroy enzymes added to feed. The stress on enzyme activity strikes mostly during the conditioning and pelleting phases of processing. For example, the feed absorbs most of its thermal energy during conditioning, prior to pelleting. However, passage from the conditioner through the pellet die also heats the feed. Many factors can contribute to temperature rise through the die, such as, feed formulation, die thickness, die speed, die specification (hole size and shape), initial processing temperature, pelleting capacity etc.

Thus, conditions during feed pelleting on an industrial scale may vary. The ability or robustness of an enzyme to withstand these variations in pelleting conditions is very important. One of ordinary skill in the art will appreciate that conditioning temperatures may vary from feed mill to feed mill. Furthermore, local law needs to be considered in determining the conditions under which the pelleting process is carried out. For instance, Danish law requires 81° C. pelleting of feed for poultry (Miljø-og Fødevareministeriet, fødevarestyrelsen, j.nr. 2017-32-31-00378).

Also, higher temperature pelleting conditions may be used in industry to increase pellet quality such as better durability and reduction of fines and to increase pellet press capacity. A need for a robust phytase that when incorporated in feed prior to conditioning and pelleting can produce pellets of consistent activity over a wide range of temperatures above 80° C. therefore exists. This is important both for liquid-applied phytases and for solid-applied phytases as described herein.

Factors beyond conditioning temperature that may influence the actual stress that a feed enzyme may be subject to include, but are not limited to, feed raw materials, geographical location of the feed mill, equipment used, die size, use of pelleting aids, steam control, temperature control and any other commercially relevant pelleting conditions such as the presence of any other exogenous enzymes that modify feed in such a manner so as to reduce pelleting stress.

These stress factors are further compounded by a trend toward high temperature or super conditioning which leads to the application of enzymes in a liquid form applied post-pelleting.

What if a robust enzyme could be engineered so that it could be applied as a liquid prior to conditioning and pelleting?

The terms "robust" and "robustness" are used interchangeably herein and mean the capability of the engineered phytase or fragment thereof disclosed herein to withstand the variations in conditioning and pelleting processes in industrial feed production. The engineered phytase polypeptides and fragments thereof disclosed herein as part of the high Tm-phytase clade polypeptides and fragments thereof are examples of such robust enzymes which can be applied to feed in a liquid form prior to conditioning and pelleting.

In other words, the novel engineered phytase polypeptides and fragments thereof are capable of withstanding such variations in industrial feed pelleting processes in an unformulated, uncoated, unprotected form when applied in a liquid form or unformulated, uncoated, unprotected solid form to feed prior to conditioning and pelleting.

The terms "liquid", "liquid form" and "liquid preparation" are used interchangeably and mean that an enzyme can be applied in a liquid form to feed in any manner prior to conditioning and pelleting.

It is believed that applying a robust engineered phytase polypeptide or fragment thereof to feed in a liquid form is beneficial as compared to applying such a phytase as a coated granule. This coated granule is the current commercial approach to make phytase products suitable for high temperature conditioning and pelleting. Benefits of liquid application of robust enzyme include; 1) the enzyme will start to work immediately after ingestion by an animal since it does not have to be released from the coated granule before it can interact with the feed, 2) there is improved distribution of the enzyme throughout the feed, thus, ensuring a more consistent delivery of the enzyme to the animal which is particularly important for young animals that eat small amounts of feed, 3) even distribution in the feed makes it easier to measure the enzyme in the feed, and 4) in the case of a robust phytase, such as the engineered phytase polypeptide and fragment disclosed herein, it may start to degrade phytate already present in the feed.

In other words, the novel engineered phytase polypeptides and fragments thereof are so robust that no special coating or formulation is believed to be needed to apply them to feed prior to conditioning and pelleting since they have been engineered to withstand the stress of conditioning and pelleting used in industrial feed production. Accordingly, the robustness of the novel engineered phytase polypeptides and fragments thereof described herein is such that they can be applied as an uncoated granule or particle or uncoated and unprotected when put into a liquid.

It should be noted that the engineered phytase polypeptides and fragments thereof can be formulated inexpensively on a solid carrier without specific need for protective coatings and still maintain activity throughout the conditioning and pelleting process. A protective coating to provide additional thermostability when applied in a solid form can be beneficial for obtaining pelleting stability when required in certain regions where harsher conditions are used or if conditions warrant it, e.g., as in the case of super conditioning feed above 90° C.

The disclosed engineered phytase polypeptides or fragments thereof were derived using a combination of methods and techniques know in the field of protein engineering which include, phylogenetic analysis, site evaluation libraries, combinatorial libraries, high throughput screening and statistical analysis.

In one aspect, the disclosure relates to an engineered phytase polypeptide or fragment thereof also that has at least 82% sequence identity with the amino acid sequence of SEQ ID NO: 1.

Those skilled in the art will appreciate that such at least 82% sequence identity also includes 82%, 83%, 84%, 85%, 86%, 87%, 88%, 89%, 90%, 91%, 92%, 93%, 94%, 95%, 96%, 97%, 98%, 99% or 100%.

Those skilled in the art will appreciate that at least 79% sequence identity also includes 79%, 80%, 81%, 82%, 83%, 84%, 85%, 86%, 87%, 88%, 89%, 90%, 91%, 92%, 93%, 94%, 95%, 96%, 97%, 98%, 99% or 100%.

There can also be mentioned the following in that in some embodiments, there is provided:
a) an engineered phytase polypeptide or fragment thereof also that has at least 81% (such as 81%, 82%, 83%, 84%, 85%, 86%, 87%, 88%, 89%, 90%, 91%, 92%, 93%, 94%, 95%, 96%, 97%, 98%, 99% or 100%) sequence identity with the amino acid sequence of SEQ ID NOs: 2, 3, 8, 10, 12, 18, 19, 24, 26, 27, 28, 30, 31, 32, 33, and/or 36.
b) an engineered phytase polypeptide or fragment thereof also that has at least 82% (such as 82%, 83%, 84%, 85%, 86%, 87%, 88%, 89%, 90%, 91%, 92%, 93%, 94%, 95%, 96%, 97%, 98%, 99% or 100%) sequence identity with the amino acid sequence of SEQ ID NOs: 1, 4, 5, 7, 9, 11, 14, 15, 17, 21, 25, 34, and/or 35;
c) an engineered phytase polypeptide or fragment thereof also that has at least 83% (such as, 83%, 84%, 85%, 86%, 87%, 88%, 89%, 90%, 91%, 92%, 93%, 94%, 95%, 96%, 97%, 98%, 99% or 100%) sequence identity with the amino acid sequence of SEQ ID NO:13;
d) an engineered phytase polypeptide or fragment thereof also that has at least 79% (such as, 79%, 80%, 81%, 82%, 83%, 84%, 85%, 86%, 87%, 88%, 89%, 90%, 91%, 92%, 93%, 94%, 95%, 96%, 97%, 98%, 99% or 100%) sequence identity with the amino acid sequence of SEQ ID NOs: 6, 22, and/or 64; and/or
e) an engineered phytase polypeptide or fragment thereof also that has at least 80% (such as, 80%, 81%, 82%, 83%, 84%, 85%, 86%, 87%, 88%, 89%, 90%, 91%, 92%, 93%, 94%, 95%, 96%, 97%, 98%, 99% or 100%) sequence identity with the amino acid sequence of SEQ ID NOs: 16, 20, 23, 29, and/or 37.

In further aspects, the polypeptide comprises a core domain of an engineered phytase polypeptide or is a core domain fragment of an engineered phytase polypeptide. A "core domain fragment" is herein defined as a polypeptide having one or more amino acids deleted from the amino and/or carboxyl terminus of the polypeptide. As used herein, the phrase "core domain" refers to a polypeptide region encompassing amino acids necessary to maintain the structure and function (such as, phytic acid hydrolysis) of the polypeptide. Amino acids in the core domain can be further modified to improve thermostability or catalytic activity under various conditions such as, without limitation, pH. In some non-limiting embodiments, the core domain of the engineered phytase polypeptides or fragment thereof disclosed herein corresponds to amino acid positions 14-325 of SEQ ID NO:1. In other non-limiting embodiments, the core domain corresponds to amino acid positions 13-326, 12-327, 11-328, 10-329, 9-330, 8-331, 7-332, 6-333, 5-334, 4-335, 3-336, 2-337, or 1-338 of SEQ ID NO:1. In other embodiments, the N-terminus of the core domain corresponds to amino acid position 1, 2, 3, 4, 5, 6, 7, 8, 9, 10, 11, 12, 13, 14, 15, 16, 17, 18, 19, 20, 21, 22, 23, 24, or 25 of SEQ ID NO:1 and the C-terminus of the core domain corresponds to amino acid position 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, or 413 of SEQ ID NO:1.

Accordingly, also provided herein are:
f) an engineered phytase polypeptide or core domain fragment thereof that has at least 78% (such as, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%) sequence identity to amino acids 14-325 of SEQ ID NOs: 6 and/or 64, wherein said amino acid positions correspond to those of SEQ ID NO: 1;
g) an engineered phytase polypeptide or core domain fragment thereof that has at least 79% (such as, 79%, 80%, 81%, 82%, 83%, 84%, 85%, 86%, 87%, 88%, 89%, 90%, 91%, 92%, 93%, 94%, 95%, 96%, 97%, 98%, 99% or 100%) sequence identity to amino acids 14-325 of SEQ ID NOs: 2, 8, 27, and/or 37, wherein said amino acid positions correspond to those of SEQ ID NO: 1;
h) an engineered phytase polypeptide or core domain fragment thereof that has at least 81% (such as, 81%, 82%, 83%, 84%, 85%, 86%, 87%, 88%, 89%, 90%, 91%, 92%, 93%, 94%, 95%, 96%, 97%, 98%, 99% or 100%) sequence identity to amino acids 14-325 of SEQ ID NOs: 3, 10, 12, 18, 25, 26, 28, 30, 32, 35, 65, 70, and/or 86, wherein said amino acid positions correspond to those of SEQ ID NO:1;
i) an engineered phytase polypeptide or core domain fragment thereof that has at least 82% (such as, 82%, 83%, 84%, 85%, 86%, 87%, 88%, 89%, 90%, 91%, 92%, 93%, 94%, 95%, 96%, 97%, 98%, 99% or 100%) sequence identity to amino acids 14-325 of SEQ ID NOs: 1, 4, 5, 7, 9, 11, 13-17, 21, 22, 31, 33, 34, 36, 64, 66-69, and/or 71-84, wherein said amino acid positions correspond to those of SEQ ID NO:1;
j) an engineered phytase polypeptide or core domain fragment thereof that has at least 83% (such as, 83%, 84%, 85%, 86%, 87%, 88%, 89%, 90%, 91%, 92%, 93%, 94%, 95%, 96%, 97%, 98%, 99% or 100%) sequence identity to amino acids 14-325 of SEQ ID NOs: 19, 20, 23, and/or 24, wherein said amino acid positions correspond to those of SEQ ID NO:1; and/or
k) an engineered phytase polypeptide or core domain fragment thereof that has at least 84% (such as, 84%, 85%, 86%, 87%, 88%, 89%, 90%, 91%, 92%, 93%, 94%, 95%, 96%, 97%, 98%, 99% or 100%) sequence identity to amino acids 14-325 of SEQ ID NO:29, wherein said amino acid positions correspond to those of SEQ ID NO:1.

In still another aspect, the engineered phytase polypeptides or fragment thereof having at least 82% sequence identity with the amino acid sequence of SEQ ID NO: 1 may also have an amino acid sequence which has a Hidden Markov Model (HMM) score of at least about 1200 (such as at least about 1250, 1300, 1350, 1400, 1450, 1500, 1550, 1600, 1650, 1700, 1750, or 1800) as set forth in Table 11 for the high Tm phytase clade polypeptides.

In still other aspects, any of the engineered phytase polypeptides or fragments thereof disclosed herein can comprise one or more specific amino acid substitutions at one or more positions within its polypeptide sequence. As such, in some embodiments, provided herein are engineered phytase polypeptides or fragments thereof comprising one or more (such as 1, 2, 3, 4, 5, 6, 7, 8, 9, 10, 11, or 12) amino acid substitutions selected from the group consisting of 30(L, I), 37Y, 45P, 89T, 182R, 194M, 195F, 202S, 228Y, 256H, 261H, and 298V, wherein the positions correspond to the numbering of SEQ ID NOs: 1 or 57.

Further or in addition, any of the engineered phytase polypeptides or fragments thereof can comprise one or more (such as 1, 2, 3, 4, 5, 6, 7, 8, 9, 10, or 11) amino acid substitutions selected from the group consisting of 3T, 6S, 9Q, 73I, 76K, 78S, 118Q, 123A, 130V, 163P, 186D, 187K, 209A, 284S, 288A, 289R, 337V, 345A, and 347K, wherein the positions correspond to the numbering of SEQ ID NO:1. In some embodiments, the engineered phytase polypeptide is selected from the group consisting of SEQ ID NO:67, SEQ ID NO:68, SEQ ID NO: 69, SEQ ID NO:70, SEQ ID NO:71, SEQ ID NO: 72, SEQ ID NO:73, SEQ ID NO:74, SEQ ID NO: 75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO: 86, and SEQ ID NO:87.

Engineered phytase polypeptides or fragments thereof containing one or more amino acid substitutions can exhibit one or more improved or enhanced properties such as, but not limited to, improved thermostability (such as any of about a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% or greater (inclusive of all percentages falling in between these values) improvement in thermostability) or improved activity (e.g. improved specific activity and/or activity at pH 3.5 compared to activity at pH 5.5) (such as any of about a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% or greater (inclusive of all percentages falling in between these values) improvement in activity) compared to phytase polypeptides or fragments thereof that do not comprise said one or more amino acid substitutions.

In yet other aspects, any of the engineered phytase polypeptides or fragments thereof disclosed herein can have one or more substitutions (such as one or more of the substitutions disclosed above) that increase the ratio between the activity (e.g., specific activity) of the phytase at pH 3.5 versus pH 5.5. Consequently, in some embodiments, any of the engineered phytase polypeptides or fragments thereof disclosed herein have a ratio of activity (e.g., specific activity) at pH 3.5 compared to the activity (e.g., specific activity) at pH 5.5 of greater than or equal to about 1.2 (such as any of about 1.2, 1.3, 1.4, 1.5, 1.6, 1.7, 1.8, 1.9, 2.0 or higher).

Also described is an engineered phytase polypeptide or fragment thereof having in-feed pelleting recovery of at least 50% when applied in MLA at 95° C. for 30 seconds using a standard in-feed pelleting recovery test. Furthermore, the engineered phytase polypeptide or fragment thereof having in-feed pelleting recovery of at least 50% as described herein may also have at least 82% sequence identity with the amino acid sequence set forth in SEQ ID NO:1.

The in-feed pelleting recovery can range anywhere from about 50% to about 100%, specifically, about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In some embodiments, the engineered phytase polypeptide or fragment thereof has an in-feed pelleting recovery of at least about 60%, 65%, 70%, 75%, 70%, 85%, 90%, 95% or 99% when applied as a solid at 95° C.

Those skilled in the art will appreciate that in-feed pelleting recoveries can vary based on the type of feed used, conditioning and pelleting conditions used, e.g., temperature and moisture content, assay used to determine activity, etc.

Any of the engineered phytase polypeptides or fragments thereof disclosed herein have a ratio of in-feed pelleting recoveries of at least 0.7 when applied in MLA at 95° C. for 30 seconds as compared to application in MLA at 80° C. for 30 seconds, using a standard in-feed pelleting test. This ratio includes about 0.7, 0.8, 0.9, 0.91, 0.92, 0.93, 0.94, 0.95, 0.96, 0.97, 0.98 and 0.99.

In another embodiment, there is disclosed an engineered phytase polypeptide or fragment thereof having a ratio of in-feed pelleting recoveries when applied in MLA at 95° C. for 30 seconds as compared to application in MLA at 80° C. for 30 seconds, of at least about 3.5, 3.6, 3.7, 3.8, 3.9, 4.0, 4.1, 4.2, 4.3, 4.4, 4.5, 4.6, 4.7, 4.8, 4.9 or 5.0, as compared a) SEQ ID NO:60; b) SEQ ID NO:60 with A25F and G157R substitutions; c) SEQ ID NO:104; and/or d) amino acids 22-431 of SEQ ID NO:104.

In another embodiment, there is disclosed an engineered phytase polypeptide or fragment thereof having a ratio of ratio of in-feed pelleting recoveries when applied in MLA at 95° C. for 30 seconds as compared to application in MLA at 80° C. for 30 seconds, of at least about 3.5, 3.6, 3.7, 3.8, 3.9, 4.0, 4.1, 4.2, 4.3, 4.4, 4.5, 4.6, 4.7, 4.8, 4.9 or 5.0, as compared to a) SEQ ID NO: 60; b) SEQ ID NO:60 with A25F and G157R substitutions; c) SEQ ID NO:104; and/or d) amino acids 22-431 of SEQ ID NO:104.

Any of the engineered phytase polypeptides or fragments thereof disclosed herein may further comprise a $T_m$ temperature of at least about 92.5° C., about 93° C., about 94° C., about 95° C., about 96° C., about 97° C., about 98° C., about 99° C., about 100° C., or about 101° C., using differential scanning calorimetric assay conditions described in Example 3 and results are provided in Example 4.

In another embodiment, there is disclosed an engineered phytase polypeptide or fragment thereof having a ratio of Tm temperature of at least about 1.08, 1.10, 1.12, 1.14, 1.16, 1.18 or 1.20 2.1, 2.4, 2.7, 3.0, or 3.3 as measured by differential scanning calorimetry, as compared to a) SEQ ID NO:60; b) SEQ ID NO:60 with A25F and G157R substitutions; c) SEQ ID NO:104; and/or d) amino acids 22-431 of SEQ ID NO:104.

In another aspect, any of the engineered polypeptides or fragments thereof disclosed herein comprise a specific activity of at least about 100 U/mg at pH 3.5 under assay conditions such as those described in Example 4. The specific activity range (U/mg at pH 3.5) includes, but is not limited to, about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 2000, etc.

In another aspect, some of the engineered polypeptides or fragments thereof disclosed herein comprise a specific activity of at least about 100 U/mg at pH 5.5 under assay conditions such as those described in Example 4. The specific activity range (U/mg at pH 5.5) includes, but is not limited to, about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 2000, etc.

In still another aspect, any of the engineered phytase polypeptides or fragments thereof disclosed herein may be stable in a liquid form at a pH about 3.0 or lower. This is very relevant when engineered phytase polypeptides or fragments thereof described herein are passing through the digestive tract of an animal as is discussed below.

In another embodiment, there is described an animal feed, feedstuff, feed additive composition or premix comprising any of the engineered phytase polypeptides or fragments thereof described herein.

Importantly, feed additive enzymes e.g. a phytase is subjected to very harsh conditions as it passes through the digestive track of an animal, i.e. low pH and presence of digestive enzymes. Pepsin is one of the most important proteolytic digestive enzymes present in the gastrointestinal tract of monogastric animals. Pepsin has low specificity and high pH tolerance in the acidic area (pH 1.5-6.0 stabile up to pH 8.0). The engineered phytase polypeptides or fragments thereof described herein are largely resistant against pepsin, which is necessary for good in-vivo performance.

The animal feed, feedstuff, feed additive composition or premix comprising any of the engineered phytase polypeptides or fragments thereof described herein may be used (i) alone or (ii) in combination with a direct fed microbial comprising at least one bacterial strain or (iii) with at least one other enzyme or (iv) in combination with a direct fed microbial comprising at least one bacterial strain and at least one other enzyme, or (v) any of (i), (ii), (iii) or (iv) further comprising at least one other feed additive component and, optionally, the engineered phytase polypeptide or fragment thereof is present in an amount of at least 0.1 g/ton feed.

The terms "feed additive", "feed additive components", and/or "feed additive ingredients" are used interchangeably herein.

Feed additives can be described as products used in animal nutrition for purposes of improving the quality of feed and the quality of food from animal origin, or to improve the animals' performance and health, e.g. providing enhanced digestibility of the feed materials.

Feed additives fall into a number of categories such as sensory additives which stimulate an animal's appetite so that they naturally want to eat more. Nutritional additives provide a particular nutrient that may be deficient in an animal's diet. Zootechnical additives improve the overall nutritional value of an animal's dict through additives in the feed.

Examples of such feed additives include, but are not limited to, prebiotics, essential oils (such as, without limitation, thymol and/or cinnamaldehyde), fatty acids, short chain fatty acids such as propionic acid and butyric acid, etc., vitamins, minerals, amino acids, etc.

Feed additive compositions or formulations may also comprise at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

At least one other enzyme (i.e. in addition to any of the engineered phytase polypeptides or fragments thereof disclosed herein) can be included in the feed additive compositions or formulations disclosed herein which can include, but are not limited to, a xylanase, amylase, another phytase, beta-glucanase, and/or a protease.

Xylanase is the name given to a class of enzymes that degrade the linear polysaccharide β-1,4-xylan into xylose, thus breaking down hemicellulose, one of the major components of plant cell walls. Xylanases, e.g., endo-β-xylanases (EC 3.2.1.8) hydrolyze the xylan backbone chain.

In one embodiment, the xylanase may be any commercially available xylanase. Suitably the xylanase may be an endo-1,4-P-d-xylanase (classified as E.G. 3.2.1.8) or a 1,4β-xylosidase (classified as E.G. 3.2.1.37). In one embodiment, the disclosure relates to a composition comprising any of the engineered phytase polypeptides or fragments thereof disclosed herein in combination with an endoxylanase, e.g. an endo-1,4-P-d-xylanase, and another enzyme. All E.C. enzyme classifications referred to herein relate to the classifications provided in Enzyme Nomenclature—Recommendations (1992) of the nomenclature committee of the International Union of Biochemistry and Molecular Biology—ISBN 0-12-226164-3, which is incorporated herein.

In another embodiment, the xylanase may be a xylanase from *Bacillus*, Trichodermna, Therinomyces, *Aspergillus, Humicola* and *Penicillium*. In still another embodiment, the xylanase may be the xylanase in Axtra XAP® or Avizyme 1502®, both commercially available products from Danisco A/S. In one embodiment, the xylanase may be a mixture of two or more xylanases. In still another embodiment, the xylanase is an endo-1,4-β-xylanase or a 1,4-β-xylosidase.

In one embodiment, the disclosure relates to a composition comprising any of the engineered phytase polypeptides or fragments thereof disclosed herein and a xylanase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 xylanase units/g of composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, and greater than 8000 xylanase units/g composition.

It will be understood that one xylanase unit (XU) is the amount of enzyme that releases 0.5 μmol of reducing sugar equivalents (as xylose by the Dinitrosalicylic acid (DNS) assay-reducing sugar method) from an oat-spelt-xylan substrate per min at pH 5.3 and 50° C. (Bailey, et al., *Journal of Biotechnology*, Volume 23, (3), May 1992, 257-270).

Amylase is a class of enzymes capable of hydrolysing starch to shorter-chain oligosaccharides, such as maltose. The glucose moiety can then be more easily transferred from maltose to a monoglyceride or glycosylmonoglyceride than from the original starch molecule. The term amylase includes α-amylases (E.G. 3.2.1.1), G4-forming amylases (E.G. 3.2.1.60), β-amylases (E.G. 3.2.1.2) and γ-amylases (E.C. 3.2.1.3). Amylases may be of bacterial or fungal origin, or chemically modified or protein engineered mutants.

In one embodiment, the amylase may be a mixture of two or more amylases. In another embodiment, the amylase may be an amylase, e.g. an α-amylase, from *Bacillus licheniformis* and an amylase, e.g. an α-amylase, from *Bacillus amyloliquefaciens*. In one embodiment, the α-amylase may be the α-amylase in Axtra XAP® or Avizyme 1502®, both commercially available products from Danisco A/S. In yet another embodiment, the amylase may be a pepsin resistant α-amylase, such as a pepsin resistant *Trichoderma* (such as *Trichoderma reesei*) alpha amylase. A suitably pepsin resistant α-amylase is taught in UK application number 101 1513.7 (which is incorporated herein by reference) and PCT/IB2011/053018 (which is incorporated herein by reference).

It will be understood that one amylase unit (AU) is the amount of enzyme that releases 1 mmol of glucosidic linkages from a water insoluble cross-linked starch polymer substrate per min at pH 6.5 and 37° C. (this may be referred to herein as the assay for determining 1 AU).

In one embodiment, disclosure relates to a composition comprising any of the engineered phytase polypeptides or fragments thereof disclosed herein and an amylase. In one embodiment, disclosure relates to a composition comprising any of the engineered phytase polypeptides or fragments thereof disclosed herein, xylanase and amylase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 amylase units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 amylase units/g composition.

The term protease as used herein is synonymous with peptidase or proteinase. The protease may be a subtilisin (E.G. 3.4.21.62) or a bacillolysin (E.G. 3.4.24.28) or an alkaline serine protease (E.G. 3.4.21.x) or a keratinase (E.G. 3.4.X.X). In one embodiment, the protease is a subtilisin. Suitable proteases include those of animal, vegetable or microbial origin.

Chemically modified or protein engineered mutants are also suitable. The protease may be a serine protease or a metalloprotease. e.g., an alkaline microbial protease or a trypsin-like protease. In one embodiment, provided herein are compositions comprising any of the engineered phytase polypeptides or fragments thereof disclosed herein and one or more protease.

Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115.

In one embodiment, the protease is selected from the group consisting of subtilisin, a bacillolysin, an alkine serine protease, a keratinase, and a Nocardiopsis protease.

It will be understood that one protease unit (PU) is the amount of enzyme that liberates from the substrate (0.6% casein solution) one microgram of phenolic compound (expressed as tyrosine equivalents) in one minute at pH 7.5 (40 mM $Na_2PO_4$/lactic acid buffer) and 40° C. This may be referred to as the assay for determining 1 PU.

In one embodiment, disclosure relates to a composition comprising any of the engineered phytase polypeptides or fragments thereof disclosed herein and a protease. In another embodiment, disclosure relates to a composition comprising any of the engineered phytase polypeptides or fragments thereof disclosed herein and a xylanase and a protease. In still another embodiment, the disclosure relates to a composition comprising any of the engineered phytase polypeptides or fragments thereof disclosed herein and an amylase and a protease. In yet another embodiment, the disclosure relates to a composition comprising any of the engineered phytase polypeptides or fragments thereof disclosed herein and a xylanase, an amylase and a protease.

In one embodiment, the composition comprises about 10-50, 50-100, 100-150, 150-200, 200-250, 250-300, 300-350, 350-400, 400-450, 450-500, 500-550, 550-600, 600-650, 650-700, 700-750, and greater than 750 protease units/g composition.

In one embodiment, the composition comprises about 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 protease units/g composition.

At least one direct fed microbial (DFM) may comprise at least one viable microorganism such as a viable bacterial strain or a viable yeast or a viable fungi. Preferably, the DFM comprises at least one viable bacteria.

It is possible that the DFM may be a spore forming bacterial strain and hence the term DFM may be comprised of or contain spores, e.g. bacterial spores. Thus, the term "viable microorganism" as used herein may include microbial spores, such as endospores or conidia. Alternatively, the DFM in the feed additive composition described herein may not comprise of or may not contain microbial spores, e.g. endospores or conidia.

The microorganism may be a naturally-occurring microorganism or it may be a transformed microorganism.

A DFM as described herein may comprise microorganisms from one or more of the following genera: *Lactobacillus, Lactococcus, Streptococcus, Bacillus, Pediococcus,*

*Enterococcus, Leuconostoc, Carnobacterium, Propionibacterium, Bifidobacterium, Clostridium* and *Megasphaera* and combinations thereof.

Preferably, the DFM comprises one or more bacterial strains selected from the following *Bacillus* spp: *Bacillus subtilis, Bacillus cereus, Bacillus licheniformis, Bacillus pumilis* and *Bacillus amyloliquefaciens*.

The genus "*Bacillus*", as used herein, includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. gibsonii, B. pumilis* and *B. thuringiensis*. It is recognized that the genus *Bacillus* continues to undergo taxonomical reorganization. Thus, it is intended that the genus include species that have been reclassified, including but not limited to such organisms as *Bacillus stearothermophilus*, which is now named "*Geobacillus stearothermophilus*", or *Bacillus polymyxa*, which is now "*Paenibacillus polymyxa*" The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In another aspect, the DFM may be further combined with the following *Lactococcus* spp: *Lactococcus cremoris* and *Lactococcus lactis* and combinations thereof.

The DFM may be further combined with the following *Lactobacillus* spp: *Lactobacillus buchneri, Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus farciminis, Lactobacillus rhamnosus, Lactobacillus crispatus, Lactobacillus gasseri, Lactobacillus johnsonii* and *Lactobacillus jensenii*, and combinations of any thereof.

In still another aspect, the DFM may be further combined with the following Bifidobacteria spp: *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*, and combinations of any thereof.

There can be mentioned bacteria of the following species: *Bacillus subtilis, Bacillus licheniformis, Bacillus amyloliquefaciens, Bacillus pumilis, Enterococcus, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Bacillus subtilis, Propionibacterium thoenii, Lactobacillus farciminis, Lactobacillus rhamnosus, Megasphaera elsdenii, Clostridium butyricum, Bifidobacterium animalis* ssp. *animalis, Lactobacillus reuteri, Bacillus cereus, Lactobacillus salivarius* ssp. *Salivarius*, Propionibacteria sp and combinations thereof.

A direct-fed microbial described herein comprising one or more bacterial strains may be of the same type (genus, species and strain) or may comprise a mixture of genera, species and/or strains.

Alternatively, a DFM may be combined with one or more of the products or the microorganisms contained in those products disclosed in WO2012110778, and summarized as follows: *Bacillus subtilis* strain 2084 Accession No. NRRLB-50013, *Bacillus subtilis* strain LSSAO1 Accession No. NRRL B-50104, and *Bacillus subtilis* strain 15A-P4 ATCC Accession No. PTA-6507 (from Enviva Pro®. (formerly known as Avicorr®); *Bacillus subtilis* Strain C3102 (from Calsporin®); *Bacillus subtilis* Strain PB6 (from Clostat®); *Bacillus pumilis* (8G-134); *Enterococcus* NCIMB 10415 (SF68) (from Cylactin®); *Bacillus subtilis* Strain C3102 (from Gallipro® & GalliproMax®); *Bacillus licheniformis* (from Gallipro®Tect®); *Enterococcus* and *Pediococcus* (from Poultry Star®); *Lactobacillus, Bifidobacterium* and/or *Enterococcus* from Protexin®); *Bacillus subtilis* strain QST 713 (from Proflora®); *Bacillus amyloliquefaciens* CECT-5940 (from Ecobiol® & Ecobiol® Plus); *Enterococcus faecium* SF68 (from Fortiflora®); *Bacillus subtilis* and *Bacillus licheniformis* (from BioPlus2B®); Lactic acid bacteria 7 *Enterococcus faecium* (from Lactiferm®); *Bacillus* strain (from CSI®); *Saccharomyces cerevisiae* (from Yea-Sacc®); *Enterococcus* (from Biomin IMB52®); *Pediococcus acidilactici, Enterococcus, Bifidobacterium animalis* ssp. *animalis, Lactobacillus reuteri, Lactobacillus salivarius* ssp. *salivarius* (from Biomin C5®); *Lactobacillus farciminis* (from Biacton®); *Enterococcus* (from Oralin E1707®); *Enterococcus* (2 strains), *Lactococcus lactis* DSM 1103 (from Probios-pioneer PDFM®); *Lactobacillus rhamnosus* and *Lactobacillus* farciminis (from Sorbiflore®); *Bacillus subtilis* (from Animavit®); *Enterococcus* (from Bonvital®); *Saccharomyces cerevisiae* (from Levucell SB 20®); *Saccharomyces cerevisiae* (from Levucell SC 0 & SC10® ME); *Pediococcus* acidilacti (from Bactocell®); *Saccharomyces cerevisiae* (from ActiSaf® (formerly BioSaf®)); *Saccharomyces cerevisiae* NCYC Sc47 (from Actisaf® SC47); *Clostridium butyricum* (from Miya-Gold®); *Enterococcus* (from Fecinor and Fecinor Plus®); *Saccharomyces cerevisiae* NCYC R-625 (from InteSwine®); *Saccharomyces* cerevisia (from BioSprint®); *Enterococcus* and *Lactobacillus rhamnosus* (from Provita®); *Bacillus subtilis* and *Aspergillus oryzae* (from PepSoyGen-C®); *Bacillus cereus* (from Toyocerin®); *Bacillus cereus* var. toyoi NCIMB 40112/CNCM I-1012 (from TOYOCERIN®), or other DFMs such as *Bacillus licheniformis* and *Bacillus subtilis* (from BioPlus® YC) and *Bacillus subtilis* (from GalliPro®).

The DFM may be combined with Enviva® PRO which is commercially available from Danisco A/S. Enviva Pro® is a combination of *Bacillus* strain 2084 Accession No. NRRL B-50013, *Bacillus* strain LSSAO1 Accession No. NRRL B-50104 and *Bacillus* strain 15A-P4 ATCC Accession No. PTA-6507 (as taught in U.S. Pat. No. 7,754,469 B—incorporated herein by reference).

It is also possible to combine the DFM described herein with a yeast from the genera: *Saccharomyces* spp.

Preferably, the DFM described herein comprises microorganisms which are generally recognized as safe (GRAS) and, preferably are GRAS-approved.

A person of ordinary skill in the art will readily be aware of specific species and/or strains of microorganisms from within the genera described herein which are used in the food and/or agricultural industries and which are generally considered suitable for animal consumption.

In some embodiments, it is important that the DFM be heat tolerant, i.e. is thermotolerant. This is particularly the case when the feed is pelleted. Therefore, in another embodiment, the DFM may be a thermotolerant microorganism, such as a thermotolerant bacteria, including for example *Bacillus* spp.

In other aspects, it may be desirable that the DFM comprises a spore producing bacteria, such as Bacilli, e.g. *Bacillus* spp. Bacilli are able to form stable endospores when conditions for growth are unfavorable and are very resistant to heat, pH, moisture and disinfectants.

The DFM described herein may decrease or prevent intestinal establishment of pathogenic microorganism (such as *Clostridium perfringens* and/or *E. coli* and/or *Salmonella* spp and/or *Campylobacter* spp.). In other words, the DFM may be antipathogenic. The term "antipathogenic" as used herein means the DFM counters an effect (negative effect) of a pathogen.

As described above, the DFM may be any suitable DFM. For example, the following assay "DFM ASSAY" may be used to determine the suitability of a microorganism to be a DFM. The DFM assay as used herein is explained in more detail in US2009/0280090. For avoidance of doubt, the DFM selected as an inhibitory strain (or an antipathogenic DFM) in accordance with the "DFM ASSAY" taught herein is a suitable DFM for use in accordance with the present disclosure, i.e. in the feed additive composition according to the present disclosure.

Tubes were seeded each with a representative pathogen (e.g., bacteria) from a representative cluster.

Supernatant from a potential DFM, grown aerobically or anaerobically, is added to the seeded tubes (except for the control to which no supernatant is added) and incubated. After incubation, the optical density (OD) of the control and supernatant treated tubes was measured for each pathogen.

Colonies of (potential DFM) strains that produced a lowered OD compared with the control (which did not contain any supernatant) can then be classified as an inhibitory strain (or an antipathogenic DFM). Thus, The DFM assay as used herein is explained in more detail in US2009/0280090.

Preferably, a representative pathogen used in this DFM assay can be one (or more) of the following: *Clostridium*, such as *Clostridium perfringens* and/or *Clostridium difficile*, and/or *E. coli* and/or *Salmonella* spp and/or *Campylobacter* spp. In one preferred embodiment, the assay is conducted with one or more of *Clostridium perfringens* and/or *Clostridium difficile* and/or *E. coli*, preferably *Clostridium perfringens* and/or *Clostridium difficile*, more preferably *Clostridium perfringens*.

Antipathogenic DFMs include one or more of the following bacteria and are described in WO2013029013.:
 *Bacillus subtilis* strain 3BP5 Accession No. NRRL B-50510,
 *Bacillus amyloliquefaciens* strain 918 ATCC Accession No. NRRL B-50508, and
 *Bacillus amyloliquefaciens* strain 1013 ATCC Accession No. NRRL B-50509.

DFMs may be prepared as culture(s) and carrier(s) (where used) and can be added to a ribbon or paddle mixer and mixed for about 15 minutes, although the timing can be increased or decreased. The components are blended such that a uniform mixture of the cultures and carriers result. The final product is preferably a dry, flowable powder. The DFM(s) comprising one or more bacterial strains can then be added to animal feed or a feed premix, added to an animal's water, or administered in other ways known in the art (preferably simultaneously with the enzymes described herein.

Inclusion of the individual strains in the DFM mixture can be in proportions varying from 1% to 99% and, preferably, from 25% to 75%

Suitable dosages of the DFM in animal feed may range from about $1\times10^3$ CFU/g feed to about $1\times10^{10}$ CFU/g feed, suitably between about $1\times10^4$ CFU/g feed to about $1\times10^8$ CFU/g feed, suitably between about $7.5\times10^4$ CFU/g feed to about $1\times10^7$ CFU/g feed.

In another aspect, the DFM may be dosed in feedstuff at more than about $1\times10^3$ CFU/g feed, suitably more than about $1\times10^4$ CFU/g feed, suitably more than about $5\times10^4$ CFU/g feed, or suitably more than about $1\times10^5$ CFU/g feed.

The DFM may be dosed in a feed additive composition from about $1\times10^3$ CFU/g composition to about $1\times10^{13}$ CFU/g composition, preferably $1\times10^5$ CFU/g composition to about $1\times10^{13}$ CFU/g composition, more preferably between about $1\times10^6$ CFU/g composition to about $1\times10^{12}$ CFU/g composition, and most preferably between about $3.75\times10^7$ CFU/g composition to about $1\times10^{11}$ CFU/g composition. In another aspect, the DFM may be dosed in a feed additive composition at more than about $1\times10^5$ CFU/g composition, preferably more than about $1\times10^6$ CFU/g composition, and most preferably more than about $3.75\times10^7$ CFU/g composition. In one embodiment, the DFM is dosed in the feed additive composition at more than about $2\times10^5$ CFU/g composition, suitably more than about $2\times10^6$ CFU/g composition, suitably more than about $3.75\times10^7$ CFU/g composition.

In still another aspect, there is disclosed a granulated feed additive composition for use in animal feed comprising at least one polypeptide having phytase activity as described herein, used either alone or in combination with at least one direct fed microbial or in combination with at least one other enzyme or in combination with at least one direct fed microbial and at least one other enzyme, wherein the feed additive composition comprises may be in any form such as a granulated particle. Such granulated particles may be produced by a process selected from the group consisting of high shear granulation, drum granulation, extrusion, spheronization, fluidized bed agglomeration, fluidized bed spray coating, spray drying, freeze drying, prilling, spray chilling, spinning disk atomization, coacervation, tableting, or any combination of the above processes.

Furthermore, particles of the granulated feed additive composition can have a mean diameter of greater than 50 microns and less than 2000 microns Those skilled in the art will understand that animal feed may include plant material such as corn, wheat, sorghum, soybean, canola, sunflower or mixtures of any of these plant materials or plant protein sources for poultry, pigs, ruminants, aquaculture and pets. It is contemplated that animal performance parameters, such as growth, feed intake and feed efficiency, but also improved uniformity, reduced ammonia concentration in the animal house and consequently improved welfare and health status of the animals will be improved.

Thus, there is disclosed a method for improving the nutritional value of an animal feed, wherein any of the engineered phytases or fragments thereof as described herein can be added to animal feed.

The phrase, an "effective amount" as used herein, refers to the amount of an active agent (such as, a phytase, e.g. any of the engineered phytase polypeptides disclosed herein) required to confer improved performance on an animal on one or more metrics, either alone or in combination with one or more other active agents (such as, without limitation, one or more additional enzyme(s), one or more DFM(s), one or more essential oils, etc.).

The term "animal performance" as used herein may be determined by any metric such as, without limitation, the feed efficiency and/or weight gain of the animal and/or by the feed conversion ratio and/or by the digestibility of a nutrient in a feed (e.g., amino acid digestibility or phosphorus digestibility) and/or digestible energy or metabolizable energy in a feed and/or by nitrogen retention and/or by animals' ability to avoid the negative effects of diseases or by the immune response of the subject.

Animal performance characteristics may include but are not limited to: body weight; weight gain; mass; body fat percentage; height; body fat distribution; growth; growth rate; egg size; egg weight; egg mass; egg laying rate; mineral absorption; mineral excretion, mineral retention; bone density; bone strength; feed conversion rate (FCR); average daily feed intake (ADFI); Average daily gain (ADG) retention and/or a secretion of any one or more of copper, sodium, phosphorous, nitrogen and calcium; amino acid retention or absorption; mineralization, bone mineralization carcass yield and carcass quality.

By "improved animal performance on one or more metric" it is meant that there is increased feed efficiency, and/or increased weight gain and/or reduced feed conversion ratio and/or improved digestibility of nutrients or energy in a feed and/or by improved nitrogen retention and/or by improved ability to avoid the negative effects of necrotic enteritis and/or by an improved immune response in the subject resulting from the use of feed comprising the feed additive composition described herein as compared to a feed which does not comprise said feed additive composition.

Preferably, by "improved animal performance" it is meant that there is increased feed efficiency and/or increased weight gain and/or reduced feed conversion ratio. As used herein, the term "feed efficiency" refers to the amount of weight gain in an animal that occurs when the animal is fed ad-libitum or a specified amount of food during a period of time. "An improvement in a metric" or "improved metric" as used herein, refers to an improvement in at least one of the parameters listed under the metrics in an animal definition.

By "increased feed efficiency" it is meant that the use of a feed additive composition according the present invention in feed results in an increased weight gain per unit of feed intake compared with an animal fed without said feed additive composition being present.

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

The improvement in performance parameters may be in respect to a control in which the feed used does not comprise a phytase.

The term Tibia ash refers to a quantification method for bone mineralization. This parameter gives indication if phosphorus is deficient (e.g. the content should be low in the phosphorus deficient negative control diets) or sufficient (e.g. the content in phytase treatments are comparable to a positive control diets that meeting phosphorus requirement in broilers)

The term "phosphorus deficient diet" refers to a diet in which the phosphorous level is not sufficient to satisfy the nutritional requirements of an animal, e.g., a feed formulated with phosphorus levels much lower than the recommended levels by the National Research Council (NRC) or broiler breeders. The animal feed contains lower levels of the mineral than required for optimal growth. If the diet lacks phosphorus, the calcium will also not be taken up by the animal. Excess Ca can lead to poor phosphorus (P) digestibility and contribute to the formation of insoluble mineral-phytate complexes. Both deficiency of P and Ca can cause reduced skeletal integrity, subnormal growth and ultimately weight loss.

The terms "mineralization" or "mineralization" encompass mineral deposition or release of minerals. Minerals may be deposited or released from the body of the animal. Minerals may be released from the feed. Minerals may include any minerals necessary in an animal diet, and may include calcium, copper, sodium, phosphorus, iron and nitrogen. In a preferred embodiment, use of the engineered phytase polypeptides or fragments thereof of the invention in a food or feed leads to increased calcium deposition in the body of the animal, especially in the bones.

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g., the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses phosphorus digestibility, starch digestibility, fat digestibility, protein digestibility, and amino acid digestibility. Digestible phosphorus (P) can be defined as ileal digestible P which is the proportion of total P intake absorbed at the end of the ileum by an animal or the fecal digestible P which is the proportion of total P intake that is not excreted in the feces.

The term "survival" as used herein means the number of subjects remaining alive. The term "improved survival" is another way of saying "reduced mortality".

The term "carcass yield" as used herein means the amount of carcass as a proportion of the live body weight, after a commercial or experimental process of slaughter. The term carcass means the body of an animal that has been slaughtered for food, with the head, entrails, part of the limbs, and feathers or skin removed. The term meat yield as used herein means the amount of edible meat as a proportion of the live body weight, or the amount of a specified meat cut as a proportion of the live body weight.

The terms "carcass quality" and "meat quality" are used interchangeably and refers to the compositional quality (lean to fat ratio) as well as palatability factors such as visual appearance, smell, firmness, juiciness, tenderness, and flavor. For example, producing poultry that does not have a "woody breast." The woody breast is a quality issue stemming from a muscle abnormality in a small percentage of chicken meat in the U.S. This condition causes chicken breast meat to be hard to the touch and often pale in color with poor quality texture. Woody breast does not create any health or food safety concerns for people and the welfare of the chicken itself is not negatively impacted.

An "increased weight gain" refers to an animal having increased body weight on being fed feed comprising a feed additive composition compared with an animal being fed a feed without said feed additive composition being present.

In the present context, it is intended that the term "pet food" is understood to mean a food for a household animal such as, but not limited to, dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms "animal feed composition," "feed", "feedstuff," and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

Engineered phytase polypeptides or fragments thereof as described herein or a feed additive composition comprising such engineered phytase polypeptides or fragments thereof may be used as, or in the preparation of, a feed.

Thus, there is described a dried enzyme composition for use in animal feed comprising any of the engineered phytase polypeptides or fragment thereof as described herein.

There is also described a liquid enzyme composition for use in animal feed comprising any of the engineered phytase polypeptides or fragment thereof as described herein.

The terms "feed additive composition" and "enzyme composition" are used interchangeably herein.

The feed may be in the form of a solution or as a solid or as a semi-solid depending on the use and/or the mode of application and/or the mode of administration.

In a preferred embodiment, the enzyme or feed additive composition described herein is admixed with a feed component to form a feedstuff.

The term "feed component" as used herein means all or part of the feed. Part of the feed may mean one constituent of the feedstuff or more than one constituent of the feed, e.g. 2 or 3 or 4 or more.

In one embodiment, the term "feed component" encompasses a premix or premix constituents. Preferably, the feed may be a fodder, or a premix thereof, a compound feed, or a premix thereof. A feed additive composition may be admixed with a compound feed, a compound feed component or to a premix of a compound feed or to a fodder, a fodder component, or a premix of a fodder.

Fodder encompasses plants that have been cut. Furthermore, fodder includes silage, compressed and pelleted feeds, oils and mixed rations, and also sprouted grains and legumes.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

As used herein the term "contacted" refers to the indirect or direct application of any of the engineered phytase polypeptides or fragments thereof (or composition comprising any of the engineered phytase polypeptides or fragments thereof) to a product (e.g. the feed). Examples of application methods which may be used, include, but are not limited to, treating the product in a material comprising the feed additive composition, direct application by mixing the feed additive composition with the product, spraying the feed additive composition onto the product surface or dipping the product into a preparation of the feed additive composition. In one embodiment, the feed additive composition of the present invention is preferably admixed with the product (e.g. feedstuff). Alternatively, the feed additive composition may be included in the emulsion or raw ingredients of a feedstuff. For some applications, it is important that the composition is made available on or to the surface of a product to be affected/treated. This allows the composition to impart a performance benefit.

In some aspects, any of the engineered phytase polypeptides or fragments thereof can be used for the pre-treatment of food or feed. For example, the feed having 10-300% moisture is mixed and incubated with the engineered phytase polypeptides or fragments thereof at 5-80° C., preferably at 25-50° C., more preferably between 30-45° C. for 1 min to 72 hours under aerobic conditions or 1 day to 2 months under anaerobic conditions. The pre-treated material can be fed directly to the animals (so called liquid feeding). The pre-treated material can also be steam pelleted at elevated temperatures of 60-120° C. The engineered phytase polypeptides or fragments thereof can be impregnated to feed or food material by a vacuum coater.

Any of the engineered phytase polypeptides or fragments thereof described herein (or composition comprising such engineered phytase polypeptides or fragments thereof) may be applied to intersperse, coat and/or impregnate a product (e.g. feedstuff or raw ingredients of a feedstuff) with a controlled amount of said enzyme.

In another aspect, the feed additive composition can be homogenized to produce a powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes. It will be understood that any of the engineered phytase polypeptides or fragments thereof (or composition comprising any of the engineered phytase polypeptides or fragments thereof) described herein are suitable for addition to any appropriate feed material.

In other embodiments, the granule may be introduced into a feed pelleting process wherein the feed pretreatment process may be conducted between 70° C. and 95° C. for up to several minutes, such as between 85° C. and 95° C.

In some embodiments, any of the engineered phytase polypeptides or fragments thereof can be present in the feed in the range of 1 ppb (parts per billion) to 10% (w/w) based on pure enzyme protein. In some embodiments, the engineered phytase polypeptides or fragments thereof are present in the feedstuff is in the range of 1-100 ppm (parts per million). A preferred dose can be 1-20 g of an engineered phytase polypeptide or fragment thereof per ton of feed product or feed composition or a final dose of 1-20 ppm engineered phytase polypeptide or fragment thereof in the final feed product.

Preferably, an engineered phytase polypeptide or fragment thereof is present in the feed should be at least about 50-10,000 FTU/kg corresponding to roughly 0.1 to 20 mg engineered phytase polypeptide or fragment thereof protein/kg.

Ranges can include, but are not limited to, any combination of the lower and upper ranges discussed above.

Formulations and/or preparations comprising any of the engineered phytase polypeptides or fragments thereof and compositions described herein may be made in any suitable way to ensure that the formulation comprises active phytase enzymes. Such formulations may be as a liquid, a dry powder or a granule which may be uncoated/unprotected or may involve the use of a thermoprotectant coating depending upon the processing conditions. As was noted above, the engineered phytase polypeptides and fragments thereof can be formulated inexpensively on a solid carrier without specific need for protective coatings and still maintain activity throughout the conditioning and pelleting process. A protective coating to provide additional thermostability when applied in a solid form can be beneficial for obtaining pelleting stability when required in certain regions where harsher conditions are used or if conditions warrant it, e.g., as in the case of super conditioning feed above 90° C.

Feed additive composition described herein can be formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent (for example, a phytase, such as any of the engineered phytase polypeptides disclosed herein); and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

In other embodiments, the granule may be introduced into a feed pelleting process wherein the feed pretreatment process may be conducted between 70° C. and 95° C. for up to several minutes, such as between 85° C. and 95° C.

The feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g. spraying, the enzyme(s) onto a carrier substrate, such as ground wheat for example.

In one embodiment, the feed additive composition may be formulated as a premix. By way of example only the premix may comprise one or more feed components, such as one or more minerals and/or one or more vitamins.

In one embodiment a direct fed microbial ("DFM") and/or an engineered phytase polypeptide or fragment thereof are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbate, glycerol, sucrose, propylene glycol, 1,3-propane diol, glucose, parabens, sodium chloride, citrate, acetate, phosphate, calcium, metabisulfite, formate and mixtures thereof.

It should be noted that any of the engineered phytase polypeptides and fragments thereof may be useful in grain applications, e.g. processing of grains for non-food/feed application, e.g. ethanol production Non-limiting examples of compositions and methods disclosed herein include:

1. An engineered phytase polypeptide or a fragment thereof comprising phytase activity having at least 82% sequence identity with the amino acid sequence set forth in SEQ ID NO:1.
2. The engineered phytase polypeptide or fragment thereof of embodiment 1, wherein the amino acid sequence of the engineered phytase polypeptide or fragment thereof has a Hidden Markov Model (HMM) score of at least about 1200 as set forth in Table 11 for the high Tm phytase clade polypeptides or fragments thereof.
3. An engineered phytase polypeptide or core domain fragment thereof having at least 78% sequence identity with amino acid positions 14-325 of the amino acid sequence set forth in SEQ ID NO: 1.
4. An engineered phytase polypeptide or fragment thereof (such as those of embodiment 1, 2, or 3) having in-feed pelleting recovery of at least about 50% when applied in MLA at 95° C. for 30 seconds, using a standard in-feed pelleting recovery test as described in Example 5.
5. The engineered phytase polypeptide or fragment thereof of embodiment 1 or 2 wherein said phytase polypeptide or fragment thereof has an in-feed pelleting recovery of at least about 50% when applied in MLA at 95° C. for 30 seconds, using a standard in-feed pelleting recovery test as described in Example 5.
6. An engineered phytase polypeptide or fragment thereof (such as those of embodiment 1, 2, 3, 4, or 5) having a ratio of in-feed pelleting recoveries of at least about 0.7 when applied in MLA at 95° C. for 30 seconds as compared to application in MLA at 80° C. for 30 seconds, using a standard in-feed pelleting test as described in Example 5.
7. The engineered phytase polypeptide or fragment thereof of embodiment 1, 2, 3 4, 5, or 6 having a ratio of in-feed pelleting recoveries of at least about 0.7 when applied in MLA at 95° C. for 30 seconds as compared to application in MLA at 80° C. for 30 seconds, using a standard in-feed pelleting test as described in Example 5.
8. The engineered phytase polypeptide or fragment thereof of embodiment 1, 2, 3, 4, 5, 6, or 7 wherein said polypeptide or fragment thereof comprises a Tm temperature of at least about 92.5° C. using differential scanning calorimetric assay conditions described in Example 3.
9. The engineered phytase polypeptide or fragment thereof of embodiment 1, 2, 3, 4, 5, 6, 7, or 8 wherein said polypeptide or fragment thereof comprises a specific activity of at least about 100 U/mg at pH 3.5 under assay conditions described in Example 3.
10. An animal feed, feedstuff, feed additive composition or premix of comprising the engineered phytase polypeptide or fragment thereof of embodiment 1, 2, 3, 4, 5, 6, 7, 8, or 9 wherein the engineered phytase polypeptide or fragment thereof may be used (i) alone or (ii) in combination with a direct fed microbial comprising at least one bacterial strain or (iii) with at least one other enzyme or (iv) in combination with a direct fed microbial comprising at least one bacterial strain and at least one other enzyme, or (v) any of (i), (ii), (iii) or (iv) further comprising at least one other feed additive component and, optionally, the engineered phytase polypeptide or fragment thereof is present in an amount of at least about 0.1 g/ton feed
11. A recombinant construct comprising a regulatory sequence functional in a production host operably linked to a nucleotide sequence encoding the engineered phytase polypeptide or fragment thereof of embodiment 1, 2, 3, 4, 5, 6, 7, 8, 9.
12. The recombinant construct of embodiment 11 wherein the production host is selected from the group consisting of bacterial, fungi, yeast, plants and algae.
13. A method for producing an engineered phytase polypeptide or fragment thereof comprising:
   (a) transforming a production host with the recombinant construct of embodiment 11; and
   (b) culturing the production host of step (a) under conditions whereby the engineered phytase polypeptide or fragment thereof is produced.
14. The method according to embodiment 13 wherein the engineered phytase polypeptide or fragment thereof is optionally recovered from the production host.
15. A phytase-containing culture supernatant obtained by the method of embodiment 13 or 14.
16. A polynucleotide sequence encoding the engineered phytase polypeptide or fragment thereof of embodiment 1, 2, 3, 4, 5, 6, 7, 8, or 9.
17. A dried enzyme composition for use in animal feed comprising the engineered phytase polypeptide or fragment thereof or fragment thereof of embodiment 1, 2, 3, 4, 5, 6, 7, 8, or 9.
18. The dried enzyme composition of embodiment 17 wherein dried enzyme composition is a granulated feed additive composition.
19. A liquid enzyme composition for use in animal feed comprising the engineered phytase polypeptide or fragment thereof of embodiment 1, 2, 3, 4, 5, 6, 7, 8, or 9.
20. A method for improving the nutritional value of an animal feed, wherein the engineered phytase or fragment thereof of embodiment 1, 2, 3, 4, 5, 6, 7, 8, or 9 is added to animal feed.
21. A method for improving animal performance on one or more metrics comprising administering an effective amount of the engineered phytase polypeptide of embodiment 1, 2, 3, 4, 5, 6, 7, 8, or 9 or the animal feed, feedstuff, feed additive composition or premix of embodiment 10 or 11 to the animal.

EXAMPLES

Unless defined otherwise herein, all technical and scientific terms used herein have the same meaning as commonly understood by one of ordinary skill in the art to which this disclosure belongs. Singleton, et al., *DICTIONARY OF MICROBIOLOGY AND MOLECULAR BIOLOGY*, 2D ED., John Wiley and Sons, New York (1994), and Hale & Marham, *THE HARPER COLLINS DICTIONARY OF BIOLOGY*, Harper Perennial, N. Y. (1991) provide one of skill with a general dictionary of many of the terms used with this disclosure.

The disclosure is further defined in the following Examples. It should be understood that these Examples, while indicating certain embodiments, are given by way of illustration only. From the above discussion and the Examples, one skilled in the art can ascertain essential characteristics of this disclosure, and without departing from the spirit and scope thereof, can make various changes and modifications to adapt to various uses and conditions.

Example 1

Generation of Phytase Molecules

DNA manipulations to generate phytase genes were carried out using molecular biology techniques known in the art. Polynucleotide fragments corresponding to the coding sequences for the various phytases were synthesized using preferred codons for the fungal expression host *Trichoderma reesei* (*T. reesei*) and randomly reassembled using PCR techniques. The signal sequence from the pep1 aspartate protease from *T. reesei* (SEQ ID NO: 63) which is artificially interrupted by a pep1 intron was introduced at the N-terminus (5' end) of each phytase gene sequence. The Gateway® BP recombination technique was used to introduce the genes into the pDonor221 vector (Invitrogen, US) according to recommendations of the supplier. The resulting entry plasmids were recombined with the destination vector pTTTpyr2 resulting in final expression vectors. pTTTpyr2 is similar to the pTTTpyrG vector described before (PCT publication WO 2011/063308), except that the pyrG gene is replaced with the pyr2 gene. Vector pTTTpyr2 contains the *T. reesei* cbhI promoter and terminator regions, the *Aspergillus nidulans* amdS selection marker, the *T. reesei* pyr2 selection marker, and telomeric sequences from *T. reesei* (for replication). These plasmids were propagated in *Escherichia coli* TOP10 cells (Invitrogen, US), and the DNA was purified and sequence verified.

All fungal manipulations, including high throughput transformations, inoculations, fermentations and harvesting were performed in 96 well microtiter plates (MTP). Plasmids were transformed into suitable *T. reesei* host strain using the polyethylene glycol (PEG)-protoplast method. In brief, transformation mixtures containing approximately 0.5-2 μg of DNA and 5×10$^6$ protoplasts in a total volume of 50 μL were treated with 200 μL of 25% PEG solution followed by dilution with equal volume of 1.2M sorbitol/10 mM Tris/10 mM CaCl$_2$) pH 7.5 solution. Then protoplasts were allowed to regenerate in a liquid growth medium containing sorbitol to maintain osmotic pressure. 100 μl of transformation mixture was transferred to 96 well MTPs, containing 300 μl of minimal medium supplemented with sorbitol (0.30M-0.84M). Plates were grown for 3 days in a shaker incubator at 28° C. with 80% humidity until fungal mycelia was formed. If necessary, 20 μL of grown cultures were transferred to a fresh minimal medium with 10 mM acetamide to enforce selective pressure and were grown for additional 2 days.

For the expression of phytase proteins, the transformed *T. reesei* strains were cultured as follows: 20 μl of the liquid cultures was used to inoculate 400 μl production medium (9 g/L casamino acids, 10 g/L (NH$_4$)$_2$SO$_4$, 4.5 g/L KH$_2$PO$_4$, 1 g/L MgSO$_4$*7H$_2$O, 1 g/L CaCl$_2$*2H$_2$O, 33 g/L PIPPS buffer (pH 5.5), 0.25% *T. reesei* trace elements (100%: 175 g/L citric acid (anhydrous), 200 g/L FeSO$_4$*7H$_2$O, 16 g/L ZnSO$_4$*7H$_2$O, 3.2 g/L CuSO$_4$*5H$_2$O, 1.4 g/L MnSO$_4$*H$_2$O, 0.8 g/L H$_3$BO$_3$) in 96 well MTPs. MTPs were incubated in a shaker incubator under the same growth conditions as described above. After 5 days of fermentation, the cultures were filtered by centrifugation using hydrophilic PVDF membranes to obtain clarified supernatants used for analysis of the recombinant phytase enzymes.

Example 2

Preparation and Characterization of Phytase Enzymes Protein Purification and Normalization

*T. reesei* strains encoding recombinant phytase enzymes were cultured as described above, and clarified supernatants were used to purify the phytase enzymes. Filtered culture supernatants were diluted 5-fold with wash buffer (25 mM Na acetate, pH 5.5) and loaded on a cation exchange resin (WorkBeads® 40S from Bio-Works) equilibrated with purified water in MTP filter plate (Millipore Multiscreen Solvinert Deep Well Filter Plate 96-well MTP, 0.45 uM hydrophilic membrane, #MDRLN0410). The MTP's were placed in centrifuge, flow through was discarded during 1 min of centrifugation (100×g). Phytase protein samples were eluted using elution buffer (25 mM Na acetate, 0.5M NaCl, pH 5.5) during 1 min of centrifugation (100×g). The samples from the protein purification step were diluted 5-fold with Na acetate buffer (25 mM Na acetate, 0.5M NaCl, pH 5.5) to a final volume of 100 μl in 96-well UV MTPs (Costar, 3635). Absorbance of the samples was measured at 280 nm, and the protein concentrations were calculated according to a standard curve of phytase protein with known concentration covering a range of 0-1750 ppm. Based on the determined protein concentrations all samples from the purification were diluted to a target of 150 ppm in buffer (100 mM Na acetate, 0.5M NaCl pH 5.5) in 96-well MTPs and stored at 5° C. until used in assays described below.

The phytase protein concentration in each sample was determined by reverse phase HPLC (RP-HPLC). Normalized samples were loaded onto an Agilent® Zorbax 300 column (SB-C3 2.1×50 mm) on an Agilent® 1260 HPLC. A gradient of solvent A (0.1 v/v % TFA in Water) and solvent B (0.07% TFA in Acetonitrile) was applied according to Table 2. The sample injection volume was 10 μl, the column temperature was 60° C. and the flow rate was 1 mL/min. The absorbance of the eluent was measured at 220 nm and integrated using ChemStation software (Agilent® Technologies). The protein concentration of phytase samples was determined based on a standard curve of phytase protein with known concentration covering a range of 0-350 ppm.

TABLE 2

HPLC gradient conditions used for determination of protein concentration of purified normalized phytase enzymes.

| Time (mins) | Solvent A | Solvent B |
|---|---|---|
| 0 | 80 | 20 |
| 0.1 | 80 | 20 |
| 1.6 | 35 | 65 |
| 1.65 | 5 | 95 |
| 1.95 | 5 | 95 |
| 2 | 80 | 20 |
| 2.3 | 80 | 20 |

Purification of samples, Phytases PHY-11895, PHY-11932 and PHY-12663 and extracts of commercial products Quantum® Blue 5 G and Natuphos® E 10000 G (extraction method described in Example 5), was performed as follows. Samples were buffer exchanged on PD10 columns (pre-equilibrated with buffer, 10-30 mM Na Acetate, pH 5.5) and subsequently purified using hydrophobic interaction chromatography HIC. Depending on the sample, one of the following HIC columns were used (Phenyl HP XK26 or HiTrap Phenyl HP or Phenyl 15, HR5/5). The HIC column were pre-equilibrated in loading buffer (20 mM Na Acetate buffer, pH 5.5 containing 1.0-1.3 M ammonium sulfate). Bound phytase protein was eluted using a linear gradient of ammonium sulfate in 10 mM Na Acetate, pH 5.5. Collected fractions from the HIC column was buffer exchanged using either Sephadex® G25 M, XK50/35 or PD10 columns (pre-equilibrated with buffer, 10-30 mM Na Acetate, pH 5.5). It is estimated that the final purity of all purified phytases samples (Phytases PHY-11895, PHY-11932 and PHY-12663 and extracts of commercial products Quantum® Blue 5 G and Natuphos® E 10000 G) exceed 95%. Protein concentration in the final purified samples was determined by measuring the absorbance spectrophotometrically at 280 nm and using calculated extinction coefficients. For the two commercial products (Quantum® Blue 5 G and Natuphos® E 10000 G) the calculated extinction coefficient of two closely related public phytase sequences (SEQ ID NO:61 and SEQ ID NO:60) were used. The molar extinction coefficients were calculated using Geneious® software version 10.2.4.

Example 3

In Vitro Assays for Phytase Enzymes

The following assays were used to measure various properties of the High Tm-Phytase clade polypeptides and fragments thereof as well as commercially available phytases.

Reference Phytase Activity (FTU)

Phytase samples were assayed for activity by reference phytase activity method (FTU). The following modified ISO 30024 procedure: "Animal feeding stuffs-Determination of phytase activity" was used: To prepare for analysis, liquid phytase samples were diluted in assay buffer (250 mM Na acetate, 1 mM CaCl2 and 0.01% Tween-20, pH 5.5) to obtain measurement within the linear range of a phosphate standard curve in the following FTU phytase assay. For solid samples, 1.0 g of sample was weighed and extracted in 100 mL assay buffer by mixing on a magnetic stirrer for 20 min. The supernatants were collected after filtration (Glass fiber filter, GA-55, Advantec) and further diluted to approximately 0.04 FTU/mL. The analysis of the samples was carried out according to the following procedure: 1 mL of the diluted phytase samples were mixed with 2 mL of a 7.5 mM IP6 substrate solution (Sodium Phytate from Rice, Shanghai AZ Import and Export, Zhejiang Orient Phytic Acid Co. Ltd #Z0201301181) in assay buffer and incubated in a water bath for 60 min at 37° C. The reactions were stopped with 2 mL of acidic Molybdate/vanadate reagent and the content of inorganic phosphate was quantified by spectrophotometry at 415 nm. The results were corrected by subtracting absorbance of a buffer blank from the absorbance of the phytase samples. A standard curve of phosphate was generated from dried potassium hydrogen phosphate and used to calculate the amount of released phosphate from each sample. One FTU was defined as the amount of phytase enzyme that generates 1 µmole phosphate/min.

Specific Activity on IP6 Substrate at pH 3.5 or 5.5

The phytases were assayed for phytase activity using IP6 substrate solution (Sodium Phytate from Rice, Shanghai AZ Import and Export, Zhejiang Orient Phytic Acid Co. Ltd #Z0201301181). For evaluation at pH 5.5, phytase enzyme samples at a concentration of 150 ppm were serially diluted to a final concentration of 0.18 ppm using 100 mM Na acetate buffer, 0.025% Tween-20 and 0.05 mM CaCl$_2$), pH 5.5 in a 384 MTP prior to analysis. 47 µL of the IP6 substrate (0.20 mM) in 100 mM Na acetate, 0.025% Tween 20 and 0.05 mM CaCl$_2$), pH 5.5 was added to each well of 384 MTP and 3 µL of the diluted phytase enzyme sample was added for a final volume of 50 µL.

For evaluation of activity at pH 3.5, phytase enzyme samples at a concentration of 150 ppm were serially diluted to a final concentration of 0.11 ppm in 100 mM Na acetate buffer, 0.025% Tween-20 and 0.05 mM CaCl$_2$). pH 5.5 in 384 MTP prior to analysis. 47 µL of the IP6 substrate (0.20 mM) in 100 mM glycine, 0.025% Tween-20 and 0.05 mM CaCl$_2$), pH 3.3 was added to each well of a 384 MTP and 3 µL of the diluted phytase enzyme sample was added for a final volume of 50 µL.

MPT reaction plates were incubated for 10 min at 25° C. in an iEMS shaker (Thermo Scientific) with continuous mixing (1400 rpm) and the reactions were stopped by addition of 45 µL of Pi Blue stop reagent (PiBlue™ Phosphate Assay Kit, POPB-DP, BioAsay Systems, US). The plates were mixed and sealed before incubated for color development for 30 min at 25° C. in an iEMS shaker (650 rpm). After incubation, the color formation was determined by measuring the absorbance at 620 nm on a plate reader (Spectramax®, Molecular Devices). The activity on IP6 substrate of each phytase sample was calculated based on a fitted standard curve of phytase protein with known concentration and activity covering a range of 0-350 ppm as the mean of three replicates. The specific activity in umoles phosphate/mg/min of each phytase sample was subsequently calculated using the activity at pH 3.5 or 5.5 divided by the protein concentration of phytase in the sample determined by RP-HPLC (as described in Example 2).

For phytase variants described on Table 3B and Table 21, the sample preparation and activity analysis was performed as described here. Aliquots of purified protein (Example 2) were diluted to a target concentration of 100 ppm in buffer (100 mM Na acetate, 0.5M NaCl pH 5.5) followed by a serial dilution to a final concentration of 0.1 ppm using 100 mM Na acetate buffer, 0.025% Tween-20 and 0.05 mM CaCl$_2$), pH 5.5. Subsequently activity at pH 5.5 and 3.5 was determined as described in example 3 except in 96-well MTPs instead of 384-well MTPs (70 µL of the IP6 substrate (0.20 mM) in 100 mM Na acetate, 0.025% Tween 20 and 0.05 mM CaCl$_2$), pH 5.5 was reacted with 10 µL aliquot of the diluted enzyme. Reaction was stopped using 170 µL of Pi Blue reagent).

Determination of Melting Temperature (Tm) by DSC

Differential scanning calorimetry (DSC) measurements were carried out using a MicroCal™ VP-Capillary DSC System (GE healthcare). DSC is a powerful analytical tool for characterizing the stability of proteins and other biomolecules. It measures the enthalpy ($\Delta H$) and temperature ($T_m$) of thermally-induced structural transitions in solution. Phytase protein samples diluted to a final concentration of 0.4 mg/mL in 100 mM Na acetate buffer, pH 5.5 were prepared. 400 µL of these protein samples, as well as a reference containing an identical amount of protein-free buffer, were added to a 96-well plate. The plate was placed in the temperature controlled auto-sampler compartment kept at 10° C. The protein samples and the reference were scanned from 20 to 120° C. at a scan rate of 2° C. per minute. The melting temperature (Tm) was determined as the temperature at the peak maximum of the transition from the folded to unfolded state. Maximum variation in the Tm was ±0.2° C. The ORIGIN software package (MicroCal, GE Healthcare) was used for baseline subtraction and calculation of the Tm values.

Example 4

Specific Activity and Thermostability Evaluation of Phytase Enzymes

Samples of High Tm-Phytase clade polypeptides and fragments thereof generated using the method described in Example 1 and Example 2 were evaluated for their specific phytase activity at pH 3.5 and 5.5 and for their thermostability, using methods described in Example 3. The commercial phytase products Quantum® Blue® (AB Vista) and Natuphos®® 10000 E (BASF Nutrition) were included in the study. These two products were chosen because they are among the most intrinsically thermostable products that are commercially available. Tables 3A and 3B provide the results for the specific activity at pH 3.5 and pH 5.5 as umole phosphate/mg/min, and the thermostability (Tm) in ° C. measured by DSC, where ND denotes value not determined. Results show that all the High Tm-Phytase clade polypeptides and fragments thereof display a Tm value well above those of the commercial products. These High Tm-Phytase clade polypeptides and fragments thereof show specific activity that is comparable to or higher than the specific activity of commercial products at pH 5.5. At pH 3.5 specific activities of the High Tm-Phytase clade polypeptides and fragments thereof are all higher than commercial products. The higher thermostability can be highly beneficial under pelleting conditions especially in MLA or when applied in a solid formulation. The higher specific activity at acidic pH can be highly beneficial under the acidic conditions that exist in the digestive tract of monogastric animals.

TABLE 3A

Specific activity measured at pH 3.5 and pH 5.5 and thermostability measured by DSC for various phytase enzymes.

| Sample name | Specific activity at pH 5.5 (μmoles phosphate/mg/min) | Specific activity at pH 3.5 (μmoles phosphate/mg/min) | Tm by DSC (° C.) |
|---|---|---|---|
| PHY-10931 | 402 | ND | 94 |
| PHY-10957 | 365 | ND | 93 |
| PHY-11569 | 335 | ND | 94 |
| PHY-11658 | 614 | ND | 94 |
| PHY-11673 | 246 | ND | 93 |
| PHY-11680 | 425 | ND | ND |
| PHY-11895 | 335 | 526 | 97 |
| PHY-11932 | 436 | 622 | 93 |
| PHY-12058 | 275 | ND | 94 |
| PHY-12663 | 363 | 741 | 94 |
| PHY-12784 | 478 | ND | 93 |
| PHY-13177 | 612 | ND | 94 |
| PHY-13371 | 263 | 572 | 96 |
| PHY-13460 | 408 | 708 | 98 |
| PHY-13513 | 267 | 624 | 99 |
| PHY-13594 | 449 | 686 | 97 |
| PHY-13637 | 319 | 654 | 98 |
| PHY-13705 | 489 | 775 | 97 |
| PHY-13713 | 261 | 589 | 98 |
| PHY-13747 | 679 | 646 | 96 |
| PHY-13779 | 744 | 880 | 97 |
| PHY-13789 | 475 | 696 | 101 |
| PHY-13798 | 288 | 602 | 98 |
| PHY-13868 | 348 | 574 | 97 |
| PHY-13883 | 387 | 508 | 95 |
| PHY-13885 | 340 | 608 | 99 |
| PHY-13936 | 270 | 635 | 98 |
| PHY-14004 | 423 | 574 | 98 |
| PHY-14215 | 430 | 410 | ND |
| PHY-14256 | 669 | 847 | 98 |
| PHY-14277 | 407 | 696 | 98 |
| PHY-14473 | 360 | 702 | 96 |
| PHY-14614 | 367 | 605 | 97 |
| PHY-14804 | 268 | 489 | 95 |
| PHY-14945 | 367 | 692 | 97 |
| PHY-15459 | 535 | 434 | ND |
| PHY-16513 | 476 | 342 | ND |
| Natuphos® E 10000 | 320 | 290 | 86 |
| Quantum® Blue | 274 | 400 | 88 |

ND denotes value not determined

TABLE 3B

Specific activity measured at pH 3.5 and pH 5.5 and thermostability measured by DSC for various phytase enzymes.

| Sample name | Specific activity at pH 5.5 (μmoles phosphate/mg/min) | Specific activity at pH 3.5 (μmoles phosphate/mg/min) | Tm by DSC (° C.) |
|---|---|---|---|
| PHY-16812 | 476 | 717 | 98 |
| PHY-17403 | ND | ND | 101 |
| PHY-17336 | ND | ND | 100 |
| PHY-17225 | 366 | 418 | 101 |
| PHY-17186 | ND | ND | 101 |
| PHY-17195 | ND | ND | 100 |
| PHY-17124 | 341 | 555 | 99 |
| PHY-17189 | ND | ND | 101 |
| PHY-17218 | 423 | 597 | 101 |
| PHY-17219 | 402 | 548 | 101 |
| PHY-17204 | 415 | 586 | 100 |
| PHY-17215 | ND | ND | 101 |
| PHY-17201 | 480 | 625 | 101 |
| PHY-17205 | 449 | 657 | 101 |
| PHY-17224 | ND | ND | 101 |
| PHY-17200 | 483 | 670 | 101 |
| PHY-17198 | ND | ND | 101 |
| PHY-17199 | ND | ND | 101 |
| PHY-17214 | ND | ND | 101 |
| PHY-17197 | ND | ND | 101 |
| PHY-17228 | 376 | 410 | 101 |
| PHY-17229 | 329 | 665 | 100 |
| PHY-17152 | 259 | 422 | 99 |
| PHY-17206 | ND | ND | 100 |
| PHY-13594 | 449 | 687 | 97 |
| PHY-13885 | 340 | 596 | 99 |
| PHY-13789 | 475 | 700 | 101 |

High resolution mass spectroscopy (MS) was performed to confirm the amino acid sequences of the High Tm-Phytase clade polypeptides and fragments thereof. PHY-13594, PHY-11895, PHY-12663, PHY-13637, PHY-13789, PHY-13885, PHY-13936, PHY-14004, PHY-14256 and PHY-14277 (SEQ ID NO: 1, 8, 11, 17, 22, 26, 27, 28, 30, 31). MS analyses confirmed the predicted C-terminus of SEQ ID NO: 1, 8, 11, 17, 22, 26, 27, 28, 30, 31. Furthermore, MS analyses revealed truncations of the N-terminus of SEQ ID NO: 1, 8, 11, 17, 22, 26, 27, 28, 30, 31. The most commonly observed N-terminal amino acid corresponds to position 4 relative to the predicted mature sequence, but also truncations at position 2, 3, 5, 6, 7, 9, 10 were observed.

Example 5

Pelleting Stability Studies of Phytase Enzymes

In-feed pelleting recovery tests of High Tm-Phytase clade polypeptides and fragments thereof were carried out at Technological Institute (Sdr. Stenderup, Denmark) pelleting facility. It should be noted that in-feed pelleting recoveries depend on several factors including; the specific feed matrix, conditioning and pelleting conditions, assay used to determine activity, etc.

The in-feed pelleting recovery of phytase enzymes: PHY-11895, PHY-11932, PHY-12663, PHY-13594, PHY-13637, PHY-13789, PHY-13885, PHY-13936, PHY-14256, PHY-14277, and the reference commercial phytases Quantum® Blue 5G (AB Vista) and Natuphos®® E 10000 G (BASF Nutrition) were measured. Liquid samples of reference commercial phytase samples were obtained by extracting phytase enzyme from powder products Quantum® Blue 5 G and Natuphos® E 10000 G using 100 mM Na acetate buffer, pH 5.5. The activity of liquid phytase enzyme samples were measured using the reference phytase activity assay (FTU) described in Example 3, and dosed accordingly into the feed. Solid samples for pelleting stability study were made by applying liquid samples of PHY-11895, PHY-11932, PHY-12663, PHY-13637, PHY-13789, PHY-13885 to a whole grain wheat carrier according to the following procedure. Ground whole grain wheat was transferred to a coupe mixer fitted with a ragged knife blade. Liquid phytase sample (max 40% vol/w) was added to the ground whole grain wheat powder while mixing. The mixture of liquid phytase sample and ground whole grain wheat powder was laid out on a tray and dried at 40° C. for 8-10 hours in an oven. After drying, the solid phytase product was milled using a Bühler mill (model MLT 204) with the roller gap setting at 0. Reference commercial product sample Quantum® Blue 5 G was dosed as solid (as is) into the feed for comparison. Analysis of the solid phytase products was carried out using the reference phytase activity assay (FTU), and the products were dosed accordingly into the feed.

The feed composition was a corn/soy diet, comprising: 62.5% corn, 31% soybean meal, 4.4% soy oil, 1.2% limestone, 0.5% VIT/MIN (Farmix Leghennen premix) and 0.4% sodium chloride. The moisture content of the feed was about 12-14% (w/w). Between 120 kg and 200 kg of pre-mixed feed described above was mixed with either liquid (MLA) or solid phytase enzyme samples in a horizontal ribbon mixer at room temperature (22-24° C.) for 10 minutes to reach a final phytase concentration in the feed of 5 FTU/g. The amount of liquid phytase sample added to the feed was between 0.2 to 0.5% (w/w).

After mixing, the phytase containing feed samples were conditioned for 30 seconds at either 60° C., 80° C., 85° C., 90° C. or 95° C. in a KAHL cascade mixer and subsequently pelleted. The term "conditioning" as used herein means mixing the feed/enzyme mixture and treating same with steam to reach the target temperature of 60° C., 80° C., 85° C., 90° C. or 95° C. for a 30-seconds holding time. The conditioning temperature was controlled manually by adjusting 3 steam valves from which steam at a pressure of 2 atm was directed on to the feed/enzyme mixture. Temperature was maintained at target temperature+/−0.3° C. at the outlet of the conditioner. This steam conditioning usually increases the water content of the feed by 2-5.5 weight % at conditioning temperatures between 6° and 95° C. Immediately following the conditioning step, the feed/enzyme mixtures were formed into pellets in a Simon Heesen pellet press fitted with a Ø 3 mm*35 mm die and a 7.5 KW motor. Feed screw rate was adjusted to achieve a production rate of approximately 300 kg/hour and the roller speed was set to 500 rpm. The system was left to run for approx. 8 minutes after the target conditioning temperature was reached to warm up the pellet die. Subsequently 5-7.5 kg pelleted feed samples were collected and cooled immediately in a cooling box with perforated bottom, with an ambient airflow at 1500 m3 air/h for 15 minutes. During cooling, the water content of the pellet drops to a level comparable with that of the phytase-containing feed mixture before steam conditioning (mash feed). Samples were downsized using a sample divider according to ISO_6497_2002 and the phytase recovery was determined as follows.

The phytase-containing feed samples, both mash feed and pellets were milled using a Retch laboratory mill (Model ZM 200 fitted with 0.75 mm sieve) and subsequently analysed to measure phytase activity using the following method which is a modification of the ISO 30024 procedure: "Animal feeding stuffs-Determination of phytase activity".

To extract the phytase enzyme from the feed samples, 20.0 g (+/−0.05 g) of the milled mash and pelleted feed were mixed with 100 mL of extraction buffer (250 mM Na acetate, 1 mM $CaCl_2$, 0.01% Tween-20, pH 5.5,) on a rotary mixer for 20 minutes at room temperature. The supernatants were collected after filtration (Glass fiber filter, GA-55 from Advantec). Supernatants were further diluted in extraction buffer to obtain measurement within linear range of phosphate standard curve in the following FTU phytase assay (0.04 FTU/mL).

One mL of the diluted extracted phytase samples were mixed with 2 mL of a 7.5 mM IP6 (Sodium Phytate from Rice, Shanghai AZ Import and Export, Zhejiang Orient Phytic Acid Co. Ltd #Z0201301181) substrate solution in extraction buffer and incubated in a water bath for 60 min at 37° C. The reactions were stopped with 2 mL of acidic molybdate/vanadate reagent and the release of inorganic phosphate was quantified by spectrophotometry at 415 nm. The results were corrected by subtracting the absorbance of a corresponding time zero sample (a sample that was not incubated for 60 min, 37° C.). A standard curve of phosphate was generated from dried potassium hydrogen phosphate and used to calculate the amount of released phosphate from each sample. One unit (FTU) was defined as the amount of phytase enzyme that generates 1 μmol phosphate/min. The percent in-feed pelleting recovery was calculated using the following formula: (Phytase activity of pellet (FTU/g) divided by Phytase activity of mash feed (FTU/g))*100.

Table 4 list the percent in-feed pelleting recovery of phytase enzymes applied in MLA at temperatures 60, 80, 85, 90 and 95° C. is shown in Table 3. Pelleting recovery at 95° C. was at least 50% for all tested High Tm-Phytase clade polypeptides and fragments thereof applied in MLA. For comparison extracted commercial reference phytases Quantum® Blue and Natuphos® E 10000 displayed much lower in-feed recovery namely, 15% and 25% respectively under same conditions. These data illustrate the high robustness of the High Tm-Phytase clade polypeptides and fragments thereof.

At 60° C., the in-feed pelleting recovery when applied in MLA is between 71% and 85% for all High Tm-Phytase clade polypeptides and fragments thereof tested. It may at first appear contradictory that the robust phytases disclosed herein lose between 15 and 29% activity when conditioned at 60° C. and subsequently pelleted, when the 60° C. conditioning temperature is more than 30° C. lower than the Tm of the robust phytases. This suggests that the initial loss is not related to thermal inactivation in the conditioner which is further corroborated by the fact that there is only limited additional loss when the temperature is raised to 80° C. Without being bound to theory, it is believed and it has been described for other enzymes (phytase and xylanase; Trial report 875: Danish Agriculture& Food Council, patent application WO2014120638 and Novus Insight, Issue 3, 2015) that there may exist a fraction of phytase and xylanase that is hard to extract/recover from the feed after conditioning and pelleting. It is believed however (again without being bound to theory) that at least some of this unrecoverable fraction is still bioactive in the animal—in other words the unrecoverable fraction may not be irreversible inactivated due to thermal stress. Rather it is believed (again without being bound to theory) that the unrecoverable fraction is bound in the feed in such a way that it is not extractable in vitro. Alternatively, it is believed (again without being bound to theory) that in fact all the phytase enzyme protein is extracted but due to conditioning and pelleting there is an apparent lower activity of the phytases when measured in an in vitro assay. Without being bound to theory, it is believed that applying the phytases in MLA compared to a dry and/or coated form will increase the magnitude of this unrecoverable-but-bioactive form of the phytases due to direct physical interaction with the feed.

It follows that an appropriate way to evaluate the thermal robustness of phytases applied in MLA is not to compare the recoverable activity in the feed before and after conditioning and pelleting but rather compare the recovery of phytase activity after conditioning and pelleting at a low e.g. 80° C. and a high e.g. 95° C. conditioning temperature which is within a commercially relevant range of conditioning temperatures.

TABLE 4

Comparison of phytase enzyme activity recovered after application in MLA at increasing temperatures, from 60 to 95° C. for 30 sec.

| Phytase sample | % Enzyme activity recovery | | | | |
|---|---|---|---|---|---|
| | 60° C. | 80° C. | 85° C. | 90° C. | 95° C. |
| PHY-11895 | 77 | 67 | ND | 66 | 64 |
| PHY-11932 | ND | ND | 68 | 66 | 50 |
| PHY-12663 | 85 | ND | 70 | 67 | 51 |
| PHY-13594 | 82 | 76 | ND | 67 | 55 |
| PHY-13637 | 80 | 78 | ND | 75 | 68 |
| PHY-13789 | 80 | 76 | ND | 77 | 74 |
| PHY-13885 | 72 | 66 | ND | 63 | 55 |
| PHY-13936 | ND | 79 | ND | 75 | 72 |
| PHY-14256 | 76 | 71 | ND | 63 | 58 |
| PHY-14277 | 75 | 70 | ND | 65 | 59 |
| Quantum ® Blue | 84 | ND | 66 | 53 | 15 |
| Natuphos ® E 10000 | 87 | 77 | ND | 67 | 25 |

ND denotes value not determined

Table 5 shows the ratio of in-feed pelleting recoveries when applied in MLA at 95° C. for 30 seconds as compared to application in MLA at 80° C. for 30 seconds. For the High Tm-Phytase clade polypeptides and fragments thereof applied in MLA, the ratio of in-feed pelleting recovery at 95° C. was between 0.72 and 0.98 when compared to application in MLA at 80° C. for 30 seconds. The corresponding number for extracted commercial reference phytase Natuphos® E 10000 was 0.32. The data shows that the high Tm-Phytase clade polypeptides and fragments thereof disclosed herein are highly robust to changes in conditioning temperature within a commercially relevant temperature range.

TABLE 5

Ratio of in-feed pelleting recoveries when applied in MLA at 95° C. for 30 seconds as compared to application in MLA at 80° C. for 30 seconds

| Sample name | Ratio |
|---|---|
| PHY-11895 | 0.96 |
| PHY-11932 | ND |
| PHY-12663 | ND |
| PHY-13594 | 0.72 |
| PHY-13637 | 0.87 |
| PHY-13789 | 0.98 |
| PHY-13885 | 0.83 |
| PHY-13936 | 0.91 |
| PHY-14256 | 0.82 |
| PHY-14277 | 0.84 |
| Quantum ® Blue | 0.22* |
| Natuphos ® E 10000 | 0.32 |

*Ratio result given as 95° C. process compared to 85° C. process not 80° C.
ND denotes value not determined Table 6 shows the in-feed pelleting recovery at 95° C. of phytases PHY-11895, PHY-11932, PHY-12663, PHY-13637, PHY-13789, PHY-13885 and Quantum® Blue 5G when applied as solid. All High Tm-Phytase clade polypeptides and fragments thereof have in-feed pelleting recoveries of at least 64% at 95° C. when applied as solid on a ground whole grain wheat carrier. Commercial powder product Quantum® Blue 5G has 58% recovery when tested at same conditions.

TABLE 6

Percent In-feed Pelleting Recovery of phytase enzymes applied as solid.

| Phytase sample | % Enzyme activity recovery 95° C. |
|---|---|
| PHY-11895 | 71 |
| PHY-11932 | 83 |
| PHY-12663 | 64 |
| PHY-13637 | 78 |
| PHY-13789 | 75 |
| PHY-13885 | 72 |
| Quantum Blue 5 G | 58 |

Example 6

In Vivo Evaluation of Phytase Enzymes
Performance Evaluation of PHY-12663, PHY-11932 and PHY-11895

The in vivo performance of the phytases PHY-12663, PHY-11932 and PHY-11895 was evaluated in broilers. The study was carried out at Texas A&M university. Eight dietary treatments were tested: a positive control diet (PC) which was formulated meeting the nutritional requirement of the broilers, a negative control (NC) which was formulated with deficiency in digestible phosphorus (0.16% point lower than PC) and calcium (0.19% point lower than PC), and NC supplemented with PHY-12663, PHY-11932 or PHY-11895 phytases dosed at 500 and 1000 FTU/kg. Table 7 provides the dietary composition of calculated and analyzed nutrient values used in this study.

TABLE 7

Dietary composition (calculated and analysed) for in vivo evaluation of PHY-12663, PHY-11932 and PHY-11895 phytases.

| Ingredient, g/kg as is | PC Starter 0-10 days | NC Starter 0-10 days | PC Grower 11-21 days | NC Grower 11-21 days | PC Finisher 22-42 days | NC Finisher 22-42 days |
|---|---|---|---|---|---|---|
| Corn | 587.5 | 609.5 | 625 | 647 | 664.5 | 686.5 |
| Soybean ml 48% | 332 | 328.5 | 277 | 273.5 | 226.5 | 223 |
| DL-met98 | 2.925 | 2.9 | 2.6 | 2.575 | 2.45 | 2.425 |
| Lysine hcl | 1.95 | 2.025 | 2.025 | 2.1 | 2.325 | 2.4 |
| L-threonine 98.5% | 0.675 | 0.7 | 0.7 | 0.7 | 0.925 | 0.925 |
| Fat, blended av | 15.5 | 8 | 24.5 | 17 | 29 | 21 |

TABLE 7-continued

Dietary composition (calculated and analysed) for in vivo evaluation of PHY-12663, PHY-11932 and PHY-11895 phytases.

| Ingredient, g/kg as is | PC Starter 0-10 days | NC Starter 0-10 days | PC Grower 11-21 days | NC Grower 11-21 days | PC Finisher 22-42 days | NC Finisher 22-42 days |
|---|---|---|---|---|---|---|
| Limestone | 14.45 | 13 | 13.35 | 11.95 | 11.95 | 10.5 |
| Monocalcium phosphate | 15.45 | 6.5 | 13.9 | 4.9 | 11.75 | 2.8 |
| Salt | 4.325 | 4.325 | 3.325 | 3.35 | 2.6 | 2.625 |
| Sodium bicarb | 0 | 0 | 1 | 1 | 2 | 2 |
| vitamins premix | 1.25 | 1.25 | 1.25 | 1.25 | 1.25 | 1.25 |
| Trace mineral premix | 0.5 | 0.5 | 0.5 | 0.5 | 0.5 | 0.5 |
| Rice bran | 23.14 | 23.14 | 34.465 | 34.465 | 44.07 | 44.07 |
| Calculated nutrients, % | | | | | | |
| Crude protein | 21.81 | 21.82 | 19.59 | 19.60 | 17.63 | 17.65 |
| Crude fat | 4.40 | 3.73 | 5.53 | 4.86 | 6.20 | 5.49 |
| Crude fiber | 2.85 | 2.88 | 2.84 | 2.88 | 2.84 | 2.88 |
| Calcium | 0.9 | 0.7 | 0.82 | 0.622 | 0.72 | 0.521 |
| Total phosphorus | 0.73 | 0.545 | 0.691 | 0.505 | 0.639 | 0.455 |
| Available phosphate | 0.45 | 0.263 | 0.411 | 0.222 | 0.359 | 0.172 |
| ME poultry kcal/kg | 3000 | 3000 | 3100 | 3100 | 3176 | 3174 |
| Xanthophyll mg/kg | 9.99 | 10.36 | 10.63 | 11.0 | 11.3 | 11.7 |
| Dig-Met | 0.59 | 0.589 | 0.533 | 0.532 | 0.496 | 0.494 |
| Dig-Lys | 1.18 | 1.18 | 1.05 | 1.05 | 0.949 | 0.95 |
| Analyzed Nutrient % | | | | | | |
| Crude protein | 19.87 | 19.74 | 18.8 | 18.6 | 17.5 | 17.2 |
| Fat | 4.54 | 4.17 | 5.53 | 5.12 | 5.96 | 5.85 |
| Ash | 5.98 | 5.25 | 4.71 | 3.96 | 4.53 | 3.97 |
| Total phosphorus | 0.74 | 0.56 | 0.73 | 0.50 | 0.67 | 0.53 |
| Calcium | 1.00 | 0.89 | 0.97 | 0.78 | 0.79 | 0.64 |

Ground rice hulls was used as phytase enzyme carrier.

Day-old Cobb 500 male broilers were assigned to the dietary treatments each containing 10 replicate pens with 30 chicks per pen. Diets were based on corn, soybean meal and rice bran, in mash form. At day 21, five birds per replicate pen were removed and tibias were collected for a fat-free tibia ash determination. Diets were formulated according to a 3-phase feeding program (starter 0-10d, grower 11-21d and finisher 22-42d). Diets and water were applied ad libitum through the 42 days study.

Data were analyzed using ANOVA, treatment mean was separated using Tukey HSD test, P<0.05 is considered significant. The following performance parameters were calculated: ADG (average daily gain), ADFI (average daily feed intake), and FCR (feed conversion ratio) from the 0-42 day study period. Table 8 shows the growth performance results for broilers fed diets supplemented with different phytases at different dosages during 0-42d of age and tibia ash measured at 21 days of age. The reduction of phosphorus (P) and calcium (Ca) in NC diets correlate with a lower ADG, ADFI, and tibia ash content and a higher FCR compared to PC. All tested phytases: PHY-12663, PHY-11932 and PHY-11895 improved ADG, ADFI, tibia ash and FCR in broilers compared to NC diet. On average, treatment with PHY-12663, PHY-11932 and PHY-11895 phytases improved ADG by 12 and 14%, ADFI by 8 and 10%, FCR by 3.3 and 3.7%, tibia ash by 9 and 9.7% when dosed at 500 and 1000 FTU/kg of feed, respectively, as compared to NC diet. In addition, all the phytases performed either better or non-significantly different from those fed PC diet on all parameters. These data show that the High Tm-Phytase clade polypeptides and fragments thereof (PHY-12663, PHY-11932 and PHY-11895) are capable of significantly improving broiler skeletal growth and performance.

TABLE 8

Growth performance over 42 days and tibia ash at 21 days of age for broilers fed diets supplemented with PHY-12663, PHY-11932 or PHY-11895 phytases at 500 and 1000 FTU/kg.

| Treatment | Phytase dose (FTU/kg) | ADG | ADFI | FCR | Tibia ash % at d 21 |
|---|---|---|---|---|---|
| PC | 0 | 69.9$^a$ | 114.5$^a$ | 1.639$^{ab}$ | 52.4$^a$ |
| NC | 0 | 62.3$^b$ | 103.3$^b$ | 1.659$^a$ | 47.5$^b$ |
| NC + PHY-12663 | 500 | 68.5$^a$ | 109.6$^{ab}$ | 1.600$^c$ | 51.8$^a$ |
| NC + PHY-12663 | 1000 | 70.8$^a$ | 113.0$^a$ | 1.597$^c$ | 52.0$^a$ |
| NC + PHY-11932 | 500 | 70.0$^a$ | 113.0$^a$ | 1.614$^{bc}$ | 51.8$^a$ |
| NC + PHY-11932 | 1000 | 71.6$^a$ | 114.9$^a$ | 1.606$^c$ | 52.2$^a$ |
| NC + PHY-11895 | 500 | 70.4$^a$ | 112.4$^a$ | 1.599$^c$ | 51.7$^a$ |
| NC + PHY-11895 | 1000 | 70.7$^a$ | 112.5$^a$ | 1.591$^c$ | 52.1$^a$ |
| Statistics | SEM | 1.11 | 1.70 | 0.01 | 0.26 |
| | P diets | <.0001 | 0.0002 | <.0001 | <.0001 |

$^{a,b,c}$different superscript in a column indicates significant difference, at P < 0.05
FCR is mortality corrected Performance Evaluation of PHY-13789, PHY-13637, PHY-14004 and PHY-13885.

The in vivo performance of PHY-13789, PHY-13637, PHY-14004 and PHY-13885 was evaluated in broilers at AH Pharma (Hebron, Maryland, USA). Ten treatments were tested including a positive control diet (PC) which was formulated meeting the nutritional requirement of the broilers and a negative control diet (NC). The NC diet was formulated with deficiency in digestible phosphorus (without inorganic phosphate, 0.24% point lower than PC), calcium (0.19% point lower than PC), digestible AA (0.04%, 0.03% and 0.03% point lower than PC for Lys, Met+Cys, Thr respectively) and ME (69 kcal/kg lower vs PC).

The performance of PHY-13789, PHY-13637, PHY-14004 and PHY-13885 was tested individually in the NC diet in two dosages, 500 or 1000 FTU/kg feed. Male broiler (Ross 308) chicks were fed the same pre-starter diet from 0 to 5 days of age and received test diets during 6 to 15 days of age. The dietary treatments were randomly assigned to nine cages per treatment, with 8 birds per cage. Diets were based on maize, wheat, soybean meal, rapeseed meal and rice bran (diet ingredient are shown in Table 9).

TABLE 9

Composition, calculated and analysed nutrient of diets (% as fed).

|  | Starter (0-5 days) | Positive control (6-15 d) | Negative control (6-15 d) |
|---|---|---|---|
| Ingredient, % | | | |
| Corn | 28.26 | 27.57 | 34.48 |
| Wheat | 26 | 32 | 32 |
| Soybean meal 48% CP | 29.95 | 21.79 | 19.4 |
| Canola meal | 3 | 6 | 6 |
| Rice bran | 5 | 5 | 5 |
| Animal and vegetable fat | 2.99 | 3.12 | 0.5 |
| L-Lysine HCl | 0.212 | 0.22 | 0.246 |
| DL-methionine | 0.361 | 0.289 | 0.276 |
| L-thyptophan | | 0.033 | 0.036 |
| Salt | 0.366 | 0.363 | 0.262 |
| Limestone | 1.84 | 1.57 | 1.51 |
| Dicalcium Phosphate | 1.27 | 1.3 | 0 |
| Vitamin trace mineral premix | 0.25 | 0.25 | 0.25 |
| Titanium dioxide | 0.5 | 0.5 | 0.5 |
| Calculated nutrients | | | |
| ME, kcal/kg | 2998 | 3025 | 2950 |
| Crude Protein | 22 | 20 | 19.33 |
| Calcium | 1 | 0.9 | 0.715 |
| Total Phosphorus | 0.689 | 0.68 | 0.422 |
| Available P | 0.45 | 0.45 | 0.209 |

TABLE 9-continued

Composition, calculated and analysed nutrient of diets (% as fed).

|  | Starter (0-5 days) | Positive control (6-15 d) | Negative control (6-15 d) |
|---|---|---|---|
| Na | 0.18 | 0.18 | 0.14 |
| Dig Lys | 1.27 | 1.1 | 1.06 |
| Dig Met + Cys | 0.94 | 0.84 | 0.81 |
| Dig Thr | 0.84 | 0.75 | 0.72 |
| Analyzed nutrients | | | |
| ME*, kcal/kg | ND | 3022 | 2955 |
| Crude Protein | ND | 19.46 | 18.77 |
| Calcium | ND | 1.36 | 1.01 |
| Total Phosphorus | ND | 0.69 | 0.53 |
| Na | ND | 0.208 | 0.164 |

ND means value not determined
*ME: metabolizable energy

Body weights and feed intake were recorded at day 6 and 15. During the last 4 days, the excreta were collected daily, weighed and pooled within a cage. Pooled excreta per cage was used for phosphorus (P) retention measurement according to AOAC Official Method 965.17. On day 15, the right tibia from six birds per cage were collected and used for tibia ash measurement.

Data were analyzed using ANOVA, treatment means were separated using Tukey HSD test. P<0.05 was considered a statistically significant difference. Table 10 shows the effect on performance of PHY-13789, PHY-13637, PHY-14004 and PHY-13885. The tibia ash was measured at 15 days of age and phosphorus retention was measured in broilers from 11-15 days of age. All phytases tested: PHY-13789, PHY-13637, PHY-14004 and PHY-13885 improved ADG, ADFI, tibia ash and phosphorus retention of broilers compared to NC.

TABLE 10

Growth performance from 6 to 15 days, tibia ash at day 15, phosphorus retention from 11-15 days in broilers fed diets supplemented with PHY-13789, PHY-13637, PHY-14004 and PHY-13885 phytases at 500 and 1000 FTU/kg.

| Treatment | Phytase dose (FTU/kg) | ADG (g) | ADFI (g) | FCR | Tibia ash d15 | P retention (% of P intake) |
|---|---|---|---|---|---|---|
| PC | 0 | 34.7 $^a$ | 44.9 $^a$ | 1.292 $^b$ | 43.9 $^{abc}$ | 57.6 $^c$ |
| NC | 0 | 32.1 $^b$ | 43.4 $^a$ | 1.349 $^a$ | 40.1 $^f$ | 57.4 $^c$ |
| NC + PHY-13789 | 500 | 33.9 $^a$ | 44.1 $^a$ | 1.303 $^b$ | 42.0 $^e$ | 66.2 $^b$ |
| NC + PHY-13789 | 1000 | 34.9 $^a$ | 44.6 $^a$ | 1.280 $^b$ | 43.7 $^{abcd}$ | 77.7 $^a$ |
| NC + PHY-13637 | 500 | 34.1 $^a$ | 44.3 $^a$ | 1.298 $^b$ | 42.7 $^{cde}$ | 67.6 $^b$ |
| NC + PHY-13637 | 1000 | 34.9 $^a$ | 44.4 $^a$ | 1.272 $^b$ | 44.0 $^{abc}$ | 78.0 $^a$ |
| NC + PHY-14004 | 500 | 33.6 $^a$ | 43.8 $^a$ | 1.304 $^b$ | 42.8 $^{bcde}$ | 68.5 $^b$ |
| NC + PHY-14004 | 1000 | 34.5 $^a$ | 44.3 $^a$ | 1.281 $^b$ | 44.2 $^a$ | 78.3 $^a$ |
| NC + PHY-13885 | 500 | 33.9 $^a$ | 44.1 $^a$ | 1.300 $^b$ | 42.4 $^{de}$ | 67.6 $^b$ |
| NC + PHY-13885 | 1000 | 34.6 $^a$ | 44.2 $^a$ | 1.276 $^b$ | 44.1 $^{ab}$ | 78.6 $^a$ |
| Statistics | SEM | 0.289 | 0.515 | 0.010 | 0.299 | 0.716 |
|  | P | <.0001 | 0.7565 | <.0001 | <.0001 | <.0001 |

$a, b, c, etc.$ different superscript in a column indicates significant differences, at P < 0.05

Phytase PHY-13789 improved ADG by 5.4 and 8.4%, FCR by 3.4 and 5.1%, tibia ash by 4.6 and 8.8%, phosphorus retention by 15.3 and 35.4%, compared to NC when dosed at 500 and 1000 FTU/kg respectively. Phytase PHY-13637 improved ADG by 6.1 and 8.6%, FCR by 3.8 and 5.7%, tibia ash by 6.3 and 9.6%, phosphorus retention by 17.7 and 35.8%, compared to NC when dosed at 500 and 1000 FTU/kg respectively. Phytase PHY-14004 improved ADG by 4.5 and 7.5%, FCR by 3.3 and 5%, tibia ash by 6.5 and 10.1%, phosphorus retention by 19.3 and 36.4%, compared to NC when dosed at 500 and 1000 FTU/kg respectively. Phytase PHY-13885 improved ADG by 5.6 and 7.8%, FCR by 3.6 and 5.4%, tibia ash by 5.5 and 9.8%, phosphorus retention by 17.7 and 36.9%, compared to NC when dosed at 500 and 1000 FTU/kg respectively. On average, the high Tm-Phytase clade polypeptides and fragments thereof improved ADG by 5.4 and 8.1%, FCR by 3.5 and 5.3%, tibia ash by 5.7 and 9.6% and phosphorus retention by 17.5 and 36.1% compared to NC. All phytases at all dosage tested performed non-significantly different from PC on ADG, ADFI and FCR despite the large reduction in nutrients (total removal of inorganic phosphorus and reduction of Ca, dig AA and ME) of NC in this trial. All phytases had similar tibia ash content compared to PC except PHY-13789 and PHY-13885 at 500 FTU/kg. Phosphorus retention as percentage of P intake was improved in all phytase treatments compared to PC. Tibia ash and P retention results confirm that these phytases are effective in releasing phosphorus.

Results from the two trials show that all High Tm-phytase clade polypeptides and fragments thereof tested are providing large improvements in animal performance.

Example 7

Identification of a Novel Clade of Phytase Enzymes

The polypeptide sequences of the High Tm-phytase clade polypeptides and fragments thereof shown in Example 3 were used to generate a Hidden Markov Model (HMM) to identify sequence similarities. The MUSCLE version 3.8.31 (MUSCLE: multiple sequence alignment with high accuracy and high throughput. R. C Edgar (20014) *Nucleic Acid Res* 32:1792) was used for sequence alignment, using default parameters. Subsequently, the HMM builder software HMMER version 3.1 b1 (available at hummer.org) was used for generating the HMM from the multiple sequence alignment. Only two parameters were used: Priors=None, and Weights=None. The command used was as follows:/usr/bin/hmmbuild --pnone --wnone Variants_for_filing_draft_5.hmm Variants_for_filing_draft_5.fsa, where wnone=No relative weights (all sequences are assigned uniform weight), and pnone=do not use any priors, and parameters are frequencies. All probability parameters are stored as negative natural log probabilities with five digits of precision to the right of the decimal point, rounded. For example, a probability is stored as 0:25 log 0:25=1:38629. The special case of a zero probability is stored as * symbol. FIG. 1 (panels A to 1BB) shows the HMM probability scores for each position along the polypeptide sequence of the High Tm-phytase clade phytases. The composite scores (COMP) for the HMM are shown on the tops 3 panels of FIG. 1A, in bold. The position (P) and consensus (C) for each amino acid are shown on column 1 under P/C. A consensus High Tm-phytase clade phytase polypeptide sequence was generated from the HMM shown on FIG. 1, and is listed as SEQ ID NO:64.

The HMM was then used to generate HMM sequences scores for a global set of approximately 7000 unique phytases, which included phytase sequences available in the public databases and patents. The correlation of ranks and sequence scores to thermostability (Tunfold and Tm by DSC) were compared for the various sequences (data not shown). Based on this analysis, the novel High Tm-phytase clade polypeptides all have HMM sequence scores greater than 1200, as exemplified on Table 11 for the phytases listed on Table 3A and 3B.

TABLE 11

Sequence scores generated from HMM for representative High Tm-phytase clade phytases.

| Sample ID | HMM Sequence Score |
| --- | --- |
| PHY-13594 | 1670 |
| PHY-13885 | 1665 |
| PHY-14945 | 1657 |
| PHY-14277 | 1656 |
| PHY-13637 | 1654 |
| PHY-13705 | 1653 |
| PHY-13779 | 1653 |
| PHY-14614 | 1653 |
| PHY-13789 | 1651 |
| PHY-13936 | 1650 |
| PHY-14256 | 1649 |
| PHY-13371 | 1648 |
| PHY-11895 | 1648 |
| PHY-14004 | 1647 |
| PHY-13713 | 1646 |
| PHY-12663 | 1646 |
| PHY-14804 | 1646 |
| PHY-13460 | 1645 |
| PHY-10957 | 1645 |
| PHY-11658 | 1644 |
| PHY-13177 | 1643 |
| PHY-12058 | 1642 |
| PHY-13798 | 1642 |
| PHY-13883 | 1642 |
| PHY-11932 | 1639 |
| PHY-10931 | 1637 |
| PHY-13747 | 1633 |
| PHY-14473 | 1629 |
| PHY-13513 | 1628 |
| PHY-11569 | 1627 |
| PHY-12784 | 1623 |
| PHY-11673 | 1615 |
| PHY-13868 | 1604 |
| PHY-11680 | 1537 |
| PHY-14215 | 1499 |
| PHY-15459 | 1330 |
| PHY-16513 | 1221 |
| PHY-16812 | 1676 |
| PHY-17403 | 1664 |
| PHY-17336 | 1667 |
| PHY-17225 | 1654 |
| PHY-17186 | 1649 |
| PHY-17195 | 1652 |
| PHY-17124 | 1629 |
| PHY-17189 | 1650 |
| PHY-17218 | 1652 |
| PHY-17219 | 1650 |
| PHY-17204 | 1648 |
| PHY-17215 | 1651 |
| PHY-17201 | 1615 |
| PHY-17205 | 1649 |
| PHY-17224 | 1651 |
| PHY-17200 | 1656 |
| PHY-17198 | 1653 |
| PHY-17199 | 1614 |
| PHY-17214 | 1651 |
| PHY-17197 | 1647 |
| PHY-17228 | 1653 |
| PHY-17229 | 1612 |
| PHY-17152 | 1625 |
| PHY-17206 | 1649 |

A multiple sequence alignment of predicted mature sequences of the High Tm-Phytase clade enzymes listed on Table11: [PHY-13594 (SEQ ID NO: 1); PHY-10931 (SEQ ID NO: 2); PHY-10957 (SEQ ID NO: 3); PHY-11569 (SEQ ID NO: 4); PHY-11658 (SEQ ID NO: 5); PHY-11673 (SEQ ID NO: 6); PHY-11680 (SEQ ID NO: 7); PHY-11895 (SEQ ID NO: 8); PHY-11932 (SEQ ID NO: 9); PHY-12058 (SEQ ID NO: 10); PHY-12663 (SEQ ID NO: 11); PHY-12784 (SEQ ID NO: 12); PHY-13177 (SEQ ID NO: 13); PHY-13371 (SEQ ID NO: 14); PHY-13460 (SEQ ID NO: 15); PHY-13513 (SEQ ID NO: 16); PHY-13637 (SEQ ID NO: 17); PHY-13705 (SEQ ID NO: 18); PHY-13713 (SEQ ID NO: 19); PHY-13747 (SEQ ID NO: 20); PHY-13779 (SEQ ID NO: 21); PHY-13789 (SEQ ID NO: 22); PHY-13798 (SEQ ID NO: 23); PHY-13868 (SEQ ID NO: 24); PHY-13883 (SEQ ID NO: 25); PHY-13885 (SEQ ID NO: 26); PHY-13936 (SEQ ID NO: 27); PHY-14004 (SEQ ID NO: 28); PHY-14215 (SEQ ID NO: 29); PHY-14256 (SEQ ID NO: 30); PHY-14277 (SEQ ID NO: 31); PHY-14473 (SEQ ID NO: 32); PHY-14614 (SEQ ID NO: 33); PHY-14804 (SEQ ID NO: 34); PHY-14945 (SEQ ID NO: 35); PHY-15459 (SEQ ID NO: 36); PHY-16513 (SEQ ID NO: 37)]; PHY-16812 (SEQ ID NO: 64); PHY-17403 (SEQ ID NO: 65); PHY-17336 (SEQ ID NO: 66); PHY-17225 (SEQ ID NO: 67); PHY-17186 (SEQ ID NO: 68); PHY-17195 (SEQ ID NO: 69); PHY-17124 (SEQ ID NO: 70); PHY-17189 (SEQ ID NO: 71); PHY-17218 (SEQ ID NO: 72); PHY-17219 (SEQ ID NO: 73); PHY-17204 (SEQ ID NO: 74); PHY-17215 (SEQ ID NO: 75); PHY-17201 (SEQ ID NO: 76); PHY-17205 (SEQ ID NO: 77); PHY-17224 (SEQ ID NO: 78); PHY-17200 (SEQ ID NO: 79); PHY-17198 (SEQ ID NO: 80); PHY-17199 (SEQ ID NO: 81); PHY-17214 (SEQ ID NO: 82); PHY-17197 (SEQ ID NO: 83); PHY-17228 (SEQ ID NO: 84); PHY-17229 (SEQ ID NO: 85); PHY-17152 (SEQ ID NO: 86); and PHY-17206 (SEQ ID NO: 87) with publicly disclosed microbial phytases: [*Buttiauxella noackiae* WP 064555343.1 (SEQ ID NO: 38); *Citrobacter braakii* AAS45884.1 (SEQ ID NO: 39); Coxiellaceae bacterium RDH40465.1 (SEQ ID NO: 40); Enterobacteriaceae WP 094337278.1 (SEQ ID NO: 41); *Escherichia coli* WP 001297112 (SEQ ID NO: 42); *Hafnia alvei* WP 072307456.1 (SEQ ID NO: 43); *Rouxiella badensis* WP 084912871.1 (SEQ ID NO: 44); *Serratia* sp. WP 009636981.1 (SEQ ID NO: 45); *Yersinia aldovae* WP 004701026.1 (SEQ ID NO: 46); *Yersinia frederiksenii* WP 050140790.1 (SEQ ID NO: 47); *Yersinia kristensenii* WP 004392102.1 (SEQ ID NO: 48); *Yersinia mollaretii* WP 049646723.1 (SEQ ID NO: 49); *Yersinia rohdei* WP 050539947.1 (SEQ ID NO: 50); EP3222714-0003 APPM phytase (SEQ ID NO: 51); US8101391-0002 (SEQ ID NO: 52); US8101391-0004 (SEQ ID NO: 53); US8101391-0035 (SEQ ID NO: 54); US8101391-0049 (SEQ ID NO: 55); US8143046-0001 (SEQ ID NO: 56); US8143046-0003 (SEQ ID NO: 57); US8460656-0002 (SEQ ID NO: 58); US8557555-0013 (SEQ ID NO: 59); US8557555-0024 (SEQ ID NO: 60); US20160083700-0003 (SEQ ID NO: 61); WO2010034835-0002 (SEQ ID NO: 62)] was made using MAFFT alignment in Gencious® version 10.2.4. Based on this MAFFT sequence alignment a phylogenetic tree showing the sequence relationships was generated using the Geneious Tree Builder in Gencious® version 10.2.4 and is shown in FIG. 2.

Example 8

In Vivo Evaluation of Phytase Enzymes in Birds

This Example assessed the utility of a representative biosynthetic bacterial 6-phytase produced by a genetically engineered strain of *Trichoderma reesei* when added to a basal diet reduced in Ca and P, on broiler tibia ash and ileal digestibility of P (AID P), when compared with a nutritionally adequate, unsupplemented diet. In addition, observations were made on feed intake, growth performance, and feed conversion.

Materials and Methods

Experimental and control diets: Positive control (PC) diets based on corn and soy-bean meal were formulated to meet the recommended requirements for nutrients (adequate in P and Ca) of the birds during starter (d 1-21) and finisher (d 22 to 42) phases [National Research Council. Nutrient Requirements of Poultry. 9th rev. ed. Natl Acad Press, Washington, DC; [1194]. Negative control (NC) diets were formulated with reductions in calcium (Ca) and available phosphorus (P) of 2.0 g/kg and 1.9 g/kg in starter phase and 2.0 g/kg and 1.8 g/kg in finisher phase diets, respectively. See Table 12. All starter diets contained titanium dioxide (added at 4 g/kg) as an indigestible marker. Negative control diets were tested as stand-alone diets or supplemented with 250, 500 or 1000 FTU/kg of a biosynthetic bacterial 6-phytase produced by a genetically engineered strain of *Trichoderma reesei* strain. Diets were provided to birds ad libitum in mash form.

TABLE 12

Ingredient and nutrient composition (g/kg, as fed basis) of the negative control (NC) and positive control (PC) diets in the starter (d 0-21) and finisher (d 22-42) phases

| | Starter (d 0-21) | | Finisher (d 22-42) | |
| --- | --- | --- | --- | --- |
| | PC | NC | PC | NC |
| Ingredient (g/kg) | | | | |
| Maize | 526 | 549 | 627 | 646 |
| Soybean meal (48% CP) | 338 | 333.5 | 242 | 240.5 |
| Canola meal | 50 | 50 | 50 | 50 |
| Soy oil | 38.9 | 31.0 | 43.3 | 36.1 |
| Monocalcium phosphate | 14.9 | 5.55 | 10.8 | 2.15 |
| Limestone | 15.3 | 14.0 | 15.4 | 13.8 |
| Sodium bicarbonate | — | — | 2.00 | 2.00 |
| Salt | 4.70 | 4.75 | 2.78 | 2.80 |
| DL-methionine | 2.83 | 2.80 | 2.03 | 2.00 |
| Lysine HCl | 2.13 | 2.20 | 1.78 | 1.80 |
| L-Threonine | 0.80 | 0.80 | 0.60 | 0.60 |
| Titanium dioxide | 4.00 | 4.00 | — | — |
| Poultry minerals premix | 0.35 | 0.35 | 0.35 | 0.35 |
| Poultry vitamins premix | 2.00 | 2.00 | 2.00 | 2.00 |
| Calculated nutrients (g/kg) | | | | |
| Dry matter | 882.73 | 880.59 | 883.353 | 881.48 |
| Crude protein | 217.61 | 217.42 | 180.83 | 181.65 |
| Crude fiber | 16.38 | 16.67 | 15.98 | 16.27 |
| Total calcium | 9.99 | 8.00 | 9.01 | 6.99 |
| Total phosphorus | 7.15 | 5.22 | 5.95 | 4.18 |
| Available phosphorus | 4.5 | 2.56 | 3.50 | 1.70 |
| Metabolizable energy (ME) (kcal/kg) | 3024.94 | 3025.25 | 3174.97 | 3174.90 |
| Available methionine | 5.87 | 5.85 | 4.67 | 4.67 |
| Available total sulphur amino acid | 9.00 | 8.99 | 7.40 | 7.41 |
| Available lysine | 12.00 | 11.99 | 9.49 | 9.51 |
| Available tryptophan | 2.09 | 2.08 | 1.62 | 1.62 |
| Available threonine | 7.91 | 7.89 | 6.45 | 6.47 |
| Available arginine | 13.03 | 12.97 | 10.45 | 10.46 |
| Available valine | 9.00 | 9.00 | 7.53 | 7.57 |

Birds, housing and experimental design: Cobb 500 broiler chicks of mixed sex (50% males, 50% females) were obtained on day of hatch from a commercial hatchery where they had been vaccinated against Infectious Bronchitis and Newcastle Disease, via drinking water. Vaccination against Infectious Bursal Disease was administered on d 11-14 also via drinking water. Birds were allocated to floor-pens on the basis of initial body weight (BW) so that each pen contained birds of approximately equal body weight. A total of 1176 birds were assigned to 49 pens with 24 birds per pen, 9 pens for NC and 10 pens for all other treatments, with each pen containing 50% males and 50% females, in a completely randomized design. Pens were located in an environmentally controlled broiler house with a lighting regime of LD 18:6 and an initial temperature of 35° C., reduced to 24° C. on d 28.

Sampling and measurements: Representative sub-samples of all diets were analyzed for dry matter (DM), crude protein (CP), crude fat (CF), ash, P, potassium (K), magnesium (Mg), Ca, sodium (Na), phytate and phytase.

Body weight and feed intake (FI) were measured on d 1, 21, and 42 on a pen basis, and used to calculate BW, average daily weight gain (ADG), average daily feed intake (ADFI) and mortality corrected feed conversion rate (FCR). Mortality was checked and recorded daily.

On d 21 and 42, 4 birds (2 males, 2 females, sex determined at the sampling point) and 6 birds (3 males and 3 females), respectively, were randomly selected per pen, killed by CO2 gas and their left tibias collected and pooled (by pen) for the determination of defatted tibia ash. Ilcal digesta was collected from euthanized birds on d 21, pooled per pen and frozen on a Labconco® Freczone® 12+ dehydration machine (Labconco®, Kansas City, Missouri). Dried feed and digesta samples were analyzed for P and Ca content in order to calculate nutrient digestibility using titanium dioxide as the inert marker.

Chemical analysis: Samples were analyzed in duplicate for all analyses. Nutrients in feed and ileal digesta were analyzed according to the following methods: crude protein, NEN-EN-ISO 16634 [NEN-ISO 6492, en. Animal feed-stuffs-Determination of fat content. International Organization for Standardization, Switzerland; 1999]; crude fat, NEN-ISO 6492 [NEN-ISO 6865, en. Animal feeding stuffs—Determination of crude fibre content—Method with intermediate filtration. International Organization for Standardization, Switzerland; 2000]; crude fiber, NEN-ISO 6865 [NEN-EN-ISO 16634, en. Animal Feeding Stuff-Determination of Nitrogen Content using Dumas combustion. International Organization for Standardization, Switzerland; 2008]. Phosphorus, Ca, magnesium, potassium and sodium in feed and P and Ca in digesta were analyzed by microwave digestion and Inductively Coupled Plasma-Optical Emission Spectrometry (OES) in accordance with method AOAC 2011.14 [AOAC International. Method 2011.14: Calcium, Copper, Iron, Magnesium, Manganese, Potassium, Phosphorus, Sodium, and Zinc in Fortified Food Products. Official Methods of Analysis of AOAC International; 2011]. Phytate phosphorus (PP [inositol hexa-phosphate (IP6)]) concentrations in diets and phytase activities in the diets were determined by DuPont Laboratories (Brabrand, Denmark), using the methods described by Yu et al. [Yu, S, Cowieson, A, Gilbert, C, Plumstead, P, Dalsgaard, S. Interactions of phytate and myo-inositol phosphate esters (IP1-5) including IP5 isomers with dietary protein and iron and inhibition of pepsin. J Anim Sci 2012; 90:1824-1832]. One phytase unit (FTU) was defined as the amount of enzyme that released 1 µmol of inorganic orthophosphate from a sodium phytate substrate per minute at pH 5.5 and 37° C. [AOAC International. Method 2000.12: Phytase activity in feed: Colorimetric enzymatic method. Official Methods of Analysis of AOAC International. 17th edition; Association of Official Analytical Chemists, Arlington, VA; 2000].

Tibia ash was measured using the method described below: fibula, muscle and connective tissue were removed and the bones dried at 100° C. for at least 12 h before defatting in diethyl ether for 7-8 h and air-drying. Defatted tibias were dried again at 100° C. for at least 12 hours and then ashed in ceramic crucibles at 600° C. for 24 h.

Calculations: Feed conversion ratio (FCR) was calculated based on total BWG and total feed intake (corrected for mortality weight) from d 0-21, d 22-42, and d 0-42. Both ADG and AFDI were calculated by correction of mortality, e.g. ADFI was calculated by total feed intake in each phase and divided by the total number of days of feeding. Mortality-corrected ADG was calculated from mortality corrected ADFI divided by mortality corrected FCR.

The apparent ileal digestibility (AID, %) of P and Ca were calculated based on the following formula, using titanium dioxide as the inert marker:

$$AID = 1 - [(Ti_d/Ti_i) \times (N_i/N_d)]$$

Where $Ti_d$ is the titanium concentration in the diet, $Ti_i$ is the titanium concentration in the ileal digesta, $N_i$ is the nutrient (P or Ca) concentration in the ileal digesta and $N_d$ is the nutrient concentration in the diet. All analyzed values were expressed as grams per kilogram dry matter.

Statistical analysis: Data are reported by pen as the experimental unit. Data were analyzed by analysis of variance (ANOVA) using the Fit Model platform of JMP 14.0 (SAS Institute Inc., Cary, NC, 1989-2019) to investigate the effect of treatments in a randomized design. Means separation was achieved using Tukey's Honest Significant Difference test. Linear and quadratic response with increasing phytase dose were analyzed using orthogonal polynomials. Differences were considered statistically significant at $P<0.05$; $P<0.10$ was considered a tendency.

Results

Diet analysis: Analyzed phytase activities in the final diets confirmed the target dose-levels (Table 13). Analyzed values of CP in the basal (control) diets were within 10% of calculated values. Achieved reductions in P content in the NC diets adhered well to targeted reductions; based on analyzed values, total P content was reduced by 1.8 g/kg in starter and 2.3 g/kg in finisher diets.

TABLE 13

Analyzed nutritional values (g/kg) of the final diets, by phase

| Ingredient | Starter (0-21 d) | | Finisher (22-42 d) | |
| --- | --- | --- | --- | --- |
| | PC | NC* | PC | NC* |
| Dry matter | 886 | 883 | 889 | 886 |
| Crude protein | 221 | 228 | 186 | 184 |
| Crude fat | 59.8 | 54.3 | 62.2 | 62.0 |
| Ash | 58.8 | 44.4 | 51.4 | 43.6 |
| Phytate | 8.32 | 8.38 | 8.70 | 9.09 |
| Phytate-P | 2.35 | 2.4 | 2.45 | 2.56 |
| Phosphorus | 7.1 | 5.3 | 7.0 | 4.8 |
| Potassium | 10.1 | 10.1 | 9.6 | 9.0 |
| Magnesium | 1.9 | 1.9 | 1.8 | 1.7 |
| Calcium | 10.3 | 8.6 | 10.4 | 8.0 |

*The values are the average values for NC and NC + phytase treatments as one batch of NC basal diet was made.

The analyzed phytase activity (FTU/kg) was 43, 24, 282, 480, 882 in starter phase and <50, <50, 253, 594, 1110 in finisher phase for PC, NC, NC+250 FTU/kg, NC+500

FTU/kg and NC+1,000 FTU/kg respectively. Phytase activity in the diets was analyzed by DuPont Feed Technical Service, Brabrand, Denmark Nutrient digestibility: The AID of P was not significantly reduced in birds fed the NC vs. PC diets (Table 14). At a dose-level of 500 FTU/kg or above, phytase supplementation increased AID P vs NC and at 1000 FTU/kg, phytase improved the AID of P compared with PC (P<0.05). Expressed on a g/kg basis, ileal digestible P in the diets was improved by phytase when dosed at 500 FTU/kg or higher (+1.39 g/kg vs. NC at 500 FTU/kg and +1.76 g/kg vs. NC at 1000 FTU/kg; P<0.05). At these dose-levels, digestible P expressed as g/kg in the diet was equivalent to that of the PC diet. The AID of Ca was unaffected by dietary treatment, but tended to increase linearly (P<0.10) with increasing phytase dose from 0 to 1000 FTU/kg.

TABLE 14

Effect of the experimental phytase on apparent ileal digestibility (AID) of P and Ca in broilers digestible P in the diets as g/kg, on day 21

| Measured parameters | PC | NC | NC + Phytase (FTU/kg)[1] | | | SEM | P-value |
|---|---|---|---|---|---|---|---|
| | | | 250 | 500 | 1,000 | | |
| AID P (%)[2] | 50.1 [bc] | 39.0 [c] | 57.7 [abc] | 65.2 [ab] | 72.2 [a] | 5.77 | <0.001 |
| AID Ca (%)[2] | 40.2 | 39.2 | 47.0 | 51.1 | 55.3 | 4.93 | 0.240 |
| Digestible P (g/kg diet)[2] | 3.55 [a] | 2.06 [b] | 3.06 [ab] | 3.46 [a] | 3.82 [a] | 0.3 | <0.001 |

[1] A biosynthetic bacterial 6-phytase produced by the genetically modified micro-organism *Trichoderma reesei* (*T. reesei*).
[2] Increasing phytase dose from 0 (NC) to 1,000 FTU/kg resulted in linear and quadratic increase in AID P (P < 0.05) and nearly significant linear increase in Ca (P = 0.052)
[a, b, c] Least square means within a row with different superscript letters differ (P < 0.05, Tukey test).

Tibia ash: The effect of dietary treatment on tibia ash was highly significant (P<0.001) and is presented in Table 15. Compared to PC, birds fed the NC diet exhibited reduced tibia ash at d 21 and at d 42 (−6.7 and −4.1 percentage points, respectively; P<0.05). Compared to NC, phytase supplementation improved tibia ash sampled at both d 21 and d 42 at all three dose-levels (P<0.05); tibia ash in all phytase treatments was equivalent to PC.

TABLE 15

Effect of the experimental phytase on growth performance and tibia ash content in broilers, by phase[1,2]

| | PC | NC | NC + Phytase (FTU/kg)[3] | | | SEM | P-value |
|---|---|---|---|---|---|---|---|
| | | | 250 | 500 | 1,000 | | |
| Starter (d 0 | | | | | | | |
| BW d 21 | 0.90 [a] | 0.71 [b] | 0.86 [a] | 0.88 [a] | 0.89 [a] | 0.010 | <0.001 |
| ADFI (g/d) | 56.6 [a] | 46.3 [b] | 54.1 [a] | 54.3 [a] | 55.4 [a] | 0.764 | <0.001 |
| ADG (g/d) | 40.6 [ab] | 31.7 [c] | 39.0 [b] | 39.5 [ab] | 40.8 [a] | 0.431 | <0.001 |
| FCR (g/g) | 1.396 [ab] | 1.460 [a] | 1.390 [b] | 1.377 [b] | 1.358 [b] | 0.016 | <0.01 |
| Tibia ash d | 50.4 [a] | 43.7 [b] | 49.3 [a] | 49.9 [a] | 50.9 [a] | 0.463 | <0.001 |
| Finisher (d | | | | | | | |
| BW d 42 | 2.70 [a] | 1.85 [b] | 2.64 [a] | 2.70 [a] | 2.74 [a] | 0.031 | <0.001 |
| ADFI (g/d) | 157.7 [a] | 121.5 [b] | 154.4 [a] | 156.1 [a] | 156.0 [a] | 1.89 | <0.001 |
| ADG (g/d) | 86.9 [a] | 58.2 [b] | 84.7 [a] | 87.2 [a] | 87.8 [a] | 1.135 | <0.001 |
| FCR (g/g) | 1.815 [b] | 2.093 [a] | 1.823 [b] | 1.792 [b] | 1.779 [b] | 0.029 | <0.001 |
| Tibia ash d | 46.4 [a] | 42.3 [b] | 46.5 [a] | 46.5 [a] | 47.0 [a] | 0.70 | <0.001 |
| Overall (d 0 | | | | | | | |
| ADFI (g/d) | 118.3 [a] | 92.9 [b] | 115.1 [a] | 116.4 [a] | 116.7 [a] | 1.186 | <0.001 |
| ADG (g/d) | 71.3 [ab] | 50.6 [c] | 69.1 [b] | 70.9 [ab] | 71.8 [a] | 0.648 | <0.001 |
| FCR (g/g) | 1.661 [b] | 1.835 [a] | 1.666 [b] | 1.643 [b] | 1.626 [b] | 0.019 | <0.001 |

[1] All performance data are corrected for mortality
[2] Increasing phytase dose from 0 (NC) to 1,000 FTU/kg resulted in linear and quadratic increase in all parameters measured (P < 0.05)
[3] A biosynthetic bacterial 6-phytase produced by the genetically modified microorganism *Trichoderma reesei* (*T. reesei*).
[a, b, c] Least square means within a row with different superscript letters differ (P < 0.05, Tukey test).

Feed Intake and Growth performance: The effect of dietary treatment on feed intake, body weight, and feed conversion is also presented in Table 15. Treatment affected all response measures during all growth phases (starter, finisher, overall; P<0.01 in all cases). No significant differences were observed for mortality (data not shown).

Compared to PC, birds fed the NC diet exhibited reduced BW at d 21 and d 42, increased FCR during finisher phase and overall, and reduced ADG and ADFI during all phases (P<0.05).

Supplementation with the experimental phytase, at any dose-level, allowed the birds to overcome the P deficiency in NC diets with improved ADFI, BW and ADG, and FCR during all phases (P<0.05) such that they were equivalence with the PC during all phases, regardless of phytase dose. A dose-level of 1,000 FTU/kg of the experimental phytase produced birds with a mean BW at d 42 of 2.74 kg and a mean overall FCR of 1.626 (vs. 1.661 in PC).

In conclusion, this study has demonstrated that the experimental variant phytase was effective at maintaining growth performance, tibia ash and ileal P digestibility equivalent to a nutritionally adequate diet, when added to diets formulated with a 1.8 to 1.9 g/kg reduction in inorganic P from MCP and administered at dose levels between 250 and 1000 FTU/kg. Beneficial effects were greatest at 1000 FTU/kg. The phosphorus replacement value from monocalcium phosphate was estimated to be 1.64 and 2.07 grams per kilogram of diet respectively at 500 and 1000 FTU/kg (equal to 1.39 and 1.76 g/kg digestible P from MCP), based on the observed increase in digestible phosphorus.

Example 9

In Vivo Evaluation of Phytase Enzymes in Swine

The aim of this study was to assess the efficacy of dietary supplementation with an representative experimental biosynthetic bacterial 6-phytase in weaned piglets fed a corn-soybean meal-based diet without added inorganic phosphate, compared to addition of inorganic P from MCP, on bone ash and mineralization and on growth performance. An existing commercial phytase was included in the study for comparative purposes. The second objective was to determine the digestible P-equivalence value of the phytase in the tested setting.

Materials and Methods

Experimental and control diets: A positive control (PC) diet based on corn and SBM was formulated to meet the nutritional requirements of piglets weighing 10 to 25 kg (NRC, 2012), containing 2.9 g/kg digestible P and 7.0 g/kg Ca (Table 16). A negative control (NC) diet was formulated without inorganic phosphate (1.1 g/kg digestible P) and reduced in Ca (5.0 g/kg). The NC was tested as a stand-alone diet and also when supplemented with 500 or 1,000 FTU/kg diet of a commercial phytase, 250, 500 or 1,000 FTU/kg of an experimental phytase, or with added MCP at 3 levels (+0.7, +1.4 and +1.8 g/kg digestible P from MCP), equating to a digestible P content of 1.8, 2.5 and 2.9 g/kg (the latter constituting the PC diet). This produced a total of 9 dietary treatments. Additional limestone was added to the MCP-supplemented diets in order to maintain Ca to P ratio within the range 1.2 to 1.3 (Table 16). The commercial phytase was a microbial 6-phytase from *Buttiauxella* sp. expressed in *Trichoderma reesei* (Axtra® PHY, DuPont Nutrition and Biosciences), described herein as PhyB. The experimental phytase was a biosynthetic bacterial phytase, described herein as PhyX. The PhyX is produced by fermentation with a fungal (*Trichoderma reesei*) production strain expressing a biosynthetic variant of a consensus bacterial phytase gene assembled via ancestral reconstruction with sequence bias for *Buttiauxella* sp. (DuPont Nutrition and Biosciences). Diets were provided to piglets ad libitum in mash form and water was freely available.

TABLE 16

Ingredient and nutrient composition (g/kg, as fed basis) of the negative control (NC) and NC with increased level of digestible P from MCP inclusion diets fed to weaned piglets (42 to 70 days of age).

| | NC | NC + digestible P from MCP (g/kg) | | |
|---|---|---|---|---|
| | | 0.7 | 1.4 | 1.8 (PC) |
| Ingredient (g/kg) | | | | |
| Corn | 400 | 400 | 400 | 400 |
| Soybean meal (48% CP) | 293.35 | 292.85 | 292.65 | 292.65 |
| Rice | 150 | 150 | 150 | 150 |
| Rice bran | 50.0 | 50.0 | 50.0 | 50.0 |
| Sugar beet pulp | 30.0 | 30.0 | 30.0 | 30.0 |
| Animal fat | 36.7 | 36.7 | 36.7 | 36.7 |
| Monocalcium phosphate (MCP) | — | 3.30 | 6.70 | 8.80 |
| Calcium carbonate | 6.70 | 7.40 | 8.20 | 8.60 |
| Salt | 4.10 | 4.10 | 4.10 | 4.10 |
| L-lysine HCl | 4.00 | 4.00 | 4.00 | 4.00 |
| DL-methionine | 1.70 | 1.70 | 1.70 | 1.70 |
| L-threonine | 1.50 | 1.50 | 1.50 | 1.50 |
| L-tryptophan | 0.50 | 0.50 | 0.50 | 0.50 |
| Noxyfeed[1] | 0.20 | 0.20 | 0.20 | 0.20 |
| Titanium dioxide | 5.00 | 5.00 | 5.00 | 5.00 |
| Filler (diatomaceous earth) | 10.0 | 6.50 | 2.50 | — |
| Vitamin-mineral premix[2] | 6.00 | 6.00 | 6.00 | 6.00 |
| Test product with carrier[3] | 0.25 | 0.25 | 0.25 | 0.25 |
| Calculated nutrients (g/kg) | | | | |
| Metabolizable energy (ME), (Mcal/kg) | 3.35 | 3.35 | 3.35 | 3.35 |
| Net energy (NE) (Mcal/kg) | 2.52 | 2.52 | 2.52 | 2.52 |
| Crude protein | 194 | 194 | 194 | 194 |
| Ether extract | 63.3 | 63.3 | 63.2 | 63.2 |
| Total calcium | 5.00 | 5.75 | 6.53 | 7.00 |
| Total phosphorus | 4.00 | 4.76 | 5.53 | 6.00 |
| dig. phosphorus | 1.06 | 1.76 | 2.46 | 2.90 |
| Non-phytate phosphorus | 1.28 | 2.00 | 2.80 | 3.30 |
| Total Lysine | 13.4 | 13.4 | 13.4 | 13.4 |
| SID[4] Lysine | 12.3 | 12.3 | 12.3 | 12.3 |
| SID Threonine | 7.70 | 7.70 | 7.70 | 7.70 |
| SID Methionine | 4.43 | 4.43 | 4.43 | 4.43 |
| SID Tryptophan | 2.42 | 2.42 | 2.42 | 2.42 |

[1]Antioxidant, containing BHT, Propyl gallate and Citric acid.
[2]Supplied, per kilogram of diet: Iron (from FeSO$_4$•H$_2$O), 120 mg; Iodine (from Ca(IO$_3$)$_2$) 0.75 mg; Cobalt (from 2CoCO$_3$•3Co(OH)$_2$•H$_2$O), 0.6 mg; Copper (from CuSO$_4$•5H$_2$O), 6 mg; Manganese (from MnO) 60 mg; Zinc (from ZnO) 100 mg; Selenium (E8) (from Na$_2$SeO$_3$) 0.37 mg; Vitamin A, 10000 UI; Vitamin D3, 2000 UI; Vitamin E (alfa tocopherol), 25 mg; Vitamin B1, 1.5 mg; Vitamin B2, 3.5 mg; Vitamin B6, 2.4 mg; Vitamin B12, 20 µg; Vitamin K3, 1.5 mg; Calcium pantothenate 14 mg; Nicotinic acid, 20 mg; Folic acid, 0.5 mg; Biotin, 50 µg.
[3]The test product is mixed with wheat carrier to get the targeted dose, the control treatment received only carrier without test product
[4]SID = standardized ileal digestible.

Pigs, housing and experimental design: The experimental procedures were in compliance with European Directive 2010/63/EU and the Spanish guidelines for the care and use of animals in research (B.O.E. number 252, Real Decreto 2010/2005). A total of 162 crossed Pietrain x (Large White x Landrace) 21-day-old piglets of mixed sexes (50% males, 50% females) were obtained at weaning (initial body weight (BW) 6±1 kg) and fed a common pre-starter adaptation diet until 42 days old (~10-11 kg BW). Piglets were then blocked based on body weight and gender and allocated to pens, with 2 pigs/pen and 9 pens/treatment), in a completely randomized block design. Test diets were administered to pigs from 42 days old until 70 days old. Pens were grouped together in an environmentally controlled animal room in which the temperature was maintained at 30° C. initially and thereafter reduced by 1° C. per week.

Sampling and measurements: Representative sub-samples of all diets were analyzed for dry matter (DM), organic matter (OM), crude protein (CP), ether extract (EE), ash, minerals, phytate and phytase.

Pigs were weighed individually before the start of the experiment, and again at d 14 and 28 to calculate average daily gain (ADG). Feed disappearance was assessed on d 14 and d 28 and used to calculate average daily feed intake (ADFI). Feed conversion rate (FCR) was calculated from ADFI and ADG.

On d 28 of the trial, one piglet per pen was euthanized by intravenous overdose of sodium pentobarbital and the right feet from the fore- and hindleg was excised in order to determine metacarpi/metatarsi bone ash and mineralization (Ca and P). Feet were stored at −20° C. until analysis.

Chemical Analysis: All samples were analyzed in duplicate. Dry matter, ash, CP and ether extract in feed were analyzed according to the AOAC (2000a) methods (925.09, 942.05, 968.06 and 920.39, respectively). Nitrogen content was determined by the Dumas procedure, by means of Nitrogen FP-528 analyzer (Leco corp., St Joseph, Mo, USA). Organic matter (OM) was calculated as the difference between DM and ash. Analysis of exogenous phytase activity in feeds was performed according to Engelen et al (1994). One phytase unit (FTU) was defined as the amount of phytase that liberated 1 mmol of inorganic phosphate per minute from 0.0051 mol/L of sodium phytate at a standard pH of 5.5 and temperature of 37° C. (AOAC, 2000b).

Bone ash was determined on both metacarpi III/IV and metatarsi III/IV from the right fore- and hindfoot, respectively. After extraction, bones were first used to characterize their integrity in a 3-point mechanical test using an Instron testing system (Norwood, MA, US) model 2519-106 equipped with a 2 kN load cell. Biomechanical parameters like extrinsic stiffness, ultimate force, displacement and work to failure were used to characterize integrity of bones (Turner, 2006). Then, bones were used to determine their DM content in an oven at 103° C. for 4 h before burnt them in an oven-dryer for 3 h at 200° C. previous to their introduction into a muffle furnace at 550° C. for 72 h and determine their ash content. Ashes from metacarpi bones were then ground using a pestle and a mortar, and send to SCT lab (University of Lérida, Spain) for mineral (Ca, P, Mg) determination by inductively-coupled plasma mass spectrometry (ICP-MS; Agilent® Technologies model 7700X) after sulfuric acid digestion. Mineral composition (Ti, Ca, P, Mg, Fe, Zn and Cu) from feeds was also analyzed on ashes samples by ICP-MS at SCT lab (Pacquette and Thompson, 2018).

Statistical analysis: Data were based on pen as the experimental unit, except for bone ash and bone strength, which were based on pig as the experimental unit. Data were analyzed by analysis of variance (ANOVA) using the Fit Model platform of JMP 14.0 (SAS Institute Inc., Cary, NC, 1989-2019) to investigate the effect of treatments in a randomized design. Means separation was achieved using Tukey's Honest Significant Difference test. In addition, a 2-way ANOVA analysis was carried out with factors 'phytase' (PhyG vs PhyB) and dose (500 and 1000) to compare two phytases at two dose levels of 500 and 1000 FTU/kg. Linear and quadratic response with increasing phytase dose were analyzed using orthogonal polynomials. In addition, linear regression was performed with increasing added digestible P from MCP (e.g. NC, NC+0.7, NC+1.4 and NC+1.8 g/kg digestible P from MCP) for metacarpi bone ash, ADG and FCR. The digestible P equivalence was calculated by applying Y values at a given phytase dose and calculate the corresponding X values. Differences were considered significant at P<0.05; P<0.10 was considered a tendency.

Results

Diet analysis: Analyzed values of nutrients in the diets are presented in Table 17. Phytase activities in the NC diets were ≤50 FTU/kg indicating the absence of phytase cross-contamination. Activities in the phytase supplemented diets were within 10% of target values, except for treatment NC+PhyX 250 and NC+PhyX 500 in which activities were respectively −20 and +27% vs. target dose. The analyzed P content of the NC diets containing added P from MCP were close to the expected values based on the intended levels of MCP addition.

TABLE 17

Analyzed nutritional values of the experimental diets

| Item | NC | NC + PhyX (FTU/kg)[1] | | | NC + PhyB (FTU/kg)[2] | | NC + digestible P from MCP (g/kg) | | |
|---|---|---|---|---|---|---|---|---|---|
| | 0 | 250 | 500 | 1000 | 500 | 1000 | 0.7 | 1.4 | 1.8 (PC) |
| Dry matter (g/kg) | 893 | 899 | 896 | 896 | 897 | 897 | 898 | 897 | 893 |
| Metabol. Energy, (Mcal/kg)[3] | 3.18 | 3.19 | 3.17 | 3.19 | 3.20 | 3.22 | 3.19 | 3.18 | 3.18 |
| Net energy (Mcal/kg)[3] | 2.33 | 2.34 | 2.32 | 2.34 | 2.35 | 2.36 | 2.34 | 2.34 | 2.34 |
| Organic matter (g/kg) | 834 | 839 | 834 | 831 | 835 | 835 | 834 | 834 | 833 |
| Crude protein (g/kg) | 200 | 200 | 202 | 199 | 199 | 201 | 200 | 200 | 199 |
| Ether extract (g/kg) | 61.3 | 61.6 | 69.0 | 65.8 | 65.5 | 63.8 | 66.9 | 66.5 | 68.1 |
| Ash (g/kg) | 59.7 | 61.2 | 62.5 | 65.4 | 61.8 | 61.6 | 63.4 | 63.4 | 59.5 |
| Calcium (g/kg) | 5.96 | 5.94 | 6.32 | 6.41 | 6.29 | 6.15 | 7.26 | 7.65 | 8.73 |
| Phosphorus (g/kg) | 4.29 | 4.50 | 4.67 | 4.89 | 4.63 | 4.48 | 5.48 | 5.65 | 6.33 |
| Analyzed Ca:P ratio | 1.39 | 1.32 | 1.35 | 1.31 | 1.36 | 1.37 | 1.32 | 1.35 | 1.38 |

TABLE 17-continued

Analyzed nutritional values of the experimental diets

| Item | NC | NC + PhyX (FTU/kg)[1] | | | NC + PhyB (FTU/kg)[2] | | NC + digestible P from MCP (g/kg) | | |
|---|---|---|---|---|---|---|---|---|---|
| | 0 | 250 | 500 | 1000 | 500 | 1000 | 0.7 | 1.4 | 1.8 (PC) |
| Magnesium (g/kg) | 2.14 | 2.20 | 2.25 | 2.42 | 2.28 | 2.26 | 2.46 | 2.26 | 2.37 |
| Iron (g/kg) | 0.21 | 0.22 | 0.23 | 0.24 | 0.23 | 0.37 | 0.24 | 0.19 | 0.19 |
| Copper (mg/kg) | 10 | 9 | 9 | 15 | 10 | 10 | 13 | 14 | 16 |
| Zinc (mg/kg) | 83 | 90 | 93 | 96 | 102 | 102 | 115 | 109 | 95 |
| Phytate-P (g/kg) | 2.6 | — | — | — | — | — | — | — | — |
| Analyzed phytase (FTU/kg)[4] | <50 | 201 | 635 | 1058 | 552 | 1083 | <50 | <50 | <50 |

[1] A representative biosynthetic bacterial 6-phytase.
[2] A microbial 6-phytase from *Buttiauxella* sp. expressed in *Trichoderma reesei* (Axtra ® PHY, DuPont Animal Nutrition).
[3] Metabolizable and net energy calculated as 0.79 and 0.58 of gross and digestible energy, respectively, according to AFZ-INRA tables (Sauvant et al., 2002).
[4] Phytase activity in the diets was analyzed by DuPont Laboratories, Brabrand, Denmark.

Bone ash minerals and bone strength: At 70 days old (d 28 of the experiment), metacarpi bone ash, Ca and P content were reduced in piglets fed the basal NC diet versus PC (P<0.05; Table 18). Supplementation with both phytases and at all dose levels improved bone ash and bone P content (%) compared to NC (P<0.05). At 500 and 1000 FTU/kg, metacarpi bone ash and bone P content were equivalent to PC. Increasing the dose of PhyX from 0 (NC) to 1,000 FTU/kg resulted in linear and quadratic increases in metacarpi bone ash at d 28 (P<0.05). Metacarpi bone Ca content was unaffected by phytase supplementation. A linear response was observed for metacarpi bone ash and P content with increasing MCP-P levels in the diets (P<0.05). Metatarsi ash content showed the same response as the results of metacarpi bone ash.

containing an additional of 1.8 g digestible P from MCP per kg diet. On comparison of two dose levels across two phytases, phytase at 1000 FTU/kg showed greater bone ash, Ultimate force (N), Stiffness (mPa) and work to failure (J) compared to 500 FTU/kg (P<0.05). No interaction was found between phytase source and dose levels.

Growth performance: The effect of dietary treatment on growth performance is presented in Table 19. Except for ADFI during d 0-14 (tendency, P=0.08), all growth performance response measures were impaired (ADG and ADFI reduced; FCR increased) in piglets fed the NC diet compared to the PC diet (P<0.05).

During the first phase of the experiment (d 0-14), both PhyX and PhyB at 1,000 FTU/kg produced a greater ADG

TABLE 18

Effect of increasing dose of two phytases or inorganic P content on metatarsi and metacarpi bone ash and mineralization (% dry matter basis) and metacarpi bone strength in piglets at 70 days old

| | NC | NC + PhyX (FTU/kg)[1] | | | NC + PhyB (FTU/kg)[2] | | NC + digestible P from MCP (g/kg) | | | SEM | P-value |
|---|---|---|---|---|---|---|---|---|---|---|---|
| | | 250 | 500 | 1000 | 500 | 1000 | 0.7 | 1.4 | 1.8 (PC) | | |
| Bone ash and minerals | | | | | | | | | | | |
| Metatarsi ash[3] | 22.1$^d$ | 26.1$^c$ | 27.5$^{bc}$ | 30.1$^{ab}$ | 27.1$^{bc}$ | 29.3$^{ab}$ | 25.8$^c$ | 29.4$^{ab}$ | 30.6$^a$ | 0.68 | <0.001 |
| Metacarpi ash[3] | 25.1$^d$ | 28.5$^{bc}$ | 29.9$^{abc}$ | 32.0$^a$ | 30.0$^{abc}$ | 32.0$^a$ | 27.8$^{cd}$ | 31.0$^{ab}$ | 32.7$^a$ | 0.63 | <0.001 |
| Metacarpi Ca[3] | 7.7$^b$ | 9.0$^{ab}$ | 8.9$^{ab}$ | 9.3$^{ab}$ | 8.5$^{ab}$ | 9.5$^{ab}$ | 8.6$^{ab}$ | 9.7$^a$ | 10.0$^a$ | 0.44 | 0.008 |
| Metacarpi P[3] | 4.9$^c$ | 5.6$^{bc}$ | 6.1$^{ab}$ | 6.5$^a$ | 6.1$^{ab}$ | 6.6$^a$ | 5.4$^{bc}$ | 6.1$^{ab}$ | 6.8$^a$ | 0.21 | <0.001 |
| Bone strength | | | | | | | | | | | |
| Ultimate force (N) | 188$^d$ | 258$^c$ | 293$^{bc}$ | 365$^a$ | 290$^{bc}$ | 373$^a$ | 251$^c$ | 328$^{ab}$ | 371$^a$ | 12.8 | <0.001 |
| Stiffness (mPa) | 112$^d$ | 158$^{cd}$ | 194$^{abc}$ | 224$^a$ | 182$^{abc}$ | 225$^a$ | 159$^{bc}$ | 202$^{ab}$ | 224$^a$ | 9.5 | <0.001 |
| Work to failure (J) | 0.60$^d$ | 0.79$^{bcd}$ | 0.78$^{cd}$ | 1.11$^a$ | 0.95$^{abc}$ | 1.16$^a$ | 0.78$^{cd}$ | 1.03$^{ab}$ | 1.11$^a$ | 0.05 | <0.001 |
| Displacement (mm) | 4.5 | 4.3 | 3.7 | 4.3 | 4.5 | 4.4 | 4.3 | 4.3 | 4.3 | 0.18 | 0.156 |

[1] An experimental biosynthetic bacterial 6-phytase
[2] A commercial microbial 6-phytase from *Buttiauxella* sp. expressed in *Trichoderma reesei* (Axtra ® PHY, DuPont Nutrition and Biosciences).

The influence of dietary treatments on metacarpi bone biomechanical parameters is presented on Table 18. Ultimate force (N) was lower in NC (P<0.05) compared to all other treatments. All phytase treatments at all dose levels improved ultimate force compared to NC. Both phytases at 1000 FTU/kg maintained the same ultimate force vs. PC. Both phytases at 500 FTU and 1000 FTU improved Stiffness (mPa) vs. NC and at 1000 FTU/kg maintained stiffness (mPa) and work to failure (J) compared to the PC that and a reduced FCR (P<0.05) versus NC, and were equivalent to the PC diet that contained 1.8 g/kg added P from MCP.

During the second phase of the experiment (d 15-28), PhyX at 250 FTU/kg or higher improved ADG versus NC, and at 500 FTU/kg or higher improved FCR versus NC (P<0.05). PhyB also improved ADG and FCR vs. NC at both dose levels (P<0.05). At 500 FTU/kg or higher, both phytases produced ADG and FCR values equivalent to PC that contained 1.8 g/kg added P from MCP.

TABLE 19

Effect of increasing dose of two phytases or inorganic P content on performance in weaned piglets (42 to 70 days old).

| Days on trial | NC | NC + PhyX (FTW/kg)[1] | | | NC + PhyB (FTU/kg)[2] | | NC + digestible P from MCP (g/kg) | | | SEM | P-value |
|---|---|---|---|---|---|---|---|---|---|---|---|
| | 0 | 250 | 500 | 1000 | 500 | 1000 | 0.7 | 1.4 | 1.8 (PC) | | |
| d 0-14 | | | | | | | | | | | |
| BW d 0 (kg) | 10.46 | 10.52 | 10.46 | 10.54 | 10.45 | 10.47 | 10.49 | 10.52 | 10.43 | 0.6 | 1 |
| ADG (g) | 436$^c$ | 480$^{abc}$ | 490$^{ab}$ | 562$^a$ | 505$^{abc}$ | 526$^{ab}$ | 460$^{bc}$ | 470$^{bc}$ | 541$^{ab}$ | 39.8 | <0.001 |
| ADFI (g) | 721 | 760 | 743 | 811 | 783 | 776 | 745 | 732 | 783 | 59.8 | 0.08 |
| FCR (g/g) | 1.65$^a$ | 1.58$^{abc}$ | 1.53$^{ab}$ | 1.45$^c$ | 1.56$^{abc}$ | 1.48$^{bc}$ | 1.64$^{ab}$ | 1.58$^{abc}$ | 1.45$^c$ | 0.04 | <0.001 |
| d 15-28 | | | | | | | | | | | |
| BW d 14 (kg) | 16.3$^c$ | 17.0$^{abc}$ | 17.1$^{abc}$ | 18.1$^a$ | 17.3$^{abc}$ | 17.6$^{ab}$ | 16.7$^{bc}$ | 16.8$^{bc}$ | 17.8$^{ab}$ | 1.4 | <0.001 |
| ADG (g) | 491$^c$ | 604$^b$ | 664$^{ab}$ | 713$^a$ | 663$^{ab}$ | 702$^a$ | 610$^b$ | 666$^{ab}$ | 708$^a$ | 37.1 | <0.001 |
| ADFI (g) | 1011$^b$ | 1104$^{ab}$ | 1160$^{ab}$ | 1181$^a$ | 1129$^{ab}$ | 1193$^a$ | 1152$^{ab}$ | 1101$^{ab}$ | 1178$^a$ | 74.0 | 0.015 |
| FCR (g/g) | 2.07$^a$ | 1.82$^{ab}$ | 1.76$^b$ | 1.66$^b$ | 1.71$^b$ | 1.71$^b$ | 1.88$^{ab}$ | 1.65$^b$ | 1.67$^b$ | 0.08 | <0.004 |
| d 0-28[3] | | | | | | | | | | | |
| BW d 28 (kg) | 23.2$^d$ | 25.4$^{bc}$ | 26.4$^{abc}$ | 28.1$^a$ | 26.5$^{abc}$ | 27.4$^{ab}$ | 25.2$^c$ | 26.2$^{abc}$ | 27.7$^a$ | 1.9 | <0.001 |
| ADG (g) | 463$^c$ | 542$^b$ | 577$^{ab}$ | 637$^a$ | 584$^{ab}$ | 614$^a$ | 535$^b$ | 568$^{ab}$ | 624$^a$ | 37.3 | <0.001 |
| ADFI (g) | 866$^b$ | 932$^{ab}$ | 952$^{ab}$ | 996$^a$ | 956$^{ab}$ | 985$^a$ | 948$^{ab}$ | 916$^{ab}$ | 980$^a$ | 34.3 | 0.011 |
| FCR (g/g) | 1.86$^a$ | 1.72$^{abc}$ | 1.66$^{bc}$ | 1.57$^c$ | 1.65$^{bc}$ | 1.61$^{bc}$ | 1.78$^{ab}$ | 1.62$^{bc}$ | 1.58$^c$ | 0.04 | <0.001 |

[1] A representative biosynthetic bacterial 6-phytase
[2] A commercial 6-phytase from *Buttiauxella* sp. expressed in *Trichoderma reesei* (Axtra® PHY, DuPont Nutrition and Biosciences).
[3] Increasing dose of PhyX from 0 (NC) to 1,000 FTU/kg resulted in linear and quadratic increases in ADG and FCR for the overall phase (d 0-28) (P < 0.05).
$^{a, b}$, Least square means within a row with different superscript letters differ (P < 0.05, Tukey test).

During the overall phase (d 0-28), both phytases at all dose levels improved ADG versus NC, and both phytases improved FCR versus NC at or above 500 FTU/kg (P<0.05). For either phytase, at 500 FTU/kg or higher, ADG and FCR were equivalent to PC that contained 1.8 g/kg added P from MCP. In addition, increasing dose of PhyX from 0 to 1,000 FTU/kg resulted in a linear and quadratic increase in ADG and reduction in FCR during the overall phase (P<0.05). A linear response was observed for ADG and FCR with increasing MCP-P levels in the diets (P<0.05). On comparison of two dose levels across two phytases, FCR was lower at 1000 FTU/kg vs 500 FTU/kg (1.59 vs. 1.66, P<0.05). A tendency of greater ADG was observed at 1000 FTU/kg vs 500 FTU/kg (635 vs. 590, P=0.08), no difference was found on feed intake (data not shown). No interaction was found between phytase source and dose levels.

Inorganic P equivalence: The dietary digestible P equivalence values (g/kg diet) of PhyX and PhyB were calculated based on bone ash, ADG and FCR as response parameters, using the observed responses to increasing digestible P from MCP as a reference. Responses to increasing digestible P from MCP were linear and positive for all three response measures (P<0.001; Table 20). Regardless of the response parameter used, calculated digestible P equivalence values increased with increasing phytase dose and were highest at 1,000 FTU/kg (Table 20). At this dose-level digestible P equivalence values were higher for PhyX than PhyB (average across response parameters 1.83 g/kg vs. 1.66 g/kg, respectively) and were highest for ADG and lowest for bone ash as the response parameter.

TABLE 20

Linear regression analysis on bone ash, ADG, FCR in response to increasing digestible from MCP[1, 2]

| | a | b | $R^2$ | P-value |
|---|---|---|---|---|
| Metacarpi bone ash | 25.0 | 4.27 | 0.99 | <0.001 |

TABLE 20-continued

Linear regression analysis on bone ash, ADG, FCR in response to increasing digestible from MCP[1, 2]

| | a | b | $R^2$ | P-value |
|---|---|---|---|---|
| ADG | 465.9 | 83.5 | 0.97 | <0.001 |
| FCR | 1.9 | −0.17 | 0.98 | <0.001 |

[1] Linear regression was performed with increasing added digestible P from MCP (e.g. NC, NC + 0.7, NC + 1.4 and NC + 1.8 g/kg digestible P from MCP) against metacarpi bone ash, ADG and FCR, with an equation of Y = a + bX, where Y is response parameters and X is the increasing added digestible P from MCP.
[2] $R^2$ is based on the regression from treatment means. The digestible P equivalence was calculated by applying the response parameters (Y, e.g. bone ash) values at a given phytase dose and calculate the corresponding MCP-P replacement (X) values.

In conclusion, this study has shown that an experimental phytase (PhyX) was effective at maintaining piglet metacarpi bone ash, bone P content and growth performance equivalent to a nutritionally adequate diet (containing 2.9 g/kg digestible P, with 1.8 g/kg dig P from MCP), when added to a corn-soybean meal-based diet without added inorganic P, at a dose-level of 500 or 1,000 FTU/kg. Responses were greatest at a dose-level of 1,000 FTU/kg, at which it was estimated that the experimental phytase could replace an estimated 1.83 g/kg of digestible P in the diet in weaning piglets fed corn-SBM based diets containing rice and rice bran.

Example 10

Design and Evaluation of Chimeric High Tm-Phytase Clade Polypeptides

A series of chimeric polypeptides were designed to evaluate the contribution of swapping/replacing regions at the N-terminus and or the C-terminus of high Tm-phytase clade polypeptides described in Example 4 (PHY-13594, PHY-13789, and PHY-13885). For the purpose of this study, the N-termini is defined at residues 1-13 according to SEQ ID NO:1, the core region is defined as residues 14-325 according to SEQ ID NO:1, and the C-termini is defined as the residues 326 to the end of each polypeptide described in Example 7, in accordance to SEQ ID NO:1. The proteins were generated using methods described in Example 1, and samples of clarified culture supernatants were used to measure thermostability by DSC and specific phytase activity at pH 3.5 and pH 5.5 using methods described in Example 3. The effect of creating chimeric molecules containing the N-terminal regions of the HAP phytases found in *Buttiauxella* sp (*Buttiauxella* NCIMB 41248, SEQ ID NO:88), *C. brakii* (*Citrobacter braakii* AAS45884, SEQ ID NO:89), and *E. piscicida* (*Edwardsiella tarda* YP007628727, *Edwardsiella piscicida* WP_015461291.1, SEQ ID NO:90), using PHY-13594, PHY-13789, and PHY-13885 phytases for comparison. Likewise, the effect of creating chimeric molecules containing the C-terminal regions of the HAP phytases found in *H. alvei* (*Hafnia alvei* WO2010034835-0002, SEQ ID NO:94), *Y. mollaretii* (*Yersinia mollaretii* WP032813045, SEQ ID NO:95 and *Buttiauxella* sp (*Buttiauxella* NCIMB 41248, SEQ ID NO:96), using PHY-13594, PHY-13789, and PHY-13885 for comparison. The phytase core regions used are as follows: SEQ ID NO: 100 for PHY-13594, SEQ ID NO: 101 for PHY-13789, and SEQ ID NO: 102 for PHY-13885. Table 21 describes the various chimeric constructs tested and provides results for thermostability, specific activity at pH 3.5 and the ratio of specific activity at pH 3.5 versus pH 5.5. As shown on Table 21, modifications in either N-terminus or C-terminus of the three high Tm phytases evaluated result in enzymes with very similar thermostability, indicating that the structural determinants for maintaining thermostability of these high Tm phytases resides within the amino acid sequence of the core regions. All high Tm-phytase clade polypeptides described on Table 21 also display greater than 100 FTU/mg when tested using the assay described in Example 2.

TABLE 21

Thermostability results measured by DSC for various chimeric phytase enzymes.

| Sample name | modified chimeric element | N-termini | Phytase Core | C-termini | Tm by DSC (° C.) | Specific activity at pH 3.5 (μmoles P/mg/min) | Ratio of Specific activity at pH 3.5 vs pH 5.5 |
|---|---|---|---|---|---|---|---|
| PHY-17434 | N-termini | *Buttiauxella* sp | PHY-13594 | PHY-13594 | 91 | ND | ND |
| PHY-17230 | C-termini | PHY-13594 | PHY-13594 | *H. alvei* | 94 | 436 | 1.2 |
| PHY-17240 | C-termini | PHY-13594 | PHY-13594 | *Y. mollaretii* | 95 | 567 | 1.3 |
| PHY-13594 | none | PHY-13594 | PHY-13594 | PHY-13594 | 97 | 687 | 1.5 |
| PHY-17041 | N-termini | *Buttiauxella* sp | PHY-13789 | PHY-13789 | 99 | 862 | 1.5 |
| PHY-17050 | N-termini | *C. brakii* | PHY-13789 | PHY-13789 | 100 | 690 | 1.4 |
| PHY-17202 | N-termini | *E. piscicida* | PHY-13789 | PHY-13789 | 100 | 771 | 1.7 |
| PHY-17117 | C-termini | PHY-13789 | PHY-13789 | Hafnia | 96 | 754 | 1.5 |
| PHY-17032 | C-termini | PHY-13789 | PHY-13789 | *Buttiauxella* sp | 97 | 419 | 1.1 |
| PHY-17126 | C-termini | PHY-13789 | PHY-13789 | *Y. mollaretii* | 98 | 645 | 1.4 |
| PHY-13789 | none | PHY-13789 | PHY-13789 | PHY-13789 | 101 | 700 | 1.5 |
| PHY-17059 | N-termini | *Buttiauxella* sp | PHY-13885 | PHY-13885 | 97 | 552 | 1.7 |
| PHY-17068 | N-termini | *C. brakii* | PHY-13885 | PHY-13885 | 98 | 605 | 1.8 |
| PHY-17174 | C-termini | PHY-13885 | PHY-13885 | *Buttiauxella* sp | 95 | 448 | 1.6 |
| PHY-17088 | C-termini | PHY-13885 | PHY-13885 | *Y. mollaretii* | 96 | 436 | 1.5 |
| PHY-13885 | none | PHY-13885 | PHY-13885 | PHY-13885 | 99 | 596 | 1.8 |

Figure 3:
FIG. 3 depicts the three-dimensional structure of a representative high Tm-clade phytase modelled using the crystal structure published for the closely related *Hafnia alvei* 6-phytase and shown as a ribbon diagram.

For illustration, FIG. 3 depicts the three-dimensional structure of a representative high Tm-clade phytase modelled using the crystal structure published for the closely related *Hafnia alvei* 6-phytase (PDB entry code: 4ARO, phytase in complex with myo-inositol hexakis sulphate) and shown as a ribbon diagram. The model was built using MOE (v2013.08, Chemical Computing Group Inc.) and visualized using the PyMol software program (version 1.8.4.2, Schrodinger, LLC). Depicted in black is the "core" domain and in light grey tones are the N and C terminal regions that were replaced/swapped in the experiments shown herein. This model is consistent with the structure-based multiple sequence alignment presented by Ariza et al (Degradation of Phytate by the 6-Phytase from *Hafnia alvei*: A Combined Structural and Solution Study, *PLOS*, 8:1-13) using the crystal structure of the *Hafnia alvei* 6-phytase.

What is claimed is:

1. An engineered phytase polypeptide comprising phytase activity comprising an amino acid sequence identical to SEQ ID NO: 1 or SEQ ID NO:26.

2. The engineered phytase polypeptide of claim 1, wherein the amino acid sequence of the engineered phytase polypeptide has a Hidden Markov Model (HMM) score of at least 1200.

3. An engineered phytase polypeptide wherein said phytase polypeptide comprises amino acid positions 14-325 of the polypeptide of SEQ ID NO: 1 or SEQ ID NO:26.

4. The engineered phytase polypeptide of claim 1, wherein the polypeptide has an in-feed pelleting recovery of at least 50% when applied in mixer liquid application (MLA) at 95° C. for 30 seconds.

5. The engineered phytase polypeptide of claim 1, wherein the polypeptide has a ratio of in-feed pelleting recoveries of at least 0.7 when applied in MLA at 95° C. for 30 seconds as compared to application in MLA at 80° C. for 30 seconds.

6. The engineered phytase polypeptide of claim 1 wherein said polypeptide comprises a Tm temperature of at least 92.5° C.

7. The engineered phytase polypeptide thereof of claim 6 wherein said polypeptide comprises a specific activity of at least 100 U/mg at pH 3.5.

8. A method for improving animal performance on one or more metrics selected from the group consisting of increased feed efficiency, increased weight gain, reduced feed conversion ratio, improved digestibility of nutrients or energy in a feed, improved nitrogen retention, improved ability to avoid the negative effects of necrotic enteritis, and improved immune response comprising administering an effective amount of the engineered phytase polypeptide of claim 1 to the animal.

9. The method of claim 8, wherein the animal is a monogastric animal selected from the group consisting of swine and poultry.

10. The method of claim 9, wherein the swine is selected from the group consisting of piglets, growing pigs, and sows.

11. The method of claim 9, wherein the poultry is selected from the group consisting of turkeys, ducks, chickens, broiler chicks, layers, geese, pheasants, quail, and emus.

12. The method of claim 8, wherein the animal is a ruminant animal selected from the group consisting of cattle, young calves, goats, sheep, giraffes, bison, moose, elk, yaks, water buffalo, deer, reindeer, caribou, camels, alpacas, llamas, antelope, pronghorn and nilgai.

* * * * *